US008715696B2

(12) United States Patent
Lee

(10) Patent No.: US 8,715,696 B2
(45) Date of Patent: May 6, 2014

(54) FULL GENOME DNA OF HUMAN CYTOMEGALOVIRUS STRAIN JHC ISOLATED FROM KOREAN PATIENT AND OPEN READING FRAMES THEREOF

(75) Inventor: Chan Hee Lee, Cheongju-si (KR)

(73) Assignee: Mogam Biotechnology Research Institute (KR)

( * ) Notice: Subject to any disclaimer, the term of this patent is extended or adjusted under 35 U.S.C. 154(b) by 28 days.

(21) Appl. No.: 13/306,080

(22) Filed: Nov. 29, 2011

(65) Prior Publication Data

US 2012/0237921 A1 Sep. 20, 2012

Related U.S. Application Data

(60) Provisional application No. 61/441,508, filed on Feb. 10, 2011.

(30) Foreign Application Priority Data

Jun. 24, 2011 (KR) ........................ 10-2011-0061865

(51) Int. Cl.

| | |
|---|---|
| ***A61K 39/25*** | (2006.01) |
| ***A61K 39/245*** | (2006.01) |
| ***A01N 63/00*** | (2006.01) |
| ***A01N 65/00*** | (2009.01) |
| ***C12N 7/00*** | (2006.01) |
| ***C12N 7/01*** | (2006.01) |
| *A61K 39/00* | (2006.01) |
| *A61K 39/38* | (2006.01) |
| *C12N 15/00* | (2006.01) |

(52) U.S. Cl.
USPC ..................... 424/230.1; 424/93.2; 435/235.1

(58) Field of Classification Search
None
See application file for complete search history.

(56) References Cited

PUBLICATIONS

C. H. Lee, et al., "Full Genome Sequencing and Analysis of Human Cytomegalovirus Strain JHC Isolated form a Korean Patient," Submitted Oct. 7, 2010, Nucleotide.

GS Jung, et al., "Full Genome Sequencing and Analysis of Human Cytomegalovirus Strain JHC Isolated from a Korean Patient," Virus Res., Mar. 2011, pp. 113-120, vol. 156.

Human herpesvirus 5 strain U8, complete genome, GenBank Accession No. GU179288, 2010, pp. 1-81.

Human herpesvirus 5 strain 3157, complete genome, GenBank Accession No. GQ221974, 2010, pp. 1-80.

*Primary Examiner* — Michelle S Horning
*Assistant Examiner* — M. Franco Salvoza
(74) *Attorney, Agent, or Firm* — Cantor Colburn LLP

(57) ABSTRACT

Provided are a full genome DNA of a human cytomegalovirus (HCMV) strain JHC isolated from Korean patients and open reading frames (ORFs) thereof and, more particularly, UL1, UL119 and RL6.

1 Claim, 11 Drawing Sheets

FIG. 4A

|  |  | 10 | 20 | 30 |
|---|---|---|---|---|
| SEQ ID NO 41 | Towne | ATGACGGTGTTTATACATG | AAGGTGCGGGT | |
| SEQ ID NO 42 | HAN13 | ATAACGGTGTTTATACATG | AAAGTGCGGGT | |
| SEQ ID NO 43 | AD169-varUK | ATGACGTTGATATATG | TGGATGCGGATA | |
| SEQ ID NO 44 | AD169-varUC | ATGACGTTGATATATG | TGGATGCGGATA | |
| SEQ ID NO 45 | JP | ATGACGTTGATATATG | TGGATGCGGATA | |
| SEQ ID NO 46 | Toledo | ATGACGTTGATATATG | TGGATGCGGATA | |
| SEQ ID NO 47 | 3301 | ATGACGTTGATATATG | TGGATGCGGATA | |
| SEQ ID NO 48 | Merlin | ATGACGTTGATATATG | TGGATGCGGATA | |
| SEQ ID NO 49 | HAN20 | ATGACGTTGATATATG | TGGATGCGGATA | |
| SEQ ID NO 50 | 3157 | TTGACGTTGAATTACA | GAGTCGAGGGAA | |
| SEQ ID NO 4 | JHC | TTGACGTTGAATTACA | GAGTCGAGGGAA | |
| SEQ ID NO 51 | HAN38 | ACGTGGAACCACGGTATTTATGGATT | | |

SEQUENCE LISTING

<160> NUMBER OF SEQ ID NOS: 51

<210> SEQ ID NO 1
<211> LENGTH: 235476
<212> TYPE: DNA
<213> ORGANISM: Human cytomegalovirus
<220> FEATURE:
<221> NAME/KEY: misc_feature
<222> LOCATION: (11506)..(11506)
<223> OTHER INFORMATION: n is a, c, g, or t

<400> SEQUENCE: 1
ccattccggg ccgtgtgctg ggtgcccgaa gggcgggggg gtgtttttg cgggggggtg 60 aaaattggag ttgcgtgtgg tggggcacgg cggtcgcgga ggacggcgac ggcgaataaa 120
agcgacgtgc ggcgcgcctg tcttgcgtgt ctgtctttgc tgttgcgtgt ctttgaatcc 180
ccggggaaaa gaggaagaag aaggggagtc cctggggacg gcagcgcgag tccctgggga 240
cgcgcagagc aactcccggg gggtgacgga cggcggccag acgcggaaaa agaggaagtc 300
cccgtcgagg acacgcggag aagacgaagc gcgcgccgcc gccactcgtc cctagggaaa 360
aaagaggaag ctgcggaccc gcgtcggggg gggggagtcg cgggccccgg ggcacactgc 420
ttccatccag ccgcgcgcac accccgccga cacacccccg acacacccgg cacacgcccg 480
cgacacaccc ggcacacgcc cgcgacacac ccgacacacc ccgccgacac acccgcgaca 540
cacccggccg acacaccccc gacacacccg gcacacccag ccgcacccgg cacacaccca 600
cccagccgca cccccgacac accccgaccg ccgccggtgc gggacagggc tcggggagtt 660
gtcagggacg taagcgccag cgcgccgacc gggctgaggg agttttgcgc tgaggcagct 720
acggagtttg tcgcgcggga cagggctcgg ggaggtttgc ggggcgtcag cgcgcggccg 780
accgggccgc gggtgtttgc acggagcttt tgcgctgcgc tttgtgcacg ctgccggtgc 840
gtggggtctc acggtcttgg tttgctcagg gatctttccg cgggtgtttg cacggagctt 900

-continued

```
ttgcgcggcg ccgcgtttgc ggcggccacg ggggtttttg ccgtgctaaa cgccggcggc    960
ggccacgggg gttgcgctag ggacgggggc ttttgcgctg gagacggggc cagggtgttg   1020
cttgcggcgg ggacggggtg ctgcttgcgg cgggacggtg ctgttgattg cggcgcggag   1080
gcttttgcgc tggactgctg gtggggacgg gggtgttgat tgcagcgggg acggggacgg   1140
ggacgggagg gggggtgtgc ggtcgcagga ctgtgcgggg acggggggct tcacctcccc   1200
tatttaacct ccacccacta caacacacac atgccgcaca atcatgccag ccacagacac   1260
agacagcacc cacacaacgc cgcttcaccc agaggaccaa cacacgttag ccttacacca   1320
caacaacaca caaccgcatg tccaaacctc ggacaaacac gccgacgaag aacaccgcac   1380
gcagatcgag ctcgacgccg ctgactacgc tgcttgcgca caagcccgcc agcacctcta   1440
cagtcaaaca caaccccaac tacacgcata ccccaacgcc aacccacagg aaagcgctca   1500
ttcttctaca gacaatcaac atcaactcac gcatctactt cacaacattg gcgagggcgc   1560
agcgctcggc taccccgtcc cccgcgcgga aatccgccgc ggcggtggcg actgggccga   1620
cagcgcaagc gacttcgagg ccgactgctg gtgcatgtgg ggacgcttcg gaaccatggg   1680
tcgccaacct gtcgtcacct tactgttggc gcgccaacgc gacggcctcg ctgactggaa   1740
cgtcgtacgc tgccgcggca caggctttcg cgcacacgat tccgaggacg gcgtctctgt   1800
ctggcgtcag cacctggttt ttttactcgg aggccacggc cgccgtgtac agttagaacg   1860
tccatccgcg ggagaagccc aggctcgagg cctattgcca cgcattcgaa tcacccccat   1920
ttccacatct ccacgctcaa aaccacccca gcccaccaca tccaccgcat cgcacccaca   1980
tgctacggct ctgccacatc acacgctctt tcctgtcccg tctacaccct cagccacggt   2040
tcacaatccc cgaaactacg ccgtccaact tcacgccgaa acgacccgca catggcgctg   2100
ggcacgacgc ggtgaacgtg gcgcgtggat gccggccgag acatttacgt gtcccaagga   2160
taaacgtccc tggtagacgg ggtaggggga tctaccagcc cagggatcgc gtatttcacc   2220
gccacgctgc ttcaccgata tccaataaac ccatcccctc gccacgacgt ctccgcgtat   2280
ctttgtagcc tcaggaatcc gtccccacgt ccacccatcc cgagcactcc acacgctata   2340
acagaccacg gacacggcaa atgcatgcaa acttctcatt tattgtgtct actactctgt   2400
gttgctacag ggagtgaagg gggtgaaggc aaagaaaaaa aaaaggaaca aaataataga   2460
ttagcagaag gaataatccg tgcgaccgag cttgtgcttc ttttcttata aggaggcaaa   2520
tatactaggg aaaacataag aataggaaga aaccgaggtt tgggagaaaa gctgagataa   2580
aatagcgcat tttccataca gaggttgttg tttttgtgga tcctaagagg tttcaagtgc   2640
gaatctcaaa gttctcacga gaatattgtc ttcaacaatc gacaactgtg gtccaagatt   2700
tttttttggt ctttttaggt tctgcgaggg acatcacgat ggatcgttgc gatgaagtca   2760
cgcgtacgcc tctggtgtgg cgcggtgtcg tgacaggaga gtgtgttttc agtgcagagc   2820
tgtcttgatt cctatatccg agtatctgtt ttctcgtaag gacggtaatc ttctttggtg   2880
taagtacatc taaaagctgc aaactatatt ttaagggctg tctctaggtg tactttgatg   2940
ctggagtttt tcgctgtgtt gatgtgaata aatctactac tactattata tgcagaaaga   3000
gtgattatgc cgagacaaga ttgcattggc tgaactgttt caaaaacgcc tacactctac   3060
ttatccgtaa acctaaggta atactatgtg taagttgttt tttttctttt tgtagtaaaa   3120
tggtgatacg tgcaattaaa actgtattcc atgtttccat cctttcattt caactttaaa   3180
ggcggctttg agagcgaaga agtgcgagga taaaaatgga tgactccttc gtgtccaggg   3240
agtcgactac tgcaacgctg attgattaaa agatggtctc cgatgatgat gttgttattg   3300
```

-continued atcgaatcat ggtgcagaac ggcgacggag aggagcgtgt ccgccgccgg gaaggtggtc 3360
tctttctctt ttctttttttc aagaaatctt ccatgtgttt atcgtagtga tcgaaatcga 3420
ctgatctcgg gttctttttg ttggtttctt ttcggttaat catgtattgt tttctttttt 3480
tacagaaaga tactttttttc atgagcaatt cctcgcccgg cgccggcatg ccgaggtggg 3540
gccactgcga tcagcggcat gccgacgccg acccggggat cttggattca ccgttttctc 3600
tcttctctct ctacatacag accgggtggc aggagcggta aggaatcatc gtcgtctttc 3660
attcttcgat gattatggta atactaaatc ttatctagga gcatatacat ctaagattgg 3720
agtactagta gtcgtttgtg gtttctattt ttttttatat ttatctatga cagtttttct 3780
gtttttcgtt ttgataataa tataataaaa actcatggac gtgaaatctg gcttggttgt 3840
ggtgatttca ttctcattat tgttgttttc tttccgtctt gcggatgaag atgttgcgat 3900
gcggttgttg ttggtgttgc tatacaccga gagagatgat ctttttgttc ttctggttca 3960
tttcctatga ttgtttggct gctgaccgac gcgtcaggat gtgcagggca tgcggggaat 4020
caggaccgga cacgggataa tttcatctac ctatacggag atcgcggtcc tcgccatgag 4080
gatcgcgaca ggcgcgtcga gggggcagga acacccttgc ggattgacat tcttggtggt 4140
gtttcgttgt tgtcggtagt tgttgttgac gatgaggata aataaaaatg accttgtttt 4200
tgttctgttt tctcttgttg ggaatcgtcg actttgaatt cttcgagtta tcggaaagct 4260
gaggtaccca aatgtctgta gctttttttct ttttaccctc ttgtttatca tctgcgattc 4320
gtggtaggta ggagagggaa atgataatcc gagattaagg aaaggagaag ataaaaaata 4380
aaaaaaaata ataaaacaga agccgaccgg ccgccgaccc gttccccagg accagcctac 4440
gaggaacgga taacgcggtg gcgacggcag cggtggtggc gctgggggtg gcggtagtgg 4500
tgctgctgat ggtagtcggg acggaggaga gacaatgcat acatacacgc gtgcatgctg 4560
catgggtgga tggtacggcc gggagacgcg gaagagaaac tcacataaaa aggtgacaaa 4620
aagagcggtt gaaaaaagaa aacgagattc gaccagacag aagagaagga ccggggcttg 4680
gcgacccttc cacgactgct gttgtcatct cggctcctcc gtcttctccc ggccacgggc 4740
ggctaagtca ccgccgttct ccccatccgt ccgagcgccg accgaccagc cggccgattc 4800
gcccgccggg gcttctggag aacgccgggg cagcagcgat ctggggaagc cgctaaaccc 4860
ctgcgttttt atatggtagc tctgccgagc gcgggctgac gcgttgagta agcggaaaga 4920
cgtgtgtgac gaaaaggggt cccatggtat ttcacgtgac gatgaggaga tgcggtttgg 4980
agcacatacg gtttagaaaa agggagttgt cgtgacaagg gctgagggac ctctgtctcc 5040
atgtgtgtat aaaaagcaag gcacgttcat aatgtaaaaa agaacacgtt gtaaacaagc 5100
tattgctgta tcattcggct gactatgctt cattcggact gattttcttt tcctaacggc 5160
gtaacttaaa gtgattaacg tatgatattt gttccccaga gttatactat agtcatcatc 5220
ctaaaattca gatataaatg aacacatgtc gtatgggagt attaagaaac cgaaactctc 5280
cacagttcac catcttcttc gtcattcaac ctatgaccca ctccgtacaa cgaatcagtc 5340
tgctgcgtca tattgcaaag cacaagcgac gtatgcgaac aacttgaaac acagactgtg 5400
gtattaacga ccgttgtacc attactagtc acattgcata gagaccctcc accgttatcc 5460
catcttttcc attcagtgga aaaccggccg ctatcatcaa ctatagtaag atttccaccc 5520
tgcgtggtat tcagtttctt catatccata ccctggattc catcattaaa ccccaatatt 5580
aagcacgtta ttagtacccc cccccccacc aaggaatgtg actggaccgg ttcttagcag 5640
ctttgggagc catcttcaag atgaaccaca gctacagcaa aaccgagtcc agtgaccgat 5700

-continued

```
aaccacgtgc aaccctgcgt atgtaccagt ccaagtacgt ccggtcattg ttccacacag   5760
gaaatctaac taggtcaacg gacaaaacca aactgtcaat ccaccatatg cgcaacacaa   5820
aagcactgac gtttatttat tgaattatca acgttactta gttacaataa gaaaccaagt   5880
atccacttgt tcaggaccgt tatcaactct ccgctttaaa tcataagatc cttcgttgcc   5940
ttgcgttacg ttgcaaaacg tcaatcctgt atgactacaa ttacacacac cgtgaatcgg   6000
cggcgttgct agcgtgtaat tcttcgtccc ctccacacta cacacgtcgg tatcattttt   6060
accatcaaaa aacgaccaaa tcgttttcag gttagcacta acggttttat catcaccggt   6120
ctttacatga acattagcca ttccctcgac tctgtaattc aacgtcaaaa ttatacacgc   6180
tataagtacc cccccccac aatggaatgc tgccaaactg gttctttccc gttatagcca   6240
tagcgttccc aagcaaaagc taacgccgaa cctagtgcag taaaccgcgc ttgcagccag   6300
aaccagctta tgtaccagcc acaataacat ccggtgattg tttccacagg aaatcctacc   6360
agggaaaacc ccgcttgttt tgttcctgac catcttgttt agcaactcgt aaactgtcag   6420
cctagcgacg tccgtttaga tcaaaagtca cgtatgtcgc gacgctgttt tcacccgttt   6480
ccccgtcccg ccatttccga acagcccacc cgggtccaga caaccaacca ccaacaggaa   6540
catacacaca gaccaccggg agttcagtta aagatttcat caggtttatt ttggctgctg   6600
ctagtctttt gcttcttaga aaaaaaatac ccatatagag aaataatgat agtttgacaa   6660
cacatatggc agggatttct tcttcatcaa taagatatgc aattcccca gggagagact   6720
ttcaacaatt gaatttacaa aaacaaaatt acatcaggag aaagagagga tacattaata   6780
aatatattat atctggtgta tatactgaat gctgctggtt cataaggtaa cgatgctact   6840
tttttaatt ccaagatggt ttttctttgt tagtcttttg ttgacttgct ggttcctaaa   6900
agttcgcaaa aacgattgtg tgaagatttt atgacgttgg ttgactagtt catgagattc   6960
tgctgtacgt gtgatggtta ttcgctggtt cgttctaaga tgagtatcgt actgtgtctg   7020
cgatggtcgt ctcttactgg cattctctcg gctgcctctt gctttcatga ttgaaaagga   7080
aaaaaggact ccgagggcgc ggtcatcttt tacttttcgg ttttctcgtt ggcgggtcag   7140
aggtagtcag atcatgagac tgtcgtggtc gatgaaactg tgtctgctca agtgacgtcc   7200
atttcttgta cggagaaaaa agtcatcggg ataaataagg ctatacaagg cgttgtcaag   7260
cgtgcggctc taaacaaatt aagcgataca aaattacagt aatatgaata ataatttacc   7320
ccctccccct gtggtccccc cgagacgaga gccacccatc gtgtactctc gcaccaccca   7380
cgaccacaga gggagacggg acgaagagac gacgcagagc gccatctcct cctggaggcc   7440
ggcggcgtta actgctacag ctgcggcggc gacgacagct gcgatttgtc ggccgacatg   7500
ccgatggtat gggcggcggc ggcggcagtg gccgcggcag cggggaggag aggagagaga   7560
agaggagcgg ggcgtccgaa ggcgaggatg gcatggtctc gccggagcgc ccggctttta   7620
tggaacactc gcgtccggtt gggtatcgcc cacaggaaga tgagtcacaa cttctaaacc   7680
atcttgagac ccgagtaacg gtttacaggt cgcacgccag tctcagctaa aaacagcgga   7740
cagtcccacg ctgtttctgt tgtggctctc tccagtttcc tcatcgccgt cccggtctcc   7800
gtcgtcatcg gaagaatacc acccgctctc atgcggcaat cgattggcct cgatgaacga   7860
gacgcggcga cgcctttcta cggccgactg gttgtggtgg tgaaagaaga gcaccagcaa   7920
tcccaggagg agcaacaagc cctcacatgt ccaggaggtc ggggagaggg cctgtcggag   7980
atggccgtga ggcatcacgt acggcagctg aggagaaacg gagaagaaag aaaaattacc   8040
gtcaggggcc ggggttctta ttagagaaac agcacgtagg tcaggatcca gatgctaatg   8100
```

-continued gcaatcatga tgacgatgat catgcaggcc aagacgcggc gcacccatgc cgaatccaat 8160
agccgccgtg cctccggttg gtggccggcg gcatctagag acatgatttg ggggggaccg 8220
gcggcgcgaa aagacaggga gatggacagt gtcacggtgt tttgttatga ttaggacatg 8280
gggaccggaa gccgagacag agtactacag ggtgttgaag ggtaacgtga gggagatcat 8340
gtcatgggcg ggctgaagac cgtgcgagga ggatcgacgt gtgcggtgct tgtggaacac 8400
ggtgttttaa tatgtatccg cgtgtaatgc acgcgatgtg ctttttagca ctcggcttgg 8460
taagctacgt gaccgtctgc gccgaaacca cggtcgccac caactgtctt gtgaaaacag 8520
aaaataccca cctgacatgt aagtgcagtc cgaataacac atctaatacc ggcaatggca 8580
gcaagtgcca cgcggtgtgc aaatgccggg tcacagaacc cattaccatg ctaggcgcat 8640
actcggcctg gggcgcgggc tcgttcgtgg ccacgctgat agtcctgctg gtggtcttct 8700
tcgtaattta cgcgcgcgag gaggagaaaa acaacacggg caccgaggta gatcaatgtc 8760
tggcctatcg gagcctgaca cgcaaaaagt tggaacaaca cgcggctaaa aagcagaaca 8820
tctacgaacg gattccatac cgaccctcca gacagaaaga taactccccg ttgatcgaac 8880
cgacgggcac agacgacgaa gaggacgagg acgacgacgt ttaacgagga agacgagaac 8940
gtgttttgca ccatgcagac ctacagcaac tccctcacgc ttgtcatagt cacgtcgctg 9000
tttttattca cagctcaggg aagtttatcg aatgccgtcg aaccaatcaa aaaacccta 9060
aagctcgcca actaccgcgc cacttgcgaa gaccgtacac gcacgctggt taccaggctt 9120
aacactagcc atcacagcgt agtctggcaa cgttatgata tctacagcag atacatgcgt 9180
cgtatgccgc cactttgcat cattacagac gcctataaag aaaccacgcg tcagggtggc 9240
gcaactttca cgtgcacgcg ccaaaatctc acgctgtaca atcttacggt taaagatacg 9300
ggagtctacc ttctacagga tcagtatacc ggcgatgtcg aagctttcta cctcatcatc 9360
cacccacgca gcttctgccg agccttggaa atgcgtcgat gcttttatcc gggaccaggg 9420
agagttgtgg ttacggattc ccaagaggca gaccgagcaa ttatctcgga tttaaaacgc 9480
cagtggtccg gcctctcact ccattgcgcc tgggtttcgg gactgatgat ctttgttggc 9540
gcactggtca tctgctttct gcgatcgcaa cgaatcgggg aacaggacgc tgaacatctg 9600
cggacggacc tagatacgga acctttgttg ttgacggtgg acggggattt acagtaaaag 9660
atgcgtgtcg cctgccgaag acctcaccat ctcacgtaca ggcatacggc gtatacaatc 9720
ataatattct atattctgca tagagttaca tgcaacagta ctactaccaa tactgcatcc 9780
atcacatcat ccaacactgc ttctaccacc tttgtgacca gcgtattttc tactccaaat 9840
cctaacacat ccacagtgtc acacgcgttc gccacctcac agacgtcaac cattggcaac 9900
atgaccaacg ttacctctgg cttaagtact gctacaactg tatattctac attcaataca 9960
tcatataaca atgcatctag tacgattacc atcacagagt ccgtttcaac agacaacgca 10020
actaccatct catctttcac caccgtaacg ccaaatgcta catcttataa cacaactatt 10080
actgcgtcat acaacgtatc tactaacagc accgtgttta ctatgagcat gcctctagtc 10140
acaaactgca gtatcgcaac aaacgcatat aatcttacta actcctccaa cgcctgtcac 10200
acgaagactg aaattatacg ttttaaagaa accaacgcaa caggaataga aggaggcaat 10260
gttactataa aaggcaatta tacatggaat tgcagttcag tctcctgggt acgacattac 10320
aatctgtcca cgcacggata ccatctaggt tatcgtcaaa atgtatatac tcaatattac 10380
tacagatggt tgcgtatcct tacctcgcat actatatgcc attcccctca tcaaaaccct 10440
acatcatatc acgacttatg tcgttcatgc aataacacag aactgtatct atacgatctg 10500
aatactacca attccggcag atatagcaga cgttgtttta aagaagacca tttaaaagga 10560
catcacgaag acgaaaattt ctacttattc gtgacacccc gaaatggaac taatcatact 10620
gaaatcatta acactacctt cgtttgtcct agaaccaaca ctaacaccaa aaataaaaat 10680
gaggaacaaa gtcaacacac taacagtaca catcaccata aacgcaatcc ccaccacagc 10740
tcacaaagaa gccgcaccgt atggacaatt atgttaattt gtgtagcctg tctgcttcta 10800
ttttttggac gacgagcttt tagtaaaaag taccaaatgt tacatgacac cgttagcgaa 10860
tccgaattca tcgtacgata taatccagaa cacgaagatt aagacacatt tccgggtaag 10920
caccccatga agctacacaa taaagtataa cacactgaaa aacggtgttc ataaatatac 10980
caatgcctac tgaataaaaa gtagtattgc aatgaactgg cggattacgg ttacgtggac 11040
gatattactg ctatcagaaa actttggatc aacgtattct tgtcagtgtc cctgtaacag 11100
tactgcttca aattattcta ccaatggcac tactactatc tcaacctctg atactaccaa 11160
tacaacagtc aacagtaaag gtacctccgg accctctaca accaccgctt atataagttc 11220
tgatacaacc acgattacat caacaaccat ccatatatcc acaaaatcac agtcaaaaac 11280
aacgtcagtc acaaatattc agaccacaac atgtaccaac actagcacga acgtcgtttg 11340
tgatagtttg aattatacgg tccataaaac atgcggccgc agctacgagg taatcaacgt 11400
aacaggacac gttggtggaa acgttattct aaaaaaatgt aatgacacga gatggcacaa 11460
tgtggactgg atccactatg gacattacac acataaaatg tgtganctag gggactacca 11520
tagaactact ctacaaagtg gcatatgttt tgaatgcaac gacacctccc tgactatata 11580
caacttaacc acagcaaacg ctggaaaata taccaggcgc cgtcgtgata atagtgatga 11640
agaaaactat tacgtgacag tgttaaccag agacacgacg acttcaactt ctggtacatg 11700
ccctgtgaaa tacaacgccg aacccaagaa cactgaaagt accatcggaa gtaatattat 11760
agaaaccatt cagaaggcta acattcccct gggacttcac gctatatggg cgggcatagt 11820
ggtatcagtg gcacttatag cgctttacat gggtagccat cgcacgccca agaaaccgcg 11880
ttataccaaa cttcccaaat acgatccaga tgagttctgg actaaaacct aatatgcaca 11940
ttaataaact tttgtatcct tagtgaataa catgtctgcg tgtgtttatt ctaaattaac 12000
cacttatagt ataaatcggg gtattcatag acattaaaaa catgggtgta caatgtaaca 12060
ataaactgct attactagtc gtactaataa caattgcaat catcctaaca ttctagtaca 12120
atttcacatg aaaagcatcc tacaggaaac ttactacaaa ctgaatatat acaaataccc 12180
atcacagtag ctgagggaaa cacaatttac tttaatgcta gcgataactc ctgtaatgtc 12240
atgccatcca taatttcaag gtctgaaatt atagaatgta actatgaatg agtcgagaat 12300
ttatacacag gacgtctatc actgtgacat tccatgtaat atcaacgatg aacgtaaaca 12360
acgtagacta ctttgacaac tgtaacaact ataaatagag ccgagtatat tatcaccgtg 12420
ttatcttcac gttattctga acacacgaac tcctacgtag ccactcacgt tgattggaca 12480
attgccgcgg caacgatgat aattatctgc atcctaacat acgtcaatgt ttcaccaaac 12540
agaagacgca gactacaaac tagaaataac gtcaagtaca taacgtaatt aaaaaattcc 12600
gacgctaatt tatccaggat aaatttttac tactttgtgt ggctctcaga aattgtaaaa 12660
ccccgctttt ccactccgtc atgaaggatc gcaatagaat actgctatgt atcatcttta 12720
tttgcattat gtgcctcatt tgtatttact tcaaacgtcg ttgtgttttt actccgtctc 12780
cagacaaagc ggatctgcga gtggaatttc cctcgttacc cctgtgtatt ggcatacagt 12840
gcgctgcatg agaacacgcg tgacacatag catacccctg gacggtacag tttatgataa 12900

-continued

```
cgtaattcag ggaaagtata cattcatacc aacatgttat cacataacac acagattttc  12960
tgcgtgtttt ataaaagagc gtctcgaagc agcttgagcc acactacggt ccagatgacg  13020
agcgtaatca aaaatatgcc gcgcagtagt cgaaagccgt actgagcgtg cgaggcgggt  13080
agagtgccga acgacggata tgcatcgttg tcatcttcga ctataaggat cgcgaccgag  13140
tcttcggcca tggtaaacgc caccctgtgt ggctggtatg tagcgtatcc ggtttggaat  13200
tgttctgctc cggctcgggg gatagtgagg aattctcagg ggatatggga cccaatgact  13260
ggataagaga agggtttttc cccgtaagat gatcctcgta tcacatgagg tctggatatg  13320
tataaatgag gagtgaaata ggcacaggga atcagatgcc agcttcgtga tgcagctgct  13380
ggttctctcg gcgaagaaat tgtcgtcttt gttggcttgc aaatacatcc caccttaagc  13440
gatgagtcca taaagcaccg ttgtccgggt acggtaaaag tgacccggat tgtagcacgt  13500
ccctttttt ttgtttttgc atcgtttatc gtcaccacta gtgcaatatt ttgatcgtaa  13560
ggctgagaga gtatcgttat gatgcttaga acgtggatat tattacagat ggtactgctt  13620
gccgcgtact gtcattgtgt ttttgggact tgtttaatca gcacgacgac tgctcctgtg  13680
gaatggaagt ctcccgatcg tcggattcca agcaatatta cttgcgctaa ttactcaggg  13740
accgtcaacg gcagcgttac atttcgaggt cttcagaaca aaacggaaga tttttgcat  13800
tggttgttag ggtggggtca taagtccatc tgctcgtttt ttccgaaact ccaagacaat  13860
aaagaacaac attataggta tggagtaacg aacctcacgt acaactgcac ccatgacagc  13920
ttaacgttgc tgaacctgac gacagaaaat agcggaaagt attatttcaa aagagaagat  13980
gtgaattcga ccttctatta ctcttgttac aacctaaccg tgtcctaaat aatacacgta  14040
aactttcaca gagtcgcgtg cctgtagcta ttgtgtttac gttgcttttg aaatgttaag  14100
cgtccttacg gcgctaacat gtttctaggc tactctgact gtgtagatcc cggctttgct  14160
gtgtattgtg tatttaaatc acgcttaacg ctcgtatttg ttgtatggtt ggtcggtttg  14220
cgtctccatg attgtgccac gttcgagtcc tgctgttacg acatcaccga ggcggagagt  14280
aacaaggcta tatcaagaga cgaagcggca ttgacctcca gcgtgagcgc ccgtacaccg  14340
tccctggcga tcgcgcctcc tcctgaccga tcgatgctgt tgtcgcgaga ggaagaactc  14400
gttccgtgga gtcgtctcat catcactaag cagttctacg gaggcctgat tttccacacc  14460
acctgggtca ccggcttcgt cctgctagga ctcttgacgc ttttcgccag cctgtttcgc  14520
gtaccgcaat ccatctgtcg tttctgcata gaccgtctcc gggacatcgc ccgtcctctg  14580
aaataccgct atcaacgtct tgtcgctacc gtgtagctag ttagccagct gtgtgtagtt  14640
gtgttttgct tttgcatatt tgttttcagt cagagagtct gaaacggggt gggagggact  14700
tttgcgggta gtgcatgcta agatgaacgg gtgggctggg gtgtgcttga taactcactg  14760
tttgaatacg cgctcacgca cttatgtagt actcaacatg ttagcttttg cccgcacgcc  14820
ccggggcgtg ccgagctgcc tttttaataa agtctgggtt tccagatacg cgctggttct  14880
gattttgatg atttgtgcct ctgaaagctc tacgagctgg gccgtgacat ccaatcgact  14940
gcctaactgt agcacggtaa ctacaacagc gggtcaagac gctgaattgc acggtccagc  15000
accgttaagc tgtaatgtga cccagtgggg acgttacgaa aatggaagca cacccgtgtt  15060
atggtgcact ttacggggat cacgcatgcg agtctcatta ggacaccgtg tagcgtttgg  15120
ctgttcttgg aaaacatttt ttatttataa cgtttctgaa agtagcagtg gcacttacta  15180
tcaaaaaggt tacaactgca ccgacaaaca tataacacta tcttgtttca acctaacggt  15240
ggttcctcga gcggttcaaa gcacaaccac cgtaatgaca cccacgctgg ttacaaactc  15300
```

-continued cacattcagt gtgtcacttg ttgcgttgag actgacgaca aattccagcg cgtttggaca 15360
cgctatttat caacgacaac agcgtgttga aaacgggacg ttatccaaga acataactaa 15420
cttggcattc acctatggca gctggggcgt tgcgatgctg ctgtttgccg ccgtgatggt 15480
gctcgttgat ttgggtttgc ctcaatcggc ttggcgacgc tggcgaagcc acgtggacga 15540
tgaagaacgt ggtttgttaa tgtaggaaat aaaaggcagt ttgagcatga ctgtttccaa 15600
accgtaacgt ggtaaataaa tcatggcttc cgacgtgggt tctcatcctc tgacggttac 15660
acgcttccgc tgcagagtgc attatgtgta caataaactg ttgattttaa ctttgtttgc 15720
ccccgtgatt ctggaatccg tcatctacgt gtccgggcca cagggaggga acgttaccct 15780
ggtatccaac ttcacttcaa acatcagcgc acggtggttt cgctgggacg gcaacgatag 15840
ccatctcatt tgcttttaca aacgtggaga gggtctttct acgccctatg tgggtttaag 15900
cctaagttgt gcggctaacc aaatcaccat cttcaacctc acgttgaacg actccggtcg 15960
ttacggagca gaaggtttta cgagaagcgg cgaaaatgaa acgttcctgt ggtataattt 16020
gaccgtgaaa cccaaacctt tggaaactgc tccagctagt aacgtaacaa ccatcgtcac 16080
gacgacatcg acggtgaccg atgcgaaaag taacgttaca gggaacgtca gtttagcacc 16140
acaactacgt gccgtcgctg gattctccaa tcagacgcct ttggaaaaca acacgcacct 16200
ggccttggta ggtgttgttg tgtttttagt tctgatagtt gtttgcatta tggggtggtg 16260
gaaattgttg tgtggtaaac tggagttata gtaatgtgct ttttatcagg gagaaggttt 16320
tgtgccaaca atgactagcc cgggactatc tgcgtcacaa aagtatgtcg gaaatcatga 16380
acttacggag atcgccaata caacgcatac aaatagcaat tattgggtaa cgttaggaac 16440
cagtgcgtcg ctgttgggaa gcacggagac tgcggtcaac ctcggcaacg cgactacgat 16500
tattccacaa cctgtggaac acccagctgg agaagtacaa tatcagagaa cggcaacgca 16560
ttattcttgg atgctgatta ttgttatcat tctcatcatt tttattatca tttgtctaca 16620
agcacctcga aaagtctacg atcgctggaa agacagtaaa gagtacggac aagtgtttgt 16680
gacggacacg gagctgtaat taactataat gtatagatac acatggttgc tttggttgac 16740
aacaacgtta ctttgtatac aacagttcca tcaatggtgg aacccagata caacgttatg 16800
cattccgaaa acgggatatg gaggtcaaaa cctcagcctg cctcctaaga gtataccaca 16860
atctaaagac tatacttttt catggtataa agattcactt aactccgtta acatgctatg 16920
tttttataac gaaaaatatg aacaagtgta taacaagtta cacattacac gacaatgtct 16980
tggaaatcat acattacttc ttattaattt gacaactcac catagcggaa tttactactt 17040
tgagtgtttc cacatgttta atacggaagt atggaaacca aatgtatgct acaatgtcac 17100
cgtgcaccct acgcatcaaa catacattca cacaactaca ttgtttcatc tgcctacatc 17160
cacacgtaat tcattaacga tatcatcatt cacctcaacc aacttcacac atgccgcggt 17220
ccatcatgcc gccagtaacg ttgaagcaca acacgatact gccactccac atacaatgtg 17280
gatcataccc ctagttatcg ttataacaat catcgtttta atttgtttca agttccccca 17340
aaaagcttgg aataaattca cacaataccg atacagcggt atgattgccg ccgctcaaaa 17400
aaaaaacaac gtcgggtaaa ccaaaacgca aatataatga atatgtacag ttatttttca 17460
gctcactgtt tgaataccgt aagcaaaatg acgtacctat acgtgataat acaacaggtg 17520
ttcatgttat gcggcgagtg attaactata tcgtaaatca tgaccttttt ctgtggtccg 17580
tcgtgaccac aatgatactt tacagatatt ctgaaacttg tatggaggtc actgtcaaag 17640
taggtgatcc agctatcctc ggcagtggac acggttatca tccaggacaa aaagtacatt 17700

-continued ggtataatca gtcatgtgtc ggcgttggca gcggcgaaaa cgtgaatcct atctgcacct 17760
acgaccctcc taaacctggc aaacataaga tgataaaaac cactccgccg ccattaccgc 17820
cgttgtacga atgtcataat tctacattaa gtatccttca tgtaaacgtt tcagatccca 17880
aaaactactg cagacgaaaa tgtccatcaa atggtaataa ctgtgagttt cctacgtgtt 17940
tccagttatc gcttatttct agaacgacga ccaccaaaaa acccggacaa aaaatgacgt 18000
caccgcgatt aaaaaccaca ccaaataaac atacacagca caaaagatca acgggaaaaa 18060
cgtcacctaa agattacaat gtcacaggtc tgccaaaagg ctttgcggac tcgtttaccg 18120
gtaacgcaga ggcacataga gccaaacatg ccgcacacag cgcatggatt ctcattgtca 18180
tcatcattat catagtcgtc attctatttt tcttcaagat tcctcaaaga ctccgagaga 18240
aatgggacac caggggatac ctttacaaag gaaccgacgg tctgcccact acggactact 18300
tatcgtgagc ggacggatat ctccggtttc aaactcactg tttgaatata gggacagtcc 18360
ctacggaacc tgagaacatg tggaaatcac ctgtggtaga atgctgctca ggtacattac 18420
ctttcatcgc gaaaaggtac tttacctagc gatcgcatgc ttctttggta tctacatcag 18480
tttccacgac gcatgcattc tggtacctgc taaagtgggt actaacgtca cattgaacgc 18540
ggtacatgtg catgacggtg actatgtgta ctggtctttt ggtggaggtg gagctaatag 18600
attaatgtgt cgctatacac caaggctaga tgaaattcac aaaaacacca atcgaagttt 18660
ttcatgtctt acaaatcaca gtctccttct catcaatgta acggaagaat atactgatta 18720
ctaccgcacc atgaccacat tcgtacatcg atcccataat tggcacaacc acggtaacag 18780
atggacttta gacacgtgtt attatgtata cgttacccaa aacggaacac ttcccactac 18840
caccaccaaa aaacccacta cgaccacgag aacgacaact accaccacaa caaagaaaac 18900
aaccaccact accaccaaga agacgacaag cactacccat caccgacact ccaatcccaa 18960
agaatccacc acccctaaaa cccacgtaga acatcacgtc ggtttaggag ccacagcagc 19020
ggaaacaccg ttacaaccaa gcccacagca ccaacacgtg gctacacacg ccctctgggt 19080
tttagcggtc gtaatcgtta ttatcatcat tatcattttc tactttcgaa taccgcaaaa 19140
gctgtggttg ctctggcagc atgacaagca cggcatcgtg ctcatccccc aaaccgatct 19200
gtgagcaagt cgcgtaggaa ataattgcat gaaatcactg tgaaacgcca actccgtgcc 19260
agctggcgcg gcggacaggc ctttgacgta tttgaagcca ggcgcgctct cgataccgaa 19320
aggatccgag gggcttttcc aaagccgacg tccctgattc ccttcataaa gctgttgacc 19380
ggccctagaa agaccaagag catgctgtgg gcccactgcg gtcgcttctt gcgttatcat 19440
ctgctcccgc tgctgctgtg tagactgcca ttcttactcc ttttccagcg gccgcagtgg 19500
gcccacggct tggacattgt cgaggaggac gagtggctac gggagataca aggagcgacg 19560
taccagctgt ccatagtgcg ccaagccatg cagcacgccg gattccaagt cagagcagcg 19620
tcggtcatga cgcggcgaaa cgccgttgac ctggaccgac cgccgctttg gtcgggatcg 19680
ctcccgcatt tgcccgtcta cgatgtgcgt tccccgcggc cgttgagacc gccgtcatca 19740
cagcatcacg ccgtatcacc cgaactgccg tcgcgagacg ggatacgttg gcagtatcaa 19800
gagctgcagt atctggtgga agaacaacgg cggcgaaatc agtcgcgcaa tgcgattccg 19860
agaccctcgt tccccctcc ggatccacca tcgcagccgg cagaggatgc acgagacgcg 19920
gacgcagaac gtgccgaatc accacatagt gcagaaagca ccgtcaggca cgacgcgagt 19980
gagaacgcag tgcggcgacg gcacgaaaga cggcgctata acgctctgac ggtccgcagc 20040
cgggactcgc tgctcctgac gcgaatacgc ttctccaacc aacggtgttt cggacgcggg 20100

-continued

```
cgtctgagac atcccgcggg aagcggtccc aacaccggcg gaccgcgacc cggcggtgcg  20160
ggactccgtc aactacgcca acaactgacg gtccgctggc agctgttccg cctacggtgc  20220
cacggttgga cacagcaagt ctctagccag atcagaaccc gctgggagga aagcaacgtc  20280
gtgagccaaa cggccacgcg agtacgtacg tggtttgtgg aaagaaccac gttatggcgt  20340
cgcacgtggg ttccgggaca gaacccggcg gccgaagcgc aagaactggc cgtcataccg  20400
ccggcaccca cggtgctccg gcagaacgag gaaccacgtc aacagcttac gggagaggag  20460
acaagaaatt caacgcacac tcaacgtgaa gaagtggagg acgtttcgag agagggcgcg  20520
agagaaggga atgatgggag ccgagcaagt ggaaacgacg agagaaggaa taatgcggga  20580
agatatgatg atgatgatca tgaggttcaa gagccgcagg tcacttatcc agcgggacaa  20640
ggagaactga ataggaggtc acaggaggag aacgaggaaa gtggaccgtg tgaatcgccg  20700
ccaatgacga caaatacgct gaccgtggcc tgtccgcccc gcgaaccccc gcatcgtgcc  20760
ctgtttcgtc tatgcttagg actgtgggtc tcgagctacc tggttcgacg gcccatgacg  20820
atttagaata caccgagcca ttcctttatt tccccccatc cccggtcgct tatgcgtgtc  20880
aaacactacc aataaagata atctgccaat cgcaccttat atataatatg tggtcgcgtg  20940
tggtcttttt aaggagctct gaaacacaga caggtatggg cggtggtcgg ctgccgccgc  21000
tgtggctgcc gctactgatc gcctggagcg agtggggcaa ctgctgcctc gatgcgcctc  21060
cggtggtgcg ttcgccctgt ctgcagccgg tgcgcgaccg caaccgcgag cggaacccgg  21120
gctcaccgca gttgctgcct tacggcgacc gtctggaggt ggcctgcatc ttccccgcgc  21180
acgactggcc agaggtctct atccgagtcc acctctgcta ctggcccgag atcgtgcgtt  21240
cgctggtggt ggacgcacgc agcggtcaag tgttacacaa cgacgctagc tgttacatcg  21300
ccggcgggcg ctggcgcttc gaggacggcg gcgcggcgca gcggctaagc ctctcgtttc  21360
ggctcatcac cgagaccgcg ggcacctaca cctgcgtgct gggcaacgag actcacagcc  21420
tggcgaccga gaccacggcg ctggtggccg acgtgcacga cctgcgccac tcggaccgct  21480
cctgcgacct agctttcgga tctcgctcac agacgcggta cctgtggacg cccgatccct  21540
ccaggttacg cagtataaac tgtggttggg agggtgaacg gcaccgcgtg gtccactaca  21600
tccccggcac ctcgggtctg ctgccctcgt gcgaggagga cgagcgcgaa ctgtgcgtgc  21660
ccttcatcag ccagagcatc gcggacaaca actgcagccg ccggcatcga gttgacggcg  21720
ctaggcggcg ctatcatcta cggagggatt actggctgac ggatccgaag atcgggctgc  21780
tggccgcggg atcggtggcc ctgacctccc tctgccacct gctgtgctac tggtgttccg  21840
aatcgtaccg gcgtctgaac accgaagagg aaaacgaggc ggcggaggaa actgccgcgg  21900
gagaagcctc tgcggtagcg gcggcggccg tctctgagga agagcagcag cgggagtaaa  21960
cgaggagagc catgaagcgg ataattcgca gtcacggcag gaaaacggaa tgtcagatga  22020
cgggcgccgg cgagcgacgc ggctccgccg tcggtgcgct catctgcggc agcggtaccc  22080
gacgcggcag cggcgccacc gaacgccgcg actccgacgt cggtcccatc gcccacagta  22140
gcggtaccag acgcggttcg acgaatgaaa cgtccgcctg tacgcggacc gatcaccaga  22200
aggcggacat tgggctgtgg ttcatgtttc tggtttttgg actgtgttcg tggttggcga  22260
tgcggtatcg cgcacaataa attttgaatc gatgtcaagg aacgcgtgtt ttgtatttga  22320
ttgggaatat tggcggggat aaaccggttt cggatgttta cccttaatct taccggggac  22380
ctcgttgtcc tctcctcctc cttcttcctc ggacaccggg ctccatgctg acgtaggtac  22440
cgactggggt caaaagcctg ggtacttatg aggagcgcgc acaaaggacc gttaggcgcc  22500
```

-continued

```
ggcatggagc gtcgccgagg tacggtaccg ctgggatggg tgttttttgt tctttgcttg  22560
tctgcctctt ccccgtgtgc tgttgacctg ggtagcaagt cttccaactc gacctgccgc  22620
ttgaatgtga cggagttggc ctcgatccgt cctggggaaa cgtggacgtt acacgggatg  22680
tgtatctcta tctgctacta tgaaaatgtg accgaggacg agatcatcgg cgtggctttt  22740
acttggcagc ataacgagtc ggtggttgac ctgtggttgt accagaacga cacggtgatc  22800
cgcaatttca gcgacatcac caccaacatc ttgcaagacg gactgaaaat gcgaaccgtc  22860
cctgtgacta aactgtacac cagccgcata gtcactaatc ttaccgtggg ccgctatgac  22920
tgtttacgct gcgagaacgg tacgacgaaa ataatcgagc gcctctacgt ccgattgggc  22980
tcgctatatc cgagaccgcc cggatccggg ctcgccaaac acccctccgt aagcgccgac  23040
gaggaactgt ccgcgacctt agcgagagac atcgtgttgg tctcggccat cactctgttc  23100
ttcttcttgt tggccctacg gatcccccag cgactgtgtc agcggctgcg cattcgcctg  23160
ccgcatcgat accagcggtt acgcaccgag gactgaacgg ataaccgcaa aggccacgtg  23220
caacgttcac gttgctataa gaaggccatg tcccccgtgg acgggtctct ttgacacgag  23280
cgcggcacgc cgttgccacg agcatggatc acgcgctcct cacacacttc gtcggccggc  23340
cccgtcactg tcggttggaa atgttgattc tggacgaaca ggtgtctaag agatcctggg  23400
acaccacggt ttaccacagg cgccgcaaac atctacctcg acgtcgcgct ccgtgcggcc  23460
cccagaggcc cgccgagatt cccaaaagaa gaacaaaggc ggccgtcctt ctattttggc  23520
acgatttgtg ctggctgttt cgacgacttt tctttcctcg ggaggactca gagccactga  23580
tgtcggatcc ggcacggtct cccgaagagg aggagtaaac aacacacggc taagaggata  23640
catcatcaaa gaagatagga ggggtcaaaa cgcggactga aagtatataa cgctgatcat  23700
gtccgaggaa ctgttaataa aacgccatga tgacaacgtg gtgtctgacg ttgtttgtgc  23760
tgtggatgtt gagagtggtg ggaatgcacg tgttgcgtta cgggtacacg ggaattttcg  23820
gtgagtcgca tatgacgttg accgtcgtgg ggatttttga cgggcaacac ttttttacct  23880
atcacgttaa ttccagcgat aaagcgtcaa gtcgggccaa cggtaccatt tcttggatgg  23940
ccaacgtttc ggcggcctac ccccacctacc tggacgggga aagagccaaa ggtgacctta  24000
ttttcaacca aaccgagcaa aacctgttag agctggaaat tacgttgggt taccggtcac  24060
agagtgtgct gacgtggacg cacgagtgta ataccacgga aaacggtagt tttgtagccg  24120
gttacgaggg atttgggtgg gacggggaaa ctttaatgga gctcgagaat aacctgacac  24180
tatggacggg ccccaattac gaaattagtt ggttgaagca aaacaaaacg tacatcgacg  24240
gtaaaattaa aaacatcagc gaggaagata ctacgacaca gaggaactat ctcaagggta  24300
attgcactca atggtccgtc atctatagcg ggtttcagac ccccgtcacc cacccagtgg  24360
tgaagggcgg tgtccgaaac cagaatgaca acagagctga agcgttctgt acatcttacg  24420
ggttctttcc aggggaaatt aatattactt ttattcatta cggtgataag gtgcccgagg  24480
atagcgagcc tcaatgcaat ccgctacttc ccaccttcga tgggactttc catcagggat  24540
gttacgtagc catcttttgc aatcaaaact acacctgccg cgttacacac ggtaattgga  24600
cggtggaaat ccccatcagc gtcacctcac ctgacgacag ttcctcgggg gaggtcccgg  24660
atcacccgac agctaacaaa cgctataaca ccatgaccat cagcagtgtc ctcctagccc  24720
tgcttttatg cgctttgcta ttcgcgttcc tgcactactt taccaccttg aaacaatacc  24780
tacgtaacct ggcctttgcg tggcgctatc gcaaggtccg gtcgtcatga ccagcaacgc  24840
cctgtatgag ctgtttcgac gtcggttacc gcgtgccccc gtcaacacgg tcatgtttct  24900
```

-continued

```
cacgcgacgc actcgtgatg ggttctgtgg tcggttgacg tctatcgcca cgaattccca  24960
ctacactatg ttcgtgttgg atcacgggtc cgtgcgcatc gagcgaccga gtcagtcaga  25020
agtggattgc gccagtttaa tggaaacgct gaagcggatt cggttacgaa attcgtgggt  25080
agcatcagaa gacgagctag atgtgagtcg cagggacgcg tgacacgaaa cgcgttcaag  25140
attaacgtag gttttcgaaa taacctacgt ccgtgagtga cgcggtttcg tgttaaaacc  25200
cgcgcccggt tctcacggtg gtttatgatg aaaccggcgt tggggatcta cgcgggttcc  25260
tcattcaacc tgcgaaaaga ggaagttgcg gtaaaactac gtcaataaag acgtcaatga  25320
cacctcaatg ttgcgttgga acggtcttta tatatacaaa cgccgttatg ctcagtgtcc  25380
ggcaagatgc tcgggataca tgctatgctg gtgatgctga attaccactg gatacagttg  25440
acaacgaaca atgacgcccg aaataataat acagatacca tctttgtatc tctccttacc  25500
gggcccaacg gaattacccg cacagccgtc gggggtctgt attcaaatta caccaactta  25560
actgaggtat tcggctttac tcaagcaaac acaacaacca actcttccgc tgagggtaat  25620
tggagcgtga tgaatttaac ggagacttgc atcaaccgcg gtgagtccta tctgactacc  25680
atttggcttc tgagttgtgc tcagaatact tcctattggt actctggaaa tgcctacaac  25740
tatacagatg ataataatac cacatgtgga agtaaaattt cgaaatatct tttaggcatg  25800
tgcaaactat gggaaagttg ggtcgctaat gatacttctc ataacactac cagaatcgag  25860
ttgctgaaaa acgaaacacg ctgcacgctg cccgctaaac agtataccct caacgccacg  25920
gtggaatggt acaacaaatc tgaaggtgac ataccaaagg aattcatgaa ttatgctatc  25980
ctgaattccg tggcggtgct tacatgcgga cttcaggaag cttatatact cgacatgact  26040
cgcagaatca cgtacttgtt ctccatgtcc tgcataggaa tcacaagtat aatatccatc  26100
atactcgcct ccttatcgct gcttatcctc atctgttact atcgctgtgg ccgacttctg  26160
atatgcccac gcggctttga acgcttgcca gaattcaccg aggaagagga ggaaaaagaa  26220
aacttgttaa cgcacaagga cattgaagtc caggtgccta tccgcacgcg gcgactgctc  26280
gtcccttgga tccgggaaag caaaatgtgg acattaccac ctccacttcc tccacgacct  26340
cctcacttaa tagaattccc accgtctcct ccgtcgtcgc ctgagcccac gcacatggta  26400
atctgcatac catcatgacg gactttggac tgagccccaa gcggtacgga ctatatattt  26460
tccacaagtc tacactgaac ttgagcacac aaatactgac aatagactgg atatatagac  26520
ttttatatga tccctgtaca gatgtaaata aaatgttttt attcaaaact ggtcccaatg  26580
ttcttcggga atcatggggt ggggacgggg aacgcggtag ggagcaaaac cgggtacatg  26640
ggggggaaca tcgtccagca gtagcaccag cggattgggt aggggttgct gcggaggtcg  26700
gtcgatgacg atgtcgatct ccatcggcag atccggcaac atctcttcgt ctccctcacc  26760
gaccagcact cggcgctgtt ctggatatat atgattctgg aaaagcctcc gacgagctcg  26820
cggcgcgtag aaagccaagc ggcgcaaggg ccggcgagcc cgaaagtcca tgcgcacaga  26880
tggcatgagt ccttgagtga cggtggtgag ctggggaaca gggctacctc ccatcgcgac  26940
ggtgacagtg gatccatgag agaggcgccg cacgctgcat ggctaaatac cgtgaatccc  27000
ctgacgtcgt ctttcgtccc gaacgcgtca tgttgggggc gaggcgtaaa ccgtcgaggt  27060
tgaaaaaccg cgtatctgcg acccgtccgg actacgttgt ttttcagaag cggccacatg  27120
acctcgagat gtcgtcaccc aaggtattta acggcacaca gccagacgcg ttcgtcatca  27180
gcgacgccga caagacctca gcatggctcg gaggctatgg atcttgagcg tactagccgt  27240
gaccttgacg gtggctttgg cggcaccttc tcagaaatcg aagcgcaggt aaacggaatc  27300
```

tggggaactc aacacaggta agaaatacaa aaaataacgt gattgtgaac gcggttatcg 27360
tgtttttgca gcgtgacggt gaaacaaccc agtaccagca ctaactccga tggtaatacc 27420
actcgtaacc aggacgtaac tctcagtcag ggggggtcca ccaccgacgg aaacgaagat 27480
tactccgggg aagagtatga cgttttgatt acagacggag atggcagcga acatcagcaa 27540
ccacaagaga agaccgacaa acacaaggaa gaacacacca aagaaaatga aaagacccag 27600
tagcagcagc agatcccaag ggttaaagac catgttgact attttatttt tttattaaaa 27660
agctgtaagg ttctgctcta aaaacacccc gcctccggtc ttttttcttt cgtattcggc 27720
acgcgaaaca cggtttcttc ccatagcctg tctaactagc cttcccgtga gagtttatga 27780
acatgtatct caccagaatg ctagtttgta gaggctatgc gggatgctgc ggcggcgcga 27840
ccttccctcc ccacccagcc ccgtcaaaac acacgcgact cgagcggttc gtatgaaaaa 27900
taaaaaacag ctttttattt acaggaacgg gaaaaaaaag gcatacggtc cgtgggagac 27960
gcgggttcac gcgtcgtcaa acagttggtg gtccactccg taaggacagg taggctgatt 28020
tagcttccgc atgctcctgg ttccgtaata aatgccgttt tcgtggcagc gtgtcatgcc 28080
gcgagtcaca aactccatca aactgtcggc cacgatgcaa acgtgctgat tgttggcagc 28140
aaagacgcgc atacagtcgt ccacgaaaag gttgatcacg tcgtaggggc tcaccaacca 28200
gcctaaaggt tccacgtggt tactgccgac catgaccctc cagtcgttaa tctcgctcca 28260
gtcgtacagc cgaatcgtgg agacgcgaat gacgctgtaa tcacccacga ccatgattcg 28320
gccgcgatac atagcacgcc actgcgcgaa cgcgtggatg tgcatgcagc cggccagcgc 28380
tctaagcgag gcggtgtgcg gcagctcctc tgggacggtg atgaagttgc agcgtcgcaa 28440
accgatgttg agaaattcag tgatgctctc ggccacaaag gtcaacgagt cagagtagat 28500
gtggtcggtc cacaggtaca tggcgcccga ggcgcccagg tacagttcag acggcacgtt 28560
gtgatcgccc ttgtgtttga gaaagttgta ggtgcagatg ctgccgacga aacgcagcgg 28620
ctcggggcag cagaggtagc tggccagacg ctgtgcatcc cgtccttcgt cgcgcaccaa 28680
gcgccagcga cgccggataa caaggcagcg gtctttgggc cagaccaggg ccacgcgttg 28740
cccgggtttc cacggtcgcg acgtcttagg aggcctccag cggtcgagca gattgagaaa 28800
acagtccttg attaccgaca tcgcggtcgc gcgccggtgg acaaaaagaa atcgggccga 28860
tccagaaaaa aaaaacgacg gcaaaacacc gccgtgctcg agcgaagggt ggcggagggc 28920
cagaagaggc ggccttgacg gcgttggcag cgaaaaaatt ggcacgcgag tcaaacggga 28980
agtagcgtcg gtgttttatg ccccaagcag cgtcgtcgtc actcgtggcg tcacagtcaa 29040
cggtgctgac gtcctttggg gcagtcgggc acgcgatcgt agatgccgtt gtggccgctg 29100
aaacgtcggt tttcaaacag caggttaagt cccagacaca tgaacgtgtt gagattatct 29160
cccacccgga tgtagcggtc gtcgcgcacg tcgcaggcgt agacggcccc ggtataggcg 29220
acgacgatgg ggataaggtc gacgggccag cgcaagtgag gaaagggcgc gttctcgccc 29280
ttgaggctga cggttcccaa gccgagaacg cgcattccga aagcggtttt gatgttgcgc 29340
agcaagtgac cgccttccac gctgttttcg aaacacctga ggttgcatag acgcagttcc 29400
gttcccggcg ggtacgtcag cggcatgaac tgcccgtggt gacggatgat gaatcgcgcc 29460
atggtatcca aaccgaggct ccaggcgcgc aacagcggac gaaagtagcg cttaaccaac 29520
gacgaggtca ggtagcgcat gcagtgcagg gtctcgacgg cgcgcagccc gacgcgcgca 29580
aactccatga ggttgcgggc caggtagtag acggcggtgt cctcgcgtac atagcaaaag 29640
acatagccct cgtccgagat gaggcacacg gcggtcttct tctgctgatc cggcgacaac 29700

-continued

```
acgccctcgt tcacgaagcg acccacgaag gccaggcgcg tctggcagca caggtagtga  29760
ctccaagctt tcacgtcctc cggtttgaag tcctcgtccg tctcgatctc ctgcagcact  29820
aggttccagc ccggcggcca gaccacgggc aacacctggc ctgcgttgat gcgcacgtaa  29880
gcttccagac agcccaggcc gaactcggct gtgagcgcca ggctagccag atcgctcatg  29940
tgacgcgccg agtcggtggg cgagcccggg ggcccgtcgc acaccacgct ccgtcttctt  30000
gtcctcaccg cggccagcgt ggcgaggaca ctttccgcgc ccgaggctgt atcttcggtt  30060
tgcccgccgg agccggccct cactatataa cgtcccgccc gggtctcctc catgtatgca  30120
ggtaagcaac tgagccgaac gcacctcagc agacgagagg atgtcgtcgc ggcgccgcag  30180
ctcgtcacgt cgctctggcg aaccctcgac ggtgatttat atcccctcga gcaacgagga  30240
cacgccggcg gatgaggagg cggaggacag cgttttcacg aacacgcggg cgcgcagcgc  30300
cacggaagat ctggatcgca tggaggccgg tttgtcgccc tacagtgtct cctcggacgc  30360
cccgtcgtcc ttcgagctcg tgcgcgagac cggcggcgcc ggcgccgcca agaaaccgag  30420
cgagaagaaa cgatcgtcgt cgcgtcggca accgcagatc gcagcgggcg cgcctcgggg  30480
ctcgccggcg acacccaagg ccggcaagtc gcctaaagtc tcgcgaccgc ctagtgtacc  30540
ctcgctgccc gagaacggcg ccggcggcgg tggcgacgat aacagcagca gcggcggcag  30600
cagcagccgc accaccagta acagtagcag aagcaccagt cccgtggcgc caggcgaacc  30660
gtccgctgtc gagggcgatg agttttcctt ctgtgacagc gacatcgaag actttgagcg  30720
cgaatgttac cgggtcagcg tggctgacaa tctgggcttc gagcccagcg tgatcgcgcc  30780
gcagcacgtt gagtatctaa aattcgtgct acaagacttt gacgtgcagc acctccgccg  30840
cctcaacgac tgcataccca tgccggcctt cgcgctcacc agtctcgtcg accccgtctt  30900
aaacaacgta gcgcctggcg agcgcgatct cacgcgtcgg ataatcacgc acgcggtgat  30960
catcaactat tactacgtgg cgcaaaagaa agcgcgccac atgatggagg ccatacggac  31020
caccgtgcga agcgacacgg tacgccgggt agccacgcag gtcaacaacc agagccgttc  31080
ggggcgtgcg gccgcgctag cgcttcactt tctcacgtca cgcaaaggag tgacggacgg  31140
ccagtacgcc acgtctctgc gacggctgga cgaagagctg cggcatcgcg gcacgcccga  31200
atcgccgcgg ctcaccgagg tctaccagac gctacgcgat tacaacgtgc tcttctatac  31260
cgcccactac acctcgcgcg gcgcactcta cctctatcgg caaaacctgc agcgtctcaa  31320
cgagaaccac cggggcatgc tccggctgct ttcggtcgaa gagatatgcg aagagcacac  31380
gctcaacgat ctggcgttcc tagtaggcgt cgagcttatg atcacgcact ttcaacgcac  31440
cattcgcgtg ctgcgctgct atctccagca ccagctgcag agcatctcgg agctgtgtta  31500
cctcatctat gtacaactgc cgtcgttgcg cgaagactac gcgcagctta gtgacgtgct  31560
ctactgggcc gtcagtcaaa actacgacta cgcgctctac gcgagcacgc cggcgttgtt  31620
tgacttttta cgcgtcgtgc gtcagcagga cgccttcatt tgcaccgact acgtgtactg  31680
cgccctgcgc ctgctggcct gtcccgacag acctattatc ggtgacaccg gcggcagcag  31740
tagctcccaa cgcctcgtag gcgagtttat ggtgcgcgat ccgctgttgc gcgacccgcg  31800
cgccacccac ctgcgccaga aactcatcac ccgcgacata tgcgtggcgc ggttgcaagc  31860
gcagccctcg agtcgacaca ttccggtcga acacacgggt gtctcctccg tcaccctgct  31920
caaaatcttt agccaggtcc cccccgacga acgcgaagaa gacacgttac gcgagatggc  31980
tcttaaagcg tttatggaag cgaacggtaa tcaccccgaa caaatctgcc gatccccacc  32040
acccccgctg ccgccgcgcg actatcctca acgcgacgag cgggaccgtc accgtcgcga  32100
```

-continued

```
ccgccgcgac agcggggaat actgttgctg atggtgggac gaagcagcag ggcggaacag  32160
tttatgatag aaagtcacag gaaagtatgt gtgttgtttt tttttaatgt accaagaata  32220
aaaatgcgtc tacgaccaaa gcggtgtgtg gacgctcgtc ctctctgtct tctccgggtt  32280
ttttttcac gtgtgttttt tttcattcct attttgttac ggcaacagcg ctgatggcac  32340
gttgccggct tcgaacatcg cgtcggtgat ttcttgcttg cccggcgtca cacggtgacg  32400
cagcagcgcg cggctcacgt agcaggccga ctcgcggatg acctggccgt cggcgtcgcg  32460
tcgcaggccc gagcggttgc cgtgacgcag tctgccctgc gcagcgcgct ccacgtcttc  32520
aaagtagctg tgtagcaggc cgcgctccag cagctgcggc agcgagtcgg cggcgcgcac  32580
cacaaagttc tcacggctga tctcgtagca cagcacgctg ccgtcggccg ccacgccggc  32640
cacgctgcgg tcccaactga aaaggttggc gagtccgatg gtgccgatga cgcgcaactg  32700
accctgggtc accaccagca gcttccagta ttctacgtcg cgcggggtga ggatggtctc  32760
ctccacgtcg cagacaaaca gcgtgtagcc gcgcggatag ggcagatcca ggtggcgacc  32820
gcgctggcgg cgcataaaat cgtctaaatt caaaccgccg tcgggtacgc gcctgctcgt  32880
catcgccgcg cctcgtcggt cgatgacccc acggtgctta taacgcgccg ccgcggcttc  32940
atgtggcgtg acctccgacc tcgtgaggcc gaaaacggcg tacatgaaga cgctcaaact  33000
tttgaatgtg ggcccggtag cgcaccgagg gccccggggc ggcgacgacg gcgggtccga  33060
gttccagcgg ggccttgcgg cggcagcggt tggcgtggtt gctcagctcg gcgtccgaga  33120
gcgccgagct gaactgcggc agccgcgtgc gatcctgcgg cgcgtccccg tgtcgcagcg  33180
agtgccagag caggcgctgg acgcgcgccg tctcgggcgt cggcggcgcg cgacagcccc  33240
ggcgcagctt gaaaacgtgc aggcacagca gctcgcgctt gatgcgcagc gacacgctgc  33300
ggtagtcggg aatccgctgc accagctcga gaaagtcgca gaaggtctcc acgaacgtgt  33360
cctcggtgaa gcgaatgcgc ttcagatcgt ggacgtgttt gcgaaaccgc gacagttctc  33420
gacgttgcac ggggttctga gcgagtccct tgcgcagcag cgcagcctcg cctttaaaca  33480
gcctgatgag ccgctgcacg tccccgctca acatacgtat acacgccgtg tactcgtgac  33540
gtatactggc gcgcagcagc cgaatgatac gcagggccag cacggcgttg gaggccaggt  33600
acatggcgta gccgcgacgc gggttggcac aggcccagcc cgcggggagc agaaagtagt  33660
cgtcgaccag cgtctgcgac cagtcggcga agcccaggtc acgtgatacg ctgttctgga  33720
cgcgggccac gtcgccggcc gtgaggtggc gaatcgccgg caggtgaaac gcacccaggt  33780
gtcggttgcg ctccagcctc agctcggcgt gctccaaacg ggaatggtga gacgccgccg  33840
cggaaagcga caaagaggag tggtcgccgc cgccgtggtt accgtcgtgg ttaccgccgt  33900
cgtcgcgccc gtcgccgcac tcgcaaaagg ccgcgtagag gtccttcaac gccgcttcgg  33960
cccgcgccat aaacgtggcg tggaaaaaaa cggcggcgcg gtgcgtccgg tacttgacgg  34020
gcaacccgcg gcacagagcc gccggcaggc aacggccgat gagttcgcgc tcctcgggct  34080
ccagaaacag gcacagggtg ccgtccaggc gcaggtacag ctcctcggtc atcgagcata  34140
gctgccgcaa gtaatgggtg cgcgtcccaa aggtcttgta atcgagcaac gtgcacacca  34200
cgtattgccc cgtggccacg gccagagcga tgcgtttggc ggcgcgactg atctctggca  34260
agtactgcgc ctcgtgcacc agacggcgga aagcgccggc gttgagccag cgaaaatgct  34320
gcggatcggg cggcaagggc acgcctcgaa gcgcggccca gacagcgagg tccgactcga  34380
gcgtcagacc gcggatgtcg tacttgccgt gcgccgtagc gcaggccgaa tggaccagac  34440
agctgcggcg aatgtacacc atggcgtgct tggggtgttt gggcgccggc gttttctttt  34500
```

tctgaccgcc ggcggccgcc agatcctcgg gcgtgcgaca caacaggccg gcgcgcacag 34560
cctcctgtcg attacgaatc ggcgtcaggt aggcgcgcag gaactggtga caaaactcct 34620
catcatcacg acagtcgtcg agatactcgt acgtggtgag cggatcgcga aataggcgct 34680
cgtcaccgtc gtcatggtct tctttaacct gctcctccgg ctgctgggtt ggcagtggag 34740
gcagcggctg atccacgggg ttcatgactg agaggaagaa gaaggtggcg acgaagcgac 34800
gcggagcgac ggcggtaaag ccagacagcg gctatatagc tagtcatcac agtctcctcc 34860
ttcacgacgc ccccgtgccg ctcacgctat ccagcacgct acggcccgaa aacacgtact 34920
cgctgacgtc gtacgcgggc gatgtatggc tgctcaccgg tttcgcggcg acggttgcgc 34980
tcgagtccaa cggcgagaag caaaaacgcc gtgggcaacg aaaccagaag gagccctgac 35040
ggataaaacc gcgcagcgtc tcggccaact taactagcat cgtaccgtac agcagtacgt 35100
gaatgccgcc gtgcgcgtcc ataaatacgg ctttgttcac gggttccatc catccgatga 35160
ctacaaagtg ggcctgttct agcacgccga tcacaaaatt gttggcctcg tcggcctcgg 35220
ccacgttcca cgatccgaaa gtgaaagtac aagcgggcga gccgcccagg cggatcttgc 35280
taccggcgtg gagctgacat acgcgcagca gattggtgcg gtcgtgcagt atctgggaga 35340
gttcgtacat gcccgcaaag gtgtgcttaa accacgcgcc ctctacgatt tcatccacgt 35400
agtcgcgctc aaagaagctg tacacggcaa agaggccgtt ctcaaaaaac tcgccaaacg 35460
agagccccag cacgtacacc ttgtcctcgc cgggcagata cgcaaaggcg tgcccgtgcc 35520
cggagaccca gatctcgggc gccgtgtttg cgtccggcac gcattcgtac acactaacga 35580
ggccgataaa gtacaagcgg ccagcctggc gcaggcacga gaagcgccgg taggtcttgt 35640
gatcgcgcac caccccaaag tactgagtgt cgcccagcat gatgccgtgc agcggcggcc 35700
agcacagcgg gagccaacga cccgccgtgg cgcgcacgta gcgctgcagg tgaaccccgc 35760
tcgcacgctc gcgcggcttc gggcgcttgt gggtccaggc atcacgcaga ccgcgccaga 35820
tgctgctgaa cttgggctgc ccgcgcagat agagcgacga gagcgagtca aagtagccca 35880
cgacgagcct gtcgggagac acaagagcgc gaaaatcaaa cctagagcga cgacggtgaa 35940
aaaaccgact ataagcgcgt gtcttaaaca cgctactttc ggttataaaa acaccgtcac 36000
cctatttctg ggcgtgtgta cactgatgac tcacctacgc tttttgaacg gcagtctcag 36060
ctcgggattg gcctcgtaca gcgagctgcg gtccacgggg ccgatgctct cgtagcgaaa 36120
gtcgtcgatg agcagcgcca gccccacgcg cacaaagccc ctgaggtcgc gcgccagccg 36180
caccaactta tcctgcccca ccagcgccgc gtacacggtg cccgtatcgc cgcagagaat 36240
ccgcacgcgg tgaaagaagg tcttgtcctc ggcgccctcg atctcgccca gcggcatgac 36300
gggctcgcgc gtgtacaacg aacgttgaaa gcggcgcagc atcgaggccg agagccccag 36360
atcgcgcgcc gtgcgcagca ccagggaatg cttctcgggc cagatgaggg tcagctgcgc 36420
ctcgcgatgc gcctctacgt aggcgcagcg agcggcggtg tcctcgcaag ccagcaactc 36480
gcggaaagcc agcagcgaac gtaggtagcg gccgcgagcg gaggcgcgcg agcggcggca 36540
cagctcggcc cgatgatcgg gatgcaccaa gggcacgttg ggttgcagac gcgcgcagat 36600
agattcgtgc accgggtcgc agcggatcat gcccttggca aaaaatccgg ccagatccga 36660
ggccaactcg tacaggcagt cctcttgcgc gtcgtaggcg aacacggcgc cgtacgcgtc 36720
cacgaacacc tggtaccggc aggtggcgtg cgagaccgtg ccaatgagat gcagagctcg 36780
gaattcgccg aaaaagtcgt tctggcagtg ctccagatcg atctcggtca gcgagtgcgg 36840
cgaatgctcg cccccgacca cgtagatgca ctgcgagggc cagcccagcg acacgcacga 36900

-continued gccctcgaag cgccgcaagt aacgccgcag gccctcatag tcgcgtcgca cgcacaggtc 36960
ggccaagtcg cgcgtgcaaa agacctcggg taccaagcag cgtttgcgac gcggtcgacg 37020
cgcgtgcccg ggcagaggag gaaggcgcga cggcggcgac gacgaggagg aagacgccgt 37080
ggccgccgag cagcccttgc gacggccgga catgccggca gtccgcgacg atccacagga 37140
gacaaaaaaa aagcagaagc agcagtagcc tcggcgaccc gctccacccc gtcctccaca 37200
cgctcagccg cgactgaacg ccggggcgcg ccgctacttg ggtttttata gccatctgcc 37260
ccccgtctcg ggcacccggg agcgatctac ggagacctga cagcagttgg gcaacacaag 37320
atagggaaat acaaagacac ttttaataaa aaacgagact actttgtgtg tgtgctccgt 37380
aaactgttta ttctccccct ccgcttcgct ctggatgggc tccgggtccg tcaacacgcg 37440
actcgcgcgg caaaaggcac gctgttgacg gcgcgagagc ccgtcgtgat agtccatcat 37500
gccccggaga tcgtgcacaa agcagctgtc gccgcgcaga aaccgacgca gcgtctccac 37560
gtgctgcagc tgccggcgcg tatcaggagc cgtcatcgct gatgtcgtca tcgccctgat 37620
aggcgcgtag atggctccgc gagatcatgc gcgttttcaa ccgccgtgac acatcaggtc 37680
catcttgagc tggcgccggg cctcgcgcag gtgtcgcacg cgttgtgagc gggaggcgag 37740
ttcggcttct tgctcgaact cctgctgctc actgtccgag agggtgcgat aaaaggcggc 37800
aaagtcctcc aagtcggcta catgcgccct gggtctgacg ctccaaagcg tacgcagtct 37860
gatgaagcgg acccatcgag cgtcacggca cgccgtcttg aacgcggggc ccgggaagag 37920
gttcttctcc ccggcgcgct cgggccggcg aggccgacgc ggtttatata caccgtctcg 37980
gacggcggga cgccgagccc gcgccgcggc cgctcatcct gagacggcgg aaaccgcggc 38040
gccggaggaa acggggaccg gcaacgacgg cggcggcggc gaccagatta tgggggacaa 38100
acccacgctt gtgaccctgt tgaccgtcgc cgtgtcgtcg ccgccaccgt cgtcgccgct 38160
gccgctcgtc agcttcacgg agctgctgtt accgccgccg tccgtcgccg ccgctgcggt 38220
ggcggcgaca gcgacgagcg aggtgggcga gaaaaccgcg gagcaagagg tagcggctgc 38280
gggtccggag accgggaatg agagaagaga aaacagggag aacgaaggag gggagacgag 38340
gacgacaggc accaccgcgg tcaaaaggtc gcacgacggt atccctcgcc aactggcaga 38400
gcgcctgcgg ctgtgccgcc acatggaccc cgagcaggac tatcgtctgc cggcgcagga 38460
cgtggtgacc tcgtggatcg aagcgctacg cgacgcggac cgcgacaact acggtcgctg 38520
cgtgcgccac gctaagattc accgttcagc ctcgcacctg acggcctacg agtcgtactt 38580
ggtgtccatc accgagcagt acaacacggc ctcgaacgtg acggagaaag cttcgtacgt 38640
gcagggctgc atctttctct cgtttcccgt catttacaac aacacgcagg gctgcggcta 38700
caagtacgac tggtccaacg tggtgacgcc caaggcggcg tacgccgagc tcttctttct 38760
gctctgctcc accagcgaga gctccgtggt gctgcaaccg ctcatcacca agggcgggct 38820
ctgctcgtcc atggcggttt acgacgagga aaccatgcgg cagtcgcagg cggtgcagat 38880
cggttttctg cacacacaac tggtcatggt gcccttcgtg ccgcacgcct gcccgcatta 38940
cgccgtgcct ttcacgacgc cgggaaagcc gggctgcgga ggtgctccga gcggcgttgc 39000
ggggttggag gaggcggcgc cctttggacg ggtcagcgtc acgcggcatg gcgcgacgct 39060
gctgtgtcgc gtggaccatc tgacctggat cagtaagcgc gtaaccacgt acggacacaa 39120
aaaaattacg cgctacctcg cgcagttccg cggcacgatg gacgacgacg aggcggcgct 39180
acccggcgag gacgaagcgt ggatcgcgtc caaaaacgtg cagtacgaat tcatgggtct 39240
cattttcacc gtcaacgtgg attcactatg cgtggacgcg gaacagcgcc aactgctggg 39300

-continued caccgtggcc acctccttct gtcaccgcgt ctcggacaag atcacggcgc gcaatatgcc 39360
gcgcgccttt tccttctacc tgctgacgag cgcgcagcgc gggtacgacc tgcgatttag 39420
ccgcaacccg tcactctttt ttagcggcga cgcgctcaac tgtccgcttc tcaatgagcc 39480
caacgtgttt tcgctcacgg tgcacgcgcc ttacgatatc cacttcgggg tgcaaccgcg 39540
gcagacggtg gagttggact tgcgctacgt gcagatcaca gaccggtgtt tcttggtggc 39600
caacttgcca cacgaggacg ccttttacac ggggctcagc gtgtggcgcg gcggcgagcc 39660
gctcaaagtc acgctgtgga cgcgcacgcg ttccattgtg atcccgcagg gcacccccat 39720
cgccacgttg tatcaaatca ccgagggcga cggtaacgtg tactcgtaca accaccacac 39780
ggtgtttcgg cagatgcacg ccgccggagc aaccacgttc tttctgggcg acatgcaatt 39840
gcccgcggac aactttctca cgtctcccca tccctgaccc tccgtccgtc ctcctttccc 39900
gacacgtcac tatccgatgg tttcattaaa aagtacgtct gcgtgtgtgt ttcttaacta 39960
ttcctccgtg ttcttaatct tctcgatctt ttggaggatg ttctgcacgg cgtccgacgg 40020
cgttttggcg ccccccatgc cggcagaacc tggttgcggc cccgtaccgc tcttctgggg 40080
cgacgatagg tcgaaagcca ccgttttcat gcccgtcgtg ctcttgacgg gggaacctac 40140
ggcggcggtc cccgtcgagc ggcgtgattg caaagccgcg ctcgcccccg gtttcaggat 40200
ggagggggag gccacaggcg gcgcattcga tacgctgctt ttggccgtag acgacggtgg 40260
gtaaacggtg gtcaccgcgg gatacgtcgg cgtggtcgag gcggcccggc tggtgccgga 40320
caggcgaccc ggcgcgctac cgctcacggg gaccgagggc ggtcgaccta ccaccgcctt 40380
gccgcccaaa gtaggtttca aggaaggaac aacaccgacg cggctacccc ggcctttcac 40440
cggagacggg ggggcactct tggccgggga cggagaggct gacgaaagca tggacagcgg 40500
cgatgtggcg ggggacacga catcatcctc cgtgggcgac aaaacggacg ccgaagctga 40560
cggctgtcga gccgaagcgg aagaggttcc cgcgccagaa gtcacgttcc ttgatgacgt 40620
tgttttagac gaagccggtt gaggttgcaa cagcgtggcg ggtaccgtcg acggcgtgcc 40680
cgacacctgt ttctctaccc ttccctgaac cggtgtcgac gtcaccgtct gcgctcgggc 40740
ggacgcgtgc ggcgtcgcga ctcgcttgcc cagcaccggt ttctggctcg tggatgtcgt 40800
cgtcattgga gacgataact tagctttacg tattctggac ggcgtcgact gctcgggcgt 40860
ctgactagga ggcgaaatga cgtcgttgta atcggacgac ggtgttgtgt gtcccaggct 40920
gacgacggag ccggtgtccg aggagtcgtc gtcttcctcc tcgctgtctt cgaccggtga 40980
ctctgcagtt tggtccctta aagcccaaac ctcatcagcg gcgttctgag acgctgtttg 41040
tgtcaccgcg gcgcgtggag tcgacggcct ccgaggggtg gtggacacgg tgttttgaga 41100
agccgtggaa gtcgtaggca tcctgaaggg attgtgagcc aggtgaggat tcctgagggc 41160
ccacgcgcgt tcgcgcggcc agttggcggg gttcatatcc ccgggcaacg gcgccgtcgg 41220
agcccagggc gagttaccgt tgaccggggt ttgggtaccc gcgaaggtag gtgtcggggc 41280
cggagcgggg gccgtagaag gattgacagg cgtcggcgtg aggatggcag cgccggcacc 41340
agcagggacg ttaactccgg cgccgaacgt caacgtcggt tgctcgaact tgtacgcggt 41400
ggtgacgggc ggtttgacgt tcgtctcggt atccgtgata tccaccagcg tgtcggtgaa 41460
acgcggatcc tgacggttgg ggggatagcc atccgagctg tcggaatcct cgtcgcccga 41520
gaaaagatcc cctctggtct ccgtgagcgg cctcacgtcc cacgcgctgt cccgacggac 41580
ccttcccggg ctggccttgg tcacctgcgg ggagacgaga ctgaaagccg cgtgacgctg 41640
ttgttgctgc gggatgttca agggaccgct ggtcggtttc tgactgcccg aggataacag 41700

-continued

```
gccgctgaaa atgctggaaa caccgttgcc actagcggcg cccttgccgc tagttcccgg  41760
tttcttgatg ggcgtaaaga tgtttttctc gtcatcgtca tcgtcgtcgt cctcatcggc  41820
actggagcca aagagcctcc gggaggcgct cggtttacgt gccgggggcg gtggttgctg  41880
ctgacgttgc tgcaggttct gctgcctctc ctcccaagcc ttcagctgct gtttctcacg  41940
ctgcaccacc tcgtcgtcca cccgtttctg ccgctcgcga cgcttttcct cttcgtcgta  42000
atagccgacg gccgccgaac gggcggcgtg ggcgtcggcg gccggtgcca gagaaccatg  42060
ggcctcgaag cggaacggtt tgtgtccctt ccagggactg gcgatccagc tccagccgtc  42120
cagcggctgc gtgggggcat gtttcttgga taccgacgag aaggccgaac cgccgccgag  42180
cgagaggaga ttggcgtcat cgtcaaactc caacgacggc gagcgcgcgc ccaaaaaggt  42240
gtgcgccgac tgcgggaagc tgtccacgta gatgtcaaag tcctcgatga gcagctccag  42300
cagcgtgtcg gccgagtcgc cgttttccac ggcgtgcttg aggatattgc gacagtagtt  42360
ggagtcaaag gaaaggcaca tgcgcagctc cttaaccagc agcttgcagc gctcctgaat  42420
gcgcgccaga catttgcgct ccagctcctc ccaagacctg cgcacgttca tgatgagacg  42480
gcccgtgtac acgagcttgt tgacggcgtt gaccagcgcc gtgttggcgt gccggtccag  42540
gttaagatcg agcggtttca cacagaacat gttacggcgc acaccctcca ggttttcttc  42600
aatgcgctgc acctccgtat ccttgaggtg cacaaaggcg atgggttccg tctggccgat  42660
ggctgtgacc agcgtctcgc gcaccgacat cttggccaga atgaccgcgc ttacgagcgc  42720
gcgctcgacg atctcggcat cgtggcgcac gtccgtatcg aattcggtat ggtctagcac  42780
agccaggtga tcgcgcgcct taccacgatc accgaacggg taagtgtagc cgcgacgcgc  42840
cacggccgcg caacgcacct cgaactcctc gagcaccgag gagaggtcgg ggttgtggaa  42900
acgcagctcg cggtagtatc ccaaccaaag catgagctcg ttgaacagca ccgtacgccg  42960
gtgcaggcgt ttttcgccac attttttcag gatcttgggg tgtgcctcga gatccacgtc  43020
gggcttttgc gtgagatggc gcagaaagtt gaccagggcc accacatcgc gccgctgtag  43080
accgataaac tgcaaactca tgctggcttt tctccagaac ccggaagcgt cgtcgccccg  43140
gactgcgccc gcggtctgct attcgcccgc gatggacacc atcatccaca actcggtgag  43200
cgtcccaccc aaagggaggg ggggtagttt aatagcggag gcggatacgc ggtttttcttt  43260
taagcgccgc tgacttgttt cttctgtttt ttcgccccgt gtgctgttcc gcccagaccc  43320
gcaacaacac tcctccgcac atcaatgaca cttgcaacat gacagggccg ctattcgcca  43380
ttcgaaccac cgaagccgta ctcaacacat tcatcatctt cgtgggcggt ccacttaacg  43440
ccatagtgtt gatcacgcag ctgctcacga atcgcgtgct tggctattcg acgcccacca  43500
tttacatgac caacctctac tctactaatt ttctcacgct tactgtgcta ccctttatcg  43560
tactcagcaa ccagtggctg ttgccggccg gcgtggcctc gtgtaaattt ctatcggtga  43620
tctactactc aagctgcaca gtgggctttg ccaccgtagc tctgatcgcc gccgatcgtt  43680
atcgcatcct tcataaacga acatacgcac gccaatcata ccgttcaacc tatatgattt  43740
tgctattgac atggctcgct ggactaattt tctccgtgcc cgcagctgtt tacaccacgg  43800
tggtgatgca tcacgatgcc aacgatacca ataatactaa tgggcacgcc acctgtgtac  43860
tgtacttcgt agctgaggaa gtgcacacag tgctgctttc atggaaagtg ctgctgacgc  43920
tggtatgggg tgccgcaccc gtgataatga tgacgtggtt ctacgcattc ttctactcaa  43980
ccgtacagcg cacgtcacag aaacaaagga gtcgtacctt aacctttgtt agcgtgctac  44040
tcatctcctt cgtggcgcta cagactccct acgtctctct catgatcttc aacagttatg  44100
```

-continued ccacaaccgc ctggcccatg cagtgtgaac acctcacact gcgacgcacc attggcacgc 44160
tggcgcgtgt ggtgccccac ctacactgcc tcattaatcc catcctgtac gcgctgctgg 44220
gtcatgattt tctgcaacgc atgcggcagt gtttccgcgg ccagttgctg gaccgccgcg 44280
ctttcctgag atcgcagcag aatcagcgag ttacagcgga gacaaatcta gcggctggca 44340
acaattcaca atcagtggct acgtcattag accccaatag caaaaactgc aatcagcacg 44400
ccaaacgcag cgtgtctttc aattttccca gcggtacgtg gaaaggcggc cagaaaaccg 44460
cgtccaacga cacatccaca aaaatccccc atcgactctc acaatcgcat cataacctca 44520
gcggggtatg agctttcctg ttactttatt cagaaagcac cagaacccgt cgccatttcc 44580
cctcatatac ggtacacgtc cccctgatct gtcatcacgg tacacagatt tcgcccgact 44640
gcggacgccg acggccaatc gcgtggcgta ggagtggcgc cccggcttca ttataacgcc 44700
acgtcggagc ccctgcgcgc cacaacgccg tccggcgcaa cttctgtctc ggcacggtac 44760
gataaaaacg acgtcccccg tcgacgttgt tttctccgag cggtgatcgt tcccgtccct 44820
ctcctccctc cgcggccccc acggcggcgg cctgctcgca cggacctata ctattaccgc 44880
cccaccaccg tcgtcgtcat gaacttcatc atcaccaccc gagacttctc caacgacgat 44940
tcagtcctgc gagccgccga gatgcgtgac aacgtggcag gctcgatttc caaagcgtac 45000
aaaggcacgg tacgcgccga aggcaagaag aagctgctgc tgaagcactt gcccgtgccg 45060
cccggcggct gctcgcgccg caacagcaac ctcttcgttt tctgcaccga gcgcgactac 45120
cgcaagttcc accagggcat cgcacagctc aagcgcgcgc cggccgaact ggacccccac 45180
gagatccagc aagtcacggc cagtatccgc tgccgcctgc agcccagtct ccgcgagccg 45240
cccacgccgg ccgacgagct gcagacggct gtgtcgcgcg tgtgcgcgct cttcaaccag 45300
ctggttttca cggcccagct gcgccactac tgcgagcacc aggacaaggt ggtgagctac 45360
gcgcgcgacg agttgaccaa acgctgcggc gaaaaatcgg cgctgggcgt ggaggtgcat 45420
caactggtag ccttgctgcc acacgagcgc caccgcgaac tgtgccacgt cctcatcggc 45480
ttgttgcacc agacgccgca catgtgggcg cgctcgatcc gtctcatcgg acacctgcgc 45540
cactacctgc agaacagctt cctacacctg ctgatgaact caggtttgga tatcgcgcaa 45600
gtcttcgacg gctgttacca cagcgaggcc taccgcatgc tcttccagat cggtcatacg 45660
gactcggtgt cggcggccct ggaactctca cacagcgcgg cggccgggcc gcccgaggcc 45720
gatgagaaca acgacgaggg agaggaggac gacgacgagc tccgtcacag cgacccggcg 45780
ccgcttcacg agtccaagaa gccccgcaac gcccgtcgtc cccgcacacg cgtgccgcct 45840
cacgagcaaa agcccgaaga aaacgaggag gaagaagagg agctgtttcc ctcctgcaag 45900
gcaaccgcag cattcctgcg ggcagaaccc tccgtctcca acgacgacga caacggcggc 45960
gaacgctgcg acacgctagc gaccgccctg cggcattgcg ccgacgaaga agacggacct 46020
ctagccagcc agaccgctgt gcgggtcgcc gcgacccccct caccttcagt caccccagcc 46080
cttacccccg tcacgtcccc cataaccccg ttgtgtattt aacgtcactg gagaacaata 46140
aagcgttgat ttctcaagtt ccgctctggt tttggtttcg ttttcaaagg gagccccatc 46200
atggcccaag gatcgcgagc cccatcgggc ccgccactgc ccgttctccc cgtggacgac 46260
tggctcaact ttcgggttga cctgtttggg gacgagcacc ggcgcctgct gctcgaaatg 46320
ttgacccagg gctgctccaa ctttgtgggg ctgctcaact ttggcgtgcc cagccccgta 46380
tacgcgctgg aggccctggt ggacttccag gtgcgcaacg cttttatgaa ggtaaagccc 46440
gtggcccagg agattatccg tatctgcatc ctcgctaacc actaccgcaa cagccgcgac 46500

-continued

```
gtgttgcggg acctgcgcac gcagctcgac gtgctgtact cggagccgct taagacgcgg  46560
ctgcttagag ggctcatccg gctctgccgc gctgcgcaaa ccggcgtcaa gcccgaggac  46620
atcagcgtgc acttgggcgc cgacgatgtg acattcggcg tgctaaaacg agcgctggtc  46680
cggctgcacc gggtacgcga cgcgctgggg ctgcgcgcgt ctcccgaggc cgaggcgcgc  46740
tatccgcgcc tcaccaccta taacctgctg ttccacccac cgccctttac cacggtcgag  46800
gcggtggatc tgtgcgccga gaacctgtcc gacgtaacac aacgtcgcaa ccgaccgttg  46860
cgctgcctca cctccatcaa acgcccgggc tcacgcaccc tggaggacgc gctaaacgac  46920
atgtatctgt tgttgacgct gcgacacttg cagctgcgac acgcgctgga gctacaaatg  46980
atgcaggact gggtggtgga acgctgcaac cggctttgcg acgcgcttta cttttgttac  47040
acgcaagccc ccgaaacgcg gcagactttc gtcacgctgg tgcgtgggct ggaacttgcg  47100
cggcaacaca gcagtccggc cttccagccg atgctgtaca atctgttgca actactgacg  47160
cagctgcacg aggctaacgt gtacctctgc ccgggatatt tacatttcag cgcgtacaag  47220
ctgctgaaaa agatccaatc agtctcggac gcccgcgagc gtggcgagtt cggggacgag  47280
gacgaagagc aggagaacga cggcgagccg cgcgaggccc agctcgatct cgaagccgat  47340
cccacggcgc gcgagggcga gctctttttc ttctccaaga acctgtacgg caacggtgag  47400
gttttccgcg tgccagaaca gcccagccgc tacctgcgcc gacgtatgtt cgtggaacgg  47460
cccgaaaccc tgcagatctt ctataacttc cacgaaggca agatcaccac cgagacgtat  47520
cacctccagc gcatctatag catgatgatc gagggcgcct ctcggcagac gggcctgaca  47580
cccaagcgct tcatggaact ccttgacaga gcgcctctgg gccaggagtc agaacccgag  47640
atcacagaac atcgcgattt atttgccgat gtttttcgcc gtcctgtgac cgacgcggct  47700
tcttcgtcgt ccgcgtcttc gtcgtcgtcc tcagcatctc cgaattctgt ttcgctgccg  47760
tctgccaggt cgtcatccac acgaaccacc acgcccgcgt ccacgtacac ctcggccggg  47820
acttcttcta ccacgggtct cttgctctcc tcttcttcct tgtcgggatc gcacggcatt  47880
agctccgcgg acctggagca gccgccccgg caacgacgcc gcatggtcag cgtgaccctc  47940
ttttcgccct actcggtagc ctacagccac caccgacgtc accgaagacg acgcagcccg  48000
ccacccgcac cccgagggcc ggcccacaca cgcttccagg gacccgacag catgccgagc  48060
actagctacg gcagcgacgt cgaagacccg cgggacgatc tggccgaaaa cctacggcat  48120
ctctgaacgc ggtttttcct ctttttctac gtgtctgtct caggacgaga cgtcgatatc  48180
aataaaaata ctgtcgacgt ggttttctaa cagtgtggtt ttctttattg accagcggag  48240
tacacagttt acgagtaaaa aagacaggga aaggttatat aaaatgctgt attatataca  48300
aaaaacatgc acatagacaa acgggaccac cgtgctcgtc atcccctcct taatcagttg  48360
ttcatgtagg cgtgtggcgg ggtgaggggc ggcatgccgt tggcggcgcc gggaataatg  48420
tgtcgtcgac cgacgtcgca caccttgaaa cgccgtcggc gcacgcagcg gtcgcaggac  48480
gggatatccc agaggaagcc catgtaggtc tcggggtcct cgtcgtgaaa gcggtaggag  48540
agttcaaagt ggtgcaacga gcccgtccga gctcgcagct tctggcgaac accctccacg  48600
tcatcggtgc acagcgacag tgctgggctg tcacacaggg cctgaagctc ctgcggccac  48660
aggtgcgtgg ccaggggcga gtccgtcgtc accagtttga cgcagtgcat caggttctcg  48720
gtgatggcgt cgtacaggcg actctcggcc tcctcgtgcg tcatcacgtt tcgaggcagc  48780
gacagctcgt cgtcgtcatc ctcgtcaaac atgatcatgg ggtcaggggt ttttttggga  48840
tgttgacaag tgggtgtctt ttccagacgc acgatggcct cacgccggcc gctgaaacgg  48900
```

-continued tggtttcggt gtcccttctt tcccatgacg caggtgaaca taaccacgtc ctcggccaaa 48960
cggtagacgg cgtccatggc ggggtcgtag ccgtagacga cgccgaaagt gtccaccaag 49020
acgtactggc gtacgaggaa ctctttgcgt tctggcacct cgtggcccag cgcgcccaac 49080
aactggtggt aacaggtgat gcgcggcacg gtacggatca tgagctccat ggtctggatg 49140
ctgccgcccg cgcggacgac gctgaaggat gtttccttga acttcataac ctctgtgttg 49200
tgggtccaga aggcgaaatg ggtgtcggga cactcatcga aagggtcgtc gatggtgtag 49260
gaagcgtagc cccgcttggt cacctcggcc gacaggctct ccacgtcacc gcggtagagc 49320
atgacggcgt tccagtagtc gtcgtactgc accatgggcc gctggtagtc gcgcatagtg 49380
tggaagtggt cgcagtgacg aaagccatgc cgcagaaagt ccttcatggt ggatgccagc 49440
tcgtagacgc agtcgcgcag gtcatcgtag cagtagatgc cgccgcgctg cccgatgagc 49500
acgatgagtt ggtagcgcat aaagcccgga ccctcgacga agccaaaggg gtgcagatat 49560
tcctgacagc agacgtaagc acctggtgga gaaataagaa aaatccacgc acgttgaaaa 49620
cacctggaaa gaacgtgccc gagcgaacgt cctctttcca ggtgtcttca acgacgtggg 49680
gcttaccttg cgaacagacg gtgcccatct tgcccacgaa gggccccagg gcgctgcgcg 49740
aacggagctg gatgaagcag cgttcgggcc aggccacgtg cagccgggtg ccgcattcct 49800
gctccagaaa gtcgttgaga ccgttaaagt ccccggctcg aatggcgatg cagccgtagg 49860
ccatcagcgt gtcccgtagg tcgtccatga cggactcctc taccttcgct cgccgacgct 49920
gcgcttctcc agccaccgct gcggtcgaca gactccttcg tccgccttcg gagaactacg 49980
gcgcggcggc acggccttta tagacactat cagcgttgac gtcagacgat ccgatgaacg 50040
tcgttttttg tgctggaact tccctcgtcc cgacaaatgt agcggaaatc ttcaagcaaa 50100
tcgcgacgaa gtccgatgag gaggatgcaa aagaggctga gcaacgcgat gctgcccgcc 50160
gccacagtac atatgctcaa caacgcccag tgtcccaacg cgcgactttt ggctcggagg 50220
agagccgaac ggcggtttct ccacatgaca gacaatctgg tccagtacgt ccatccttga 50280
cactctgacg tccagatggg aagcgtcgtc atgttatttc ccgtaaatgt tgtattgcac 50340
tttgttttgt ttttcataaa cttaagggtt ctcctgagaa atcgcgggca catgtcttgc 50400
aaaaagatgt aatcactttc cgcgtatcta gccaacgttg acgtcacagt agtagtgttt 50460
tccgaaaaag tagcgttgtc agtgacgttt gtttcttccc aacgtacgta tgattcgaat 50520
ggactcgtgt gtgctattgc ccgcaatacg taactgtgac cggtaaagtt gaacgtcagt 50580
tgtcccatag tcacgtttgt ggcgttcgta gagcacgcga cttccccacg gacctccgtg 50640
acgtttatct cacggctttc attcagaatt cgcaggggaa accagccttc caaatgatac 50700
tgaaaaccaa atttaagcat gacgctgtgc cactcccgtc gtgattgtcg aaatgtcaca 50760
tttaagggta atctggcttc ggtcccggca cagggcccgc tgtaaattag cgtatgattg 50820
cgcgtgcagt ttagctggca gttcatactc gtggtgttgg aagtgcgatt aacgtccgtg 50880
ccgtggtacg tacatcggac agaaacaccg tgtcccgtgc tccaaaacag cgtcaacaac 50940
agccacacag acacctacgt ggggacgaca cgggactttt tattgacgga gactcacgtt 51000
tctaccctcc cctttcccgt aggtaaaaac ccacgtttat cacacacgtt gtttttacct 51060
gaaacccgcg cagcccgtgg acgcgacaaa aaaccgcggc actagaaaga aaatgaaaca 51120
agtatgttta ttaagcagca tgtggggcta atagggggaa taactgaggt atagcaacta 51180
tgaaaaaaac actaaaaaaa aaagctgaac atggtcatct agcagcaaag ttctccttct 51240
agaccacgac caccatctgt accacgtcgc cctccccggc cgtgtacacc acatccttca 51300

-continued ccacgaccgg cggcagcggc ggcgacgagg acaactcgct ctcaacggag gccgggacga 51360
cagaggacgg gggggtggtg gcggcggagg acggaggggt ggcggcggca gcggggtctt 51420
cttccgacac gggcgacggc aggctcggcg gcgcggacaa cacccgttgc gccggggcgt 51480
gagaaggctg agccccggtg gcctggatgt gggccaacga attggctcgc agcgagtcgc 51540
gatccacgaa ggtcatagga attttccctt cgcggatccg ccgctcagat tccaggatgg 51600
cgcgcacgta gctgttcacc gacttggcaa aagtgcgcgg cccctccgta ttcttgtcgc 51660
gacgcgcttc cagcacctgc ttttcgtagt ccagttggtg gaagaccatc accaggtcgt 51720
ccatggtgtg cgcgtgctga cggacgtggg agcgcacctc caccgggaac agagcgttcc 51780
aatactccag cactatggca ccgtgccaga actgcgccat gctgggagcc aggaaaaaca 51840
ggataccgga gtcgtaggcg aacacgtccc acttgggcgt catgaacaac accagctgac 51900
gcgtgggccg caccgaagct tcctcccagg cctcgatgac cccgaacatg atgagctcct 51960
ggtccaacgg ggggcagtgt cgctccagcc aactgatctt gctcaggttc atctgcagaa 52020
actcgtagga ggggtcgcag atgcacacgt agagacccga gtcatgccgc agcctggctc 52080
cgcgcttcat cagtttcctc accgcgtagc gaagcgccac cttgcccaac gccgacgcct 52140
ggatcagtcc ccccacgtcc atctgcgtct gtcgccactc ggcctcgtcc agcaggctca 52200
tgatagcggc ggtgctatgc gtggtcgtag tcatcctttc tatccttctc tatgaatagc 52260
agcaatagcg gtaaagtccc ttcttatact atcccggagt ctgtggtttt tttgtttacc 52320
cctgcttact ggtgagactg ctgggggccg ttgtgctgca gcagctgagc tcgtcgccgc 52380
cgttgccaca ggaaccggtg cctccgcagg gcctttttga gggcctcgca ggcttctcgc 52440
gcaagtcctg agaggccttc ggcgtcgatg gggttcacct cgggcgtctg agcctcgttt 52500
tcttcttctt catcctccct ttcctcctcc gtgtcctctc gctctgtgtc ctccgttacg 52560
ctctcctccc cggcctcggc caagagcgcg gccaccaagt ccacggaccg ctcggtctcc 52620
gagttctcac cgtcaattac gccatgttgg cggcgtaacc ggtgccgaga acgccgggtg 52680
agcgcacatg ctttttttctt tcttaaccaa ggcgggagag gatcttcaag gcgttttcgc 52740
tggatccagc ggtagctaaa gtaccaaaag gccagcaggc ccacgctacc taacagattc 52800
acgtagactg gagacataat taaagaaaga agtgaaaccc gcgtgtgggt ctcacgtcgt 52860
cttgaaacac cgtcttatat acatgaagat gccggacatg acgcgcccaa gacacgtggg 52920
gttttcccct taggcgaccc ggtttcttaa gatgtttttc atcttcgcac gcgatgtact 52980
acatcaaagg gtcggctgac cgaccgcatt gacgcacact ttccgagtac gcgcgtctcg 53040
gagcacctga cggtgagcca cccagctcac gcggataggg gacaacactg acgtgagggg 53100
cgattcacgt cactgacggc tgacgggaat aagacgggtg agggatctcc accttttttct 53160
taagtgtgac tctccttacg gtaaatcgca cctgtgacct tttaacccct cctccctggt 53220
acccaataac agtgaaaaac acacaccaca cgtcacgaca ctgatcgatt ttctttattc 53280
ttagtgtgat gataggtaag ggcactcgtg aggatgtgca gttatcatta tcaagccttc 53340
ttcaaggcgt agtgatgatc gttgggcaga acccccaggc tcctagcgat ctgggaatag 53400
aaggaggaga acgaccccag ggccagaatg cccacagtgt acatggccca ggtctccaga 53460
ccgaacgtgg cgggtcgcag cttcagatgg taggccaccc gctccgagag ttgtgaatgc 53520
tcgttcaggc aacaggactg caggtgggtg agcccaaaag cgctttcgtt tacgccgcgc 53580
acgtgcaccg tctgggccgg gcaatcctgg tgttgcgcgc gaaaatggtc ctgacaggaa 53640
attccgtcta cgtggcggcg cgtgttgtta cccacttcga tcagcagcgt gttatcggca 53700
ggatgatgcg agaacgcgac gacggtgttg ctggaggtct ggcggcagca gtacacgtcg 53760
agcgtcatga gggccatgtc gccttggtgg tacacggcgt acgcccaacc ctggaacacg 53820
agcggacata acggaccgtg agcggacgtc acggcggcgg ttgttaccgt cgtctcggca 53880
ggagaagaca ataaactcct gatcctcata cacaggagtc caagcgtcag aactaaagtc 53940
cgcggagcca taaccgcgca agtgaagccg atacgagtgt tgctgaattt gttcattctg 54000
ccgactgttg ctcacgagcg ttcggagacg gtgccacagg ctgttggcca ttaaaaagtc 54060
ctggcccgaa tgacgacgag acagagcccg aggcgaagaa aaaggcgccc gtcatgaaga 54120
cgtaggcagg ggaattccca tatttttatg gcttctttta aaagtctgta tccgactcca 54180
tccggcgctt ttcccaaacc gtggtctcct cgtcgtccga ctcggtaccc aggaggtggt 54240
aagtcttttg ccgcacgtag aaagctttca acgtggagca aaagatgaga ataaagaccc 54300
cgaaaacgaa acaaaccacg ccgatcatgc cgatgcagac gttcatgtcg acgtagccgg 54360
cggtgctgtt ggcggtgcgg caaaagagtg tcatgtcgtg cgtgcacaaa aaacaacaca 54420
caccacaggc caggtcgtag cgtagttatt attccgtagc agcaatgatg gtacagtcaa 54480
gcacatgctc tatttcccgt taccccgatg atgatgatga tgatgatgtc cccgttgcag 54540
tggaattgtc ccggttaatc accacggtga acaccacggc caagaaaatg atccctaata 54600
tagcgaccac taagagagca aaagtccatt tccagccgtt gtcaaagtac gcccccgtgg 54660
tgggatgcat ggtggcgggc atttccatca tatccatgtc gaacgtgtgt cgcggcgacg 54720
gcgaactaac caggcagtac gggggtcgat agggcggtgg gctgcagtcg ggtggtggcg 54780
gcggtggcgt ggaaaccgtc gtcgggcaca gacccatggc ctgctcgtag gtggggggcg 54840
cgtcgtcgtg atcccggtcg cggagcatcg gcgtgggctc catgtcggtg gcagtgacgg 54900
cgactgtggt aactgtggtg gagacggtac cgacggcgtc cgcggctcac cttcgagcaa 54960
agagcccctt ctttttgcgc aaacgacggc aaaacagttc tctgggacag ccggtggcgc 55020
ggtaagcggg tgccacgctt tcagggtggg taaaacagtc gcgggcgaag cagtagttgt 55080
tgcagaaccg caagaacccg acgcgaaaaa agcccaggag tccgcgcgcc agaaagtgcg 55140
cctgccgcgt ctcgggatgc acgccgaaga cggcgccgct ctcgttcacc agtatggaga 55200
tgtccaggcg ctgctgcgac tccaccggca cggcccgcac cacaaatacc tgcagcacgt 55260
tcagcgagca cgtctctttt aaccagttgc cgtgggccgg atcctcgtaa gtctggctcc 55320
cgttcaagac gaccgtcgtc agcgcctcat taccgtctcg ccaactgaag attgaaccct 55380
cgcgcttcat gcacaggcgc cacagggcca gcaggtcgcg cgccaacatg aactcgcgac 55440
ccacgtcgcc gccggtctcg aagcggacat agcccagttc ttcgcgcagc ggcgcgtagt 55500
tgcgcaggcc ctcctgcacg aagccgcgga aaccggaccg cgacaccagg tacagcgatt 55560
ccaccacggg cgagtagacg tagacgcggc cgccctcgcc gatgagtacg ggtagcggtg 55620
ggcggccgat ggcttcgcaa cgactcacag tgcccaccgg cagcaggaac ttgtcgcagc 55680
acaggaaggt cttctccaaa cctttaatat tgagatgtcc aaagtagccg acgcgtaaca 55740
ggtcgcagta ggtgaaaaac caaccgttcg gccagctgag acgcagcacc gtgccgctga 55800
cgcgacgaac cagcttctgc aggtccttgc gggcgtcggc ggtgacagag cagcggaagg 55860
tctcgttgac cagctcgaca gccagcgcgt cctccagcgt acgttccttc atctcgtcgt 55920
tgatgctctg gcggcgccgc cgaatttcgt cgaaacgggc cgcggaggcg gcgaccgacg 55980
cggaggtcgt ccgaacgccc tctgtgacgc tgtcgtccgg ccagtcaaga aagctaaggc 56040
tggcgctgcg ccgcctaaag tgtccgatcc gcgcgggacg tcgctgaggg acggtggctg 56100

-continued

```
gtctgctggg gcgggtacgg ccgcgggtgt ccgcggacac gttagttata cacggaattg  56160
agtcacgtgg cacgttgcca gctgaaaccg ccgtcgtctc cgccggcgtt ttctccatca  56220
cgggaccgcg ccgtgcgcgc gttcccaagc acgcggccca cgctctaccc gcacttttgc  56280
ttcttggtgt tagggacgaa ctcgaacgtt acagaatcct cactgtcgct ctcctctttc  56340
gcgtcgttga agtaattgcc ggagttgcga tccaaaccgc cgcctcctcc tcctccgccg  56400
ccgcccgatc cacctttgga cgtcaggtag ctggtgatct tgtgctgctc gtatttttcc  56460
ttggaggaaa gaccgtggtc gtgatcaccg ccgccgccac cgctgctcat tttccgcgta  56520
ccggaaccac cgccaccacc gcggtcgtgc ttcttgccgc caccgccgcc acctcctccc  56580
agaccgccaa gacccatggg ctcgttcatg agatcgttat ccagacccgg gccgtcgtcg  56640
tgcagaccgc cggcattggc cagcgaagag aggctgccgc caccaccgcc gccgccacgc  56700
gacttgccgc tgttcccgac gtaattttta tcgaagggat cgccacgctg gaaaggttcc  56760
tcagtgagaa aattctccac ggcgaacaga ccgttgcgac tggccacgta caacagcgtg  56820
tcgtgctccg taactatacg caacgtgcac ggcagtttgg tgacggcgca attgagcagc  56880
gtctgataga agttcttcag ctgcacgttg atacgcatgt tttttacgcc gtggaaactg  56940
acgcggttat tggccgtgaa ttccagctcg ctgccgttgg tcaggataaa cttgatggcc  57000
ggtggaccgg cgtgcaccag aatctgcacg gtgcccgtag ggcagggcgc tttttttaacg  57060
ttacgcttga cgcgggtatg cggcccgatc cacttaagca ggtcggccac cacgccgaaa  57120
tctagatcca cgtgcacggc cgaattctcg ctttcgcgca caatgtcttg gccgtgcacg  57180
caggccgagc tgaactccat attgaaatcg ggcgcgcaca tggagatctt ggccgaaagg  57240
tccgagatgt cctgcacgta gaacttggtc aggtccttgc tggaagtcag gtacatgaaa  57300
ttaccgagca gcggcgtgga attgttaatg gtcttgggct gaaacgactt gtcagtgatg  57360
tagagacatg agctgttaaa agtgattttt gacacgcagt gactgcgtac cgtttgcaag  57420
ataagcgacg gcgttggcaa gaaggtaacc gtggtgttct ccttgagcgc acggatcaca  57480
gatcgcagct gctggatagc cgtcttgtac ggcttcagcc gcagcgccaa cgtcggcggc  57540
tccgagaggc gcgtcttgcg atccatcccg gacagcgtgc aagtctcgac taaggagcgg  57600
gcgcgagcga gcgaaagttt tatagagagc acacacgacg accgggaacg ctgcgaagac  57660
gcccggcgtc taataataca gccgcgccga gccagcgggc ccccgactaa gaggcacagt  57720
acttatatac tccgacctta aagcgccagt ggtaccactt gagcatcctg gccagaagca  57780
cgtcgggcgt catccccgag tcatagtaga aaaccagggc cacgcactga tccacaaaca  57840
cgctcaggtt cacagccgcc atttccacgt cgttttggat cgccggcgcc gcctggaaca  57900
gacactgcgt cgccttgccc tcctcctggt gctgctccaa ccacgcgtaa ttcaccacgg  57960
gcacgcgcag cggcctccgc accacggtgg ggaagtaaca ctcacggttg ggcgggcaca  58020
atgaccacac cgtctcctcc tcgaacacgg tgccgcgcga agcccacacc gacggcgtca  58080
cgccccacag atgcgccacc tcgtcgtcag gacccaccgc cagaaactga cagttgcgca  58140
atccgaactc gagcatgtcg gcgcgcagcg cttcccagcg cgcgctggcg atggagagcc  58200
gcggcaaccg atacaactcg aagatgaatt tgccctcttg atagatggtc cgttcgaacc  58260
actcgcagcg tggcaaaccc gacttgcaca aatcgacgct agcgcgcacc gcggcaaaat  58320
acatgtgttc aaagatgcgc tcgatcaagt cccaagaggc aaagtacgtg aaccctaacc  58380
gcatgagcgc cgtgtgcaag ccggccacgc cgatgtgcag cggacgcagt ttttccagcg  58440
cgctctctac ccaccattcg gacgccgaca ttagcgcgtc caggcgcgcg ttgccccaaa  58500
```

-continued

```
ccaccgcctc ggtcaccaac tcgcgcagca cgctcaaatc aaagtaacgt cgcgtgttcc  58560
ccaaaaccac gtcgggtaga tgcagcttct gttcgtcgct acgtgcaaac acgcagcgag  58620
ccacgttcac cgtcagccgc tgcaccggca tgtcacactc gccaaagtgg cacgacgcca  58680
tatcgggact caagcacggc ggcaggcaca cgctgtcggc cataatcgag tacttgacta  58740
cgtgatggac aaagaccacc gaggcacggc ccttgagagc gcacagcaac atctttttca  58800
gaaaatcgtc cgtgttcacg accaccttgg ggcacgattg ctcgcagcgc gaatattctt  58860
tctcaaaagc cgactcctga cccaggtccg agagccgccg ggagacaggc cgcccgaaca  58920
gcgagtagcg ctgctcacgc gcacggtagc gcttcattaa cacgctaggc acgttgaaag  58980
cgtagcaaac ccccgtcaac tccgacgtgc tttctttgag aataaagtta atcacgcgga  59040
tagcggccac gtcccacatg tccacaaaca cacgtaccac gggtcgatgc acctccttct  59100
cgcgtatcaa atcgcagtat ccccccaggc aacgaatcac gctgttcacg tcggcgttaa  59160
gtcgcgttac gttcaccgac acagaaacgc cgcaactcaa ggtgctcatc catttgcaca  59220
tagccgccca actggcgtca cgcgaaaaag gatcggccga gatcagaaag tcgtactgcg  59280
gcacgcgatc aaaacccacg gtagacatgg tgaaggtgga cagcgacagc tgcccatcgc  59340
gacagcgctt caacaccgag tccaacacct cgccctcgaa acgcgcatcc agatggaagc  59400
gatagatgcg cgagtgccta ctgttctcga tagcggccgt caacgccacg gcaatgcgca  59460
aaaacacgcc gcccgggctc tcgtcctgtc cgtgcagttg gcggcacacc ttatccaaac  59520
acaaaatggc cgcgtacaag ccccagcaac cggccaattc cacaaaacgc gccgtctcct  59580
cggccagctt gggtagatcc tccatgtgac gcaacacaaa acggcgcacc gactcatcgc  59640
acagctccga agcgtaacac agtggcgtgc ggctttcgcg cgcccagttg gctttgaaat  59700
aaaagcgacc caacagtaga tcgcaacgcg gcgagtgacg gatcagacag ggaccatggc  59760
gcatgataag ctgaaacagc ctgaaactgc ccaaaccggc actatgccgt gacacggtgt  59820
ccatctcgcg ccacagcgcg ttcctgtcgg acggcagctc ccgcgccggc tcctgtacac  59880
cgcaaaagcg aaacttgccc caatagccgt gacaatgaca ctttttgccc atcaacatgc  59940
gcgtagcctg tatcggcggc gacactttgc agagcgaagc cccgaaatcg tcctcctcct  60000
cgacactgtc cagctccatc ctggtcgcgc cggccggatt gaaggtgctc agaccgctac  60060
tcacacgtcc accgcgactg ggcacgacgg gaccgctgtc acgcgtcaac gacagcacag  60120
acggcgtgcc gtcgggagac ggcgactcgg gacgccaact gacgacgccg ccaccactcg  60180
taaaacccgc tacacacgct acgccgctcg atacgttggt atttccagcg gacgcttcct  60240
tgtcaccccc gggcagcggc ccctcctcga gctcgctgtc atctcccccg gtagtatcag  60300
cggcggcttc tgccgacgat tcctccgtct cggtttccgc gccgcggctt ggaatcctac  60360
ctggccgaca ccgatgtgcg ggcaccgagg acacccgctg ttcctcgtcc gcgtcagccg  60420
gagtcataag tttacgagga aaagaacaaa gaaatcaggt agatttcaat aaagtgagtc  60480
tagatggcgc cgataactac ggtttataaa gtctgtgtgc gctgtgttta tttttctttt  60540
tgtgtctcct ccccgtatgc tgtcagcgcc gctcagacga attctcgaaa gtctcccaat  60600
tcgacgctaa agttgtccaa acggacgacg gacagtttga gttctttgtg taccaggaac  60660
gaggtgtgaa tgtcgtcagc caggcaccag cccagctttt gtatgacccc ggtacacaga  60720
gggatctggc gtgggcgcgt gatgcgacgg ttgacaaagc tacagcgctc gcgggcgaac  60780
tttccgcgtg caacgtcgac tagggtctgc cagtgtgcga tgctggaggt gagcacgtag  60840
atgccgggac gtgtttcggg cccgtcatag tcatagacga tgattaaata cacgtattgc  60900
```

-continued

```
agccgtcccc gggtctcttc ccacgtcaga tacatgtctt tcggtatcat caacgcgaac  60960
acctccgttt tgagcgtgtt gtaaaggtag ccgcgcatga cgcaggtgag caacgaggtg  61020
atgcccagcg agacggtctt gacgcagccc agcgtctcga ggcggcggtg cagcagatgc  61080
gggcccaagt ccagccactg cagcgcggcg cgcgcggccg aggccgtgta cacgctttcg  61140
agcaggcagc gcgtgctggc cgagacgttg gaggcgcgaa tgcctaacag gtagaggctg  61200
atgtagaggt gtcgcggcga gtcgcaaccc gtctccatgc ggatgagcag cgcgcccggc  61260
tgcgcctcga actctaccag gccctcgggc acgaagaaac gcgccgtgag cgcctggtga  61320
tcggcgtggt agaggtagcg caccgatata gtatttacct cgcgtttggc tttgagcgcc  61380
gtcactagtt cattgtcctc gtcggccggg tcgcgcggcc gtttggccac cgcgcgcgcg  61440
tccatgatgg cgaggcgcac ggtagatttc aaaaagttga tagagcagct gcgggcacgg  61500
gccacggaca aagcggaggc gttaaatacc gtgagccaat tggagatcgg cgcggtggat  61560
gcccaggacg tgaccgcgag cgccgtgcgc gccttcgtgg gtgcgttgcc gagctcgggc  61620
taccactttg gcttcgtgcg tcagaacgtg gtcttttacc tcctaagcca cgccacggta  61680
cagacggcgc gcgacccgct gtacgccgcc gagcagttgc acgaacagct ggaccgcttc  61740
ctgcgacacc agcacgacgg cggcggagac gaggaccggt tgccgttcta ccacaacggg  61800
gccacgctga cggctttcca gaagctgttg cagaccctgc gcgagatcca gaccgtaata  61860
gccgaacaga gcggcggcac cgcggcagcg gcggacttga tcgccagtaa caacgcgtcg  61920
accgagcgcc gcgccaagaa gggcggttcg agttccgggg gccagcagcc gctggtccgc  61980
cgggtgatca cgcagctgga aacggctgcc acggaggcgc ggccctacgt caattgtcgc  62040
accgtggccg aactcctgga cctgacctac cagcggctca tctactgggc ctgcacgctc  62100
atgccctacg tgttgtttcg gcgcgacacc gacaccgaac tggacacggt acttctgatg  62160
catttttttt acacacacta ccgttcggtt aacggcgatt tggccgtgga gtttcaaaac  62220
tacgtcaaga acagcgtgcg gcacatgagc tctttcgtca gttccgatat cgacggcgac  62280
cagaagcccg gtgccgaaca catgcgtgac gtcagctaca agctgttcgt gggtaatctg  62340
caggcgcgtg acgccagcgg cctcatgttt cccatcatta gcacgcgcat ctccaccgtg  62400
aacctttacc tgtcgcccga acgtatgttt ttccacccgg gtctgatctc gcgtctgttg  62460
agtgaggaag tttcgccgcg cgccaaccta gacgcttacg cgcgcgtgtg cgatcgcgtg  62520
ctggaagacc acttgcatac gccgcgacgc gtgcagcggt tactggatct gacgcagatg  62580
gtaacgcgac tggtggaact gggtttcaat cacgatacct gcgcggccta cgcacaaatg  62640
gcgctgatcc agccggccag tcagaagagc tcgctctttg tcagcgagat tcgcgagaaa  62700
ctcatacaga tcatctacaa tttttacacg tttttcatgt gcctctatgt gtacagcccc  62760
acgttcctgt tcgaccaccg gcggcggttg attttggagc agcatcgatc cacgttgatc  62820
ggctccaagg aggaactaca gcacgtctgg agcaacgtga cactgaacgt caatacgcac  62880
tttgcggttc agtacacgga agaagacttt gaggcacata cgaagggtgc cacggaggcg  62940
gagcgcgagt acctgtatcg ggacctgcac agcaagtggg gcgtgcacct gtttaccttg  63000
cgtccgtctc gcggcgcggc cggcgcggcc tcgcctttgc ctccgcttga cggcgtcaca  63060
cgctccgaca tcttacgcga atgcgcgctc gttaatctga acgaaggccg cgtcaactac  63120
gcctccctgc tagccttcag ccatcatccc gagttcccca gcatcttcgc gcagttggtg  63180
gtggtaactg agttttcgga gatctttggt atcccgcagg gcctgtttca agccgtgggt  63240
tcgccgcgtc ttttcgcgct cattcagtta tgccgtgtat tgttgcccga gcaggtgacg  63300
```

-continued

```
ctgtaccaga acctggtctc catctacaac ctgaccacct ttgtcaagca catcgacgcc  63360
gcggttttta agacggtacg cgattgcgtc ttcgacatcg ccacgaccct cgagcacctc  63420
agcggtgtac ccgtcacgcc caatgtggac ctgctggccg agctcatggc gcgctccgta  63480
gcgcataacc tgtacaccac cgtcaacccg ctgatcgagg acgtgatgcg cagcagcgcc  63540
ggcagtctga gaaactatct gcgacacacg cgactctgtt tcggtctggc gcgtgggcgg  63600
gcgcgcctct cggaggacgg cgtgacggtg tacgtggagg tacagggtca gtacggactg  63660
cgcgtaccta ccacgcgttt cgtagaacag ttgcgcgagc tggttcgccg cgatcggctg  63720
ttggccgaga atctgcgcgg cttgaatgag cgcctgctga gtgttcgcgt gcgcgtacgt  63780
cagatcagca gcgacacaga ggaagtaagc cgacacgcca agggtcacct cacggtggcc  63840
cagatgagca aggcgctcaa aaagacggcc tccaaaatca aagtgttgga aacacgcgtg  63900
acattggcgc tcgagcaggc gcaacgttcc aatggcgccg tcgttaccgc ggtgcaacgc  63960
gcgctagccg tctttgacgt actaagtcgc gagaacttgg aacgccgcgg cgcacagctc  64020
tgtctgacgg aagcgacgag cctactgcac cgacatcgcg cgctagcgcc gatgacctgg  64080
cccgcgggca cgggcgttgc ggcggcggcc gaagcggatc gcgccttacg cgagttcttg  64140
gaggcgccct gggaatcggc gccccaaccg ccgcgactcc gcatgacgcc cgacaccgat  64200
cacgaagaat cgacggcagg cgcgacgtcc gtaccggagg tcctgggtgc gcgctacgaa  64260
cccgcacacc tggccgcgag cgacctatta aactggtaca tcgtccccgt aagccaggcg  64320
cagcaggaca tcttgtcttc gatcgacccg cccgccggct cgacatcggt gtccctgccg  64380
ccggcctcgc catgaaagtc acgcaggcca gctgccacca gggcgacatc gctcgctttg  64440
gagcgcgagc gggcaatcaa tgcgtctgca acggcatcat gttcctacac gccttgcacc  64500
tgggtggaac gagcgccgtc ctgcagaccg aggcgctgga cgccatcatg gaagagggcg  64560
cgcgtctaga cgcgcggcta gagcgcgagt tgcaaaagaa gctgcccgcc ggcgggcggc  64620
tgccggtcta ccgactgggc gacgaagtgc cgcgccgcct ggagtcgcgg ttcggccgga  64680
ccgtgcacgc gctctcgcgg cccttcaacg gcaccaccga gacgtgcgac ctggacggct  64740
acatgtgtcc gggcatcttc gactttctgc ggtacgcgca cgccaaaccg cgtcccacct  64800
acgtactcgt caccgtcaac tcgttggcgc gcgccgtggt cttcaccgag gaccacatgt  64860
tggtctttga tccgcacagc tccgcggaat gtcacaacgc cgccgtgtat cactgcgagg  64920
gtctccatca ggtgctgatg gtgctcacgg gcttcggcgt gcagctgtcg cccgctttct  64980
actatgaggc ccttttctc tacatgctgg atgtggcgac cgtgccagag gctgagatcg  65040
ccgcgcgttt ggtctccacc tatcgcgacc gcgatatcga cctcaccggc gtcatccggg  65100
aaagcgcgga cacggcggcg acaacgacca ccgccgcacc ttccttacct ccgctgcccg  65160
accccatcgt cgacccgggc tgccctcctg gcgtggcgcc cagcattccc gtctacgatc  65220
cctcgtcctc acccaaaaaa acacccgaga aacgccgcaa ggacctcagc ggtagcaaac  65280
acggaggcaa aaagaaaccc ccgtccacga cgtccaaaac actggccacc gcctcctcct  65340
cctcctcagc gatagcggcg gcctcttctt cgtccgcggt accaccgtcc tacagctgcg  65400
gcgaaggggc cctgccggcc ctgggccgct accaacagct ggtcgacgag gtagagcagg  65460
agttgaaggc tctgacgctg ccgccgttgc ctgccaacac cagcgcctgg acgttgcacg  65520
cggcgggtac cgaaagcggc gctaacgcgg caacggccac ggcgccgtcc ttcgacgaag  65580
ttttcctcac cgatcgtctc cagcagctca tcatccatgc cgtcaatcaa cgctcgtgtc  65640
tgcgtcgccc ctgcggcccg caatcggcgg cgcagcaggc agtacgcgcc tatctgggcc  65700
```

```
tatccaagaa actggatgcc tttctgctca actggctgca ccacggcctg gatctgcggc  65760
gcatgcacga ctacctgagc cacaagacca ccaaaggcac gtactcgacg ctggatcgcg  65820
cactgctgga gaagatgcaa gtcgtcttcg atccctacgg acgtcagcac ggcccggcgc  65880
tcatcgcctg ggtggaggag atgctgcgct acgtggaaag caagcccact aacgaactgt  65940
ctcaacgact gcaacgtttc gtaaccaagc gaccgatgcc cgttagcgac agcttcgtct  66000
gcctgcgacc cgtagacttt cagcgtctga cgcaagtcat cgaacagcga cgtcgggtgt  66060
tgcaacgtca acgcgaggaa taccacggcg tttacgagca cttggccggc ctcatcacca  66120
gcatcgacat tcacgaccta gacgccagcg atctgaaccg acgcgaaatt ctgaaagcgc  66180
tgcagccgtt ggacgacaac gccaagcagg aactctttcg cctgggcaac gccaaaatgc  66240
tagagttgca gatggacctg gaccgtctga gcacgcagct gctgacgcgc gtgcacaatc  66300
acatcctcaa cggctttttg ccggtagagg acctgaagca gatagaacgc gtcgtcgagc  66360
aggtactgag actcttttac gacctgcgcg acctgaaact gtgtgacggc agctacgaag  66420
agggattcgt cgtcatacgc gaacaactga gctacctcat gacgggcact gtgcgcgaca  66480
acgtaccgct actgcaagag atcctgcagc tgcgacacgc gtaccagcaa gccacgcagc  66540
aaaacgaggg tcgcctcacg cagattcacg acctgcttca tgtcatcgag acgctggtgc  66600
gcgacccggg cagccgcggc tcggcgctga cactggcctt ggtacaggag cagctagctc  66660
agctggaagc gctaggcggc ctgcagctac ccgaagtgca gcagcgccta cagaacgcgc  66720
aactcgcgct aagccgcctc tacgaagagg aagaggaaac gcagcgtttc ctcgacggac  66780
tctcgtacga cgatccgccc accgaacaga ccatcaagcg acacccacaa ttacgcgaga  66840
tgttacgtcg cgacgaacag acgcgtctgc gactcatcaa cgccgtactg agcatgttcc  66900
acacattagt gatgcgactg gcgcgcgacg agtcgccgcg accgacgttt tttgacgccg  66960
tcagtctgtt gttgcagcaa ctgccacccg actcgcatga acgtgaggat ctgcgtgccg  67020
ccaacgccac gtacgcgcag atggtcaaga aactggagca gatcgagaaa gccggtaccg  67080
gcgcatccga aaaacgcttc caagcgttac gggagttggt ttactttttc cgtaaccatg  67140
aatatttctt tcaacatatg gtcggacgac tgggcgtcgg acctcaggta acggaactct  67200
acgagcgata tcaacacgag atggaagaac agcacctgga acggctagaa cgtgaatggc  67260
aagaagaggc cggcaagctc acggtaactt ctgtggagga cgtgcagcgt gtcttggccc  67320
gggcaccgag ccatcgtgtc atgcatcaaa tgcaacaaac gttaaccacc aagatgcaag  67380
actttttaga caaggagaaa cgtaaacagg aagaacagca acggcagcta ctggacggct  67440
accaaaaaaa ggtgcagcag gatttgcaac gcgtggtgga cgccgttaag ggcgagatgc  67500
tctccaccat cccgcaccaa ccactggagg ccacactcga gctgctcttg ggcctagatc  67560
aacgcgccca accgctacta gacaagttca accaggactt gctgtcggcg ctgcagcagc  67620
tgagcaaaaa actagacggg cgaatcaacg agtgtctgca cggcgtgctg acgggtgatg  67680
tagagcggcg ctgtcacccg caccgagaag cggctatgca aacccaagcc tcgctgaacc  67740
acttggacca aattttgggt ccgcaactcc tgattcatga gacgcagcag gccctgcaac  67800
acgccgtcca tcaagcgcag ttcatcgaga agtgtcaaca gggcgatcca actacagcca  67860
tcacgggcag cgagttcgag ggcgactttg cacgctaccg cagcagtcaa cagaagatgg  67920
agggacaatt acaagagact agacaacaga tgaccgaaac tagcgagcgg ctggatcgct  67980
cgctgcgcca ggatcccggg aacagctccg tcacgcgtgt acccgaaaaa cccttcaagg  68040
gtcaggagct ggcgggtcga atcacgccgc cgcccgccga cttccagcgg cccgtcttca  68100
```

-continued aaacgctgct agatcagcaa gccgacgcgg cccggaaagc gctcagcgac gaggccgatc 68160
tgctgaatca gaaagtacag acgcagttgc gacaacgcga cgagcagctg agcacggcgc 68220
agaacctgtg gactgatctg gtcacgcgcc acaaaatgag cggcggactg gacgtgacca 68280
cccccgacgc caaggcgctg atggaaaagc cgctggagac acttcgcgag ctgttgggca 68340
aagccacgca acaactgccg tacctgtcgg cggagcgcac ggtgcgctgg atgctggctt 68400
ttctggagga agcccttgcg caaatcaccg cggaccctac gcacccgcat cacggaagca 68460
ggacccacta ccggaacctg caacagcaag ctgtcgagag cgccgtgacg ctagcgcatc 68520
aaatcgaaca aaacgcggcc tgtgaaaatt ttattgcaca gcatcaagag gcgactgcca 68580
acggcgcgtc cacgccgcgg gtcgacatgg tccaggcggt agaagcggtc tggcagcgac 68640
tggaacccgg acgcgtagcc ggcggcgccg cgcgtcatca aaaagtgcag gaactgttgc 68700
agcgcttggg tcagacgcta ggcgacctag aactgcagga aacgttggcg acggaatact 68760
ttgcgctgtt acacggaatc cagaccttca gctacgggct ggactttcgg tcgcagttgg 68820
aaaagatccg cgatctgcgg actcgttttg cggaactggc caagcgacgc ggtacgcgtc 68880
tctccaacga gggagccctg cccaaccccc ggaaaccgca ggcgacgact tcgctgggcg 68940
cctttacacg cgggttgaac gcgctggaac gacacgtcca gctgggtcac cagtatctgc 69000
tcaacaagct caacggctca tcgctagtct ataggctgga agacattcct agcgtgcttc 69060
cgccaactca cgagaccgat cccgcgctga taatgcgcga ccgcctgcgt cgcctatgct 69120
tcgcgcgtca ccacgacacc ttccttgaag tggtagacgt cttcggcatg cggcaaatcg 69180
tcacgcaggc cggcgaaccc attcacctgg tcaccgatta cggcaacgta gcctttaagt 69240
acttggcgct gcgagacgat ggccggcccc tggcatggcg gcgccgctgt agcggcggag 69300
gactcaaaaa cgtcgtcacc acacgttata aagccatcac ggtagccgtg gccgtctgtc 69360
agacattgcg cactttctgg ccgcagatct cgcagtacga cctacgaccc tacctcacgc 69420
agcatcagag ccacacgcac cccgcggaga ctcacacgtt gcataacctt aagctctttt 69480
gttatctggt gagcaccgcc tggcaccagc gcatcgacac gcagcaggag ctgacgaccg 69540
ccgatcgcgt aggaagcggc gagggtggtg acgtagagga acagaaaccg ggccgcggta 69600
ccgtgctgcg cctgagtctg caagagtttt gtgtactcat agcagccctg taccccgagt 69660
acatctacac cgtcctcaag tacccggtgc aaatgtcact accctccctc acagctcacc 69720
tacatcagga tgtgatacac gcggtagtca ataacacaca caaaatgccc cccgaccacc 69780
tccccgaaca ggtcaaggcc ttctgtatca cccccaccca atggcccgcc atgcagctca 69840
ataaactatt ttgggaaaat aaactggtac agcaactgtg ccaggtaggc ccgcaaaaaa 69900
gcacaccacc cctaggcaag ctatggctct acgccatggc caccctggtc tttccacaag 69960
acatgctgca atgtctgtgg ctagaactga aaccccagta cgccgagacc tacgcctcgg 70020
tgtccgaatt ggtacagacg ttgtttcaga ttttcacgca acaatgcgaa atggtgaccg 70080
agggatacac gcaaccgcag ctccccaccg gagagccggt gcttcagatg atccgcgtgc 70140
gacgccaaga cacaaccacc acagacacaa acacgaccac ggagccagga cttttagatg 70200
tttttattca aacagaaacc gccctagact acgcgctggg ctcctggctt ttcggcatac 70260
ccgtgtgtct cggcgtgcac gtagccgacc tgctgaaagg ccaacgtgta ttagtagcgc 70320
gccacctcga atacacgtcg cgagaccgcg acttcctccg catccaacgc tcccgggacc 70380
tcaatctcag tcaactgctc caggacacgt ggaccgaaac gccgctggag cactgctggc 70440
tacaagccca aatcagacgg ctacgcgatt acctgcgttt ccccacccgc ttggaattta 70500

-continued

```
ttcccctagt catttacaac gcacaggacc acaccgtcgt acgcgtgctg cgaccgccct  70560
ccacgttcga acagaatcac agtcggctgg tgttggacga ggccttcccc accttcccgc  70620
tgtatgacca agatgatgac ttatccgcgg acaacgtcgc tgcgtctggc gccgctccaa  70680
caccgccggt acctttcaac cgcgtgccag tcaatattca gtttctgcgt gaaaacccgc  70740
cacccatcac gcgagttcag cagccgccgc gccgacatcg tcatcgagcg gccgcggccg  70800
cagacgacga cggacagata gatcacgtac aagacgatac atcaaggaca gccgactctg  70860
cattagtctc taccgccttt ggcgggtccg tctttcaaga aaaccgactg ggagaaacgc  70920
cactatgccg agatgaactt gtggccgtgg cgcccggcgc cgccagcacc agtttcgcct  70980
cgccgcctat cacggtgctc acgcagaacg tcctcagtgc tctagaaata ttgcgactag  71040
tgcgattgga cctgcgacaa ctggcgcaat ccgtacagga cactattcaa cacatgcggt  71100
ttctctatct tttgtaaccg acattgacag tagcgggtaa taaaaacaaa aggattgtta  71160
tcgtttttta tgataaaaaa caacgtgtca ctttcacggt gatttattct tgctattatt  71220
ttttccccat gggctgtcag cgtcgggtgc gcgacacggc tatcatgcgc aacaggtcca  71280
gcttaaaggc gcacttgtcg ttaaacagac tggacatgcg tgtatacttg ctcagcatgg  71340
tggccagcac cgggtgggtg gcctctgaga tctcggtcgg caactccaaa acgacgttga  71400
cgacgtgacg gtgtttttca tcccgcttgt tggccaccgt gggtcccggt gcggtgttag  71460
acatggggcg ggccgtgggg ggaggacgag gaggaagtcg ctgctaaacc gccgcgcgcc  71520
tgctgcacaa tgtggccgcc gacgtggcag gcggtctgtt taaccagcgc gcagccccga  71580
cacagcgggg cgccgtcttc gctttccaaa cagctgtcgc ggtactcgcc cgtctgacag  71640
cgcgcgcaca gcaggccgtg cccgtgcgaa gtgaggcgca ggagacgcgg gaccgtcacg  71700
ccgcgtacca ccacagtgga gtcgcaggtg cgtgccgcgc agggcagaat gacgtcgaaa  71760
gccagccggt gatcgtacac ggcacaagcc gcgttgaggc ccagcacagc tttccagccc  71820
acgcgtacgc agcgctgtcc aaagagcgtc tcggagacga gctcgtagac gcgctgccgc  71880
accacccgct gactgccgca gagcgagcag tgtacgagct cggcgtgcgt gttgaagatg  71940
acgctctttt cttgacggtc ccgataatag aacatcgagt tgagcggaaa attttgctgg  72000
cagtgtagct tttccttacc caggttgagg cagtgtccgc actgccgaca gaccacggcc  72060
accagcgagc gcgcgtccag atggcgctcg cacttgagtc gacacagaca ccagagcggc  72120
aggtcgatga cgctgccgat gaggccgccg cgcagcgcgg cgctgagtgc aaagaggacg  72180
atcttggtgg gctctacgtg acgcgcctgc tgtccggcgc ccgcgtgtcc taccgccgca  72240
gctgccgccg tcgagcctcc tccgcgcgtc tcgttgtgca gacccagtgc ccgcaacggc  72300
accaggtatc gcggacacgt gtcgcaaaac gtctgcaccg cttgtcgggc cagtacgtag  72360
agcgggtttc cgcagggtac cttcccggcg tgccggcgca aggctgcgat gaggccccgc  72420
agctgcggcg accgcggctg ccgttggtga caccactggt tacggtggta tacggccaaa  72480
tcagcgcggg cgtcgaagcg cttggcgcgt agtagtgcta ggcacggcga gctggtgggg  72540
tgaagcacgg gcagtcgaag gtccaccccg aaaaggaaac ggtgaaggtc acctagcagc  72600
gaggcggtga caccgtccaa caacgcgtgc agccgctcgg gcgggtagat ccgcagacgg  72660
cgcagcaggt agtcggtgtc gtagcattcg aaacgcagaa aggccatcgt gcggacggcc  72720
acggtgtgca gacagtccat gctgtagacg taagcgagaa acacaaagta gggcttggtc  72780
ataaccatac gctgaaagag cgccgtcacc gcctccccgct cggcctgccg acacaccagc  72840
cattcgcgca ggaagcgttg gtagagacgg tcgcccagct cgcgattcag aaagcgctta  72900
```

-continued

```
tccgtcacga agagatgaag gacgcaagaa cgtggcacgt gatgcaccag ctgctgctgg  72960
aggaccgccg acgtctgcgc cgcaaactgc gccggtggct gcgacgtttc taccgccgct  73020
tcctccggct gcagcgcacc gcggccgatc accagctgca catggaaatg gtcctcgtga  73080
acgcagaggg gcgcgaagag acggcgcaga gcctgatgga actcatcagt cgcggtgtgc  73140
ggagcgtgtc ggagacgacg attggccatg accgcgccac agcagagcca gcaccagcag  73200
aagagccagc accagcgggc ccagagtcgc aaagcgcgcg ggcagccacg gcccagactg  73260
cggtcgcgat gggccggagc gcgctcgcca ccacgatgac ggtgcccaac gataaccagt  73320
ccgctccaag gacggcgcgc acggcggaga cggcggatga cggtgatggg tcgacacccc  73380
tcgccgacga ctcacgtgct cctccagagg ccgacgcgcg gaccctccga cgtcctggcc  73440
cgccgctgcc gctgccgcct tcccttctcc cgccagagcc agcaactcct cctcctcttc  73500
atcagcgtct ccctcgcttg cgcatccgca tcgtcccata caggcctcac aacgacacag  73560
ccgccacgac cccgccgcca tgggtggcgg cggcggccga ggcccggcag cggcgccgcc  73620
agcggcgacc atggtgggag agcaactcgg atgacgagga ggaggagggg gagatgcggt  73680
ccgagaggac cgctttcccg ccgttcgcgt gagcgcggcc gacatgcggg cgcgccacag  73740
ggacggaccg ctgccgctgt gactgcttac ggtgacgtga ttccggaccg ccaacgacgt  73800
cgacgcggct ttcttggcgt acagctcgcg cagcagattc tcgtactctc cctcgttttc  73860
gggtccgaag gcgatgagct cgatgttgaa gaccgacgcc gaattggatt tgcgcaccac  73920
gcacttcgtc agcactccgt aggccgaggg cttgatctcc tcgatgtcct tgagcgtgac  73980
gatgagcgac tcgttcacct taagcacatt gaactcacct acgtggcgcg ccggcgagac  74040
gagcttgacg ggcgctcgca cgaaacagca gagggagacg gcgcagccag tgtttttaaa  74100
aataaaacaa ggcacgtggt ctgtgcggct ctcccagtag ctgagcagat actcgacaca  74160
atagaccgtg tctgtcttga gcatggcgtc gcacaccgag taattgggat ttttacagat  74220
aaggccggcg tcggtgacgc gcagctcgct ggggcccaac ttgaggatac gccgcgtggc  74280
ctgcaccaga tcctgatgga gaaccttgtt catctccatc gcaccgacgc caccgccgat  74340
ttatttaccc ggcgccggct cgtcttttcc ctccaggatt ccgttaatgt ccatgagctt  74400
gctgacgatc gccgttaata gttgcgtctt ctcacggagg atctctccgt gactgcaggt  74460
cgcgcagtcg ccgtgcacgt acttgaggaa ggcggcgtac ttctgacccg cgttcacgaa  74520
atttaagcgc gcgtccaggg agggcagcaa cagatcgtag acgcgcggca gcatcggctc  74580
gaactgtaat agcagatcgt cgtcaagatc gggtagcgcg cgcccgtctt caccgtcctc  74640
gtcgtcacca cctccccct cgagcccacc gctagtacca gccgcgggct ccgcgtcctc  74700
gtcgatcacc agcggtcgcg tcggcaccgg agaatccacg tcatcctgca cgtcgttttc  74760
ctcctctccg tcgtcatcgt ccagaaacgg cacccgctgc ttagcccagg acattctttc  74820
tccgcgtcct caatcagcgg cgccgatcgc catgaatccg agtacccacg tgagcagtaa  74880
cggcccaacg actccccccc acggggccca caccacgctt tttcccccga ccagcccggc  74940
cccgtccacc agctccgtcg ccgccactac cttgtgcagt ccgcaacgac aggccgtttc  75000
gcgttacagc ggctggagca ccgagtacac ccagtggcac tcggacttga caactgagct  75060
gctatggcac gcgcacccgc gtcaagtacc tatggacgaa gcgctggccg ccgcggcggc  75120
cgcctcatac caggtgaatc ctcaacaccc cgccaaccgt taccgtcatt acgaattcca  75180
gacgctcagc ctcggcacct cgggggtaga cgaactgctc aactgctgtg cggaagaaac  75240
cacgtgcggc ggcacgcaat ccaccgtact caccaatgcg accaacacca ccaactgcgg  75300
```

-continued

```
cggagccgtc gccagcagta gcaacgcagg acctgccggc gcttcggccg cctgcgacct  75360
agatgcggaa ctggccggcc tcgaaacctc ggcggccgac tttgaacagc tgcggcgact  75420
gtgcgcgccg ctggccatcg acacgcgctg taacctatgc gccatcatca gcatctgcct  75480
caaacaggac tgcgaccaaa gctggctcct cgagtacagc ttactgtgct tcaagtgcag  75540
ctacgcaccc cgtgcggcgc tcagcacgct catcatcatg tccgagttta cgcatctgct  75600
gcagcagcac ttttccgacc tgcgcatcga cgacctgttc cgacaccacg ttctcacggt  75660
cttcgatttc cacctgcact ttttcataaa tcgttgcttt gaaaaacaag tgggcgacgc  75720
ggttgataac gagaatgtca ccctgaacca tctggccgtg gtgcgggcca tggtcatggg  75780
cgaagacacg gtgccttaca acaagcctcg gcgccacccg caacagaagc aaaaaaacaa  75840
cccttatcac gtcgaagtgc cgcaagaact gatcgataac tttctagaac acagctcacc  75900
cagccgcgac cgcttcgtgc agctgctttt ctatatgtgg gccggcaccg gcgtcatgag  75960
caccacgcca ctcacggaac tcacgcacac taagttcgcg aggctagacg cgttatccac  76020
ggcctcggaa agagaagacg caaggatgat gatggaagaa gaggaggatg aagaagggga  76080
agaaaaagga ggagacgatc cgggccgtca caacggcagt ggcaccagcg gggggttcag  76140
cgagagcacg ctaaaaaaga acgtgggtcc catttaccta tgtcccgtac ccgccttttt  76200
taccaaaaac caaaccagta ccgtgtgtct gctgtgcgaa ctcatggcct gctcctatta  76260
cgataacgtc gtcctgcgcg agctgtaccg ccgcgtcgtc tcgtactgtc agaacaatgt  76320
gaagatggtg gaccgcattc agctggtatt ggccgatctg ttgcgcgaat gcacgtcgcc  76380
gctcggcgcg gcgcacgagg acgtggcgcg ctgtggactc gaagcaccca cctcgcccgg  76440
aggcgactcg gactatcacg gcctgagcgg cgtcgacggc gcactggcgc gacccgaccc  76500
ggtattttgc cacgtcctgc gtcaggcggg cgtcacgggc atctacaagc acttttctg   76560
cgacccgcag tgcgccggca acatccgcgt caccaacgag gccgtgctct tcggacgcct  76620
gcaccccac  cacgtccagg aggtgaaact ggccatctgc cacgacaatt actatataag  76680
tcgacttccg cgacgtgtgt ggctctgcat cacactcttc aaggcctttc agattacaaa  76740
acgcacctac aaaggcaaag tgcacctggc ggactttatg cgcgatttca cgcagctgtt  76800
ggagagttgc gacatcaagc tggtggaccc cacgtacgtg atagacaagt atgtctagcg  76860
tgagcggcgt gcgtacgccg cgcgaacgac gctcggcctt gcgctccctg ctccgcaagc  76920
gccgccaacg cgagctggcc agcaaagtgg cgtcaacggt gaacggcgct acgtcggcca  76980
acaaccacgg cgaatcgccg tcaccggccg acgcgcgccc gcgcctcacg ctgcacgacc  77040
tgcacgacat cttccgcgag caccccgaac tggagctcaa gtacctcaac atgatgaaga  77100
tggccattac gggcaaagag tccatctgct tacccttcaa tttccactcg catcggcagc  77160
acacctgcct cgacatctcg ccgtacggca acgagcaggt ctcgcgcatc gcctgcacct  77220
cgtgcgagga caaccgcatc ctgcccaccg cctccgacgc catggtggcc ttcatcaatc  77280
agacgtccaa catcatgaaa aatagaaact tttattacgg gttctgtaag agcagcgagc  77340
tactcaagct ctccaccaac cagccgccca tcttccaaat ttattacctg ctgcacgccg  77400
ctaaccacga catcgtgccc tttatgcacg ccgaggacgg ccggttgcac atgcacgtca  77460
tcttcgaaaa ctccgacgtg cacatcccct gcgactgcat cacgcagatg ctcacggcgg  77520
cgcgcgaaga ctacagcgtc acgctcaaca tcgtgcgcga ccacgtcgtt atcagcgtgc  77580
tgtgtcacgc cgtctcggcc agcagcgtca agatcgacgt gactattttg caacgcaaga  77640
ttgacgagat ggacattccc aacgacgtga gcgagtcctt tgagcgctac aaagagctca  77700
```

-continued

```
ttcaggagct gtgtcagtcc agcggcaaca acctatacga ggaggccacg tcgtcctacg  77760
cgatacggtc ccccttaacc gcgtcgccgt tgcacatagt ttccaccaac ggctgcggcc  77820
cctcctcctc gtcccagtcc acgccgcctc atctccaccc gccgtcgcag gcgacgcagc  77880
cccaccacta ctctcaccac cagtctcagt ctcagcagca tcatcaccgt ccccagtcac  77940
caccgccgcc gctgtttctc aacagcattc gtgcgccttg acactgtacg gcagaaaagc  78000
cggctccaag tgcaagcgcc gcggcagcac catgtgcaaa aacttgtcct tgcgcgcggt  78060
ttcgccgccg ggaaagacgg gcgacagcac gttggttaca gccttgagaa cctgctcaaa  78120
gtacttgtcg gcgtgaatgg gcacgccgtg ctcgcgcacg tagctcggat cttcggctac  78180
ctcgtagttg cacacggccg acggtggttt ccgcgccctc ttctttgccg gctctcctcc  78240
tctcctgttg ctctcctcta ccccgctgcc gtcagcgtcg tcgtccgtgc catcaatcgc  78300
gtccgaccgg gaaaccacgc cggcggttac agaatcaccg ttgtcggagg aaccctgcgg  78360
cgccgtccgg acaccgggcg ccgtcaggac gtaaaagacc cgatccccga ccgagggtag  78420
ctcctcagaa cgggccgcca gtcgcttaat gacggcaatg tgcggcaggt tagattgacg  78480
gtacaacgag atgtccttag aaagcaccga cgaaagcacc aggtcctcga cacgcacacg  78540
gtgcaggtac agatcgtcgc gggcctgcac caggcggcgc aaaatacgcc agaaaccgcg  78600
tggcacgccg tatttcttga cttcatcgag tgagaggcgc gacaggcgca cggctgcttc  78660
cgagacctcg cgatcctcaa agagcagcga gaggacgtca cgcgtgacgc ccttgacgaa  78720
ctcgcaggcc gtcttgcgca ccagatccac gcccttcatg ctcagacccg aggcgccctc  78780
cactttgccg atgtaacgtt tcttgcagat catcataaga gagacgaaga ccttttcaaa  78840
ctccagcttg acgggctcca caaaaagaca ggccgtcacg tagtgcgcca agctgggccc  78900
acgcgccacc agagcctgcg gcgtcaggcc acgaaagcgg acaaacacgc tgtccgtgtc  78960
cccgtagatg acccgcgcct ccacccgccg ttcgtccgag ccccctgacg atgtttcgag  79020
cccctccggt aacgtgctgc tctcctccga atccccctcc cgcgttccca ctacatagtc  79080
ttcctgatta aaaaaattgt gcaaaaaaca cggctctgaa aagttgtctt tgatgaaccg  79140
cgccgtgcgc tctagcatgt cgcgaccgat gcgcgtgatg ctggcggcga tgggcagaca  79200
cggcatcatg ccgttgacca cgccggtaaa accgtagaaa gcgttgcacg ttactttgag  79260
cgccatctgt tccttgtcga gcagcatacg gcgcacaggg tcttgacact cgcgcatgca  79320
ttcgcgcacg gcacgccgct gcgaaaccca cttgttcagc agttccgaaa gcaccgagac  79380
gcgcaccgaa gcacgcacaa agcggtgggt cacgccgttc tctagcgtga cgctgtatac  79440
gtcggcaggg tccacggggt actcgccacc cggcaccagc agggtggagt agcagaggtt  79500
gtgggccatg atgatggaag ggtagaggct ggcaaaatcg aacacggcca cggggtcgtt  79560
gtagtaaccc acctcgggct caaacaccgt ggcgccttgg tacgaaaccg ccgcggtacc  79620
gccgacgccg tgactgtcgt tggaaacgcc gacgccgcca ctactgccgg agccgacgct  79680
gaaaacaccg acgctgctac tactgttact gccggagcct ggtgaaacgc cgtcctgact  79740
cgacggcgca gattgcaagg gcggcgacat ctgaaacata gccgccacag aacccgcgtc  79800
gccgggcacg gcggcggtag agatgatagc ggcgttaggt gacacggcaa cgctattcgt  79860
ttcgggcacc gtcgtacctt tgctgtagtg gttaggcagg ataaaatcgc ggcaggcgca  79920
ctcgtccagc agcgaggtgt agatacggat ctgctgtcca tcaaagatga cacgccgcaa  79980
cggaatctta gccagccgcg cgatggcccc ggcctcgtag tgaaaattaa tggtgttgaa  80040
cagatcgcgc accaatacgg cgtcctgcag acagtaacgg cctacctggg cgcggccctc  80100
```

ggcattagcc acgaaacaac gcgggatgtc cttgtaggac aggtcatcct tgcgttgccg 80160
caggtaaagc tcggccatag tgttgagctt atagttgggc gagttggtct tggccatgca 80220
tacggggtac atgtcgataa ccacagaacc cgcaatatac accttggtgg cggccgtact 80280
ggccggattg ttgtgagaag ccgagggaaa ggcggcggcg tactgccgct taaaacccac 80340
ggcggggctg tgtaaaaaga aacggccgcc ctgcgccgtg ggcaacttgc agaagcgctg 80400
cgagtccacc ttatacaggt actcgaggcg cgtgaggatg tacttcaagt caaaggagtt 80460
gatgttgtaa ccggtcacaa aggccggcgc gtaccgttga aagaaaagca taaagcccag 80520
cagcagctca tattcggaag ggaactcgta aacgtccacg tctgggccca cctgcccgca 80580
ggtgccgatc gtgaagagat gaagacccga gtgcccaaag atcgcgccct ccgaagtgca 80640
gccccgacca tcgttcccgt ttgggatccc ctgatccacg gcggtgtttc cccccgtctc 80700
gtagcacacg cacgagatct gaatgacaat gtcatcggac ttctcggcac agggaaagcc 80760
accctcgccg ctcatgcact cgatatcgaa ggacaggcac cgataacgcg gccacgagct 80820
gtcgtcgggc acggctacca ggtcggagac atcgcagtcg acctcgatat cacaagtcga 80880
cgcgcgaccc tgctgccgcc agtcgtaacg attcacggag caccagccga acgtggtgat 80940
ccgccgatcg atgaccaaac gcgtcagcgg atccacacgg acctcgtaca cgggaaaacc 81000
ctgctccagc agatactcgc cgatttttct ggccatggtc cagttgctga tagacacaca 81060
ctgcaaatcg ggtacgggtc gcgtcccgta cccgtagatc gaagtcttgg tggccggcgt 81120
gacagacacg gcgtatggcg tccgcggttc gggcactagt tcgcccacgc tggcaatgac 81180
ctcacgcagc ctatcggtgt cgctgtactc acagtaaaag tagctgcgct gcccgaaaac 81240
gttgacgcag atactgtagc cgtgttctgt ggccccgaag aaacgcaaca cgttccccga 81300
aggcaccaga tgctgacgat agcgcggcga cacgttttcg ggcgagtcga aaaagagcac 81360
ggcgtccgtc tgatcgtagg tgtgaaaacg aataggtccc accacgcgac ccaccagggt 81420
ctcgcgccaa ggacacggcc aaaccatgtc atgactcaac aaatgtttaa tctctcgata 81480
gaacatgaga ggcagccgtc ccgtcttatg cttgatcaac cccgtctgac cgtcgaacat 81540
gacgcctcgc ggcacgatct gcaaaaactg tttctgtggc ggccgcttgc ccgagccctg 81600
cgcggagccg ggctgcgaac gctgacgccg gccacccgcg accgcaccgc cggtcacgcc 81660
gccgctcaga tacgggttga aaaacatagc ggaccgtgag aggctgacag cttacgaagc 81720
aaaatcacaa agaaaataca catgcagcac ctagatatcc agtttaaccc cgtatatcac 81780
aagtctctgt gtcacttttt ttgtcttttt ttttcttctc ctggttcaga cgttctcttc 81840
ttcgtcagag tctttcaagt gtcggtagcc gtttttgcga tgtcgcagtc ggtctagcag 81900
gttgggcttc tgtcccttgt cctgcgtgcc agtctgtccg tccaaagaat ctgtaccgtt 81960
ctgctgcgct cgctgctctg cgtccagacg ggccagggcc agaagcatct ggtaagcctg 82020
ctcgttggtg taaggcggag ccgccgtgga tgcatcagac gacggtggtc ccggtccttt 82080
gcgaccagaa ttataaacac tttcctcgta ggaaggcgga gcctgtaacg acgtgtcttt 82140
ggtgctgccc gacgtcacgg tggtcccgtc ggcggacacc agatagggaa agaggttctg 82200
cagcggctgc atgcacagac gccgctgtcg agtatagatc aaataaatga taatgacgac 82260
ggctatggcc acgaggatga tggtgaaggc tccgaagggg tttttgagga aggtagcaac 82320
gccttcgacc acggaagcca ccgcgccacc cacggcccca atggctacgc caacggcctt 82380
tcccgcagcg cccaggccgc tcatgaggtc gtccagaccc ttgaggtagg gcggcagcgg 82440
gtcgactacc ttgtcctcca cgtattttac ccgctgcttg tacgagttga actcgcgcat 82500

-continued

```
gatctcctcg aggtcaaaaa cgttgctgga acgcagttct ttctgcgagt aaagttccag  82560
taccctgaag tcagtgtttt ccagcgggtc gatgtccagg gcgatcatgc tgtcgacggt  82620
agagatgctg ctgaggtcaa tcatgcgttt gaagaggtag tccacatatt cataggccga  82680
gttcccggcg atgaagatct tgaggctggg aaactgacat tcctcagtgc ggtggttgcc  82740
caacaggatt tcgttgtcct cacccagttg accgtactgc acgtacgagc tgttgacgaa  82800
attaaagatg accacgggtc gtgagtagca gcgtcctggc gattctttca cgttcatatc  82860
acgcagcacc ttgacgcttg tttggttgat ggtcacacag ctggccagac ccagaacatc  82920
acccatgaaa cgcgcggcaa tcggtttgtt gtagatggcc gagagaatgg ctgatggatt  82980
gatcttgctg agttccctga agacctctag ggtgcgccgt tgatccacac accaggcctc  83040
ggcgatctgc gccaacgccc gattgatgta gctgcgcaac gtatcatagg tgaactgcag  83100
ctgagcgtag agcacatttc gtacagattc gctttcaagc gacagggtgg tcgtattgcc  83160
cgtacttctc ttggttctac gcgtggagtt cacaccggaa ctattggcca aacgttccag  83220
ttccaacaaa gatttttgct tgataccttg ccagaacacc accagaccgc ctgtggtttc  83280
aaaaaccgac acgttaccgt acttttcgta tgtttgattg tacgaggcgt tgaagatctg  83340
ttgtagctta tttagagcct gatcacgcac acaatccaac acgggatcgg acatgttcac  83400
ttcttgtttc ttagacagaa aagttgcagt cattttagca gaagaaaagt gatacgagtc  83460
ttcggcttcg gaacgaatag tacgttccga ggcttcccag aaggtgagct gacaggtgac  83520
attcttctcg tcctgtatat cccaggagat caccgagtcc gcacgttcaa gaaaagccac  83580
caacctgtgg gtctctggcg cagaattcgc tcttccaaag tcagagacaa tagtgtagtt  83640
agggaaaatg aaaaacttgt cggcgttttc tccaaagtag ctggtattgc gattggttcc  83700
gttgtagaaa ggagaaatgt caaccacgtc acccgtggac gtggcgaaaa aatggtaagg  83760
atacttggaa cgcgcagtag tgatggtcac catacagttc agattacagg tctcacgata  83820
gagccaggtg ctaccgcggc tgtgccactg atccttgacc gtcacgtaac gggtgctgtg  83880
ggtgttggaa taatcgtcga gcattaattg catggttttg ttttcatagc tgtccctatg  83940
atacgccacg aaaaccgtgc ctgctataac gcggctgtaa gaactgtagc actgactgtt  84000
cctgttgata tgatgaatct cccacatagg aggcgccacg tattccgtgt tgctgcctag  84060
cagataagtg gtgtggatgt aagcgtagct acgacgaaac gttaaaactt tttggtagac  84120
ccgtacctta aaggtgtgcg cgacgatgtt gcgtttgtag accaccatga tgccctcgtc  84180
caggtcttca ttgatgggct tcatcggggt gcagacgata ttacgttcaa agcgaataag  84240
atccgtaccc tgggccatgg aacacacgcg atagggggtac ttggtggtgt tgaccccccac  84300
cacatctcca tacttgaggg tagtgttgta gatagtctcg ttggctctat gactgacggc  84360
ttcagaagac gttacgtgtt gagaagaaac tgaccgggtt tgagcagacg tcgtacgaga  84420
agtatggctt ccattgtgag tagaagaagt tgcatgagaa gtagaagaag aggaaaccgc  84480
agcacccaga cagacgatac acaggttaac gcagactacc aggcaccaga tcctggattc  84540
catgttcgtc gcgggccaaa tccagcagcg atgaggcgcg tcgtggtctc ttgcgtgttg  84600
cgcggaccct ccgggaaacg cccgcggtcg aggaggaggg gtacggactt ggcagccaag  84660
gtcggtccgg ctccctgaag gcacccgaga cggccgcggc ggccgtcagg gtggagggct  84720
tggccacggg agctgttggc acgtcgccac tctcatccgg tctggacaga tgcctgtaga  84780
ggaggagata tagatctttg gacttataaa gacttccttc gtgacgaagc agcaacggcc  84840
actctttgtt atacgtgaga atcacatctc tgtccgggtg cagttcgtcg cgcaggcacg  84900
```

-continued

```
cgatcgagag ttgtttcccg aaagtttcat tatatagtgc gacggagagc acgagctccc  84960
gcacgtgcat ccacatctcc ttctgcagca cgtttagatc ctgacagtcc gaaaaattga  85020
aaaaacccat gtacttcacc accatccact cactgggata cacggtacct tccgcgcatt  85080
tgaccaaatc gtccttgacg tggggtagta cgcccgcgtt gtcgcaggca taggccatgt  85140
ccacattgtg agagagggga tagcgatcgg tacagtgtgt gaagaggggc ccgttacaca  85200
actcgtagat ctgctgaccc agtagcggga gggattccac aggcagactc ttgtggatca  85260
ggttattgac cacatacagg tgctcatcgt acgtgaactg atcccccacg tccaccacgt  85320
cttggtcctg gtggtattgg ctgcggtata gaaacccatt catgagctta gagataaagt  85380
ccagacacaa gggccccact aggttgacat cgatgagttt gctagtcaga cgctcctgcg  85440
ttttgatgca acggatcacc ttgccatagc ccacctccga gaccttctgc aggtaggcgc  85500
gtttgcgcac gttcacctcg cgggtgacgt tgtggatgcg ggaacgcgcg tccaccaagt  85560
cgagagcctc gtgttcgtcg cagttgcgca cccgtaagcc gttctcgctg ccgtcgccgt  85620
cctgcccatt cgcccctccc cctacagctt tcttgcctcc tccacgagtc cggccgccgc  85680
caccgttatt cctctgactg tgagtactgc tgttgctgct gctggccgtc atcaaagtcg  85740
tacccgtccc cgacatcgcc tcccgtccac gcaggtgaat agcctcgccc tcggggccgt  85800
cgccccccgt gccatcgggc agcggacgtc gaatctcctc gagaatatgc ttgattttgg  85860
tgtacatctc gttgctttcg tggagcttgt tgaacaccgg gttgtcctcg aaagcttgaa  85920
tgctgaggga tgtgatgagg tcgatgatcc tgttgggggc ggcaaagacc gaccccacga  85980
acatgcgctc ctccccgtcc aacgcctttt ccccgagcac gaagatgtcc tccacgtcct  86040
ccccgtacag atggcgactg atgccgttca tgagcgcccg gcacagctgg tgatacacat  86100
ttagctgctg gatggtgatg cccacccgct tgacgataac ctccgaggta cgggaccagt  86160
aggtaaaatc cgacaaggaa tatattcgtt ccggtatatc cgtaaacagg ttgtactccc  86220
tcagcgcctc ctccgcctcc tggatgtagc tgtggtaggc cgatgaagaa gagaataggc  86280
ttttgagggc cgaaaggact ccagccaagt gggggatgcg cgttgtcagg tccagcaggt  86340
cctgctccac cgtctggata ttcacatcgg actggcttga cggacggtgg accgctatat  86400
ggttgcacag caagccctgc agccgcttgt tcagcgagcg gccctgattc gggatgatgg  86460
tcagctcctc gtagcattgg gcgcatgtcg tcccttcgac gtacacttcc tgacgcgcca  86520
ccggcgagat gccgcatagg cgacggagga gctccagcag ctgcgcgcag acctccaggc  86580
cggcctccgg cgccaggatc ccgtacacgt agttcatttt gcacaggaag cgctcgatgt  86640
cgttgagtgt ggccagactg acgctgaaac ggacgttgtc cgtaaactgg agctccacgg  86700
tgtgatggcg atcgcagcga tccaaacgga ggacggtacg gtagaaggcc gcccggtccg  86760
gctggcgcga gtaggccatc agcgcccgat ccagcaaagc cgtatcctcg tgcagcgcct  86820
tcagcagcat ctccagatag agagtcagca gcgaactctg cgtacgattc tgcgccacca  86880
cctccgggta gatcttccgg tacagataca ctatagccgc cgcgtttctc ttgaacggcg  86940
tggactccgc cagtaacacg ttcggatcgc agtactttag acactccagc tccatggcgt  87000
attcgttgca tttcgaacac actacgcata gtttctgtaa caaattcatc tccatgactc  87060
gactcgctca cgtacgagac gctgtcgtcc ggtctggcgc cggccagaga catggagtcg  87120
gtgcacaaat aactcgcggg ccgctcgcta tgccgactga cgttgacgtt aatatataac  87180
gacgtcgtcg acgacgcggg ttctgctccc gaagctgttg ccgccgcttg cggcgcaacc  87240
tcctccacca ccgccgccgc cggctcctcc gcctcgggcg acgggggctc ggagatgact  87300
```

-continued

```
ggctgtgtct gacactcctc cccttcctca ggcggcccgg gcgccgacgc gaatgtcgga  87360
gtttgccagc gcggcggcgg tctctgtctc tggtgccgcg gcgctaacct tcggggctgt  87420
tgctgctgtt gatgatgcga cgccgtctgt cgccgctgtt gcggcggtaa ctgatacggt  87480
gtcgcctggt gctgctgtgt cggtggctgc tgttgttgct gttgttgcgg tctgaaaagc  87540
ggccacgggg gctgcgactg ttgctgctgt tgttgcgatg ctcgtggctg cggcggccgt  87600
tgtcgcggcg tttgctggcg gttacaaccg gctgcgtttg gccggcaata acccgctgcc  87660
cccgccgccc ccgctgctcc cgccgacgcc gccagcctcg tcttcgccgg cgttcacgag  87720
aaagcagcca cctcccgtct cgccgggcac gccgaagcaa atggagttgc ccgcgacgga  87780
ctcgccgaga agaagaccgc cacccccgac gccggacgcc gcgccgacgc cactgggcgc  87840
gaagagcgcc gacaggtcgt gcacctcccc cccggcggcg tccgttaatc gctgggcgtc  87900
ggcgtccagc acgcgtcgca agttctccag cgaaaagtcc tccacgccct gctcctgcaa  87960
cgcggcaaac ttgtccatca gcgacgcggc cagcgcctcg cagccatcca cgaagaagag  88020
cacatcgtcg gacgcgggga tctcctcgcg cacgctcaga atctcgtaca cggccatcac  88080
ttcggggtcg caatccaagt tctcggcgtc cagcgccagc atgacgcggt tttttataag  88140
atccgcgtca aaaagcacgt tctcgcggcg cgagcgtttg atgagcacgt cggccagacg  88200
cgtagccaag aggtagcgct ggcgcatgaa acgataatct tggccgctca tagagctcac  88260
gttaaggctg cgttccacac cgttgcccga aaagtagccg atctgcccaa actgatagat  88320
ctccttgctg ttgttgatac ccgcatattt ttccacgctc acgggcacgg tcaccaagga  88380
acgatgctca aaaacgctcc gtaccaacga ttcacgcgcc acagtggcgg ccatgggcgc  88440
cggcacgcct gcggtcttca agcccttgac atgcaacgca aattcggcgg gcgacgagaa  88500
acgcggacta gcacctaaca cgtgaggaaa ctgcgcgtgg ttctgcgtcg ttaagcgcgt  88560
cgtcaacccg tgcagcgagc cgatgtagtc tttgaagccg tagtagcaga ggaatttgtt  88620
gtggaaacgg ctttccacgt aactcagcac acagtctggc gccacatcca gcagatcgtg  88680
ctcctgatag tcagccgtca cagccaccag aaatttgacg aaagcattga actcgcccat  88740
gtcacctatg ggcacattct tgggcaacgc gttggaacag accttctgcc aaaactgtaa  88800
gcaggggaga ccacattcag gaaaaagtcg ctcgtgatgt cgatacagca gaaatcccaa  88860
gcagccctta gccggattgc gacgcggaac gtgatcgcgg cgaaaaaaca cgctacccgc  88920
gttgcccttg cccgcgcggt agatgggtcg gtttttcacc cgcaccatga tcaacgtggg  88980
taccgacagc cgcgagagct taatctccat gggcaccacg gcgtacgtgc cctgcgcgta  89040
cagcctaaag tccagcaggc ggtcgtgatc cgaattcttg gacgacttga tctgcttggt  89100
gaagagaaag cccttgcgcg acgacgtggt ggagaacgcg ccgtgaatgg attgaaaatg  89160
ctgcgtcatc catttggata ccaagttggt ggtcaacgga ttgtccacaa tgtatgaggt  89220
agcggtaata agcgccacgt tctggatcac gtaaaagacg gatctgaaat aggcgtaggc  89280
cagcagcggc tggaaggcca cggcgtaggg attcagatcc aggttgaagg cctgcgtggc  89340
gcccgccacc tcgtcgcggc tgctcttgag gcgcacctcc gaaacgaaac ccagggcctc  89400
gtcgtccaca aacttgttga gcgccgaaaa gacggccaca aagtcgcttt tgccgtgcgc  89460
gctaaaggta tcctcgcccg tcacggggtc gatgagccgc atcttgcggc agtaatccaa  89520
gatgcgatta agccgatagg tacggtccac gctagcgccc agcatgcgac cgccgcgccc  89580
catcattccc ccggaatccc cgccaccccc accaccacga ccgccgccca gaccgtcgct  89640
cgggccccccg ctcacgtccc gtccaccacc cccgccagca ccgccgcccg gaaccccgtc  89700
```

-continued gtcacctttg ccgtccaaac ccccgtcctt ggcgtcgacg ttgtaacgcc gaccgaagct 89760
gcccaaaata tccacgtcgt tgagaaaacg cgactgcacg gtgatcacgc agggctcctt 89820
cttgggctgc ttgggcacca cgggcaagcg ggtgcgcacc cgcacgaagg ccgtctgata 89880
acacgtgtgg caacaagtac ccccacaggc ctcgcacagc cccgcggcgc agcccaccag 89940
gtgattcgtg agcgtcgacg aacccgacaa gcccgtgtta tacaccgaga cacgatttag 90000
ataccagacg aagcccgaaa ctagctgcgg acacgtgcca cacaccaacg ccaaatgctg 90060
cggcccatag cgttcgtcct tgagcggcgc gccttgaaat ttgagcacct tgcgcgcgtc 90120
gttgtagaca tcttcgcagg ccgccgacaa cccgttggtg aactgaatag ccttgagcaa 90180
cgtctcctga ctggccgtac cgccggcgct gggatgccgc gccgacgact ggagatacac 90240
cagcctgtgc tggtagagca ccgaattagc gctgaagacc aaggcggcca cgtgcgtcga 90300
gagatgcaac ttaagctcgg tcagcgcgcg gatcagatcg cggtgatcgg ttgcgttggt 90360
cactaaaggc cactcggaaa agagcataga ctcggcaggt tggtaggccg aatcgaaaaa 90420
taccgaggca aaactgaagg ccaactcgca aaccaccgcg tcactcagca tcagatgatc 90480
cttttccaga ctgctgagtc gctggctcat gtaccccaag tagcgcttat gtggcgccag 90540
cttcaccgac tgctgactgt cgtgcacaaa ctgccgcaac gccgcctcga tcagcacacg 90600
cggctccgag aagcgcagcg attgacacca tgacgtgtac acgtagtaga aaagcgtctc 90660
gcttacggcc ggtacgtaga accctcgcgc ctccacaaaa gcgctgcgcg catccagcga 90720
gacctcgtcg gcttcggcgt caagctgcag cgaattaaag agcgtaggcg ggtacaacgg 90780
cacgcgcacc gcctcgccgc cgtgcagtcg caccgtggtc gcctcctcca cgcatggaat 90840
cagctgaccg gcaaagagaa actccttcaa gccgttgccc accaccacgt gcacagtcgt 90900
ctcggacgcc tgacagccca ccgccgcgca caacgccgcc agatcggtag gcacgcgatc 90960
cgcctcgggc gtgtaggcct ccaacgcgta cttctggcgg gcgtcctcgc acagccgatg 91020
cacgtctccg tgatcctcgg taaaagccac gatgccttgc gtatgatgaa agtagagcgc 91080
aaaaggacag aaggacgtga ctttcgtgag caccccgccg tcgtaacaaa gcacaggcgt 91140
gcgcacagaa acgccgaaat ccgcctccac cgtgagcccc gccaacagag gagcgatcac 91200
cacgctcgag gaacggtcgc atagcgagag agtggccaga atctcctgcg tttctgcgtt 91260
caacctgctg aagtagagaa aagccgcggg ccccaccggc gctagcgcgg ttagttcctc 91320
gtggctcatg gtggatgaac ggaagacaat ggctacgccg ccactgagtg aattttatac 91380
caaggaaaag ttcagcacgt catgtttgac gcacgacgtc tgatacacca ccgtggccac 91440
cactgcggtc tggctgcggt tgcggaccac caaaggcgac aaccgcaacg atcccagcaa 91500
ttcgtaagaa aagctaaccg ttacggtcgg gcagcctctc gcagccagac cgctagccga 91560
cgcacccgcc cgcgaaaata gcgtgatgtt cgggacggct tcgcgtcacc gcaaactaac 91620
gtcggtagtc gcgcacgtcg tttatcctca gcacaccgtc cgatcacaac ccgttgtccc 91680
actcagtcgc acaagcagca cataaaaacc ccacacaggg cacgtgaaaa caacgtccct 91740
agaaaacggt gttttctgtc ctaccgtcac cgggccacac aggcaaatcc cgagcccgat 91800
ccccgaaaac accgtacggt gtttgtggcc tccaaaatca catcagctaa caaaccgtga 91860
aaagtcacgt ttcacgaaca cggtgttttt aaatcacaaa gaaccacctg acggtttaca 91920
agcagaaaca ccgcaccacg gtggtacaag cgcgattgat ctggtctcgc aacctcaatc 91980
gccgctatca ccaccgactt tcgctacgct ccgccgacaa aacgccgtac aagctacaca 92040
ccccaaaaac ccgcgcgcct atgagcgcca aacgtgtgta ttatctcaac gtcacaacac 92100

-continued

```
gacacaaacc gcgtaacgtg gtttcccgaa cacgtacgcg gcacagaccc ccgacacgta  92160
ctcgaagacc ttacagttta cgagtcaata aaacaggaaa agatccgaac tttaaaattg  92220
tgtattttta ttttcccatc cccctctttt taccaaaaaa cacatttttc gtcttgtaaa  92280
aagtaacttt cgcccattgt catgaaacac cgtgatgggg aacggtgttg tgtgtcgact  92340
gacgtcacta cggcgatcag tattgacgtc gtgtatacat aacggtgccc ggtgttttta  92400
ttcggggcgt tgtcgcgtct tgatgtaatg taacctgaaa ccgccgtgtc caagaatgcg  92460
gaagccagcg tgtaatcata acaaggtttt gggtacaatc tgacgacatc tggcggcgag  92520
cgtacaccat cgaatgtggc gatcgccggc tctacgtcac aatgacgcaa aaacacactg  92580
taaaacccgc gtagacagct ttcctggtaa acgagcgcca tctggtgtcg gcataagaac  92640
aggcatcaac cccgtggccg gcgaggcggt gagcactttt gttggtcacg tgaccatcag  92700
cgcaggaagc gaggcccgta gaaccgccca agaggcggtg ccagatgcta acgtcataat  92760
cacaaggtga tttgttacgt cacgcgcgcg cgcacgcacg cgcgcgcggt agaatacagc  92820
gatccctagt gaagccacac ccattacgtg tagccatatc cgcttacgta tacagccaca  92880
cccctaggta cgccacctta tctaccaatc acagaaacgg atatacaatg acccctccct  92940
agactccacc ccttgtacgg aaatttcaga taggtggaac ccgttagggt tccaccgtcc  93000
tcggtgtacg tacaggcttc tccgtctacc ggaaatatac acctgctgac gtagacgcta  93060
ctcccggata cgcgtcataa gctactggac cctagggggg agtgtctaca gggctacgtg  93120
cacgcccccct tacttagggt atccgccccc ttcctctgtt ttggcctagt aaacttaacg  93180
ccgccgcttc tcacgtgacc cctggcaagc ctacgtcaca ctcgcgtgac cacacccact  93240
ccggatatac gtcatcctgt ggaattccgg acatacggtg acgtagcgag cgtagcgagc  93300
tacgtcacgt atgcgtgcgt cacctccggc ggaaatcatc tctgatgacg tagcgagcga  93360
agcgagctac gtcatcagtc cgttttacgt ataccggatg ctaggcgacg ccccgtaggg  93420
gcggagccta gcttccaccc ctaggatgca taccctatat agcataattc ttctaacgaa  93480
acgttctacg aaaacggact ggcggaacgg gaaccaccgt aacccccccc ctcaccccccc  93540
cccttctcct ccggaaccgg ggggggcaaa tttttaccaa atttgggcaa ccatgatttc  93600
caatgggacg gcgttttcgt gcgcatgcgc agtcggggca aatttttggt tgtcagggcg  93660
ttgccacgcg gattatggga tggggactcg agtgcgcatg cgccggggat gccgcatgga  93720
aagcctatat ataaggaggg gtgaaccagg ggccccggtg cgcatgcgcg ggccctggcc  93780
cgcgggaggg tcgccctgcg catgcgccgg taagattcca ctgggtgtgt gttgtgcgca  93840
tgcgccagta tttttccacc gggggtggtc agtgcgcatg cgtcggtaaa attccactgg  93900
atgtgcgccg tgcgcatgcg ccggtatttt tccactgggc ggccgcacct agggagcgcg  93960
agccccgtgc cgggcatggg ccgcggcggt ggaaaattac cgctccgccc atataggcgg  94020
ggcatctgaa aacctataaa acccggcgtg cccgccgccc cccggcgcag tccgcggcag  94080
ggttccggcc gtgctgcggt ccgcacgctg cgcccgctcc cgcctgcctc ccgccctacc  94140
ccccaccctc cccggccgag gcccggcgcc ggtccgtccg cgggcccgtc ccaccgccct  94200
ggagcaccat ccggggccgt gggccgggca ccgggcgcgg cccgctccgg acctcggccg  94260
ggggtccctc ccctcccccc gctcgacccc ccatccgacg gcccggccgg gctgggaccc  94320
ccgcaccggg gtcccggttc ccgtccgcgg cccgggggga cccgagcggg ggcttcccac  94380
ccccaccccg ctcctccccg ggctccggcc cgggatccct cgctgctccc ggcgacctcc  94440
gccggcttcc cggtccaccc gccgcggaac ggacgggacc cggggtccgc acccttcccc  94500
```

-continued

```
tccccccacg gggggctggg tcgcggaccc cgggtcctag gctcgttccg cggtgggcga  94560
ccggggatcc cccacccagc tccccttccc ggtccgcccc gctggctttt gggcccctcc  94620
gggctttttt tccggctggg ggtcgcggcg gtcggccgac gacgacggta ggtgggccgg  94680
gtggacggtg gtggggacgg gcgacgcccc ggctcgacgg cagtcggtcc cggaaggttg  94740
ggggctgggg gcccggtcag gagctccggg agcggggtcg accgcgacgg ctttcgggtc  94800
tcgctgcggc tccctctcgg cggctccggt tgggctcccc tccccccctct cgagggtccg  94860
gccgccagtc gtgaccgggg gtccctcggc ctagccgccg gctctcgggc cgccttatcc  94920
tgggcgttgg ccggtcccgt gacgctcccc tcccccgctg ctccccaaaa aactccgccc  94980
gaaccgtcgc ggcttgctgg tcctgggcgt ggtcccccac tcccctcccc ccatcggccg  95040
cccagccggg gtcggcgcct cggaccccac caggctgtgg cgtgtgtgct ggccgatgcg  95100
gcggcgaggt tgggtgtggc cggaagcgct cggggtcgac ggtgggtcgc catgacacct  95160
caattgccgt cagtacgccc ctccacaatc accgtcccca cacgatgggc ccggcaggtc  95220
acccaacgtt ggttcaggcc cagtcgggtt tttccccggc acgaacgcac gaccccgtgg  95280
gctccacgcg ttttccaccc tttcctggag gggtcaggaa caccgtgaat ccacggggag  95340
ggtcccggca cgggccgagg agaccacgac cgtcccaccc ggcgtgtcga ctcgtccgag  95400
acccgagaag ggaacaggcc ccaccttttt ttccccttct ccgatttgcc gtggaaaacc  95460
cgtgaaccga tacgggtgca gacggccgaa aaaattcgag acgacattac gacggcaggg  95520
cgtgattttc tcccccatcc gacaaaaccg tgtccctcaa aattccccac ttttctctgt  95580
tcaaatggcc ccgaaactgt aaaacaccgt ttgaccgcac cccaaccggc gccatcttgg  95640
tgaccttctc gacggttctc tcgctcgtca tgccgttctg agctccgaca tggcggacga  95700
gagaaaatgg cgtcgagagc ctaggagcgt tttcgctcca ggcgggtaaa aaaatagcac  95760
gataactttt ctgtgctttt tttgagacgt tttagaagag cttttttttct gctcagagcg  95820
aaaaaatgat agccctgaaa atctcgacga gtctggccga gcggcgccat cttggaggag  95880
gggcgagtcg cgggcaccgc ctcggtaccc cctggccgag gcgagtccgc ggtcgccgcc  95940
tgtttcgtga tgctacctag agggcgccgt cgaggcgact cttcctgttt tcgccctaag  96000
ggctaacggt cgctgacgtc aaaccatctc gtgctcgctg agtcacatcc ggttgttgac  96060
aagcgatgga ggaccgcacc caaagtgcgc cctctagtca tcgcgcctga ccccttttat  96120
aaactgctcg aagaaaagaa caccttatgt gaaaaaatac agaatgatga caagttcatc  96180
caacacaacc gctcaacaac gccatatcta tcagtgtcca aaaactatct tctatccttt  96240
gaaactataa atgctgccta tatacatatt tagtatccaa gactcttacc acgtagacga  96300
aaagaagtga tacaatgatc ttgacgtgta tcgtctatat cgtgctagat atattcagat  96360
aagacgcgca aaccatagat ttctcatcag tatcatgaaa gacctatagc tctatatacg  96420
aacctagtca ttttaggaca gccgccggag aagccgacga gggatcgggc gggtgcagcc  96480
agaacctcac gcccgatccc gcctccggta ggcgatttgc atctgtttgg taaaaagctc  96540
ataagtctgt atgtgaccta tatatatatt atacgctatg tacaccgaac tgtcgctgtt  96600
gtataagaag aaaaaactct ccatatttat atcgtctgaa tttttgcttg atagacacgt  96660
gtttggaact ctgtcccccc cacgttttca ctgtgtataa caaaaatatg tgtttctcaa  96720
aagatcttga ggtgtttgaa aacgggggaa acctgcgttt gggtgcgcta agccccggac  96780
tgggacgtag ccggcgtccg gcacctatat tttttctatt tttttttttt tttttttttt  96840
acaaaatata tgatgaacca agaataaaac tctagctctc gtctattttt aatatgctct  96900
```

-continued acttagaacc tttttaatga cagaatgaac tccatgttat acgctcttta tatagtttct 96960
ctgcactaac ctttaaaacc gtatccttcc ctgttgtaca aatcatcttt tgatacacaa 97020
tgatgacctg atatccctcc atatatatga tcggatatta ttccgttaga cttgtcctcc 97080
tttttttttc ctcatctcct gtatctggag atatatgttg accaccaccg ccatgaccac 97140
caaaaagcta gccgtcacga ctagaaatgt gtaggattcg gactttccgt tcgagaagaa 97200
agagaccgcg tctctggacg ctctttttgt cggtctgaat cgacccggga tacgtaagag 97260
agcggcccta catcgggggg cgctcgagac cgacgacgtt ccatctgacc agaaaaaaaa 97320
aggcacccct cggtagcgac ctctcaccat cgtttgcccg tccgcccgtc cttcgtagcc 97380
atcatcatca tctcaggctc tatcggtacc atcgttgtca tctgaaaaaa aaactgcctc 97440
acccacctgc gtaaaaacac catctttccg gaggtgcggt aagacgggca aatacggtcg 97500
tgccgaggca aaaaaaacgc accatcgaca ccacaccctc atgagcacca cctgtcggtg 97560
ttggtcgtcc tccatcgttc tctacgaaca tctcgacgcc cgggtgacgg acgacggcaa 97620
gacgtcccgg agaagacggt gttctctcgg gcggtacgct ctctggatct ataatatcta 97680
tagtagctaa acgagactgt gagtacgacg aaccacatca tctttttttt atgttgcttc 97740
tttagaaaat gacttatgtc gacgacactc ggcatcagcc atctcgtgaa acacgctcgc 97800
ttttcgtctc tccaaggaac actgggtccg ctgaaaggga ccgtgtaccg accaaagcaa 97860
aaaacacaca cgtagtaaca tgatcaacca cgtctgaatg acacgaaaac acaatcgtat 97920
aacgctctat tcatggaacg aacttggaat aaaaaaacca tcgcaggcca gaggctaagc 97980
cgaaaccgtc cggggaagcg ggcgcgagtt ttccgactta gtctctggtg ctcgttgagc 98040
ctcttttttt tttctgattc tctgaagaat caccgtcaca gccctatgac gcgaaatcaa 98100
ttgctagaac ataaacgttc tcaacaggta tgaaatgaac aaactagatg atgctataac 98160
cttatattgt gtgtatatag ataggtgtga aatttgtagg ataaaaagtg tcgttgtatg 98220
atgcacaacg atcgtgaaac tggagactgt agctctctac cgaatgcaaa tacacaaatg 98280
acatcgattc ccgtccccac ataaagaaat gtgctttact gtgaaagaat gaagaagatt 98340
cttgttcctc gtacgacggg gccctcgctc gtcgtgcctc ttccccccctc cgggagaggg 98400 gacgtcgggg ccctctgtcg caccgggccg aagccagtga aatgtttact acactgtcat 98460
cagaatatat gatgtatatt atttcctcca aactcctcac catagccacc aattcgcatc 98520
acttaagaaa gtagtagcaa ccgcggcggc ggcgaccggc cggtcgtcgt ctcctcgtcc 98580
tcaaatgttg tacatgtgca gaaaaatgtg taaatacgtg ttatttatcc catgcgtctt 98640
gtacatagat atatgttttt atatacgcta tttatacttt atatatcctt ttgcataacc 98700
atagacagtc aaggatttta atgatttgct catccgcctt tgagccatcg cttaggagtt 98760
agttcctcta tgttctcggc ccaccttttc gactacagta gcaaaccctt gtactaccac 98820
cccgataaaa accacatcat catcgtcacc acgacctgga aacgacacac gttccccccc 98880
aatcttgggc atgtgtatat atatataaag aatgggaggg agaggacgtg gggctcgaga 98940
agaaataaac gccaagctcg attcgaacca aaaaaccaca tgtgtattgt gctttttttt 99000
ttacggtggg gaaaaggagg gggccgtcat taacggaaac cgtgtatggg gtccggacac 99060
gaacagtaca cagcttatgg ggaaaaaagc tcacagagag aaaaaaacac caagctcagg 99120
cacgcgtaca tcattatcat catcggatat ctcaccacga gtcatagtag taccaaggag 99180
tgtgtaacac catttttctt tttcttttg taacgggata agggacagca atcatcacgc 99240
acaacaccct tcactctctt tttagtcatc catatcatcg ctgtaacaca gcatgtcctc 99300
gtaatcgggc gtctggcagc gcattaccac cgagtcgtct tcttgcggta ccggtggtgg 99360
cggcggcggc ggctgctgct gctgctgctg ctgggttgcc gtcgtactgt gattaccgtt 99420
ggcggactgc accgggatga tgggctgctt gtggggaacc tggggtggac tgccgccgtg 99480
agaaggcgac ggcgtcatca agttaagctc accacggtga ctccggacac cggcgagggg 99540
cgccggggga ctgggaggga ccgcggtcgt cttgtagacg acggtgtccc cgtgtcgatc 99600
cgtggctcgt accagatctt gactgctagc gtcgtcactg tcttcgtcct cttccagctc 99660
gccctcagag tagtgctgct gtggttgcga cggtggctga gcgggaggag cggcggcgat 99720
cattggagag ggatgtcgat gactcccttc tctgtccttt ttatcgtagg ctgtcagcgt 99780
tgctgggtcc gtcctgcttt ccatatttgc gcattgctca tcggtgggat gaatttggtc 99840
tcctccccgc tgttgtccgc cggcagtggc gtggttgctg gcggttgtcg ttgtcgtacc 99900
ggcaaagacg gtgagatcca atagcgactg ctcgtcgaag ggacagtacg ctatcatgaa 99960
acgatagggt gccaacgcgc gttggatgcg cagttcgcac atctcgttct gacactcgtg 100020
gcactgcagg gcgcctagga tcaggtccga gacagcgccg cagcggtagg tacccatggc 100080
gttgttagta tcgaactggt caaaaaattg gggcgtaccg gtgacttgca atgcgcgacg 100140
gcgtagcgag acggccacgc gcgagaagga gcacacgtag gccatggcgc ggtgcatggg 100200
ttgcgagaag gtctcgggcg gacgcttctg cagatcgcag acgtcgtcgc gtagccaggc 100260
gctcatttga ccgggcttct tgactagccg tttgagcgtg ctgcaatggt cgccccagcc 100320
gtcctggtgg tccaggatgc agcccaggtc caggttgttg agtttgttga agagcagctg 100380
acgcatgccg cccaccgtct ccagataggg atcgtgcggg ttgacgggta gcccgtgcag 100440
gtggtggtac ttcatgtagc tgagcgtttc gtcgatgatg gccagcaacg tgtgcaagtt 100500
gggagcgttg tacacggcga agatcttttc caccaccagc ttgcgcagca acggttcctc 100560
cagccaatcg aactgttgac ggatgtgcaa caggtagtcg gtgtgcatga gctcgtcgtg 100620
tgacagcagg atgcgaccgc gcggctgatg atcttgcggg aaggcggtgg ggaccttgag 100680
atcggcgggg tagggtgcca gacgtagact ctcggccgtg tagcgctgaa ggtcgtagac 100740
gggcgaggta gaactcggtg aggtacccga cgaggcggcg ccgcgctgca gacgcgctct 100800
ttttttcttt tcgatcaaac ggctgagttg ctgtagttcg tcttcgtcca tggcgtccag 100860
ttcgtcgtca ataagcgcca gcatctgttg ttgttgcggt ccggcggacg atccgtgatg 100920
attattggct gaagaggggt gagaagaacc gaaagtcgta ggacaactgg gaactcggcg 100980
acgaagatgc gtcgaatcgc cgccgtgatg gtgcggttcg ccgtcatcgt cgtcgtaaga 101040
cttaccgtag tgggggttaa ggggcaccga ggcggacgcg gccacgcgtc gcttgaaaga 101100
ggaggacgcc ctatgtccgc cacggaagcc cgcggtgccc atgatgatgt gtccgccggt 101160
gcccccgagt gcgtggcggg aggagggtgg aaggggagga ggatagtggt ccggatcgcc 101220
ttcggtatca tcgtctttgc tgtagcgggg tcgtcgtgcg gggacgcagg gtcggtgatg 101280
atgcgaggcg gcgccgacgg tatcttccgc gagatggtat tcgctggcgg ctgctccgtt 101340
ccgtgtcgac ggcgaggttg gacttcgctc gcgtcggaac ttccgtggca cgggttcgta 101400
atccagacag aagcgccgtg cgcgacgggc gcggcgttcg cgctcgctca gggaagataa 101460
cgacggagcg tcgtgacggc cgcgtgagtg cagctccatg gccgccgtcg ctaggaaggt 101520
cacgttcggg cacgctgatg tatatataga tgagaccgct gccgggggc gggtcaccgg 101580
cgccgtggaa agtgaggctc agacggcggt cgccggcggc atgggcgcgt cgggcggtct 101640
gattttgatg gaaatgtgga cgtttttggc gttggagtga cactttttgg tgaaacagcg 101700

```
gctccagagg ctggcccaga gcgcgtagct gtgctcggtg cgcaggtcga tgaacacctg 101760
cacggtctct tgcgggttgc ggtgcgtgta gttgagacag cgaaaatccc gcgtgcgcgc 101820
gccgtcgcgc cgcttgacgg ccacgcagca ggcgccgtgg ggctgaaaga ggaggacgtg 101880
gggcgcggta aactgctcgc tgacgtgcgg ctcgtagtgt tgcgtgaggt gctcgagcag 101940
cggcggccac acgcgggtga cgacgagccg ctgcaagtcc gtgtcggaaa tcgcagcggc 102000
agtggcgccg tcgccaccgt acaggtgata ggcgagcacc tcggtgagac cgcggcgtcg 102060
ataacgcgtc acgttaagcg agcgcgtctc gataaagttg gcttcggtcg aggggcagat 102120
tttgtcgcgt acgctgagaa tgacgcgtgg cggcggcgac aggggcaacg cgggcaggtc 102180
gtgcggcggg tggtggtgaa gcaggttacg cagatccagt tgggcgcgca caaagcctag 102240
cgggtgttcg cggtaggcgt cgggtacgat gaacagcggc aacagacggc gatgcatgaa 102300
atagccgtcg tcttggtcca ttttatacat gtagggcaga cgtacagagc gtccatggtg 102360
gtagatgcct gtgtctaggc tgctctcggg atgcgagatg ggtccagca gcgtgtgcag 102420
ttcggcgtcg agacagacgg cgtgattgag cacctgcgcc acggcgcgta aaacgctggg 102480
gtgtacggct acggtgcagg cggggaacgg cgtgatgatg cgcagcccca gtttgccctt 102540
gcagcggcag taagggggtg acgtgtcaat gaaagacgtt ggtttttgaa aaacgccgtt 102600
atctggaacg ttatttttgt cctctttccc gtcttcgtct tcctctgtgt cgcgctcgtc 102660
ccggtaatcg agatagtcgt cgtcatcgaa aggcgcgccg gccgcgtcca cgggcacgct 102720
gttgggtggg cacgcgcttt tgaagaaata gaccgggtgc cggtcggggt gcgtgtagcc 102780
aaagaggctc gcccatacgg tcatccagac gcgtcgtagt ccgcgacata actcaaagac 102840
ggtgtgtcgc gccagaccgg agacgccgtc gcgcagccgt aaatcaaagt cggccacaaa 102900
attgaagacg ggcagacgtt cgttgaagac ttcgtgtcgc gtgtagtaga actgtgtctc 102960
ggggctggtg ctggccacgt cgtcgtcgtg tagccacacg gtctcggtca gggcctcgtc 103020
cgagaaacgg ctgtcgggta cgtgacggag caggtcgcgc ggaaagaggc tgcgatgcca 103080
ggtttcggag gccacggcgc agaagacgtg ctggtcattg ggcaggtgta cgcggtagac 103140
gggcagcggt cgctccagca gcggtgccag cgcgggctcg ggtagcaggt agcgacgttg 103200
cgagtaacgc gttagcgtgc cggtggtgta ggtctgagct gtgcgcagcg aggcgcatag 103260
acgtaacaag ccggacaggg agcgttccag cggcgagaag acagactcgg aaagcgtgtt 103320
gatgcgttcg agctggcgcg ccagctgcgt ggaggtgccg aagaagcccg ccaggtgcgt 103380
gccgtcgatg cggccgccgt agccggccag ccccaggccg tgcgggctgg tcgccgagtg 103440
gggggattcg tcgagacgta gtagatgcgt ctccacgtaa tcgtgtagaa agttgtcgag 103500
cgagaagtat ttttgcatga cgtccagcag ctcggtggaa agccggcggc ccagaaaacc 103560
cggttcgcgc gtacactgcg cttcgggcgc cgcgtcagcg tcgtaagcca ccacgcgccg 103620
gtactcgagc aaccgcgcgc gtgccagcgc cgtgcggtag gccaggtaga cgtagtgcac 103680
gcagaccgtg tcgggcagac gcgcacgttc gcggaacgcg ttgatctgcg tgtccacctg 103740
ctctagctcg gtgtagtcgc ggcggttgcg cgccacggcg tacgccacga aagcggacac 103800
gcgctgacgg aagggcgagc ccagtagcag acgcgcgaac tcgcccatgg aggcgtgcgt 103860
ggggatgatg gtgcccaggt cgcgcgtgca gaagctgcgc acgtactcct ccacggtgga 103920
gatggtgctg tactggccct cgaataggta gtaggccatg gtcagcagca cctggccctc 103980
ggtgtgcccg aagacgctga tgaaccacga gggcgaggtg gggcagagga agacctggtt 104040
gaggtgacgt agcacggccg cgtggtgaaa gtacaccagg tgcttgaatt cgcgcacctc 104100
```

-continued gccgccgtgt tcgggcgaga gcacgggcgt gcggaagaga tgccggtaga gcggccgcgt 104160
ctcggcctcg tccagactgg cgatgagcgc cgagaggggg atgggctggc gcgcggccag 104220
gtagcgcgag agctgcagcg tttcgttgtc cacggcgaag acgggcgcca cccgccgcga 104280
gtccgagcac ttttgcgtct gtaggcagaa ataaacacgt cgcgagacct ggtgtttgac 104340
cagcaggggg aagacgcagt ggtccgtcgg tgtctgcgag agtacgttgg cgactatatg 104400
agcagaatca tactctgttg cgaacagaac gagcgtcatc gtcgcgccgg cacgatgcag 104460
ctggcccagc gcctgtgcga gctgctgatg tgccgtcgca aagccgcgcc tgtggccgat 104520
tacgtgctgc tgcagcctag cgaggacgtg gagctgcgcg agctgcaggc gtttctggac 104580
gagaacttta agcagctgga gatcaccccg gccgacctgc gaaccttttc tcgcgacacg 104640
gacgtggtga accacctgct gaagctgctg ccgctctata ggcaatgcca gagcaagtgc 104700
gcgttcctca agggctatct ctcggagggc tgtttgcctc acacgcggcc ggcggccgag 104760
gtggagtgca agaaatcgca gcgtatccta gaggccctgg acattctcat cctcaaactg 104820
gtggtgggcg agtttgccat gtccgaggcc gacagcctgg agatgttgct ggacaagttc 104880
tccacggatc aggcctcgct ggtggaggtg cagcgcgtta tgggcctggt ggatatggac 104940
tgcgagaaaa gcgcgtacat gctcgaggcc ggcgcggctg cgacggttgc accaccgacg 105000
ccaccggcgg tcgttcaggg ggaaagcggc gtccgcgagg acggggaaac ggtcgccgcc 105060
gtgtcggcct ttgcctgtcc ctcggtttcg gactcgctga tccccgagga aacgggggtc 105120
acgcgtccta tgatgagttt ggctcacatt aacaccgtct cctgtcccac cgttatgagg 105180
ttcgaccagc ggctgctgga agagggcgac gaggaggatg aagtgaccgt gatgtcgccg 105240
tcacccgagc ccgtgcaaca gcagccgccg gtcgagcccg tgcagcagca gccccaggga 105300
cgcgggtctc accgtcggcg ctacaaggag tcggcgccgc aggagacgct gcctacgaat 105360
cacgaacgcg agattttgga tctcatgcga cacagccccg acgtgcctcg ggaggcggtg 105420
atgtcaccga ccatggtcac catacctcct ccccagatac cttttgtggg ttccgcgcgt 105480
gaactcaggg gcgtgaagaa aaagaaaccc acggcggcgg ccttgctgtc ctccgcgtga 105540
acagcctggc acgttttgga aaacgtacgt gatcacggac acgacgagta cggggtttct 105600
catagacgta ctttattagg tcagggatga cggggaggtt tcgggccgac gtcaaaaata 105660
acgtcactcg tgttgacagg gctttctgcg tcggagctct tttcatcttc ttctgtctcg 105720
tcgacgtcat cgtctaccgg cgagggtgtc cgttgcagca acgcgtgctc gggcgtgtgg 105780
gtgaaaccga tgtcgggggt gggcggcacg atcatctgtc ctagggggtg actgcccacc 105840
ggcagatagg taaaacgatg ggtggtaaaa accgctttgg ctacggtggt gtgtggggag 105900
atgcagacgg tggtgtgcga agtgttgacc accgtcacgc cggccgcggt acccgggagc 105960
cagatggtgg gtcggatgat gagatccgat tgactaaact ggcgcacgcc cactatgagg 106020
gcgcagatac cgggcgcgtg cacgtaggcc gcgtcaaaat agacggtttg cgtgtgaccc 106080
ggaccgatca ccagcgtctg acgggtacgt aatgaaaaga aacggtgttc gttgggcggc 106140
ggcaagttca tgagctgcca aggttctggc acaaaacagg ggaaaacgcc gatatcgcct 106200
tcgatggtgc ccggaaagat ggactgaaaa gtgtcgttga ggttgacgac atccaactgc 106260
gggacttgca gcccggattc cagcagctcg ggcatgcaaa cgaattgcgc gtccaggcat 106320
ttgtaaaagg taatgccaaa aaaaccttcg gggatataga ggctgacgcc cagcgaggtg 106380
ggcactttgc gctcgcgtga cagccaaatg atgtgtttat tgtaaaaggc cagctgcgtg 106440
tggcattgtt tgacgatgaa actggaaggc atccacttgt agggaacttt gagcggcgac 106500

```
ggtaatgacg acgacgcttc atcctctccc ggatgctgct ctttgtcgta tttctcctcg 106560
gtcgattggg gcagcgtaaa tgtggtttga aaatcgctat cactagcgaa acgcacgcag 106620
taacgcatgt tgacggattt ctcggctagg atgatggagc ctgatgacgg tgcggactct 106680
tccttcatta ttaacgtagg ggtctcccag aatcgctgaa aacgggagcg cggcagccgc 106740
gacagtacca gttgagagtc gattcggtcg gtcaacatcg taagcatcgt ggcggtggtg 106800
tgatggagtg gaaaacagtg atactaggtg tttttgtttt atcggtggca gcggggagtt 106860
ctggtaacag ctcatccacg tcaacctccg caactacgtt aaaatcgtcc agttctagcg 106920
tgtcaacaag caaattgacg acaactgcga caactacgac aactacgatg agtacgacct 106980
catcgacaac taccactaaa ccaagttcca ctactcacga ccctaatgtg atgaaacgac 107040
atactcacga tgatttttac aaggcacatt gcacatcgca tatgtatgag ctttcactgt 107100
ccagcttcgc ggcttggtgg actatgctta acgctctcat tctcatggga gctttttgta 107160
tcgtactacg acattgctgt ttccagaact ttactgcaac caccaccaaa ggctattaag 107220
ggtggacaga tttacagctc gacggtgttc cggcggggta aggtttccat aagtgggtga 107280
ctggagacta aagttacgga tctcatctag aaatagcagc gagtctagat agtcccacag 107340
gggatctata aacgttctct gaaatcccgt tgatggtgac gtaggtgtag tttcggaagc 107400
cgttttgttt tccacgaaca tggtttcgtt ataatataag gagctcatat caagagtacc 107460
gtaaatagtg tacggtgttt cattacggat tagtacatgc gtgtttttca taaattctga 107520
tacggcggtt cggttgcggc ttgattcaca aaaagggttt tgccggtaac gtagagtggt 107580
atacacccac gtcgctaggt cccttaattg cgtggtcata atggacttca taaagctact 107640
atcaggacga taagcaattg tagacgtgga aacccgcctt gcggtggtag taacactata 107700
agttgcgtta gtagtgacgt tcagagcggt tgacgttgta tagggagaat atggcgtagt 107760
agtactttga gatttcttac tcttttttc tgattgttct ttgactggag cttgtttacg 107820
cttgagtttt cgcatagtgt ttttcaactt agtaccgtta atatacttag ggacgcgaaa 107880
taaatttcgg ctcatggcgt taaccaggta gaaactgtgc gtacagttgc gttgcgcgta 107940
acgtagaagc aaggcggtta ggcctaaaaa gtagatcgtt tgactatcca cgtttacttt 108000
cttggaacct acatataact tcgtgttcca acgtggcaca ttgaaaaaca tggggttgaa 108060
cgtggtgaaa ttgccgcagc cttgttcgcc agtatcatta cgtttggaaa cgtttagcat 108120
ttcggaaaga caagtcatgg aaggcaccgt accgcaagat gggggtctga atgttattgt 108180
tttagccgta tgattgtatt ctgagaaaac gtacttagcc ggttttcgaa gctgagtgct 108240
ataaaaatcg aaccaaagat aggtaacact gttattttga atgggtcccg ctaaaatgta 108300
ataccgtgga aactcggtca tgttcatagt cagattttta atgtgttgtc tggtcatatt 108360
aaagtatttt gtatagatat ccttttctag ttgtttcaaa atctctaatt tgaacttgtc 108420
tagtctttgc ttgcctatcg tagacagtac tttacctgac cagtaacgtc ctacggataa 108480
tcgtaccgca gccctacagt ttatgaaaga gaatagcagg aaagttagtg acataaggaa 108540
gaataaatta aaaacacctc tcatctctcc ttttctcccc atgacagagg aggagacccc 108600
gcaccgtccg tctgccttgt ggtttggctt gcctgcgtgt actcactgct gattctggtc 108660
gttttgctgc tcatctaccg ctgttgcatc ggcttccaag acgacctagt ctcccgcact 108720
ttggctgtgt accgagcttg tatccagggc ccgatatgta accagaccca caacagtacc 108780
tcgtaaataa agacgcacag acctcacgca tatagtacca tcacaccgtg tggcgtgtac 108840
tttattacaa cgagcaagag tgccccctaa ctattggggc ccgtaccgtt ttagaaggtt 108900
```

ttgtgtgaat gtctttaact tctctgtccc ttttctcata aactgtcagg tcctacagtc 108960
agcatgtctt gagcatgcgg tagagcagat agatgccgat gatggccgat agcgcgtaga 109020
cggacatcat gaggagacga ctgtcggtgg cgtccacgac aacgtcagtt acttctagga 109080
ccgtaccgtt tttcaaaagc atgaggtagt gagttcgcgg agatgagacc accacttcgt 109140
tgtagggatc cagggcgaaa aggacgtcgt ccgagtcgtg catgtacatg atgttgatga 109200
cgccttgcgt gtcgtcgtat tctagcaggg cgctttggca aaaggcgcag ttttctaggg 109260
aaatgttgag cgccgctgtg atgctgtgtg tggtatgcat gttgcgcgtc agttcgcatt 109320
tagtttgact gtccgtctgg gtgatgatga ggctctggcc tacgacggtg gtggagacag 109380
ggtaggagat acctttgatc aggtactggt ttgttacgac ataactgacg tgttcggaga 109440
cggtcagcgc ggagaaggat tcgcctagtg gcagacaaaa caggtcgggg aaggtttcca 109500
acgtgcttgg ttgcatggta gataggatgg agagggcggc gggaacggta gtggggacgg 109560
tggcatcggg gaagagacgt gtgaggcgtt cgagcgagtg atcgcgtcgc ccgctactgg 109620
aacagggtgt gtacaggtcg ctgaggtatt cgtggtgcgg atgagctagc aactgcgtaa 109680
agtgtgatag ctcggccaat gaacagaggc ccgtttctac gatgaagatt tcgcgtctct 109740
ccgtcgtatg taccagcatg gagtggacga ggctgcccat gaggtagagt tcttgacgcg 109800
cgaaggctga aagaaaagag gccaggtgcg ttttgtgtag ttttagggca aagtcggcga 109860
tctgtcgtag tgcccactgg gggatgagat gttgctgatt ctgtttagag agtatgtaga 109920
ccaggcgtac gaggctggtg atgtcggtga tctgattcgg tgtcaaaagg gctcgtttgg 109980
ccaggtccac ggccgtggga tacagtagca acgtggtgcg tggtggtgtt tgtgagaggc 110040
aggtgatcat aaattcttgt atttgtaaga gtgcggcctg gcggtctagg gcccgtggga 110100
cggagacttg ggcgccggcc tcttcttgtc gggctgctgc gaacagtgct aatgcgtagg 110160
cgaaggccat ttctaccgtg cggcggtcca gcatctgaca tcgaccgctc ttgagtacat 110220
ccacggcgta acggtgaaag ctgttacgta gtagtgcgct gaggtctagg tagttgaagt 110280
caagtgcggc gtcaagaaag tccgggtctt tgagataaga gtgacggttc agttgatctt 110340
tcttaactag caccaggagc tcgtgttttt cagtttgtcg tagtataaag ttgtcgcgtt 110400
gatagggcgc tttgaaaagt acgcgtggaa gatggccgaa gataagcagc atgggtgtgt 110460
cgtcgtctat ggacaccgta actacgaaga agtcctcggt cagtgtgatt ttaacgtaac 110520
gtagttcgtc gatgaggtaa aagccttggt gcaaacaagg tgtgacggtg ctgaatagta 110580
gatcgtgtcc atcaaagagg atacaggtct ggttaaagtg tggtcggtgt agtcctgagg 110640
tggtatgtga ttctgtccag ccgtgtggag tggtttgcgg tggcatccaa acgtgaggta 110700
ttgacaggtc aatgggcggt ggcacagtgg tgggctgttc acctaggctg tcttgtgcct 110760
ttagctgctg cgaaaaagat cggtagctgg ccaggtcttt ggataccagc gcgtaagtgt 110820
taagtctctg ttggtatctt tccagggttt cggtcagatc tacctggttc agaaactgct 110880
ccgccagagg acccgcaaaa agacatcgag gcatatggaa tacatagtat tgattatagc 110940
tttggaaaaa gttgaaactg atggcgtttt ccctgacgac cgtgctgtta cggaggctgc 111000
tgttgtaggt gcactgggtg gtgttttcac gcaggaagcg gatgggtctc ccgtaggtgt 111060
tgagtagtag gtgaaacgcg tgagggtcca gcgcttcgga tgcggcgtct gcgccatatc 111120
gttgcgaagg taggtgactg aggaggtaga cggcgaagac ggtgaggtag gaggggaggc 111180
cgggccgcat agcgcggccg cgccgctggg ttcagcggcg tgatccaggt ggtggttggc 111240
gttacacccg agagaaggag aaaaaggatc ccaggaagga gcacccgggt gcggcgctac 111300
gggttacaaa agtcgcgtct ccgtctattt aatacgatgt cattggccgc tgcgaaggga 111360
gaagagggga cacgcgaata agccatgccg tccgggcgtg gggacgacgc tgatttgacg 111420
gggaacgctc tgcggagatt gcctcacgtg cgtaagcgaa tcggtaagcg caagcacctg 111480
gacatctacc gtcgtctgct gcgggtcttt ccctcgtttg tggcgctcaa ccgcctgttg 111540
ggaggccttt tcccacccga gttgcaaaag taccgtcgcc gtcttttcat cgaagtacga 111600
ttaagtcggc ggattcccga ctgcgtgttg gtgtttttac cgccggactc tgggtcgcgc 111660
ggcatcgtgt attgctacgt gattgagttc aaaaccacgt actcagacgc cgacgatcag 111720
tccgtgcggt ggcacgccac ccacagcctg cagtacgccg agggcctgcg ccagctcaag 111780
ggcgcactgg tggactttga ttttctgcgt ctgccacgcg gtggcggtca agtctggagc 111840
gtggtgccca gtctggtttt ttttcagcaa aaggccgatc gcccatcctt ttatcgggct 111900
ttccgctcag gccgttttaa cctgtgtacc gattctgtcc tggactatct agggaggcgt 111960
caggatgagt ctgttgcaca ccttttggcg gctacccgtc gccgtcttct tcgagccgca 112020
cgaggaaaac gtgctgcgct gccccgagcg cgtgcttcgg cggttgctgg aggacgcggc 112080
ggtggcaacg cgcggcgggg gctggcgcga ggacgtgctc atggaccggg tgcgcaaacg 112140
gtatctgcgt caggagctca gggatctggg tcacagggtg cagacttact gcgaggatct 112200
cgaagggcgc gtgtccgagg cggaggcgtt gttgaaccag cagtgcgagc tcgacgaagg 112260
accgtcgccg cggacgctgc tacagccacc gtgtcgtccg cgttcgtcgt ccccagggac 112320
cggcgtggca ggagcttccg ctgtcccaca cggtctttat agtcggcacg atgccatcac 112380
gggacccgcc gccccgtctg acgcggcgac cgcgtcagcg gccgccggtg cttcttctac 112440
ctggctggcg cagtacgccg agcggccgtt gcccgggaac gtacctagct actttggaat 112500
cacgcagaac gatcccttta tccgctttca caccgatttt cgcggcgagg tggtcaacac 112560
catgttcgag aacgcctcca cttggacttt ctcctttggc atctggtact atcggctcaa 112620
gcgggggttg tacacgcaac cgcggtggaa acgaatgtac catctggcgc agatggacaa 112680
cttttccatt tcgcaggagc tgctgctcgg cgtggtcaac gctttggaaa acgtgacggt 112740
gtatccgacg tacgactgcg tactctccga tttggaagcc gccgcctgtc tgctagtcgc 112800
ctacggacac gcgctttggg agggccgcga tccgccggac tccgtgacgg cggtgttgag 112860
tgagctgcct cagctgttac cgcgtctggc cgacgacgtg agtcgtgaga ttgccgcttg 112920
ggaaggcccc gtcgccgcgg gtaacaacta ttacacgtat cgcgactcgc ccgatctacg 112980
ctactacatg cccctaagcg gtggtcgtca ctatcacccg ggcacttttg atcgtcacgt 113040
gctggtgcgg cttttccaca aacgcggcgt tattcagcat ttgccgggct acgggacgat 113100
aacggaggag ctggtgcaag agcgtctgtc gggccaggtg cgtgacgacg tgctttctct 113160
ctggagtcga cgtctgctgg tcggcaagct gggtcgcgac gtgcccgtct ttgtgcacga 113220
acagcaatat ctgcgttcgg gcctgacctg cctggctggc ctgctgttgt tgtggaaggt 113280
gaccaacgcg gatagcgtct tcgctccgcg cacgggcaaa tttacgttgg ccgacctgct 113340
gggttcggat gccgtagccg gcggcgggtt gcccgggggg cgcgcgggcg gcgaagagga 113400
gggctacggg ggacggcacg ggcgggtacg taattttgag tttctggtgc agtactacat 113460
cgggccgtgg tacgcgcgcg accccgcggt cacgctgtcg cagctctttc ccggcctggc 113520
tctgttggcc gtgaccgaaa gcgtgcgcag cggctgggat ccctcacgtc gcgaggacag 113580
cgccggaggt ggcgacggcg gcggcgccgt gctcatgcag ctcagcaaga gcaaccccgt 113640
ggccgactac atgttcgcgc agagctccaa acagtacggc gatttacgtc gcttagaggt 113700

-continued acacgatgcc ctgctctttc actacgaaca cgggctaggg cggctgttgt cggtgaccct 113760
gccgcgtcac cgtgtgtcca ctctgggctc gtccctcttt aacgtcaacg atatttacga 113820
actgttgtac tttttagtgt tggggtttct tccgagcgtg gcggtgttgt aatttccacc 113880
acgtgtcgct cgctgcataa agggcgaacg tccccggaga gggtatattc gttcggcgag 113940
agcgggcggc ggtggtgggt atgtcccctt ctgtggagga gactacctca gtcaccgagt 114000
ccatcatgtt cgctatcgtg agtttcaaac acatgggccc gttcgaaggc tactctatgt 114060
cggccgatcg cgccgcctcg gatctactca tcggcatgtt cggctccgtt agcctggtca 114120
acctgctgac tatcatcggt tgcctctggg tgttgcgtgt tacgcggccg cccgtgtccg 114180
tgatgatttt tacttggaat ctggtactta gtcagttttt ttccatcgtg gccaccatgt 114240
tgtccaaggg tatcatgctg cgtggcgctc taaatctcag cctctgtcgc ttagtgctct 114300
ttgtcgacga cgtgggccta tattcgacgg cgttgttttt cctctttctg atactggatc 114360
gtctgtcggc catctcttat ggccgtgatc tctggcatca tgagacgcgc gaaaacgccg 114420
gcgtggcgct ctacgcggtc gcctttgcct gggttctttc catcgtagcc gctgtgccca 114480
ccgccgctac gggttcactg gactaccgtt ggctaggctg tcagatccct atacagtatg 114540
ccgcggtgga cctcaccatc aagatgtggt ttttgctggg ggcgcccatg atcgccgtac 114600
tggctaacgt ggtagagttg gcctacagcg atcggcgcga ccacgtctgg tcctacgtgg 114660
gtcgtgtctg caccttctac gtgacgtgtc tcatgctttt tgtgccctac tactgcttca 114720
gagtcctacg cggtgtactg cagcccgcta gcgcggccgg caccggtttc ggcattatgg 114780
attacgtgga attggctacg cgtacccttc tcaccatgcg tcttggcatt ctgccgctct 114840
ttatcattgc gttcttctcc cgcgagccca ccaaggatct ggatgactcc tttgattatc 114900
tggtcgagag atgtcagcaa agctgccacg gtcatttcgt acgtcggttg gtgcaggcgt 114960
tgaagcgggc tatgtatagc gtggagctgg ccgcgtgtta cttttctacg tccgtccgag 115020
acgtcgccga ggcggtgaaa aagtcctcca gccgttgtta cgccgacgcg acgtcggcga 115080
ccgttgtggt aacgacggcc acgtctgaga aagccacgtt ggtggagcac gcggaaggta 115140
tggcttccga aatgtgtcct gggactacga tcgacgtttc ggccgagagt tcctccgtcc 115200
tctgcaccga cggcgaaaac accgtcgcgt ccgacgcgac ggtgacggca ttatgagcgg 115260
cggcgctgta cggcagcggg gagaaaagtg gcagataaat cacgtcaggt tcacacgtcg 115320
ttagccagcg tcggcatatg aagggcgcgg gcggccagta cggcctctgg gctgagacag 115380
gacgaggcag ggtgagaaag aggaggatgg gggggaccgg ggtggtggtg ctgctgctgt 115440
tgtgggtgtg gacggtgcgg atgccgggac agcgtgccgg cgaacgttct gtaatcttcc 115500
ataataaagg taaaaatgcc cgtctcgtgt cgactccgct ggatctcgaa ggcgtcgggg 115560
gtaatgcgca tcttgccggt gccgatgaga taaaagtacc acattttttg acagatgatg 115620
cgaatcaagg gttcgtacgc ttcggcaccc cagtggcgcg tgaagaaggc cgccagacga 115680
aacaagcggt gtccgtagag cgtgcctagg gagaagagga tgttgccgtt gcgcgccagg 115740
tcttcgggga aaacgaccgg caggccggtg tggcgctgca caaagcgcgt cagcagtccg 115800
ccgctcaagc gcgggtgaca caggcgctgg ctgagacggg cggcgcgcgt ttcatcgaac 115860
acggccgcct caaagtccag ccccgggaag gcctggcgca gttcgcggta cagatgaggc 115920
cagtagggtt gcggcgtctt gcgactaagc acggcgtggt ccgagacgcc caggttgttc 115980
atggtttcgc gcagtagcag cgtttcgaga ccgcggtgaa agaggaggac gcagatgagg 116040
cgtacgattt tgagttcttc caaacgcagc gagctcagcg gctgtccgcg cgacatcttc 116100
tcgctaatct gtaatattag atgattggcg caagtaaagg agaatttgcc cgtgcggacc 116160
cgcgggacgg cggggttctc ttcgtcgcgg gccatcatcg ttcgctcggt gagcgggtag 116220
cgacggtgag gacaatgacg atggacgagc agcagccgca ggctgtagcg ccggtctacg 116280
tgggcggctt tctcgcccgc tacgaccagt ctccggacga ggccgaattg ctgttgccgc 116340
gagacgtagt ggagcactgg ttgcacgcgc agggccaggg acagccttcg ttgtcggtcg 116400
cgctcccgct caacatcaac cacgacgaca cggccgttgt aggacacgtt gcggcgatgc 116460
agagcgtccg cgacggtctt ttttgcctgg gctgcgtcac ctcgcccagg tttctggaga 116520
ttgtacgccg cgcttcggaa aagtccgagc tggtttcgcg cgggcccgtc agtccgctgc 116580
agccagacaa ggtggtggag tttctcagcg gcagctacgc cggcctctcg ctctccagcc 116640
ggcgctgcga cgacgtggag gccgcgacgt cgctttcggg ctcggaaacc acgccgttca 116700
aacacgtggc tttgtgcagc gtgggtcggc gtcgcggtac gttggccgtg tacgggcgcg 116760
atcccgagtg ggtcacccag cggtttccag acctcacggc ggccgaccgt gacgggctac 116820
gtgcacagtg gcagcgctgc ggcagcactg ctgtcgacgc gtcgggcgat ccctttcgct 116880
cagacagcta cggcctgttg ggcaacagcg tggacgcgct ctacatccgt gagcgactgc 116940
ccaagctgcg ctacgacaag caactagtcg gcgtgacgga gcgcgagtcg tacgtcaagg 117000
cgagcgtttc gcctgaggcg gcgtgcgata ttaaagcggc gtccgccgag cgttcgggcg 117060
acagccgcag tcaggccgcc acgccggcgg ctggggcgcg cgttccctct tcatccccgt 117120
cacctccagt cgaaccgcca tctcctgttc agccgcctgc gcttccagcg tcgccgtccg 117180
ttctccccgc ggaatcaccg ccgtcgcttt ctccttcgga gccggcagag gcggcgtcca 117240
tgtcgcaccc tctgagtgct gcggttaccg ccgctacggc tcctccaggt gctaccgtgg 117300
caggtgcgtc gccggctgtg ccgtctctag cgtggcctca cgacggagtt tatttaccca 117360
aagacgcttt tttctcgcta cttggggcca gtcgctcggc agcgcccgtc atgtatcccg 117420
gcgccgtagc ggcccctcct gctgcttcgc cagcaccgct gcctttgccg tcttatcccg 117480
cgtcctacgg cgcccccgtc gtgggttacg accagttggc ggcacgtcac tttgcggact 117540
acgtggatcc ccattatccc gggtggggtc ggcgttacga gcccacgccg cctttgcatc 117600
cgtcttatcc cgtgccgccg ccaccatcac cggcctatta ccgtcggcgc gactctccgg 117660
gcggtatgga tgaaccaccg tccggatggg agcgttacga cggtggtcac cgtggtcagt 117720
cgcagaagca gcaccgtcac gggggcagtg gtggacacaa caaacgccgt aaggaagccg 117780
cggcggcggc gtcgtcgtcg tcctcggacg aagacttgag tttccccggc gaggccgagc 117840
acggccgggc gcgaaagcgt ctaaaaagtc acgtcaatag cgacggtgga agtggcgggc 117900
acgcgggttc caatcagcag cagcaacaac gttacgatga actgcgggat gccattcacg 117960
agctgaaacg cgatctgttt gccgcgcggc agagttctac gttactttcg acgtctctcc 118020
ccgctgcggc ctcttcctcc ccgactacta ctaccgtgtg tactcccacc ggcgagctga 118080
cgagcggcgg aggagaaaca ccgacggcac ttctatccgg aggtgccaag gtagctgagc 118140
gcgctcaggc cggcgtggtg aacgccagtt gccgcctcgc taccgcgtcg ggttccgagg 118200
cggcaacggc cgggccctcg acggcaggtt cttcttcctg cccggctagt gtcgtgttag 118260
ccgccgctgc tgcccaagcc gccgcagctt cccagagccc gcccaaagac atggtagatc 118320
tgaatcggcg gatttttgtg gctgcgctca ataagctcga gtaagagaga cgctatattt 118380
agggtttccc tctctttttt ttttctacac cgtgataccc taataaagca cactgcggtt 118440
attatcaacg tctctgtgtt tttattattt agaaataaat acagggaatg ggaaaaacac 118500
gcgggggaaa aacaaagaag tctctctcta gatgcggggt cgactgcgtg gggtgctgga 118560
agtggaagcg gtgctgatgg gtgagggtcg tggcgcgggc acggaccgca acgtgctgct 118620
gatgtctgcc gcggtacgca cgtcgccgtc catgtcgctg cgcagataag aggtaggtcg 118680
taatgcggcg tgctgcacgc tcaccgttaa tggtaccaag tcgtcaaggc tcgcaaagac 118740
gtgccacgag ggatgacga gcgtgagagc cccgttgtta ccgcttcgac gtctttgtcc 118800
ggtcaggatc agtgcccggg acagtccggc ttgggtgtcc gagtcctcgt cgccgctggc 118860
ctcctcgaag ccggcaaaca tggcttcgga cagggggtc ggcgtcggtg tggaggagag 118920
gtcatcttcg tcgtcctctt cctcttcttc ctcctcttcc tcggtgggtg gtaatccggg 118980
ggactgcggg agaaactcgg agacggcgcc gcgcatgacg ttgctccgtg gaaagagacc 119040
ggcgcgcagc tgcacctggg gacgcttgat tttgtccggt ttaccgggtg tgagagtcca 119100
aaacccacgg cggaaaaagt ggatgcggcc tagcggctgt cggtgttcca aatgaacggc 119160
ctggtcgccg gtcagcgtga cgcggagggt gattcgcaca cgatcgggta gcgggccggc 119220
ttctatggag acgcccggga tgttttccgg gaaaaagatg gtgtcgtgag tctgattggt 119280
ttcgaaagca ttctggatct gcacgatgta ctcgggatgt atgcgcgtca gcgtaaaact 119340
tttgggaatc aacagctgga agccgttgtc cggcaagcgt cgtaggtgcg ggtacggatt 119400
gtgtcgcgcc accacctcgg cgcgatgcgt gtaaaccgaa aagtgcagaa acacgctggt 119460
cggcgggtgc ggtgagtcgt gatgcagaaa cagcatgatc cattggcctc gttcgtccgt 119520
ctccgttttg tggatgtacg tgttagggtc cgaacaggcc agctgctcca gggcgtctac 119580
cagcgtcagc gggatggcgc cggcgcgaaa ggcgaactgg ctgacaaaga tctgccctgc 119640
ctccaaactg ctgtcggttc tgcggcgcca gttcggcgtc acggtcagtc gcacggccca 119700
gtggtgagcc gtgcggcgga tgatggcgcg cgcttccatt cgcggccgat tttcttcgcc 119760
gccgcgccgc tggctctgaa agaggtgcaa tccgctaacg ggcacgcggt ctagcggcag 119820
cgcaaaggcc agcaccgaga ccgtgttgtt ttctgagcct ggcgtcaggc gtcgtgggcc 119880
aaagttgttg aggtccacca gcagtcggtc ctgttcgccc accacgcagc ggcccttgat 119940
gtttaggtcg gtcaggtcta cggtgtcgtg cggagatttg ttctcctgaa aacagcagag 120000
aaccgagggc cggctcacct ctatgttggt acgcaggtcc aggagtcgca gacgaccggc 120060
ttccagcgag ccgccttcca cgttggtgat gagccgaagc acctggcagt gcaggcgacc 120120
aaagctgccg ctggcggctt cggcctcgct gatcgcggcc gcttccgacg agggtccctc 120180
accgggcgag gacgatgcct gagacattgc gaaggcggga tggggggagg gtcaggggat 120240
gcgcaaaggt gaacgggtct tcgtgggagg tcgggaaggg ttccggcaac tgtcgcaaat 120300
atagcagcgg cgacaggtgt ggcggccaaa agttgcgtgt ctgagtggac gtgggttttt 120360
atagagtcgt cctaagcgcg tgcgcggcgg gtggctcaac ctcggtgctt tttgggcgtc 120420
gaggcgatgc atggcccggg caaggcgtct tgccggtggc ggcgacgttt gggttgcgca 120480
gcgggctgcc atacgccttc caattcggcg aagatgcggt agatgtcgtt ggcgtcccag 120540
aagaactcct ggtacttcag attctgaccc tgaaccgtag ccaccatggg caccaggttg 120600
cgggccagga tgccggcctg ccagggcggc caggtgaaca cggccggatt gtggatttcg 120660
ttgtcggaat cctcgtcggt gtcctcttcg ggcgcgacgg tggactcggc cttaaggcgg 120720
ccgcgtgtca taacgcccga cgtgcacgcc gtcgccgagg atgctgattt gcgtttgcgg 120780
cccgcggaag tggaggcgcc cgccatggcg ccgccgccgg tgacgcgggg cgtcttgcgc 120840
tcggtggtta cgagttcttc gtcggagtcc gatccgctgg tccagacgtc gtcgtcgccc 120900
tgggcggcac cctcgtcgtg ccggtcccag gtgtgtcggt actcaagctt gccctggatg 120960
cgatactggc tggtgaaggt ggggtgctcg ctgtactgag gcccgcgctg cagcagcaag 121020
tcgatatcga aaaagaagag cgcagccacg ggatcgtact gacgcagttc cacggtctcg 121080
cgtatcgctt gtacctccag gaagatctgc tgcccgttca tcaacaggtt acctgagatg 121140
ctcaggcccg ggatgctctt gggacacagc agcccaaaat gctcgtgtga ggtaaaagcc 121200
acatccagca tgatgtgcga gatcttgccc ggtttgatta tcatattttt gggacacaac 121260
accgtaaagc cgttgcgctc gtgggggcgc atgaagggtt gcgggttgcg ggtcatcgtc 121320
aggtcctctt ccacgtcaga gcccagcgtg acgtgcataa agagcttgcc ggagggcacg 121380
tcctcgcaga aggactccag gtacaccttg atgtactggt cacctatcac ctgcatcttg 121440
gttgcgcgcg tgttctccat ggagcaaacc agctcgtgcg cgcacaccac gtgccgcagt 121500
gccacgtcct tggtgggaaa cacgaacgct gacgtgtagt agacgtcggg ctctttccac 121560
tggttctgct gacgcgtcca ggccagtccc gagaccgtga gacgcgcctg ccacatctgc 121620
ttgcccgacg cgtgaatcac agcgtcagct acgggcaggt gtcggtgttt gcgctcggcc 121680
gccgacgggt agtggtgcac gttgatgctg ggatgttcca gcatcttgag cggcagcgcg 121740
tacacataga tcgacatggg ctcctggctg gggcagatgc ttcggcccgt agggttgtgc 121800
acgttgaccg acacgttctc cacctcgctg cccgtaaagt acgtgtgctg cacctgcagc 121860
tgattgtcgc cgcggtggca tggcgtcgag tcgggcgtgt actgcgacac caggatcagc 121920
gagggctggc tcacgcgtac gtggataccc gtctgcagga gtcgcgtctc gtgcggcagc 121980
accggcgtat cgccgcgact aaacacggct ttcagcacgt gccccgaaat gggacccagt 122040
acggatatca tttcgggaca acggcgaccg cgcgactcca tgctgcctgc gcgtacgggt 122100
gtaggcgact gagcggcgcg ccctctgcgg ccgccgcctt acataggcag gcgaccaaac 122160
gcggaacccg aaataaaaac gttctacaca gagacaaccg cggattattg agtgtctttt 122220
tttattacaa aaaaaaagag gcgaagcccc accgtcacca caccccatca cacaccacca 122280
ccgatttttt ttgttttaac cccgtatcac gcggacgcct agtgtccgtt tcccatcacc 122340
agggtcctct gtttagagat cgccgcagac catggctaga gtgacaggac tcgttttctc 122400
tgtcgtattt tccgtaagct tacagtcttg cggttccgtc tccggggacg ccagtcgcat 122460
gggcagcagg tcctccagcg cgatggaagc gcccagcacc gagagctgct gttgcgacgg 122520
cgaatgggac gtggaccgcg agtgtagcgt ggatttgact tggtgcgtca ttgctgacag 122580
gcaaccgcga ttcagcgtat gctttgacga gataaaatag aggcgcccca ggagcgcgtc 122640
ccgtgggaac gtggcgccgt tctcgtcgct caccagtacg gttaattcca accaggagcg 122700
cggtagccag accgtaacgg gcattttgag tccctgacgg ttgtgtggta caaaaacacc 122760
cagataaggc ccgtaaaagc ggcggtagat acgtaacgtg tgcgagttct tcagtgtcaa 122820
ttcgtaaggg acgcgcacct ccagtccctc gtccgccgcg ccggagcgtg gcggtacaaa 122880
gtaaggcagt ggcgcgtccg aaaagaaggg tcgtcgcacc gtttcgcgtc gcagccgcag 122940
gcgaaacgcc actgggtcgg ctggcgcctc ggtgcggtcg caggtcacgt tgaaacgtaa 123000
catgccgtct tggtatagcg tgagtgacga cagcgtcagg tccggcggtg attcgttcgg 123060
atctagctcc aatcgtccaa agacggaggg tcccaatgtc ttggccgtgg tttccgagag 123120
gcgtgccgaa atacggctag tgagtccacg cggccccgag atgccgcctt ccactcgatg 123180
ccagcacagc gcgtgtcgta cgcgcactgt cagcgtgggc gtcagatccg cgtccgttga 123240
ttccgcggta tcagcgacgg aagccgcgtt ctccgttacg ttgtttatat ccagcgtagg 123300

-continued ctcgaacgtg agttctggca gatgcagcgc caggcagtcg tgtaacgccg tgtgatgcgc 123360
ggctttacgt cgtagcggta gccgtttcag cagcggcgtg atgatacgga gcgcgaagag 123420
attgagtgat aagcgcacga tggccatgcg cgtcagttgt tggtcaatta ccgagcgcag 123480
gatatggcag cctgggcgtg cgggaaagag agagaaggcc gggcgcacgt cagaatcctc 123540
gttagagacc acgcatagaa tgccgcgttc acgatcgtcg ttgcggtcat cctcgtcctc 123600
ttctttcttc tcttcttttt ccttttttt ctcgggctcg tgggaagccg ccgtttcttc 123660
ttcttgcgac gtcgcggggg cggtttgaga ctcgccgttc gcttccccca attgcagcgg 123720
cgtagagagc agaatctgga agggatcccg caattcttcg ggtcggaggt cgaggtgcaa 123780
ctggatcaga tggtaggtgc cgcggtgcac ccgaggctga cggatgtcgt gtttatccgt 123840
cagtgtgagg atggtctgcg gcgagccgct gtgcttgtcc agctcgtccg gcgttttcag 123900
gaggagactg tcgtcgtcgg tactggcgac gcccatcata gtcgtggtgg tagtggtggc 123960
gaggaaagtg agtggcggcg ctgacagagc tcggcgttgg cggcggcatt tgccgctgtg 124020
tcggctgcta ttgctgccaa cgccgccgcc gccgccccgt ctggctcgtg gccggcgggc 124080
ccgattccga aggttggggt cgacgcgtgg catgcttggt gtctgcgggc gcgagagggc 124140
cggctcagcc tttaaatatg caggtcgcgg atttgttatc gggtgaaacg tcacacaccg 124200
tgaagacgac ctgttcgcgg atgaggtcat ccagctgtcg cagcatgacg aaaagcgccg 124260
acagccgcgc gatctcgtcg tcgggcgaca cgtgctgcgg ccgcgcgggc gtgcgcggct 124320
cgccgacgct gcgctcgcgg tccagccgca tcagcagctc ttggcacttg acgagcagca 124380
tggagctgtc ctctagcgct aacttgcgca cgtaggtcat ggtcagctcc gaggctaggt 124440
tggccaccat ggacatggag aggcaggcgg tcttcatgtc gatcagcagg tgctggtcga 124500
tgaccggatc ggggatggtg aaggtggcgt cgcgaaaagt aatggtctgc agctgctgca 124560
cggcagcctt tacctcctcg tacgaacggt cgagcgagaa gaggcccatg atgagtagtc 124620
gctggttgat ttccagcgcc agtggcatgg gtacgatcca gggcagcacc agctcccact 124680
ggcccagcgt cagcaggttc tcgcgcgcca gcggtccgtg gaagagcggc ggcagcacgc 124740
atagcgcgtc gcccttctcc caagtcacgg gtcccgtgtt gaggacggtg tagagcagtc 124800
cgtgcgtggg tacgtgtagg aggatctggt tgccttctac gcgccgcatc aacgtcagcg 124860
tcatattgcg cagcaggccg cgcagtcgta cgtaaccgcg ggtgtgatct acgaactggt 124920
gtaggcccag ctggtagtgc ttgatgagat gtagacgctg cggaatgggc acaacggccg 124980
ctactagctt ggtcagtttg cctacgtcgg cgatgctgag cttgtggtcg aaagtgcaga 125040
agatgttggc ctccatggcc gccatagcgg cggtgaaatc ctggccgcga cagaggagaa 125100
gcagagacga acaacgtctg caccgggcgc ggcgtcagag cgagcgtggc gcgtccgggc 125160
ccgcgtttgc gtctaggtga ctcgccgcta acctgcggtc gtcgccgtcc tcctcaccgg 125220
acggcctcac gagttaaata acatggattg ctgcagcggg atgatttcgc ctacgacgta 125280
gttaccaaag tgcgtttcgg acgtagcaaa agccccggcg ccacccttga gtttggtctc 125340
catcagcgcc agcgtggtgg tgctgaggat cggtagcgct tcctgcgtca gacggcacgg 125400
gttttcgatg agttgttccg tgccttcgac gcagacgtac tgcgtgtccg tgtcgccgcg 125460
gatgcagtcc ttggcgcgta gcaggtactc gtcgatggtt ttgaagagcg ttttgttggc 125520
cgcgataatc tcttctgtgt taaagtactg cgcgcagggg ctgtagaatt tggagttgta 125580
gcctagacgt tcgcgatgtc gggtgttgta gagtacgtcg ctcagacagc cggcttgcga 125640
ggcccagggg ttgtgtgtgg ccgcgaaagt ctgtgcgtcc gcttcgcgat ggtcgtagat 125700

-continued ggccttggtg gcggcctccg tgtcgtacgg atcgacggcc agcatgcagg aggcacgccc 125760
gcgcgggttg ttggggatct taaagtaatt aacgtccatc gtcaccggcg taaggattag 125820
ttcgcacgcg gccttttgtc cgtgcaccgt ggcggcggca ttgcgctcgg acatgctgcc 125880
gaacgtcagc atggagatgg tctccgtgtc taacagttgc ggccgttcta cgccggccgc 125940
gtgccggatc cagcggtcca cctcgtcgtg ccggtacacg ttcataggga agacgcgaaa 126000
gaggtcctgc acgcggacgc ccatgtcggt tcgcacgcgg tttacgtagg ctacgcaggt 126060
atttgacgtg taacccagac ccatgtctac ggtgttaatg ttctgcgtga cgtggtacgt 126120
ggtgctgatg tcgcgttcct ccttggtcac gatagggttg ttgatgataa ctgacgtgca 126180
cgatttgccg ctgtagagca gcatgtccac ctcgaaggtg tcggtgcgta cggccgtgag 126240
tgcgaatccc gggtggatgt gcgccttggt ctgcagcacc agtgaaactg gtgagatttt 126300
gtataacatg gcggccagcg tcatgactga gtgcaacacg ttgggacagg tggccgagta 126360
acgcgaaaag ggcgagcgca gccagttgtg gtactcgtgt gcgaaggctg tgggtagcgg 126420
gaaaccaccg tcgtgacggt gatagtgcgg gaactcggtc acgtagcgtt taatgtcgtc 126480
gctcaacgcc gcgcagatgg tggggtttga gtagaaacgg tggaaaggta cgggtaggct 126540
gtactcgatc aacgtcttag gcgccgtcac ggcgcagcag ccattgtaaa gcacgtgctg 126600
acgtgagata aagtccggca ggccctgacg ctgcgcgtgg tccagaggcg cgcgcacttc 126660
gagcaccttg acgtgctcgc ccacgaattg cacggccaaa aacagttcac gacaggcctg 126720
cagcagcggc gtatgcgcgt cggtggcgac gtcctccacc agctcggtca gcatctcgcc 126780
tacggcttga cgttgcgccg ctatcgagtc ttcgggggtg acgccgcttg tgctctcttt 126840
cgacgtcgta cctgatgtgg agaccgcggt ggcggccggc atcaggagaa acgccggtcg 126900
gtaaaagagg tctactagca gcgtcttgag gttgagtccc aggccacagg cccggttgtt 126960
ggtcatggcg ggcatgaggc agagataaaa gaccttttgt aacgtccatt cgtcgtcggt 127020
ggcacggtaa tcgtccacaa acagcggctc gtcggcatcc atggcgccca aacgcggtac 127080
gtccgaaacg ccgtggtgtc gcgcctcgat gttggccggg ttcaacggtt gccggtcggc 127140
cactacctgt acgccttcca tgttacgcgg caggtgcgta acgaaggggg gccacagccg 127200
gtggtcgtgc agcgcgttca cgtaagccga tagcggttcc tcagccagtt gaccgttgtt 127260
aagtcctggc agcgctgaga tgcgcgttac cagacgcagc acggcgacca gattgcggta 127320
gtgaaagagc aactgcggtg gtagggcgcc atcagccagg tgttcggcga tcaacgtcac 127380
cagcgcgtag ctgtgcgcaa aaaccagcag ctgacgtgtg tgaaacatgt tgacgataca 127440
acgtgctacg aaagtgcgga ttagcaaaaa agcgtcgacg ttgccgtgta ccagcacgtc 127500
gaccaggtag cagagctcag ggtaattggg gcttgtcacg gtggttttaa aaagtcgcaa 127560
cgtctcttcg tagtcgggtg gtggccgcag tcgcatgtgt tccatgatct ccaaggtgcg 127620
cagttcgtgg aaggggcccg gtgccagtcc atctggcaaa ttaccgatga cgatacgcgg 127680
tgtacacagc gccaccgttt cgctgttttc ctggcagtgc gtaaagtcga agaaggggtg 127740
cagctcggtg tagagcgtga tgttgcccac cttgtagaag tcggtgacca caaagtcctg 127800
cttcatttcg ttcaccgtgc gcgggacctc gcgtcgtacg cggtaaaaat gcggtatgcg 127860
gcgcgccgca ccgcccatgg gttcctgctg aaaacgacac tcgagcagtc gttgcatggc 127920
gggttccgag ggcggtccgc gttccgtgaa ggtctgtaga cagggcgcgg gctcgtgcag 127980
caccgggtgg cacagcgtct tgagcgcgtc cacaaagtct atcttttgta cggcacggtc 128040
ccggtttagc aggtaggccg tggtgggcaa cgcgttgcga acggtgtcgt taagcttaac 128100
tttgctttcc accgtggtgt aaccgcgatc ctcgggcaga tacagcccta cgggaaagaa 128160
aaacgtcagg tccacgttac gttctagcgg atctttggta tcggtgtttt tgtagacgcg 128220
ccgcaagttt tccataatca ccgtttttttc gcccagtcgg atcacgtcca tgctcagcgg 128280
cgttaagctg tgcgccccgg cctgcgaaag cgagtcgttg ggcaaatgcg gttggcccga 128340
agtcagatga gccttgtacg agttgaaatc ggccaggatc gagtgatagg atatggcggt 128400
gacggcattt tcgggactga gtacaaaatt gccgtaggtg gccggcgccg agaccgtttc 128460
tttggtgatg tggcttgaga gcagcgacat gatgatctgc ataacgttgg ccgtgcttac 128520
catcacgccg ctgatcttgg cccccgagct cgtggtgtac gtggtggggt tgtctaggat 128580
gctatcggtg gccgcttcgg ctagacgcgt gaggaacttg agcacatagt cgcgatcgcg 128640
cgtgcgattc agcaaaaaga gcgtggccag cattttggcc ttgaagctct gcaagatgtt 128700
gcttcgctgg atgcggttca gcgcctgtcg cgccagcgtg gcgttctcta ccagcgtctg 128760
caccacaaag tacggcggcg ccttgcgtag cagtgtctgt aaaaagctgt gaatcaagcc 128820
gcgttccatg gcgtcggccg tgtttttgag cgcgcgcagc accgtgtgca tagcttccac 128880
gttaaggatc ttgtccagga tggtgccttc gaacgtctcg cgcagatacg tgaggcaggc 128940
tgcgctgagc tcaaagggga tggtgatggg ggatttttca ctgtatttgg tgaccataat 129000
ggtggtctga cgactggtag gtaaaccggc gccgctggcc acacgcggca cctgcacgtg 129060
gaacagcatt tttcccgtag tcagtttatt gaggtcgtgg aacttgatgg cgtgcgccgc 129120
cgcggccaag ccgctggtca aaaaataaac ccattccagg cgattgcaga aggtgccgaa 129180
gatggcttcg aagtgaatat tgtaacgctc ggggtcgtcg ccgtagtaga tgcgtaaggc 129240
ctcgaacatc tcctcgccgg cgctggtctt gacgtgcgtc agaaagtcag tgggaatgcc 129300
tactttaggc aggagctcga gcgccgacca gttctccatc gcggcggcgg cgtgagcgcg 129360
aggcgtcgga gctcggggaa agcagcgcga cccggagaat ggccggcgct gcgccgcgcc 129420
gcctcggctg tgacgctcta atagtcgtcg gcggctccgc tacgccgcgc cgggttttac 129480
acgtccccgt gcacgttcgc gcctgcaacc tcacccaaga gctatcgacg ggcgaggacg 129540
cccgcttctg tcgtccgcga cccgttaacg tcgaacgggt gcgcgctgtt tttgcagctc 129600
tctaccgtgc ctgtccggtg cacgtgagga ccgagcccga gcgtgtcaag ctggtactgg 129660
gtcgtctgtt actgggaccc gtggccgtac cctgtttttg cgacggtgaa gtggagggcc 129720
acggtgaaca tttggtgcct acgacgcagt tttgtcgcgg gccgctgctc tacgtgcacc 129780
gacgttgttg ttgcggatcc gtgaccgccg ggcgcgcgtt gtcctaccac gttctcgaaa 129840
accacgtggc cacgcatgtg ctacgcggat tgctctcgct gacggaatgg aatcgagaat 129900
tgccgggcct cttttgcgac tgtcctggcg gcggtggcgc ctcgggaacc gaggaacgct 129960
acgccatggc ctgcctgccg cgcgacctca gcctgcacct ggacgactat ccttacctga 130020
tggtggaaat cggacgcgta ctcagtgtca gtgaggtaga cgactacgta accgccgtct 130080
ccggctacct gggcgaggcc gcggcgccgc gcattcaggt tcactacaag ctgctctttg 130140
gactcaacgt gcgtccgcaa gcgccgtgcg cgttggacgc tacacgcgac ttttttctgc 130200
tggagctgca aaagctttgg ctgggcgttg aatatcacca cgaagtgacg tcggagtttt 130260
tcggtcgcgt gctggctcag ctgcatcgcg accgcgcccg cgtcatgatg gcgcttcgct 130320
tgcccgagca gacggtgtgc cacctgagca ccttcgttct cagtcgcttc aagcgacagg 130380
tactgtattt caagttacag gtgagctacg gcaagtgccg gactggccac gctgacagaa 130440
gtgggggagg gggaaacggt ggaaatcagg gacaccacaa cctactgtgt tatcgacgcc 130500

-continued ttagcgtcac atttgccgac acagacacgg tgtggagaaa ccttttctac gtttattacg 130560
aactagctcg ggatctgggg tcccatggga cagagaaccg acccgtaaac cgcggttacg 130620
gtgtttcttg cgctccgagg acgtcgcggc tatcaccgtc agaatcgacg gtggtttcgg 130680
cgaacggaca cgcgctgtct tccaccgcgc tcccgacgac gagcgcgggt cacaagctgt 130740
cactgccgcg cgacccggcc gccgatcgcg ttcgacgtta cgtgtgcatt atctcgcgtc 130800
tcatgtacgc tcggtacggg gagagatggc gtaaacaccg tcaacggcgg tcggagacgg 130860
gagaagagga ggaggaagag acgctggaat cgggggagac tgacgccacg ccgccatttg 130920
actttacggg gcagcagctg cgccgggcct atcaggaaca ccgacgtcgt aaacatctag 130980
ccgtgcagcg ttacgcgccg tgccgtcgta agctcatcgg cgggatggag tttgccgagg 131040
tgacgggcgt gagtctggac cgcatcgccg tcaacgcttt caacaccaac cgcgttatca 131100
atatgaaggc cgcgctctcg tccatcgccg cgtcgggtct cggcgtgcgc gcgccgcggc 131160
ttcccaagaa catgacccac agttttgtga tgtacaagca cacctttaag gagcccgctt 131220
gcaccgttag cacttttgtt tccaacgacg ccgtctacat caactcgctc aacgtcaata 131280
ttcgcggttc ctatcccgag tttctgtact cgctgggcgt gtatcggctg cacgttaata 131340
tcgatcactt ttttctgccg gccgtggtgt gcaacagcaa ctcctcgctg gacgtgcatg 131400
ggctggagga ccaggcggtg attcgctcgg agcgcagcaa ggtgtactgg accaccaact 131460
ttccgtgcat gatctcgcat actaacaacg tcaacgtggg ctggttcaaa gcggctacgg 131520
ccattgtgcc gcgcgtctcg ggcgctgacc tggaagccat tctgctcaaa gaactctcgt 131580
gcatcaagaa catgcgcgac gtgtgcatcg attacggtct gcaccgcgtt ttcacgcaac 131640
tagagctgcg caattcgtac cagatcccct tcctggccaa gcagttagtg ctgtttctgc 131700
gtgcttgcct gctcaagctg cacggtcgag agaagcggct gcagttggac cgcctagtat 131760
ttgaggcggc acagcggggt ctctttgact acagcaagaa cctcacggcg cacaccaaga 131820
tcaagcacac ttgtgcgctc atcggcagtc gtctagccaa caacgtgccc aagatcctgg 131880
cccggaacaa aaaagtcaaa ttggatcacc tgggccggaa cgccaacgtg ctgacggtgt 131940
gtcggcacgt ggaagcccac aagatccctc gcacgcgcct caaagtgtta gtcgaggtgc 132000
tgggcgcgtt gcagagtatc agcggtacgc cgcacacgcg cgaagtgatc caccagacgt 132060
tgtttcgatt gtgctcggcg gccgcagcca catcgggcct gtgttcatcc cctcccccat 132120
tgtgtgtatc atcgtcttcc tccgtccctt ctgtcccaac ctccgtcagt gttgacggca 132180
gttctgaacc cacgtcgccg cgagcgcggt ttgcatcacg atgatggaag ccgcggccgc 132240
tgccgccgcg gcgtttcgtc cggaggagcg tccgacgccg ggttggcacg acgcggcgtt 132300
gttaatggac gacggtacgg tgcgcgagca cgcgtttcgc aacggaccgc tgtcgcaact 132360
gattcgccgt gtgttaccgc cgccgcccga cgccgaagac gacgtggttt ttgcatccga 132420
gctgtgtttt tattgcagcg gtcgttttaa ccgcaggtcg tcagtcttct ccatctattg 132480
gcagaagcat agcgatctgg tgtacgcgct tacgggcatt acccattgcg ccaagttggt 132540
ggtggaatgc ggtcagttgg ggagcagtag gctacggtgg cgcgacggtg atgcgagtgg 132600
tgaggagcgc cggggagacg acgacagcag ggacgagctg tacgacgtgc cgggcattta 132660
tatgattcgt gtcaacgacg gcggcagcac cggccccaga cacgttattt ggccgggtac 132720
cagcgtgctt tgggcgccgg acgttgtgat cactacggtg cagcgacgaa tctcggcggc 132780
gcgcgccctg gtgaacacgt tccgccaata tttttttttg ctggaacggc gctcgcacga 132840
ggagttggtt ctttgtccgc ccgagatgga ggagcgtcta gcgccgttgt tgcagagtgc 132900
cacgcgcggt gattcggaca tgtttgacgg tgtggtggcc agcgcttatc accgtttgcg 132960
aatgagtaat attccgcgtt catccgcccg gctgctggag cactgcgtgg ggctggcggg 133020
tgctaagaag ctgctcttgc tcgacgtgcc gcgtctggag aactattttc tttgtcaagt 133080
ctgtctttac gagctggacg aggacgagat gggcgaggag atgctgggca tgttggccgg 133140
aaagcccgag gatgccgccg tctcgggcgc aagcggcggt tttctgctac atcgcaagac 133200
gatgaagctg gccgcctgtc tgtgtttgtt gctcaattcg ctgcatttgc accaggaggc 133260
gctggaggcc ttggatcctc cgccgccgcg cgtcgaggag aacgaccttg tcaacgtggt 133320
gctgcgccgt tattatcgca gtcacggcgg cgtgcaggcg cggacgctgg cggcggcccg 133380
ggctttgtta gccgactacg ctgaaacgtt ttcgcctttg ggaagtttta cgcgcctggg 133440
ttacgatcgt ctcgtttctg ccgatgccgg cgtcagtcgc cggcacctgg tggctctgct 133500
gcgtgcctaa ctgaccctga aacggatggc gtgtatatcg tcacacaggt aggtggccat 133560
gatgacggcg atgataagat cgtccgagat acgattctgg cgcttggccg agtagcgtgc 133620
cgtcgtgcct tcggccagcg tgacgcggtg caggttctga atctgctcca gaagatactc 133680
gatggggtcg tggctcagct tgatggtgta ggagacgagc tcttgcgagg ctttgatgta 133740
gcccgagttg aaacgcgaga tgaactgttc cacggccagc gccttgtcgc ggcccatgag 133800
gtagaagggc tgttcgatgt ggttctggtc gggcgtgtgg tagaagagca cgcggatgag 133860
cgtgctgctc tgcacgctct gtcggatgag gcaggcgatg cgcacggccg ccgcctggtt 133920
ggtgttgccc tccacggcga tacgcagttc gtccaggtaa gggtgcaggc tcagcaccga 133980
gatgatcatg tgcgccgcgc actcggcgat ggctacctca gaactctcgg agaggtcgcg 134040
caaaaagaaa tgctctaggc cgtaaatgag aaactggtgt cggtaggcgc ctacggccgc 134100
cacgcccgtg cccgaggcct tgcggttggt ggtgaaggcc gggtccagat acacgtaaag 134160
cgtcttgccg aaataatcgt aggcgttggt gttgagcgtg ctgtaacgca aaatatcgaa 134220
ctcttcgcgg ctctggtccg tgatgagcac ggtgttctgc gagattttat tggtaccgcc 134280
gatgatctcg tccatgaaag cgcccggcat aaacatgttg gccgtcttgc gcacctgcga 134340
gttgaggctg atgaaggtgg gcttgtgcag tcggtagcaa ggacacgccg tggcgtcgcc 134400
cttctccgtg aagctgtgca ggtgctcttc gcacacgtaa gagaccacgt tgagcatgtc 134460
aaagggcgca ttgttgaggc gcgtcaagaa acacgtggcg tcactggtag tgttggtgga 134520
cgatatgaag atgatcttgg tggtattctg ggccaggaac cccagaatgg tgttgaaggc 134580
ctctttcttg atgaagtgcg cctcgtccac cagcagcaag tggaagtttt gtcctcggat 134640
gctctgtgta gagaggaaac agaaaaggga ctcttatgat tacgcacgct cggctggaag 134700
cctacagagt cggggtgggg ccggacaggt gagccaggtg agccgccagg tgaggcggga 134760
tcgccgtgtg ccaaccgggc tgcgacctga aaaccggaac caatccgccg acaccggcgc 134820
cgcgtgacgc gcgcccataa aaacgaaagt gtcgtcgtcg cgacccgcca cagccgccat 134880
gaactcgttg ctggcggaac tcaaccgact gggggtcgcg cacgccacta cggaggatgt 134940
ttttatcttt gtcgaccgcc tctttcaaca cttttccttc cttttccagg ccgaggagtc 135000
aggcccgcgc cgcttggaac tggtcgcgtc cgtgttcgag cacctgacgg tggagtgcgt 135060
caacgacatc ctggacgcct gcagccaccc ggacgtgaac gtcgcggaga caagcaacac 135120
ctgtcgtccc tgcccttctc ctgttccctc cgcccccaaa actgtcagcg acgctcagac 135180
gtcatgtgcg acgcctcggg cgcctgtgac atgaggcacg tccagaacgc gtttaccgag 135240
gagatccagt tacattctct ctacgcgtgc acgcgctgct ttcgcacgca cctgtgtgat 135300
ctgggcagcg gctgcgcgct cgtctccacg ctcgagggct ccgtctgcgt caagacgggc 135360
ctggtatacg aggctctcta tccggtggcg cgtagccacc tgttggaacc catggaggag 135420
gcctcactgg acgacgtcaa catcatcagc gccgtgctca gcggcgtgta cagctacctc 135480
atgacgcacg caggccgtta cgccgacgtg atccaagagg tggtcgagcg cgaccgcctc 135540
aaaaagcagg tggaggacag tatttacttc acctttaata aggttttccg ttctatgcat 135600
aacgtcaacc gtatttcggt gcccgtcatc agccaacttt ttattcagct tatcatcggt 135660
atctactcaa agcagaccaa gtacgacgcg tgtgtcatca aggttagtcg taagaagcgc 135720
gaggacgcgc ttctgaaaca gatgcgttcc gaatatggaa acgcacctgt attcggatct 135780
ggcgtttgaa gcgcggttcg ctgacgatga gcaattgcct ctacacctgg tgctcgacca 135840
ggaggtgctg agtaacgagg aggccgagac gctgcgctac gtctactatc gtaatgtaga 135900
cagcgctggc cgatccgcgg gccgcgctcc gggcggagat gaggacgacg caccggcctc 135960
cgacgacgcc gaggacgccg tgggcggcga tcgcgctttt gaccgcgagc ggcggacttg 136020
gcagcgggcc tgttttcgtg tactaccgcg cccactggag ttgctcgatt acctacgtca 136080
aagcggtctc actgtgacgt tagagaaaga gcagcgcgtg cgcatgttct atgccgtctt 136140
cactacgttg ggtctgcgct gccccgataa tcggctctca ggcgcgcaga cgctacacct 136200
gagactggtc tggcccgacg gcagctatcg tgactgggag tttttagcgc gtgacctgtt 136260
acgagaagaa atggaagcga ataagcgcga ccggcagcac cagttggcca cggccacgaa 136320
tcaccgtcgg cggggcgggc tgcgtaataa cttagacaat gggtcggatc gccgtttgcc 136380
cgaagcggct gtggcttctc tggagacggc cgtcagtact ccattttttg aaattccgaa 136440
cggagcagga acctcctccg cgaacggcgg cggcagattc agtaacctgg agcagcgggt 136500
agcgcgtttg ttgcgcggcg acgaggaatt catctatcac gcgggtccat tggagccgcc 136560
ttccaagata cgcggtcatg agttggtgca gctgcgcctg gacgtaaatc cagacctcat 136620
gtacgccacc gatccgcacg accgcgacga ggtcgcgcgt acggacgagt ggaagggtgc 136680
cggtgtctcg cgtctccgcg aggtctggga tgtgcagcat cgcgtgcgcc tccgtgtgct 136740
gtggtacgtc aattcctttt ggcgcagtcg cgagctgagc tacgatgacc acgaagtcga 136800
actataccgg gcgttggacg cttatcgggc gcgcatcgcc gtcgagtacg tgctgattcg 136860
cgccgtgcgc gacgagatct acgctgtact acgacgggac agcggcgcgt tgccacagcg 136920
tttcgcctgc cacgtgccac ggaacatgtc ctggcgcgtt gtttgggaac tttgccgtca 136980
tgccttggcg ctctggatgg atcgggcgga cgtgcgtagc tgtattatta aggcgctaac 137040
gcctcgtctg agccggggtg ccgccgctgc cgctcagcga gctcgtcgcc agcgcgagcg 137100
ctcggcgccc aaaccgcagg agctgctttt cggaccgcgg aacgagagcg gtccgcccgc 137160
cgaacggact tggtacgctg acgtggtgcg ctgcgttcgc gcgcaagtgg atttgggcgt 137220
ggaagtgtgc gcggcgcgtt gtcctcgcac cgggctttgg atcgtccgta atcgccgcgg 137280
acgcctgcga cgttggctct cgcagcccga ggtgtgcgtg ctctacgtca cgccagactt 137340
ggacttttac tgggtgctgc cgggcggctt tgccgtctct tcgcgcgtca ctcttcatgg 137400
cttggcgcag cgggctttgc gagaccgatt ccagaacttt gaagcagttc ttgcaagagg 137460
aatgcatgtg gaagctggtc ggcaagagcc ggaaacaccg cgagtatcgg gccgtcgctt 137520
gccgttcgac gatctttagt ccggaggacg acggctcgtg tatcttgtgc caattgctgt 137580
tgctctatcg cgacggcgaa tggatcctct gtctttgctg caacggccgt tatcaaggcc 137640
actatggcgt gggccacgta catcggcgtc gtcgacgcat ctgtcattta cctaccttgt 137700
accaactgag cttcggaggt cctttgggtc cagccagcat tgatttcttg ccaagcttta 137760
gccaggtgac cagcagtatg acgtgcgatg gtattacgcc cgacgtgatt tacgaggtct 137820
gcatgttggt gccccaggat gaagccaagc gcatcctggt caagggtcac ggtgccatgg 137880
acctgacctg tcagaaggca gtgacgctag gcggcgccgg cgcctggttg ctgccgcgtc 137940
ccgaaggcta cacgcttttc ttttacattc tgtgctacga cctgtttacc tcatgcggca 138000
accggtgcga tatcccttcc atgacgcgcc tcatggcggc ggccacggcc tgcgggcagg 138060
cgggttgcag cttttgcacg gatcacgagg gacatgtaga tcccactggc aattacgtgg 138120
gttgcacccc cgatatgggc cgctgtcttt gttacgtgcc ctgtgggccc atgacgcagt 138180
cgctcatcca caacgaggaa cccgcgactt ttttctgtga gagcgatgac gccaagtacc 138240
tatgcgccgt aggttctaag accgcggcgc aggtcacact gggagacggc ctggattatc 138300
acatcggtgt caaggattct gagggccgat ggttgcccgt caagaccgat gtgtgggacc 138360
tggtcaaggt agaggaacct gtgtcacgta tgatagtgtg ttcctgtccg gtgcttaaga 138420
acctagtgca ctaacggggt ctgacagttc acggggagaa gaaacaagaa ataacaaaaa 138480
aaaagaggac atggactcgc cacggtttgt ggcaaggcgt gtgttatcat catggagcta 138540
ctcacgttgg tgttgtagca actggcaaaa agcgccgtgc tcttggcgcc gcggtggtcg 138600
atgctgatca cgttgtcctt gttctcgacc acgtagtcgc gcgcgaaggt gtggcggcag 138660
cggaactcga cctctttgag cacaaactgc gacacgtgct tttggtgcgc cacgtagccg 138720
atgctgatgc cgatcatgtg cttaagcaga aacgagataa tggggatgat gaaccaagtc 138780
ttgccgtgac gtcgcggcac caggaacacg gtggctttct gcttaaagat gtcgatggag 138840
gtctgcgaga ggaagtcgat ctggaaggcg tggatgaggt actgcagcac gcgattggcc 138900
agcacgggga tcttggtcac ggctataaaa aagatgacgt gtatcaataa attcttttga 138960
aacggttcga gtcggatggc ttttgcgtcg ccctcgacgg cggtactgaa gccgccgtcg 139020
agccactttt taaagtcggt catgaagttg ttgatctgct gaaactgcgg atcgcggtag 139080
agctcggtca acgcgtccag cttctggtag gaggcgcgct gctcctcgga gcacgggcga 139140
aacgtcagtt catcgagcgc actcttgagg cgctcgtgaa acagcagctc gcgctggctt 139200
tcctcgggcg agttgtagtc gcggtggcgg ccgcagaagg ccatgagcgg caggaaggcc 139260
tcgttgcacg agtgggccag cccgagttcg ggtgcatca tctggtagcg cttgcggcac 139320
agcgccgcca cattggtgaa ggccgtggag atgcaggagg tggggtggct cttgcgcttc 139380
tgcagctccg cgtagcgctc ctggatcttg gcggccgaat ctccgcgcaa catgatggcg 139440
gcggcggtgg tgcgagcgga ggttaggcgg cagcggcgag aggagaggaa aaagatggcg 139500
tccgcgagga cgacggagga tccacccgaa aaccacgttg tcgcggacgt ggcttgtggg 139560
acgggcgccg tcactcgttc gtcttcgtcg tccctagtgg tgtcgtcttc ctcggcgtca 139620
ggctcagacg aatcttcctc cgcctctcct ctcagtttcc ccgtctcctc cccctcaact 139680
gccgtcaggt ctccggggtc cgccggggtt tcaacgtccc tgtgctcggt ggaacggatg 139740
gtcgagctgt cggcgcagtc tccggccgcc gatttctcgg tctccgaggc ttggcgcttc 139800
gaggaggccg taaatatggc gctggtggcc tgcgaggccg tgtcacctta cgatcgcttt 139860
cgcctaattg aaacgcccga cgagaatttc ttgttggtca ccaacgtaat tccgcgcgag 139920
tcggccgagg tgccggtgtt ggatagcagt agcagcggtg gcgatagcgg gccggaggat 139980
aaaaagaaaa acgtcgggaa taaaaccgcg ggggaaaaga acggcggtgg gtctcgggcc 140040
aaacgccgtc gtagacgacg cgctccgaaa aacgacgccg ccacgccgtc ttttctacgt 140100

-continued cgacacgacg tgctggagcg tttcgcggcc gcggctgagc ctttgccgtc gctttgtgtg 140160
cgtgattatg cgttacgcaa tgctgaccgt gttacctacg acggcgaatt aatctacggc 140220
agttacctgt tgtatcgcaa ggctcacgtg gagctgtcac tctccagcaa caaggtgcaa 140280
cacgtggaag ccgtgctgcg acaggtgtac acgccgggct tgttagatca tcacaacgtg 140340
tgcgacgtgg aggccctgct gtggctgctg tactgtggac cgcgcagctt ttgcgcgcgt 140400
gacacctgtt tcggtcgcga aaagaacggt tgtcctttcc ccgcgttgtt gcccaaactc 140460
ttttacgaac ccgtgcggga ctatatgacc tacatgaatc tggctgagct gtacgtcttt 140520
gtttggtatc gcggctacga attccctgcg ccgacgccgc aggcgacgac ggcgggtggt 140580
ggtggtagtg gtggcggcgg ggccggcgct tgtgcggtcg agacgagcgc gtcagcaggc 140640
cgggtcgatg acgccggcga cgaggtgcat ttgcctttaa agcccgtctc gctggaccgt 140700
ctcagagagg tgttacaggc ggtgcgcggc cgcttctcgg ggcgcgaggt gcccgcctgg 140760
ccggcctcgt cgcgcacctg tttgttgtgc gcgctctaca gtcagaaccg tctctgttta 140820
gatctcgcgc gtgacgaggc gcggaccgtg agttatagcc ccatcgttat ccaagactgc 140880
gccgcggctg tcaccgacgt cactttgagc cacatcttgc ccggccagag caccgtctcg 140940
cttttccccg tctaccacgt cggcaagttg ctggacgctc tctcgctgaa cgacgcgggt 141000
ctcatcacgt tgaatctatg acgtcggtca acaaacagct cttaaaggac gtgatgcgcg 141060
tcgaccttga gcgacagcag catcagtttc tgcggcgtac ctacggaccg cagcaccggc 141120
tcaccacgca gcaggctttg acggtgatgc gtgtggccgc tcgggagcag acccgataca 141180
gtcagcgaac gacgcagtgc gtggccgcac acctgttgga gcaacgggcg gccgtgcagc 141240
aagagttgca acgcgcccga cagctgcaat ccggtaacgt ggacgacgcg ctggactctt 141300
taaccgagct gaaggacacg gtagacgacg tgagagccac cttggtggac tcggtttcgg 141360
cgacgtgcga tttggacctg gaggtcgacg acgccgtcta acaggtatag caatccccgt 141420
cacgcctctg ttcagatttt attaaaaaaa aaacacaaca taacgacagt gtcggtgtgg 141480
tagctagtgc agccctagga acagggaaga ctgtcgccac tatgtcctcc gcgcttcggt 141540
ctcgggctcg ctcggcctcg ctcggaacga cgactcaggg ctgggatccg ccgccattgc 141600
gtcgtcccag cagggcgcgc cggcgccagt ggatgcgcga agctgcgcag gccgccgctc 141660
aagccgcggt acaggccgcg caggccgccg ccgctcaagt tgcccaggct cacgtcgatg 141720
aagacgaggt cgtggatctg atggccgacg aggccggcgg cggcgtcacc actttgacca 141780
ccctgagttc cgtcagcaca accaccgtgc ttggacacgc gactttttcc gcatgcgttc 141840
gaagtgacgt gatgcgtgac ggagaaaaag aggacgcggc ttcggacaag gagaacctgc 141900
gtcggcccgt ggtgccgtcc acgtcgtctc gcggcagcgc cgccagcggc gacggttacc 141960
acggcttgcg ctgccgcgaa acctcggcca tgtggtcgtt cgagtacgat cgcgacggcg 142020
acgtgaccag cgtacgccgt gctctcttca ccggcggcag cgacccctcg gacagcgtga 142080
gcggcgtccg cggtggacgc aactggcgtt tgcgtccgcc gttggtgtcg ctggctcgca 142140
ccccgctgtg ccgacgtcgt gtgggcggcg tggacgcggt gctcgaagaa aacgacgtgg 142200
agctgcgcgc ggaaagtcag gacaacgccg tggcatcggg cccgggccgc gttccgcagc 142260
cgctcagcgg tagttccggg gaggaatccg ccacgacggt ggaggccgac tccacgtcac 142320
acgacgacgt gcattgcacc tgttccaatg accagatcat caccacgtcc atccgcggcc 142380
ttacgtgcga cccgcgcatg ttcttgcgcc ttacacatcc cgagctctgc gagctctcta 142440
tctcctacct gctggtctac gtgcccaaag aggacgattt ttgccacaag atctgttatg 142500

-continued ccgtggacat gagcgacgag agctaccgcc tgggccaggg ctccttcggc gaggtctggc 142560
cgctcgatcg ctatcgcgtg gtcaaggtgg cgcgtaagca cagcgagacg gtgctcacgg 142620
tctggatgtc gggcctgatc cgcacgcgcg ccgctggcga gcaacagcag ccgccgtcgc 142680
tggtgggcac gggcgtgcac cgcggtctgc tcacggccac gggctgctgt ctgctgcaca 142740
acgtcacggt acatcgacgt ttccacacag acatgtttca tcacgaccag tggaagctgg 142800
cgtgcatcga cagctaccga cgtgcctttt gcacgttggc cgacgctatc aaatttctca 142860
atcaccagtg tcgtgtatgc cactttgaca ttacacccat gaacgtgctc atcgacgtga 142920
acccgcacaa ccccagcgag atcgtgcgcg ccgcgctgtg cgattacagc ctcagcgagc 142980
cctatccgga ttacaacgag cgctgtgtgg ccgtctttca ggagacgggc acggcgcgcc 143040
gcatccccaa ctgctcgcac cgtctgcgcg aatgttacca ccctgctttc cgacctatgc 143100
cgctgcagaa gctgctcatc tgcgacccgc acgcgcgttt ccccgtagcc ggcctacggc 143160
gttattgcat gtcggagctg tcggcgctgg gtaacgtgct gggcttttgc ctcatgcggc 143220
tgttggaccg gcgcggtctg gacgaggtgc gcatgggcac ggaggcgttg ctctttaagc 143280
acgccggcgc ggcctgccgc gcgttggaga acggcaagct cacgcactgc tccgaggcct 143340
gtctgctcat tctggcggcg caaatgagct acggcgcctg tcttctgggc gagcatggcg 143400
ccgcgctggt gtcgcacacg ctgcgctttg tggaggccaa gatgtcctcg tgtcgcgtac 143460
gcgcctttcg ccgcttctac cacgaatgct cgcagaccat gctgcacgaa tacgtcagaa 143520
agaacgtgga gcgtctgttg gccacgagcg acgggctgta tttatataac gcctttcggc 143580
gcaccaccag cataatctgc gaggaggacc ttgacggtga ctgccgccaa ctgttccccg 143640
agtaaccggg acgcggaacg tgacggttgc tgaggggaaa ggcgacagag aaggtacaaa 143700
cccaccggcg gggaaaatac cgaggcgccg ccatcatcat gtggggcgtc tcgagtttgg 143760
actacgacga cgatgaggag ctcacccggc tgctggcggt ttgggacgat gagcccctca 143820
gtctctttct catgaacacc tttttgctgc accaggaggg cttccgtaat ctgcccttta 143880
cggtgctgcg tctgtcttac gcctaccgca tcttcgccaa gatgctgcgg gcccacggta 143940
cgccagtagc cgaggacttt atgatgcgcg tggccgcgct ggctcgcgac gagggtctgc 144000
gcgacatttt gggtcagcgg cacgccgccg aagcctcgcg cgccgagatc gccgaggccc 144060
tggagcgcgt ggccgagcgg tgcgacgacc ggcacggcgg ctcggacgac tacgtgtggc 144120
tcagccggtt gctggatttg gcgcccaact atcggcaggt cgagctcttc cagttgctgg 144180
aaaaggaatc gcgcggacag tcgcgcaact cggtgtggca tctgttgcgt atggatacgg 144240
tctcggccac caagttctac gaggccttcg tcagcggctg tctgcccgcc gccgcggcgg 144300
cggacggttc gggtggcggc ggctcgcact acacgggctc gcgcgccggc gtctcgccgg 144360
gcatccagtt cggtatcaaa cacgagggct tagtcaaaac gctggtggaa tgttacgtga 144420
tgcacggacg cgagccggtg cgcgacggcc tcggtctgct catcgacccc acgtcggggc 144480
tgctgggcgc ttccatggac ctgtgcttcg gcgtgctcaa gcagggcagc ggtcgcacct 144540
tgctggtgga accgtgcgcg cgtgtctacg agatcaagtg ccgctacaaa tatttgcgca 144600
aaaaggagga cccctttgtg cagaacgtgc tgcggaggca cgacgcggcg gccgtggcct 144660
cgctgttgca gtcacacccg gtgccgggcg tggagtttcg cggtgaacgc gagaccccgt 144720
cggcacgcga gtttctgctt tcgcacgacg cggcgctctt cagggccacg ctcaagcgcg 144780
cgcgcccgct caaaccgccc gaaccgctgc gcgagtacct ggccgatctg ctgtatctca 144840
ataaggccga gtgttcggaa gtgattgtgt ttgacgccaa gcacctgaat gacgacaaca 144900
gcgacgggga cgccacgacc actattaacg cgagtctcga cctagccgcg ggcgacgccg 144960
ctggcggcgg cgctgatcac cacctgcggg gcagcccggg cgattcgccg ccgccgatac 145020
ctttcgagga cgaaaacacg cccgagctgc tgggccggct taacgtgtac gaggtagcgc 145080
gcttttcact gccggctttt gtcaatccgc gtcaccagta ttactttcag atgctcattc 145140
agcagtacgt gctcagccaa tactatataa agaagcatcc ggacccggag cggatcgatt 145200
tccgcgacct gcctaccgtc tacctggtct cggccatctt ccgcgagcgc gaggaaagcg 145260
aactgggctg cgagttgctg gccggcggtc gcgttttcca ctgcgaccac atcccgctcc 145320
tgctcatcgt cacgcccgtg gtctttgacc ctcagtttac gcgccatgcc gtctctaccg 145380
tgctagaccg ttggagtcgc gacctgtccc gcaagacgaa cctaccgata tgggtgccga 145440
actctgcaaa cgaatatgtt gtgagttcgg taccacgccc ggtgagcccc tgaaagatgc 145500
tctgggtcgc caggtgtctc tacgctccta cgacaacatc cctccgactt cctcctcgga 145560
cgaaggggag gacgatgacg acggggagga tgacgataac gaggagcggc aacagaagct 145620
gcggctctgc ggtagtggct gcgggggaaa cgacagtagt agcggcagcc accgcgaggc 145680
cacccacgac ggctccaaga aaaacgcggt gcgctcgacg tttcgcgagg acaaggctcc 145740
gaaaccgagc aagcagtcaa aaaagaaaaa gaagaaaccc tcaaaacatc accaccatca 145800
gcaaagctcc attatgcagg agacggacga cctagacgaa gaggacacct caatttacct 145860
gtccccgccc ccggtccccc ccgtccaggt ggtggctaag cgactgccgc ggcccgacac 145920
acccaggact ccgcgccaaa agaagatttc acaacgtcca cccacccccg ggacaaaaaa 145980
gcccgccgcc cccttgccct tttaattcat aaactttcag gtctcgcgta cgattcgcga 146040
gtcgggaatg ggacacccgt gggtgtttct ccgtgtgtat attattattt tttttgtgtg 146100
tgtttgcgcc cccgtgtgtc taatgtgctg tttgaaacac gtaaagtagc tggtggaaga 146160
acagataaac ctttaataaa aaaaaaagta tgtgctcccg acccacggtc tgcgtgtctc 146220
ttttttatgt ccatgtctcc aagtctggtg cgggtggcgg cggggtcaag cgtcctcgaa 146280
gtcttcatca tcgtcgtcgt cctcttcttc gcgaaggcga cggctttcca agctgtcgtg 146340
gtgactgagc gcagcgactt cttcgccgga ggctgtggcc agcgcctggt acttgacact 146400
gccgctaccg cgtccgcgaa agtagcggac ggcgcgacac gtcgtaaaca tggcccatat 146460
gaaaaagagc atgccgaacg accagctgat gccggtgcgg tattcgttgc tgaggaaggt 146520
atcgtactgc acgatggggt agatgaggcc gcagagtcca aagaaggcgc ccaggtggta 146580
gccgaattgc accttgacgt attgaaaaaa gacggcctcg attagtaaaa agtagatgat 146640
ggagatgata gcgtagacca cgaagacggc taacaccatg tggcctgtac gcacgaaaaa 146700
gttgtttccg aagccgtagc acagggccat ggctaccacg gtggtgttga aaccaagcgc 146760
tacctccacc aggttgacga tgagcgtgcg gaactgcacc gtacctttga gcttggggtg 146820
cagacgcgag aagaaaaaga gtgagcgttt gtagctgcgg tactgcgtga ccatgctcac 146880
gttgaaaatg gtcaggcaga aaaagtgcac ggcggccatg aaggcgatca tgctgggcag 146940
ccgaaatgac atggtcagtg tgaatagttg gaacgtgtcc atgctgagaa tgaagaggaa 147000
ggctgtgagg ctgtcgccca tgtacgaaat gtcgcgtgtc gactggttta ggctcatgcc 147060
tttgtccttg cgcatgctga tcttgatcca gcataccagg tagtagatgg tcacggctaa 147120
aaagacgagc tgcatgaaca cggcgtagca caccaactgc accgagtcta agaagagcat 147180
aggcgtgtgc aggtgcatta cgttgtaggc cgacatgttg agcctttcaa agtccacgac 147240
gtgatagtag acgcaggggt agcccaggtg cggaaaattg ctcagcacca gatgcacgct 147300

-continued gacgttgaca aaagtcagca ccatgaaaac gatagaagcg ctccatgtcc gtgtattcac 147360
cttatccacg tgcgaggggg ccatggcgat agcggcggcc cgctcgctcg ggaggcgatg 147420
ggggcgcgcc gatgacgaca ggctcgcggg tcgttaaata ctacgatggg agccgccgcg 147480
gctcacgacg cggtttgagc acgtccgggc ggtcggtgaa aaaagacccc gcgggccttc 147540
gcgactctct tctgtccgag gatgaccgct cagccgccgc tgcaccaccg ccaccacccg 147600
tacaccctgt tcgggaccag ctgtcatctc agctggtacg gccttctgga ggcctcggtg 147660
cctatcgtac aatgtctgtt tttggatctg ggtggcggcc gtgccgagcc gcggcttcac 147720
acgttcgtgg tgcgcggtga ccgtctgccg ccggctgagg tgcgtgctgt gcatcgcgcc 147780
agctacgccg cgctggcttc ggccgtgact acggacgccg acgagcgccg gcgcggccta 147840
gagcagcgta gcgccgtgtt ggcgcgcgtg ttgctagaag gcagcgcgtt aatccgcgtg 147900
ttggcgcgca ccttcacgcc ggtgcagatt cagacggacg ctagcggcgt ggagattttg 147960
gaggccgcac cggcactggg cgtggaaacc gcagcgctgt cgaacgcgct tagtcttttc 148020
cacgtagcca agctagtggt catcggctcg tatcccgaag tgcacgagcc gcgtgtggtc 148080
acgcatgccg cggaacgcgt ctccgaagag tatggcaccc acgcgcacaa aaaattgcgt 148140
cgcggttact acgcctacga tttggccatg tcgtttcgcg tcggcactca caagtatgtg 148200
ctggagcgcg acgacgaggc cgttctggca cgcctctttg aggtgcgcga ggtgtgtttt 148260
ttgcgcacct gtctgcgtct ggtcacgcct gtcggtttcg tcgccgtggc agtgaccgac 148320
gagcagtgtt gtttattgct gcagtcggcc tggactcacc tttacgacgt gcttttccgt 148380
ggtttcgctg ggcagccgcc gctacgcgac tacctggggc cggacctttt tgagacgggc 148440
ggcgcccgtt ctttcttttt tcccggtttc ccgcccgtgc ccgtctacgc ggtccacggt 148500
ctgcacacgt taatgcgcga gacggcgttg gacgcggcgg ctgaggtgct ctcgtggtgc 148560
ggcctgcccg acatcgtggg ctcggccggc aagctggagg tggaaccctg cgcgctctcg 148620
ctcggcgtgc ccgaggatga gtggcaggtc ttcggcaccg aggccggcgg cggcgccgtg 148680
cgtctcaatg ccacggcttt tcgcgagcga ccggccggcg gcgatcgtcg ctggctgttg 148740
ccgccgctgc cgcgtgacga cggcgacggt gaaaacaacg tcgtggaagt cagcagcagc 148800
accggcggtg cgcacccgcc gagcgacgac gccactttca ccgtgcacgt tcgcgacgcc 148860
acgctacatc gagtgctcat cgtggatttg gtcgagcgcg tgctggccaa gtgtgtacgc 148920
gcgcgcgact tcaatcccta cgtgcgttat agtcatcgac tccacactta tgcggtttgt 148980
gaaaagttta ttgaaaatct gcgttttcgc tcgcgacgcg ccttctggca gatccagagt 149040
ctgctgggct acatctccga gcacgttacg tcagcctgcg cttcggccgg cctttgtgg 149100
gttctgtcgc gcggacaccg cgagttttat gtctacgacg gctattcggg tcacggaccc 149160
gtctcggccg aagtgtgcgt gcggactgtg gtcgactgtt attggcgcaa actttttggc 149220
ggcgacgatc cgggtcccac ctgtcgtgtt caagagagcg cgcccggcgt gctgttggtc 149280
tggggcgacg agcggttggt gggtcccttc aacttcttct acggcaacgg cggcgccggt 149340
ggtagtccgc tccacggggt ggtgggtggt ttcgcggcgg gacattgtgg cggcgcttgt 149400
tgcgcgggct gcgtcgtcac tcaccgccat tctagcggcg gcggcggtag tggcgtgggc 149460
gacgcggacc acgcgagtgg cggcggtcta gatgccgctg ccgggagtgg tcataacggc 149520
ggtagtgatc gggtttctcc ctccacgccg cccgcggcgt tgggtggttg ttgctgcgcg 149580
gccggtggcg actggctctc ggccgtgggt catgtcctgg gccggctgcc ggcgctgtta 149640
cgagagcgcg tgagcgtgtc cgagctggaa gccgtgtacc gcgagatcct ctttcgcttc 149700
gtggctcgcc gcaacgacgt ggacttttgg ttactgcgct tccagcccgg tgaaaacgaa 149760
gtaaggccgc acgccggggt gattgactgc gcgcccttcc acggcgtgtg ggccgagcag 149820
ggccagatca tcgtacagtc acgcgatacg gcgttagcgg ccgatatcgg ctacggcgtc 149880
tatgtggaca aggcttttgc catgctcacg gcttgcgtgg aggtctgggc gcgagagtta 149940
ttgtcgtcct ccaccgcttc caccaccgct tgttcttctt cttccgttct ctcctccgcc 150000
ttgccgtccg tcacttcgtc ttcttcgggc acggcgacgg tgtctcctcc gtcttgttct 150060
tcttcgtcgg cgacttggct cgaggagcgc gacgagtggg tgcgtttgct ggcggttgac 150120
gcgcaacacg ctgctaagcg agtggcttcc gagggcctgc ggtttttccg gctcaacgct 150180
taacgagtca cgtaggggaa ctacgtgggt aagtgacgtg gatactagta aaaaaaagtg 150240
cgtcaaagtt ctcagcgtgt gacgtggata ctagtaaaag ggacgtcaaa gctcactacg 150300
tgttgcgtgt tttttttct atgatatgcg tgtctagttc gcttctcact cttcctctcc 150360
ccgttcccag cgcggtggca gcttgggggg tgagggcaaa ttggggtagt tggcgttgag 150420
cacgtctagc aggcccaggc ccacgggcca accgtccacg gtcttacgct cggtcagctt 150480
gaggctaaac gagtgtgcct cgtcttgacc ggtaaggcgg aaaaagaagc gtgctaccag 150540
ctgcaggcag gtatgccgcg tctgctggaa gagcacgaag gtagcgggca cgtactgcac 150600
aatgtgcggc tctttttcct caaagagcag gtagagcgcg ctgcagatca gccgccgggc 150660
gctgtggtgc agcagccggc cgaagctttc gcgcacgttc accgcgtcca ggtactggag 150720
caggtcgtgc aggcacttgc gcgttaagtt gcaattttcc acgcatgaaa taacggtaca 150780
gagcgcgaag tgcagcaagt tgtcggcctt gacgatgccg cagcggtgtt tgagccgtag 150840
atccgagagc ctcacctgcg tgacggcgtc ttcggtctcg agcaaaaaca cggcggagta 150900
gcccagaaag gccgaggtgc acagcaactc gctgcggtac tcggccatgg aaaccagcag 150960
cccgtgctcc gtgtgcagcc acagcttgtc gccgcgcacc gtaaagtcga gcacttgcgg 151020
ctccatgatc atcacattct gtctagtgaa atccgtatgg acctccagca cgccgcggat 151080
catcagggcc tccatttcga aatcggccga cacgctctgg gccgcgccgc tcctcgtctg 151140
ccgtgatcaa gcggcgcggc gcggaccttt caagcgttcc tgggccgccg ctcgaggcag 151200
ttcccctttc tggcactccg cccgccgctt cgcggctcat ttggcgccgg cgcgccttct 151260
cgcggctgca aatcagctcc acgtatcggc aaaacttgct gtcgtcgtag gcggcggcca 151320
cgatctcgcc gaaggagagc tgcaggtagg cctcgggtac ggggtccagc gtgcccagcg 151380
ccaggatgtg acacagatag ggcagggtta cgcgctctac cgtgtaattg gagtagacga 151440
tggcctcttc ggcccccctga tgcgtgacca gacgccgcag gcgaaaggtg cggaaatact 151500
cgttttccca cagctgcgtg aggaagcgtt ctagcgactc ggtgccgggc acgaactgcg 151560
aaaagaagct gttggccacc aggcggttgt cttccaccgc cagcggacgg aagggcgccg 151620
cgtcgcgcgc cttgcgcacg gcctccaaca cgggcaggtg gtacagttcg gcgtcgcgcg 151680
cgcccaggct catggagtcc tcgcgccgcg aggcgtagcg tgtgagcagg tcgcgcagtt 151740
cgcgcacgcg attctcccag gtctggttaa gcgtgcgcag gtcctggatc tcgtccacct 151800
gcgactggat ctgctcctcc aggcacttga tgacctgctt cttaaacagg tcgcggatgt 151860
cccgctcggg cgccgccggg ccgggtggcg gcggcagcag cccgacgtgg cccgcgggtc 151920
ctcccaccac ggcgccgccg ggtcccacca cgccggttcc acccggacca cgcgcgggta 151980
gtagacggtt ttggtccacc agcgaggggg tcaggtcctg cagaaaggac tcgacgctgt 152040
cctcgatgcc gatgcgcgat ttgctgtccg agacgttaag caaaaacttc atgatggact 152100

-continued

```
ttttggcgtc gctgcctcgg tcgtgctgct ccatcatctc caccagcttc ttgcagttga 152160
gctcgtggcg gctggcggtc accactttca caggaaaggt attgagcaac tggcagatct 152220
tttggtggcg gcagagcccg tcgtagcgca gaatctcctc gtgcaggtgt gccaccggcg 152280
tggtgaacag cagcttgtcg cgctcataag ccagcggttc ggtcgccacg tacaagcgga 152340
tgtgcttgcc gcgcagctgc gcctccagcc gctccgagcg caccttcttg aagacgcgta 152400
cctcgggcgc gttggctacg cgcacggcgc ccaggcgctc ggccacctgc agcagcagcg 152460
ccaggttagc ctgcagcagg tcctgcgcca gcgggtgtgt ctcggtggcc cgctgcacgg 152520
ccgcgcgtac aaattgcgcc cgctcggccg cctcgctcgg cttggtcttc acgtccagca 152580
gcggtaccag tcccaccgtt acgcaccaat ccacgtagag accatagtcg tcgttatcgg 152640
cgtactgata taaaatgtcg cggagcgcgc ccagcacgcc cgtttgcacg ctctggcgca 152700
acgaggcgct ccacaccaac agatactgct ccaggtcctc ttcgtccagc gcgcggtagg 152760
gaaacagcgc cgcgtgcaac ttccactcct cggccacgcg ccgcaccgtg atggtgtcaa 152820
agagcgtctt gcacactccg tagagcagct gcttgcgcag cacgcacggg tcgcgcagca 152880
cctggtgcat gctttggccg cgacacgtcc ccagaaagcc gtgcagcaac cgcaggaagc 152940
tcatcgtctg gcccgtgggg aaaatgtcga tgacggcctc gtcatccacg ccgcggccca 153000
cgcccaagta cgacgacgct ttgatcctca acctctcgtc ggccgccaag atcgaacgga 153060
tcgtcgacaa ggtcaagtcc ctctcgcgcg agcgctttgc gcccgaggat ttttcgttcc 153120
agtggtttcg ctccatcagt cgcgttgaac gaacgacaga tagcaacccc tctgccgcaa 153180
ctaccgccgc ggcaacgacg accgttcact cctccgcctc ctcttctgcc gccgctgccg 153240
cttcgtccga ggccggcggc acgcgcgtgc cctgcgtcga ccgttggccc ttctttccct 153300
tccgcgcgct gctcgtcacc ggcacggcgg gcgccggcaa gacttccagc atccaggtgc 153360
tggcggccaa tctagattgc gtgatcaccg gtaccacggt gatcgccgcg cagaacctca 153420
gcgcgatcct caaccgcact cgctcggcgc aggtcaagac catctaccgc gtcttcggct 153480
tcgtcagcaa acacgtgccg ctggctgata gcgccgttag ccacgagacg ctggaacgct 153540
accgcgtgtg cgagccgcac gaggagacca ccatccagcg cctgcagatc aacgatctgc 153600
tcgcctactg gccagtcatc gccgacatcg tggacaaatg cttaaatatg tgggagcgca 153660
aggccgcttc ggcctccgcc gcggccgcgg ccgccgcctg cgaggacctc tcggagctgt 153720
gcgagagcaa tatcatcgtc atcgacgagt gcggccttat gctgcgctac atgctgcagg 153780
tggtggtgtt tttttactac ttttacaacg ccctgggcga cacgcgactt taccgcgaac 153840
gccgcgtgcc ctgcatcatc tgcgtcggtt cgcccacgca gaccgaggcg ctggagagcc 153900
gctacgacca ctacacgcaa aacaagagcg tgcgcaaggg cgttgacgtg ctctcggcgc 153960
tgattcagaa cgaggtgctc atcaactact gcgacatcgc cgacaactgg gtcatgttta 154020
ttcacaacaa gcgttgcacc gacctggact ttggcgacct gctcaagtac atggagttcg 154080
gtatcccgct caaggaggag cacgtggcct acgtggaccg cttcgtgcgg ccgcccagct 154140
ccatccgcaa cccctcgtac gccgccgaga tgacgcggct tttctctcg cacgtcgagg 154200
tgcaggctta cttcaagcgg ctgcacgagc agatccgcct gagcgagcgc caccgtctct 154260
ttgatctgcc cgtctactgc gtggtcaaca accgcgcgta ccaggagctc tgcgagctgg 154320
ccgacccgct gggcgactcg ccgcagcccg tcgagctctg gttccgccag aacttggcgc 154380
gcatcattaa ctactcgcag tttgtcgacc acaacctctc cagcgagatc accaaggagg 154440
cgctgcgccc cgcggccgac gtcgttgcca ccaacaactc ctccgtccag gctcacggag 154500
```

ggggaggatc tgtaatcggg agcaccggcg gcaacgacga gacggcgttt ttccaggacg 154560
atgataccac caccgcgccc gatagccgtg agacgctgct caccttgcgc attacctaca 154620
tcaagggcag ttcggtggga gtcaactcta aggtgcgggc ctgtgttatc ggataccagg 154680
gcacggtcga acgtttcgtg gacatcttgc aaaaggacac gtttatcgaa cgcacgccct 154740
gcgagcaggc ggcctacgcc tactcgttag tttcaggcct gctcttctcg gccatgtact 154800
acttttacgt gtcgccctac acgaccgagg agatgttgcg tgagctggcg cgcgttgagc 154860
tgcccgacgt gagttcgctc tgcgccgctg ccgccgccac ggccgccgct cccgcttgga 154920
gcgggggaga gaatccgata aataatcacg tcgacgcgga ttcttctcag ggcggccaga 154980
gcgtgccggt atctcaacgg atggaacatg gccaagagga gacccacgac atcccctgcc 155040
tgtccaacca ccatgacgac tcggacgcca tcacggacgc cgaactcatg gatcacacca 155100
gtctgtacgc ggatcccttt tttctcaaat acgtcaagcc acctagcctg gcgctgcttt 155160
ctttcgagga gacggtgcac atgtacacta ccttccgcga catttttctc aagcgctacc 155220
agctcatgca gcgtctcacg ggcggtcgct tcgccacgtt gccgctcgtt acctacaatc 155280
gccgtaacgt ggtgttcaag gccaactgtc agatcagctc gcaaaccggc tccttcgtgg 155340
gcatgctttc gcatgtgtcg ccggcgcaga cgtacacgct cgagggctac accagcgaca 155400
acgtgctcag tctgcccagt gaccgccacc gcatccaccc cgaggtggtg cagcgcggcc 155460
tttcgcggct ggtgctacgc gatgcgcttg ggttcctctt tgtgctcgac gttaacgtct 155520
cgcgcttcgt cgagtcggcg cagggcaaga gtctgcacgt gtgcaccacc gtggactacg 155580
gcctcacttc gcgcacggcc atgaccatcg ccaagagtca gggcctgtcg ctcgagaagg 155640
tggccgtgga ctttggggac catcccaaga acctcaagat gagccacatc tacgtggcca 155700
tgtcgcgagt cacggacccc gagcacctca tgatgaacgt caacccgttg cgactgccct 155760
atgagaagaa caccgctatc accccctata tctgtcgcgc gctcaaagac aaacgcacca 155820
cgcttatttt ttgacacaac accgtgtaag gaaaacgtga ctttattgag cagggtaaaa 155880
accacgtaca agaaccacgt tgtctatccc caaaaaaaca cacaccgtca gggaacacat 155940
cgcctataga tagcggcact ttacataaaa ccaccgtacc tgcatcacgg tggctcgata 156000
cactggaaat ttaataaaaa ccaccgtgtc tccgttacgg tacttgccgg gtcagcgtct 156060
ttctcttgag atttctgttc gtaaacttat ccgtttcccc ggtccgcggt gtctcctcgc 156120
gaggctgaca gtctacgagt ggtatctaca agagaaagaa acccgggtgg gagcgacgcc 156180
gtcgctgggt atcaaccccg cggctgaccg tcgtccggta aaggaacaac ccgtcgtcgc 156240
aagccgggtt cgaccaagag aaaaaacccg ggtgcggggg gagacgggtc gtcctttgct 156300
tgttcgcgga cggcgtacat gccgcgtggg tcagtcgacg gcgtcgctcc gtgcggtcgg 156360
tcatcattct gcttcacata tatgggttgt ttgtgttttt tttataatga atacgcactg 156420
atcctatccg tgactgcgcg tgtggcagag aggatgcttt ataacatgta ttttgaaaaa 156480
ttgccaacag ctataatttc tctcatgtag cagaatagag accttttgtc gtctttttgt 156540
ttgtcattac ttgttttcca gggaattaga gagagggaac cgcgcctccg gcggcggtgc 156600
ccgcggaccc cggccccttc tcgcgtgcgc ggtgtgactg gttgagcgaa tgagcagcta 156660
ggcttggtgg tgctccgcgt gcgggggaga agacgattaa caacaaaaaa taagtggaag 156720
tggccggtgg gtctttgtcc gcgtgcgcgc ccatccgtcg ccgggaccga gcagaaagtg 156780
atgtggtggt acattgattt tttccttgac aggaaagaaa aaaaagagtt ttgttttcct 156840
atgtgagagg agaaaggtat gtgaggagat gttcgatgat cgtatgttac agttatgctg 156900

-continued taaggaagct tttatcgtgc gtcctgtttt tcatttgatg tatatgacac aattgaaacc 156960
tatcgatagg cgtatatcga ggattcatca attcttagaa tcgtcgtctt tttggctaat 157020
tggactttgc ccatgttggt tgtcattcgt ggcctgaggt catcgtcgtc cacgacgacg 157080
tgtctatagc gtgcggtgtg atcattgtgt cgagccagag aaagtgcgcc tcgcacgacg 157140
tttgcggatc ggctcgcggg tgtgtggaat tcctaagaac ataatcagct ggtcgtcttt 157200
ctttgatgtg ttgctgtcgt cgaggtcttg cttcgttttc ttttttcttt ttagtcgatg 157260
gaacttttct tcggtacggg ttcttgttat ggaagcttgt gttttcgaac atgaattcga 157320
aaaaataaaa aggcctatct tcgtttcaaa aaaaggacag atatcaatct tcttaactta 157380
tatcatggta aattcagaat cctatggtgt cttattatct ctaaagtagt caacattatg 157440
gtctaacttg tatttccctg acgagatata tatgatcctt ataacctggc tactatcatg 157500
aacaacaata tccttactta cagtcatctt cgtgagttaa tgaagtataa tatcggtcat 157560
ctatcaactt atctgctatg taacgtaccc ttttaggtat tttgcgtttc ttaacgagtg 157620
tacccgcctg tgtgaggcga aactctgaga agtctaccga gtcgagttac aagtcactaa 157680
aacacttaca cgagttatct atactaaaat cactatctat gttgtttgct tacctaatta 157740
ttatcctaca tgacgaagct acctcccaac gtaaggtagg gggagaggag acagaacaat 157800
aaaaagtaac taatgtttct tagaacttac ccgctaagga cttaccaaac tatattcacc 157860
aaaaaaaaca acagctacgt gtttcatttg ttttaatcta ccgaagtaaa aaaaaaaaga 157920
ttagctatcc agaacctact tacttcttaa tgttttaact aaggatgcct atgggattgg 157980
aaaaaaaatc acagcaactt gctactaatc agttgacagc gaagagactc ataacaaaga 158040
tttctgggta atacggttat aataatgctt atggactaaa ggatacttgg aaaaaaagaa 158100
cgggctatga ctatagagat tcgtcgagat atcaaacttc aaataggcgg ctatcattca 158160
tggttgtggt gactatatcg tggagaaaaa atgtgatcgt tagttagcta ggtgagactt 158220
acagctatcc atccgtctag tttttcgttg taatgatgat agtacgtcta tggtggtgat 158280
cgattttggt taacaatttg ttcgtttaaa ggcttaatgt acttatgcta catgatgtat 158340
tattctttga ttcatcgttc ctcctaaggg ggtgtatgta tgtactagtc gtatagtgtt 158400
cctaacatca tgactattca gactatggct tcatctatcg tgtctaaagt tcacctattc 158460
tactattact atatatatgc actactatgt aactaggata tggtcctata aggtgtcttc 158520
tatcacggtg gcttgtttat cgcttggcgg ttacgagcaa gagttcatca cggaccagcc 158580
gtgaggcagg gcacacgcgg gtcggcggcg atgatgtccc ccgcgaaggg gacaacaaaa 158640
acaagacaag aggccgccgg ccgcggccac ggacgcgtag cggttacaca atgtttggtt 158700
gagcgttttg tttcatcgtc gtggtggtgg ttttgttgtt ctctgtatat atcgtgtggt 158760
ggctttatcg tcatcattat tatcatcatt cttgtttcca tcatcacgat gagttttctc 158820
cgttttcctc tcctccagtg gtagtcgtgt atcatcatca atcatcgtag tgacgtcgtt 158880
gctgctgctc ttgccttcat ggcggtattt ctcttcctcc cccctaaccc catattaact 158940
cgttagtgtg atggttagag tggctgcttg ttttttttc ttttctcttt ggaacaacaa 159000
aagaggataa agatggtcgg tgaatgtatt attattatta tcatcattat gatacggtcg 159060
cggtcttctt cttcttcgat gacgaaacct gcgcacatcg aagaaaagac gagcgcgcga 159120
accgatagcc gtccgtctgg gacgaaggag aagatgatgg ggagaggagg agagccccag 159180
aagccagagc gagaagggag acgacagaca tacgtcgtca ccgtcctctg gaggaggcac 159240
ggcggcgctg tttgttgttt ggatgcttga ttatatcctg ttctatgggg tagattatta 159300
tcaataggct tggttttcaa aggtcagcct gtgtattgtc gtgtcttttt tttcgttctc 159360
ttgatcgcgg agaccacaca gacgtgcgcg tctcccaatg gctaggcgtt ctttttaggt 159420
agtaattttt tgatcttttt ttttcttaac aagtctggct tgatttcttt tatctatgat 159480
cgattcttct ttttctcggg ggttgcatct tccgtgaaag taaagtgaca ctactctaaa 159540
tggtaaccat attatctgtt gattaggaga aaaaataatt ttttcgcacg aaatcgatcc 159600
taagtgaggt gatttacttg ctatcacacg aaatgattat cttttgctgc taacgtactg 159660
aattttttaa cagaattgct tctccgtaac tatttccgca gattcagaca gattgtcaaa 159720
aaaaatacgg cacagaaata gtgggtctgt ggcttttggt tcgtgtacat tcgcgtttgc 159780
gtgtcgagat ttctacggta tgtttattct tcctgcgatg atgtagggtc cttggtgtaa 159840
gtaggatttc gagtatctct cttagagcga acaaaataat caaaaaacaa cagctaggaa 159900
atcgagggtt actctacgat aaagtgtctc tacaaagtga agaatgttac gttgtggtgg 159960
aataataaga ctcgcgtgat cgatgagtga tcgagagcgg ctcgaacctt ctttaagagc 160020
tttgtttagt gcaactttaa attacaagga gtagaaagct gaaatgaatc tatgaaggtg 160080
ctattctttg aatatcttac tttgtacgct tcacattcgt tatttggata gagagttgtc 160140
tagagaaaat ctgtgattct ctatgagtgt tatttttatt atccttttgg ggactacgat 160200
ttttcttctt gttctacata ccactactac tcgtaatcac atacatggac gaaaaaaaaa 160260
ttcgtcaggc agtagatacc agattctccg acgttacggc gtcttttttt cttttgagag 160320
agtatctgct gagattgtcc gtggtgtatc tagtcgctat ttttgttgtt actagtagtt 160380
ttgcacacag tttattcagt atagtttttc ttcttgccat gatcaattga gcccaccacc 160440 ttttttttt agagaggagg aatttcgtct tgatctccag ccggagacaa cggcggcggt 160500
ggtggtggtg gcgggagaga cttcaaggca atgaaaaaaa aaaatttcgt tttgccatca 160560
agtggtgacg ataacccgtc agattgataa ttggttccta cagaaactat tctaaccgcg 160620
gaagaaagaa attgaaaaaa aaaattgaca aaaacatcat aacataaagg accacctacc 160680
tgggacgcgc agttgggcgg cggactgggg cggcatgctg cggcgatgct gtcggtgatg 160740
gtctcttcct ctctggtcct gatcgtcttt tttctaggcg cttccgagga ggcgaagccg 160800
gcgacgacga cgacgataaa gaatacaaag ccgcagtgtc gtccggagga ttacgcgacc 160860
agattgcaag atctccgcgt cacctttcat cgagtaaaac ctacgttggt aggtcacgta 160920
ggtacggttt attgcgacgg cctttctttt ccgcgtgtcg ggtgacgtag ttttcctctt 160980
gtagcaacgt gaggacgact actccgtgtg gctcgacggt acggtggtca aaggctgttg 161040
gggatgcagt gtcatggact ggttgttgag gcggtatctg gagaccgtgt tccccgcagg 161100
cgaccacgtc tatcccggac ttaagacgga attgcatagt atgcgctcga cgctagaatc 161160
catctacaaa gacatgcggc aatgcgtaaa tgtctctgtg gcggcgctgt ccgcgcagag 161220
gtaacaacgt gttcgtagca cgctgtttta cttttgtcgg gctcccagcc tctgttaggt 161280
tgcggagata agtccgtgat tagtcggctg tctcaggagg cggaaaggaa atcggataac 161340
ggcacgcgga aaggtctcag cgagctggac acgttgttta gccgtctcga agagtatctg 161400
cactcgagaa agtagcgttg cgatttgcag tccgctccgt tgtcgttcac ccagttactt 161460
taataaacgt actgtttaac cacgttgcgt cgtgacgttg tttgtgggtg ttgctaggcg 161520
ggctggaaag atgatgtata aatagagtct gcgacggggt tcggcgctct gccggctgcg 161580
gcggcactcg ctccacggcc tccgacgagc gttgcgctcg cgctttgcgc cgccgcgtca 161640
tggatctgcc tactaccgtc gtgcgaaaat actggacttt tacgaatcct aaccgcatcc 161700

-continued tgcatcagag cgtcaatcag actttcgacg tgcgccagtt cgtctttgac aacgcccgtc 161760
tggtcaactg cgtggacggc gatggcaagg tgctgcacct caacaagggc tggctctgcg 161820
ctaccattat gcagcacggc gaggcttcgg ccggcgccaa gacgcagcag ggcttcatgt 161880
ccattgacat tacgggcgac ggggaacttc aggagcacct ctttgtacgc ggcggtatcg 161940
tctttaacaa atccgtctcc tcggtggtgg gctccagcgg acccaatgag agcgcgctgc 162000
tcactatgat ttccgagaac ggtaatttgc aagtgactta cgtgcggcat tacctgaaaa 162060
accacggcga atcctccagc ggaggcggtg gttgcggtgc cgcgtctacc gcctccgccg 162120
tctgcgtgtc ctcgctgggt ggcagcggcg ggactcgcga tggcccttct gcggaggaac 162180
agcaacggcg aaggcaggaa cagcgtcacg aagaacggcg caaaaaatcg tcctcgtctg 162240
ccggtggtgg tggaggcggc ggcactggtg gtggcggtgg cggcggcggg agcggcggtc 162300
agcactcctc ggactccgcc aacggactgc tgcgggatcc ccggttgatg aaccggcaga 162360
aggagcggcg gccgcctccc tcctccgaga acgacggtga gtcccggccc tcctcgcgtc 162420
acggtgcttt ccgagtggac tcgtgagccc cccgtagcgc acgagcgagc aggcgagcgg 162480
tgttggtgcg ctggtggttg tgtggatgat aaccatgtgc tttttcgtgc gctatgtgtc 162540
gtcccgtctg taggctctcc tcccctccgg gaggcgaaga gacaaaagac caccgcacag 162600
cacgaaggcc atggcggcgg cggcaagaac gagacggagc agcagtccgg tggtgctggc 162660
ggtggtggtg gcggcggcag cggccgcatg tcgctgccgc tggacacgtc tgaagcggtg 162720
gcctttctca attactcgtc ctcatcctcc gcggtctctt cttcctccaa caaccaccac 162780
caccatcatc accaccataa cgccgtgacg gacgtggccg ccggcaccga cggtgcgtta 162840
cttctaccca ttgagcgcgg agcggtggtt tcgtcgccgt cgtcgacgtc gccatcgtca 162900
cttctttcgc tccctcgacc cagcagcgcc cacagcgcgg gcgagacggt gcaggagtcc 162960
gaggcggcgg cgacggcggc ggctgcgggg ttaatgatga tgaggaggat gaggagggct 163020
ccggctgagg cggcggaggc accaccgcag tcggaggagg agaatgattc caccactcca 163080
gtctctaact gccgtgttcc tccgaattcg caggaatccg cggcgcctca gcctcctcgc 163140
agtccgcgtt ttgatgacat tatacagtca ttgaccaaaa tgctcaatga ttgtaaggag 163200
aaaagattgt gcgatctccc cctggtttcc agcagactct tgccagagac gtcgggcggg 163260
actgtcgtcg tcaaccacag cagcgtcgcg aggaccgccg cagctgtctc cacagccggc 163320
gttggccccc cagcagccgc atgtccgcca ctcgtcacca ccggtgttgt accctcaggt 163380
tccgtcgccg gtgtcgcgcc cgttgccgcc gcagtcgaaa caccagctgc tcctccccgg 163440
cccgtgtgtg aaatcaagcc ctacgtggta aaccccgttg tcgccaccgc cgcggctgcc 163500
agtaactctt cctcgtcttc ttcggctcca ctgccgccgc cgccaccacc gccgggcgga 163560
cgtcggggtc gggcccggaa caatacccga ggaggcggcg gtggtggcgg tggtagaaac 163620
agccggcggc aggctgcatc gtcgtcgtcc tcctcctctc ggagatcgcg acggagaaac 163680
aaccgccatg aggacgagga caacgatcct ctgctccggt tgtcgcaagt cgccggcagc 163740
ggccgccggc gagggccctc gttcctcgag gacggactcg aaattatcga tcccagcgag 163800
gaggctgcga tcgccgccgc ctcgatcgcg gcgtttttcg acgattaaaa aaccgagccg 163860
agaccggaaa aattatgaaa caggacgcgc ttggacattt gggtttccac ccctttcggt 163920
gtgtgtctat atatattgtg gtcactgatt tttttttaca ataaagagat agacatcaca 163980
gttcaccatc ttgtctcccc ggtgtgtcta ttatcatcaa tcacccacag agtcgccagt 164040
ccatggtctc tcggtaatgc gtgtccagat acgcgttagc cagtataaag tggtcgttgc 164100

-continued ccacgaaggc gcgggtggtg ttgcgcggcg acgggtggca ggacttaagt accaagtgcc 164160
gccgtcggtc gatcaggtac tcgcaggtgt gcgcgtcggc gccccacagc atgaacacca 164220
gatgctcccg gcgctctgac agcctccgga tcacatggtt actcagcgtc tgccagccta 164280
agtgacggtg agatccaggc tgtccgtgca ccacggtgaa cacggtgttg agcagcagca 164340
cgccgcgtcg cgcccaggcg tccaggcaac ccgaggccgg acgctgaaac ccgtccaccg 164400
tacgcgccag ttcgcgaaac acgttgttga gggagggcgg cggcggtcgg cccgccagcg 164460
tgccgaaggc caggccgctg gcgctgccgt cgcagtacgg gtcctggccc acgatcacca 164520
cgcgcacctg ctcgggcgga cacagatagc tccagcggtg tacgtgctcg ggtgccgggt 164580
acaccatctc gagttgccgc gcgccctcca ccgccgccac cgtgtcgcgc aacagcaccg 164640
tgtcgtggtc gggcaagctg aggaagcgga tccagtcggc gctcagacaa aacacgcgag 164700
cctgctcgtc gggggttaac agagagcctt tattatcagc aatgttagcg agcatccact 164760
gcttgagggc catagcgcga gtgagccggc aggttgacgc gcgtctgctt cagctcgggc 164820
ggcagtccgg cgtagtattt atctaggtgg cgtagcagcg gcgggtccag ctggtgacgc 164880
aggcagaatt ccttcaccgc gttgtacagg ccgtaaaaga gcgtgatgcc ctcgggcgcg 164940
gcagcggtgc tcacgggcag acgcacggcg cggttggtac gcgtggcttc gttgcgtatg 165000
gccaccacca cgttaaagag agacggtggc accagctcga agcctaacac gtgttccgtg 165060
aagatgctgc gcccgtatga cagtcgcgtg aggtcgtagc cgcggcacag gtcgtccacg 165120
cacgtgtaca cggccggcga gccatcgccg cactcgctgt agccgcgcat taccgtcatc 165180
cagcgcggcg ctgtgtctga gctcaacagc gtcagcaggg cccgcaattg atccggattg 165240
ttgtacagca gggccagagt gtccaggaaa gcctcgtcca acagcacgga gttggcggcc 165300
tccggcgtaa cgggacggta acggataagt tgcgatagcg ggccatcgcg cccggtaaca 165360
ttcaccaacg ggcgtagcca actttcatac ttgtcaccct gaaacacctc acccaacagg 165420
catcggcgcg ttagttcggg gcactccgcg gggactttct cggcggcggt aggagcgacg 165480
ctgacggcgg ctgaggaaac aatgggcagc agaaggcaac accacagcag tatcaccggt 165540
ccaggtgaga aagaaaagcc gcaatccggg cggcggcaca tcaagtctgc ggcacgatga 165600
gagtgtgacg gtaaggagcc agttggcgcc gaaagttggc actcaggtct tcgatcccta 165660
aaaagttata tattgcatcc agcaggtgag ccaggctaaa cggattcacg taccaggttt 165720
ggttacccgc gacgatgacg gccagaccgt gggcgctaca gttggagagg ttcctgggta 165780
cgaaggtaac tgagtcgatg tcgcgccacg gggggaatga gacagacgac tggcgcacgc 165840
tgtaatcaca actgtgattg acgtgttgta gcgtgtaatt taggttgcac tcagcctcga 165900
agtagagggg gaaccacagt tcgtcgtact cttcgtcgtc gtcctcttcc aactctgact 165960
cttcttcacc caccgtaatg tccacgctgc tctgagattc ctcttcgtac aggatgattg 166020
acaggttatg gctacacagg tcctgggcgg gaggacgcgt gggagcgcgg gtggtggtaa 166080
tgttttccag gtcaaaagtt ggagtgtagt cggatgttac atccccattg ttggaggtgg 166140
tagaagttgc ggccggtgtc gcggtggtaa gtatggatac agaaggggag ggggaagtag 166200
cgttcgtacc gatggttgtg gtattattat tccctgtgtt tcttgttcca gaaaccgttg 166260
acgttgaaac gggaatcgac gtggtgctgg acgtcagatt gctgaccaag gaaaccgtgg 166320
tgggagtggt gacggtgtta ctcgtggttg aagtgacgtt aggggaggta gtagtggtac 166380
cggtggtggc gacggtagtg tttgtcgtgg cggcggcagc ggtggtactg gtaacggtgg 166440
tcgcgttggt ttccaccgct tcacacagta agcaaaagca cagggccagg aaaagcaacc 166500
agccccgcca tcgccgccgc cgcttcatga ggtgggcagg cgaaagctgg tgaattcgtt 166560
gtacagcggc aagtggggcg ccgcgatcga agggtacgtc aacaagctga cgttgatatt 166620
aaatacgtct ggctgctttt ctacgatgga agcgcacagg gttacggcgt caaacaggtc 166680
tttcttggtg gcgcctgaga cccacatctg gtatacaccc gtctcgtggt acgaagtaga 166740
gcgcggcacc accggacgga tgcagtccag aacgcggttg ggatcctggt gaaagaattt 166800
gaacgtggct acggcctgtg gcgtgtgcgg catcgtctgc gtgatgagct gctggcccgc 166860
taacacggtg acgttgtgca acttgagcag ggcactcttg agggcctgga aagcgttgcc 166920
gcacgaggcg ctgatctgca gctgcacggc cgtggagtcg tgcagccgca tgagacgtga 166980
cacctcttcg aagacgtact tgtatttgct ggcaaagagt ggcgcgtacc gacagtcggc 167040
cggcaaaatg taggtggcgt taccgccgtt ggtggccacg gcgggcgcag cggccgcgga 167100
ggccggcgta aacagcgtca gcggccggtg gtggctggta aggtcgatca tgggcggcgt 167160
ggtgaccgtg gcggtggcgg gcatgacggg gtttgcggcg acgggcactc cggccacagc 167220
ggcggcagcg gcggccacgg cggcgctggc cgagcccaca cccgccggca gtcctccgcc 167280
acccatgacg ccgccgggca gagcgtcgcc cagacagact tccacagtgg cgggcgcgct 167340
ctcggcggtc agtacggttt gccgatcgac ctcgcgacga aagctggtga ggaactcact 167400
gtgatccatg gccgcagggc ccgagatccc ggaattctgc ggatgctgac cgagtgcggg 167460
ccgagttata tggaagacga ttagcttgga gcggagtttt gcgtccctag ctgacctgcg 167520
gatcagcgac gtgccatagg gatagactgt gagcggcggc cgcaacggcg gggtcggccg 167580
ccgctcgtcg tcacggggcg gcgcgaggga ggaggtggtg gtcggtacga tcttgacgtg 167640
gttgacgtcc tgcccgtccg ggggaatacg caagaaaccc cgccgcggcg ctaccacgat 167700
ggtgcgatgg gtctttctct tgttggctgg ggccagggac ttgcagatac gtgtggagcc 167760
gtagacgatc tggacgtggt cctgggagaa catgaccatc gccgccaacg ctcagcgggg 167820
ggacgcgttg ggaacacaga gggtgagaga aaaccccgta gaagtcagcg aaataaagac 167880
aacacagcag ccactcctct cgtctcgggc cctaccactg cttgaagtag ggcaccgggt 167940
gtttcttttc ctcaacgggc tcctccagtc tcttatagga ccagtcccgc cggcgcgcca 168000
gcatgtaggt cacgtacaaa agaataatca ccatgaacac caggaaagcc agcacgccgt 168060
aggccagcag ccggtcctcg aacagcgggt cgctcttgat aaacacgtag gtggtggtaa 168120
aacttcggcc cgcaatctga acgtggagac gcacgacagt atacgtgccg ttgaggtaga 168180
agacaaactc gcgtaaccgt tgtccgttat acgtcacgtt actaatattc cacggcggaa 168240
tgagctggtt gccctgatgc agatgcacgg tgctgttggg gtgatagagg ctgctaccgt 168300
tgagcaagca gtgttcgtgt tcttgaagca gcacgcggac ccgcatcgtg gtggcgttca 168360
agcgagtccc gtacacggcg tagatgggat aggtgaaaag gtcccaagtg gcgttgtgat 168420
ggcggcccca gctgaagaaa gagcacgtgt actcagtggt ctcctgcggc ctgagtcccg 168480
agataagcag ctcttgagca gtagcgttgt aggagagatg tagttttcct gtggataaaa 168540
ttcataaact gtttattttg atgtcaggtt agcgggggag gaaggggaat agacggaaag 168600
gtaggtgcta cttaccttta tcgtcggagg ggaaagcgct aagatacccc acctgagtga 168660
aaggaccttt gcagtttgtc cgtgcataac aggtaactga taaaatgtct ggatttttgg 168720
tgttgttcaa caggttaact ttgcaggtgg cgttcagaga cacctggttg tagctgtagc 168780
tggcttcgca attcacatta tacaggtgcc cctctttctg cgtcgtggtt gccacggagg 168840
tagaggcgga cgtggaggta gagccggacg tgaaagtaga ggtttgtacc gtggtggtga 168900
cggtagaagt aacgttattg ggggtactta tcgacgtagt ggatgtgacg gtgatattag 168960
gggaagtgac ggcacttgta gtgctacttc ccattcctgg gtgcgtgtta ctcaggagcg 169020
cggctgcgag cgcaatcgcc agtgcgggac acatgttgcc gtgtggcaag acggcgggtg 169080
gacgagctat atgtggcgag aggccgcgtc acctcttatg acgcttaaat gtccagctcc 169140
agataaaaga ggcgttaata atgaacacca caaaaaccac ttgcgtcagt atgacaatca 169200
taaaggctcg atgattactg cgcctaaagt atgcaggatt ctccaccaat tcatcctgtt 169260
gaacaaagtg gatgattgac gtgctggtgt taccggccgt cgtattgatc atggatttta 169320
ctaagaaagt tttggcacca aaagtcccgt tagagcccca gcaggtaacg ctgccgttca 169380
cataggctcc cggtgcccct gtcagcatgc gtttcagttc atgagtataa tttttcctat 169440
cgttatacat atcatcactg tagttgactt tgctggtgag aaactgtgtg ttctgtggaa 169500
tactgatcat catccccgag gccaaaaagg gcgaatcgca agctgtagtg ttacagaaaa 169560
tagtcaggtt agtgtcatta tgctcataca tataagccac gctaacctgg ggctcatacc 169620
acccaatcgc aaccgccagc acgtcccatc tcccgacatt tatcaccgcc accactaaca 169680
acgtcacccc cgcacggtac atagttaccc tctcgacgtc gccggctgtc aatgacgtgc 169740
ctgcgtcagt ggctatgatt tatagctttt gggcacaacc gcaacggatc tgtcgtaatc 169800
taccttccac agggccgccg cgacgatgct gaacgacagg atcagacaga cggcgtatag 169860
gagtcctagg tcggcgtcga cgcggcaggt gcggatgtct cgcagggtgg gtagatgggc 169920
gatgcacaac tctttctccc cccgcccgta catcccatct cgtatcagca gccgtagcgt 169980
ggcattgatg gtcagcgggg taaccaaaga aatcacatag ggatgtgtac aggaagtgca 170040
gtgacgggta tccgtgagat gtaagtcatc acccttctca ccgttatcat gaaagaccag 170100
gactcgggta agacgacccg atgaatactg gatctcccac cacagtcttt ggtccaacac 170160
cgagagggca caagagattc taagtctccc tgggttgggg gagcagatgt aagccccgtg 170220
tgtgcccctc gccatcagag ccatacacat gagggggaga agaacaagta tccgggacca 170280
cccgcacccc cacatcacga gaccagagac ggagatgtat aaaaaaaagc tacttttatt 170340
aaacagcatt ctcaccacac gttaatactg tcacggggaa tcactatgta caagagtcca 170400
tgtctctctt tccagttttt cacttactga gacttgttcc tcaggtcctg gatggctgcc 170460
tcgatggcca ggctcagggt gtccaggtct tcgggagggg tctcggtggg ctgctcaaac 170520
tgccccacgg cgtaggcctt cgcggccgtc tcgtagatag gcagcatgaa cccaccctgg 170580
ttggtggaga agatgcgcac catgacctgt ttggggaact tttgcatcag gggcaggcac 170640
aggttgagag cgcccaacag gtccacgggg gtggcagcgt ggatgatcat gttgcggtaa 170700
tcggaggaac gggggcataa ttggtgggtg tgcaattctt tgaggctcca cgcggccttg 170760
acgccttcgt tacaagcatc ggccgtgcgc tgcgccactt cgggtgggtg tgtcacaggc 170820
atggtgtgct ccatgaggaa gggagtggag agggccaggt tgcacatggt gcccaggcga 170880
caccgcaccg catccacctc actcttcacc tcatgattgc gggtgtagat gatctggatg 170940
cccttgttgt tcacctgcat ggttttgcaa gctttgatgg cctcatctaa cacctggtgc 171000
atactgggaa tcgtgaaggg caggttcttg tactcaagag agcgattggt gttgcggaac 171060
atgcggctca cctcgtcaat cttgacgcga ccccgccgag tctgcacgtt gggtgtgcag 171120
aagggggtgt tcttatcttt catgatattg cgcaccttct cgttgtccaa ctcggagatg 171180
cgtttgctct tcttcttgcg gggtccggtg ctcgccccgc cgctgctctg atggccgcag 171240
ctcagcagag aggaggaggc cgcgccacca aaaccgccgc gcccatggtg gctcgaggtc 171300
acggatgctc ctccgccact gctgcatttc atctcctcgg actcactctc cgagtccgaa 171360
gccgaactgc aggaggagga agacgaagag gaactatctt catcgggccg ggccaaggga 171420
tcgggaagag gagggtggtt catctgggag agcgggtgcg tgggagaggt cactcgcggc 171480
gtgccgctgc cggtggaagg ggaagacgcg gtagcaccgc gggtttcgac ttcttcaccc 171540
tgttcttcct cgctatcaga gatcacgata cagccggcgg tatcgataat cttgttgcgg 171600
tactggatgg taaagtcggg ctcgggcttg atgtcttcct gtttgatgag gggcagcatg 171660
ataggcgcgg gaggcacggg cggtttaata atcaccttga aaggacgcgt ggttttgcgc 171720
ggtttcttac gcgggctgag ctcgggagta gcggatgccc cggggatagg agtgttagta 171780
accgcgacgc tggtgggggt cggcttgtta agaggggcgc tgctaacgct gcaagagtgg 171840
gttgtcagcg tggggccggt gctactggaa tcgataccgg catgattgac agcctgggcg 171900
aggatgtcac ctgatggtga taagaagaca cgggagactt agtacggttt cacaggcgtg 171960
acacgtttat tgagtaggat tacagagtat aacatagagt ataatataga gtatacaata 172020
gtgacgtggg atccataaca gtaactgata tatgtacaat agtttactgg tcagccttgc 172080
ttctagtcac catagggtgg gtgctcttgc ctccagaggt ggtgggttcc tcagcaccat 172140
cctcctcttt ctctgaggca acttcctcta tctcagacac tggctcagac ttgacagaca 172200
cagtgtcctc ccgctcctcc tgagcaccct cctcctgttc ctcatcactc tgctcacttt 172260
cttcctgatc actgttctca gccacaatca ctgaggacag agggatagtc gcgggtacag 172320
gggactctgg gggtgacacc agagaatcag aggagctagc accagcggtg gccaaagtgt 172380
aggctacaat agcatcttcc tcatctgact cctcagcgat ggcccgtagg tcatccacac 172440
taggagagca gactctcaga ggatcggccc ccagaatgta ctgggcaaag accttcatgc 172500
agatctcctc aatgcggcgc ttcatgatat tgataacctc aggcttggtt atcagaggcc 172560
gcttggccat catcacacta gtctcctcta agatatagca gcacagcacc cgacaaaatt 172620
cacttaagag agagatggac ccgtacatgg tcatcataca agcgtcactg gtgaccttgt 172680
actcattaca catggtttcc acacatgtag tgaggatatc cataaatatg tgatcaatgt 172740
gcgtgagcac cttgtctctc tcctcatcca aaatcttaaa gattttctgg gcataagcca 172800
taatctcatc aggggagcac tgagacaagt tctgcaatgc cgccatggcc tggctgcagc 172860
cattggtggt cttagggaag gctgagttct tggtaaagaa ctctacattc ctgtagcaca 172920
tataaatcat ctttctctta agttcatcct tcttagcacg ggccttagcc ttcagtgcac 172980
cccctaactt gttagcggcg cccttggtca catcatgcag ctccttaata caagccatcc 173040
acatctcccg cttatcctcg ggtacaatgt agttctcata catgctctgc atagttagcc 173100
caatacactt catctcctcg aaaggctcat gaaccttatc taagatatct aaggcattct 173160
gcaaacatcc ccccatcatg ttaaaggcgc cagtgaattt ctcttccgtc tgggtatatt 173220
ttttcagcat gtgctccttg attctatgcc gcaccatgtc cactcgaacc ttaatctgtt 173280
tgactgtaga ggaggataac aacacatata agtatccgtc ctcctgactc atttatcgct 173340
atctcgatgc cccgctcaca tgcaagagtt aatcttcact ctatctgaca tacacaagta 173400
aatccacgtc ccatgcaggt tagtatatat cacatacatg tcaacagact taccgagttc 173460
tgccaggaca tctttttcgg ggttctcgtt gcaatcctcg gtcacttgtt caaaggtttt 173520
gagagattct tcggccaatt ctgggaacag cgggtctccc aggctcagct gactgttaac 173580
ctccttcctt aacatagtct gcaggaacgt cgtggccttg gacacgggtg tctcgggcct 173640
aaacacatta gaaatagagt cataagcaca tgggtcacat acaggagata tgtatataac 173700
attaatacaa ctttattaaa aaaaaaggag gcacaaaccc agacacgtac cgtggcacct 173760
tggaggaagg gccctcgtca gggttgtcag ggtccatctt tctcttggca gaggactcca 173820
tcgtgtcaag gacggtgact gcagaaaaga tccatggaaa ggaacagtct gttagtctgt 173880
cagctattat gtctggtggc gcgcgcggca gcaacgagta ctgctcagac tacactgccc 173940
tccaccgtta acagcaccgc aacaggagtt acctctgact ctcaacagaa cacaactcag 174000
ctgcctgctt cttctgctgc tgctgcctta agtcttccat ctgcgtcagc gctgcaagcc 174060
cattccccga gctcattttc agacacatac cctaccgcca cggccttgtg cggcacattg 174120
gtggtggtgg gcatcgtgct gtgcctaagt ctggcctcca ctgttaggag caaggagctg 174180
ccgagcgacc atgagccgct ggaggcatgg gagcagggct cggatgtgga agctccgccg 174240
ctaccggaga agagcccatg tcccgaacac gtacccgaga ttcgcgtgga gatcccacgc 174300
tatgtttaat aaaaactgcg ggcactgggg acggtggtgt tgtatatgtg aatttgtaaa 174360
taataaatga gaccccatcc tgtaaaaata cagagtccgt gtcagtctct gaaggacaga 174420
gtattggcat atagccaata aagagagtta tggcaaagag ccatgttatg gattagtaat 174480
ggaaagtatc gtcaccaata ggggagtggt caataatggt caataaccca cacctatagg 174540
ctaagctata ccatcaccta tagcataagg aagcgggggt gtatagaccc caagccaaaa 174600
acagtatagc atgcataaga agccaagggg gtgggcctat agagtctata ggcggtactt 174660
acgtcactct tggcacgggg aatccgcgtt ccaatgcacc gttcccggcc gcggaggctg 174720
gatcggtccc ggtgtcttct atggaggtca aaacagcgtg gatggcgtct ccaggcgatc 174780
tgacggttca ctaaacgagc tctgcttata tagacctccc aacgtacacg cctaccgccc 174840
atttgcgtca atggggtgga gttattacga cattttggaa agccccgttg attttggtgc 174900
caaaacaaac tcccattgac gtcaatgggg tggagacttg gaaatccccg tgagtcaaac 174960
cgctatccac gcccattgat gtactgccaa aaccgcatca ccatggtaat agcgatgact 175020
aatacgtaga tgtactgcca ggtaggaaag tcccgtaagg tcatgtactg ggcataatgc 175080
caggcgggcc atttaccgtc attgacgtca atagggggcg tacttggcat atgatacact 175140
tgatgtactg ccaagtgggc agtttaccgt aaatactcca cccattgacg tcaatggaaa 175200
gtccctattg gcgttgctat gggaactcac gtcattattg acgtcaatgg ccgggggtcg 175260
ttgggcggtc agccaggcgg gccatttacc gtaagttatg taacgcggaa ctccatatat 175320
gggctatgaa ctaatgaccc cgtaattgat tactattaat aactagtcaa taatcaatgt 175380
caacatggcg gtcatattgg acatgagcca atataaatgt acatattatg atatggatac 175440
aacgtatgca gtggccatta gccaatattg atttatgcta tataaccaat gactaatatg 175500
gctaatggcc aatattgatt caatgtatat atcgatatga attggccatg tgccaacttg 175560
atgtcgcctc tatcggcgat atggcatcat atcgtctgtc acctatatcg aaactgcgat 175620
atttgcgaca cacagaatcg cccaagtcgc caaagtcgtc tatcgccatc ccccgtaaac 175680
gatataagcg ttatcgtcag atatcgcgta tgcccaaaaa tcacttttta aaaaatggcg 175740
atatcaggtg cacagaaact cacatcggcg acattttcga tataccatat tttcaaatat 175800
cgctttttcc aatatcgcca tctatatcgg cgataaacac cactatcgcg cgacatgaat 175860
ttagtcggcg acagaaatct caaaacgcgt atttcggaca aacacacatt ttattattca 175920
ctgcagcata tagcccattt tagcgcggca cacatccagc cgtttgtgtt tcttaacgct 175980
ctccaggtac tgatccaggc ccacgatccg ggttatcttg tcgtattcca ggttgatcca 176040
tcgataggga acgctgccag cggcgcccag caggtactgc gccttgtcgt tcactttgcc 176100
gcagcgtatt cgcccgtcag cttcgaggta taacctacaa cacggaaggg aagggggggta 176160 caaaacacgt gaaattagac ttttttttt aaatgatgtt ttgtccctct ctgtcttact 176220
ctcccatagg ctgtaaggcc ttcgaggaag agacttacgg attgtagttg cagctcgtca 176280
gtttgttgtg tacgacctgg cgtgtcaatg aatgggttat ggtggtgacg atcccgcgaa 176340
tctcagccgt tttctcggga ctgtagcaga cttcgccgtc cggacaccgc agcctgtgga 176400
ttcatgaaaa tctactctgg cattcccgag gatcgtcgat ggaacatggc tatcagaaac 176460
gtcgagagac agatccagac gcaccacaga acgcagacaa tcatgaaaat acgtacgcga 176520
cggtgaagcg attgcacatt ttgaaatcgt aacagcgttc cggcgggtgg ttgacgttta 176580
tgaattcgca acattcttct gcgcgtaccc gcggcacgcg gctgtgaccc aatagcagcc 176640
acaacgccgt caagaacggc gtcaggtttt tgggactcat gacgcgcggt tttcaaaatt 176700
ccctgcgcgc gcgacgggct caaacgatga gattgggatg ggtgcagaag gtgtaagtct 176760
ggttattggc ctcggtgaac gtcaatcgca cctgaaaaga cacgctgtag tcccggaaga 176820
cgtgggccca gctctccagt ttcatcacac acatctgata acgtgtgcca tcgttgacga 176880
cgaagcgtag cagcttggtc tgcttgggca ccatgtgcgc tccaaaaatc ttggcgtctt 176940
ccacgctgat ctgcacgttt ccgtcgctcg gttttgaagc cgttcggggc attcgttgaa 177000
ggatggtctg gttgcgaccg ctcaggtacc agatcacctt tttcacccag gtggagcttc 177060
tctccaccaa ggtctggcct tcccggttgt acagcagata cagggtctcg ttgcgacact 177120
cgggacccgt tgatacccgc tggaaccccg agaattgcga gggggaccgt gggggcgagg 177180
gatagagaaa aggacagtaa aacgtcgccg cgtcatgcgg tttggaatac gtcagtttgg 177240
accatggcgg ggacggattc tggttcgccg ttagcgtcga ccacgaagac gccagacagg 177300
gcgttgccca aaccgcgcac agaagcaggc agtgaaagta gtgacgaagc agaagccgca 177360
gcatattatt tcccgtgacg caggctagtt ggcaaagagc cgcacgctga actcgaggct 177420
ccgggcgtgc ggcgccagcg aaccggcggc gttgaacgtg gtccttttgt tggtgccgcc 177480
gcgacggttc tgacgtctaa agtcgctgat gagcaacgac acctcggtca cgttgattct 177540
gcaagcacag gttccgaacg tcatttcaca ccccatgcgg ttacctaccc gttacccgtt 177600
cgcccttacc ttcccgttgt tcatacacct ttagcgcgta ccctcacctc ttgagcacgt 177660
caaagttgtc caagccgtgg ctcgcatcgt agtggtagtt caacgtgagg tccacgagct 177720
gttccacata cttgtaacga gtttggtcgg gcagcgcgcg agagcacggg tcccagtaat 177780
gcggtactcg gtaataatcg tttttttctg cggtctcccg ctggcactga cccagcacca 177840
cggcgcacag acaaacagac agccacaccc gacacagccg catgttgcag actgagaaag 177900
agagctttat tatgagacat catacacata gtataggcga ggtaatgggg cggggaaaga 177960
gttggaactg aaagacaaaa aaaaaaagcc tagtcgtact cgggatctct gagcgagacg 178020
ggttgcgtag caactttcat tagtttggga atctgccagc tggtgctgtt cgaaggttct 178080
tccatttccg aggcggtcag ttcatcgtac accgagacgt agtacctgat ggggtcctcc 178140
tcattgtccg agaggtgaga ttcgatggtc aaaggcgagc ctctcccata attgggattc 178200
acgaacgacg tgtccaagtt gccatccttt ctgaaataga tgacgttctc aggatcatgt 178260
ttcatgcgct cgcgggccgc ggacgcctcc tcctcctcgt cccagtcccg agtttccaac 178320
cgctgataag ggctcgagga acaaaatccg gcggggatct gagaacctcg tcgggaaccg 178380
ctgccaaacg ggctgctgcc gccactgtcg tccgtgtcgt ccaacaggtt gacggcttct 178440
tcgtcggcga aacgaaagcg gcccgggtgc ttgcaacacg aggagtaaac taccgcgatg 178500
agtaccgcta tgaagctgaa aatggaggtg cctgtcacga tgtagaagag gatagccagc 178560
actttcatga tttcgtcatt gcgcgcgtcg tgaacggaag attcgcgggc ggtggttatg 178620
ttggtttcgg ttgtaggttc gctactcgtg gtgctctcga cggtatttct gctgctggtg 178680
ctagtaggga cgtttgtgct gctggtcata tttgtagcgt cgctgaagtc catgtgaagc 178740
agcaacccga acgcgaccag gaccaggaat gttgcgcgaa ggagaccccg cggggccagc 178800
attcttgaga cgtggcgacg tggatttctt gttatgtccg cgaacgacgt gtgacgagga 178860
cgtggtttcc gcaagcctct accgacgccg cgacaccagg taggttatca aaacgcgagc 178920
ccatatcgcc gccatcattg taatcagcaa tgtgttgagg tactgcacga tgaatctgtc 178980
tagtgacacc agccaaccct ctgcttttgc gggcaagcgc gctttcggtg acagggtgta 179040
tcgtacgtag ccgcgggtca ggcgcgcgtt gtagcggtac acgcagaaat ctatccacag 179100
gccaacgccc ggctgtagct taggatggtg gataatagcg cggtgacgta cgccgcgggg 179160
ctttagaatc tccacctgta aggccatctc ctccaggtag tgggtctgac tgcgacgcag 179220
cgtccaattc atgtaaaagt cggtctcgcc gtgtccggcc acgaagaggc tgcttactaa 179280
atcgggcgcc agagctaggt caggcgtatc aaattccact gccaggcgac ctgattctaa 179340
cggttccacg atccgggaga gcgtttctag atatagagca aagcgtacca cgtctacttg 179400
cggtgtaaaa aactgctgtg ggcgttcacc gtcgttgacc acgtaggcca cgtagaggcc 179460
aacattttcc accacgggtt ctagctgcag gcggcacgta aagcttagaa acgacggctg 179520
tacggtttgg ttcccgtgaa gctgaagcgt cacttccttg ccggggctca ccgtgctgta 179580
acgccgcacc gagtcggtca tctgctccag atcggtagac cagaaaggcg tgcaatgcat 179640
actgtcccag tcgcgacacg cagcccagcc tagctcggtg aagggtcgac gcacacccga 179700
aaaagtgtgc ttgaagacca gggggtcgcc tcggtagctc agtagccgaa catgcacata 179760
gtcgcggcta gcgttgacag acggcccgtg gagggccagt aggacgagcg tgaacagcaa 179820
gcgcaacatg ctgcgcgggt taggaaatgc ggcgtgccgg ccaccgcccg actcataaac 179880
gctaccagca tgacgtctca gatcacacaa gtgacgagga gcgtaccgca aatcaccagg 179940
gaaaaggcca gcagagcccg atagtcttgc tcttcgcgaa cgatctcgtc cggttcctcg 180000
cactcttcgt ggtccacaga agacgaggag caggattctt cgttgatctt cgccagggta 180060
ctagtgctgt accacaccag agcgcttagc gtacctaggg ctaccacacg gtaaaatagg 180120
gacatgatca ccagcgcagt ctgaagtggt ggtagttcaa tttcttggcg tatttccaga 180180
gaaaggcttt gtaggccgta gggactggcc aggcaccaaa ctcaatattg gtagacacta 180240
cgtcgtaaat gcgttgttct tcgtctaaga ttaaccgaaa aaatagccgg ttgatgtgac 180300
gacgcacggc ttgcgcgtta ggattgagac acttggtgcc cttgtccttt aaaatagcca 180360
gcacttcctg acgattgcag ctttcgctcg ctccgattgg cttaagcagt tgagttccga 180420
ctggcagggt attcaacaga atttggttgt tgcaacgaca gcgcttgtcg taatcttcca 180480
attctaagag atagacgaat aggggacacg tggaaagtaa cacatatgcg gtcaaataca 180540
ggtatcgtac cgataagagt ttcatatgcg agttcagaat cgtagggtgt agccatgtta 180600
gcatctctaa aacactgtta tctttttcca taaaaatctt attaaccgtc acgtgtatga 180660
atatcactct gatttatcgt aaatatgcaa aattaactca accgtttctt aatttcagct 180720
tttttgtcta catgcggtcc actaccacct cccgttgtta ccacaacttt gtaccatgag 180780
ttactatttt gagcatccaa ccattttgat aaatggtgat cgggattcaa acatgcacgt 180840
ctaccattgg gaggcaccaa ataatgttga tatttggtac aaccgggagg acggggtgga 180900
tcacgaccaa ccagaaatac accgctgaga ggatcgcgta aaccattact accacatgga 180960
caacgcaatt ctacgctttc gaccccataa tagcacacaa tcaaaatact aattaacgaa 181020
ccaaaaatta atcgcattat aattttatta tctacgtcac tatcagtaat tcgtaatatc 181080
cggtattccc ggaaaatcac tcaaaactgc gtccatgaca catcaattcc cgataagtac 181140
ccccctttga aatcggatcc ccccacatac caatcaatca cacaacacac aggtttaaaa 181200
atcgatcaca cgtcaatcag gtttcaaaat cgatactgtt tattatcagg aatctagact 181260
aattctacaa tgacagctct gaatttctct ctcgtctttc ttgtcaggtt ctcatcatca 181320
gtcatcactt ccacccatcg aggagtcatc gtcgctccaa aatcctttgg ggtcgctagt 181380
tggaaaagtc tctgacacga tccaggcacc ccgcacccag tccgactgat ctagcttgcg 181440
gagcatctca acaggcatga gctgcagggc cacggctgtc acggcactgt atcgatgtaa 181500
cactagggac tttctttgcg atgtagccat caacacggcg tatgccccat agttcgcgtg 181560
atacgacgca tgatgggtta aacgttccca tccggcagtg ccgtctcggg tccgtgcaca 181620
caacagctgc acagcgttat gatgcttaaa attaaccata acgctgggac tactgatgaa 181680
ggagtagtaa tgagccagga cgccgtacat cgaaggcaac aagaaagagt gacagcacga 181740
tagcaccggg ctcttatgta ggcgacagct tatttttcat gacgtcggca aaaagtacct 181800
aaattcccca cagatattca gacacggttc cgtaaagtgc ttcttttttt agtgcaggaa 181860
ttggaaaaaa taataaaaaa tatgaacagc tcatctgtaa ttatctgtgt gacttcatcg 181920
taccgtgatg taaaaacaac aacaggaagc ttacagggtg cggtaaaaaa ttttgccgat 181980
tgagcaacac tgttggcatc tctcactccg ataggcggct ataagataga gaattaaaag 182040
tatgataccc acaagaaaga taaagagaga caaccaggct agagtatgac gaccgctttt 182100
tccttgtttg acggttatat gtgcggtatg attttgctgt cgttgcttgt gatgttggac 182160
gcctggagtg ggaaagtacg tatggttctt aggtgcgcat acggtattat tggtggaagt 182220
gcagttacga atcatgacct gagtgacgtt acattgagtg caatcggtac agttgtaaag 182280
tcccgataca tacgtgccgt tggggcaagg ggtacacgtt acactggtat aatccgtgca 182340
tactttagta actctttgtc ccgaaccaca cggagggcag cactcattgc ccagttgcac 182400
ttcattatgc tgacacactt tagtcactcc aagctgcaat aatatcacag caaagcagat 182460
gagcattatc agaggcttca tgcctcctac cggaagaata aaaataactc atagggccga 182520
acggtgtcat cctctccgcg gtttgtaata cgagattgca aacgtaaata aatgacataa 182580
cttcactaac ccgcatacta caaagtccac ctacgacgct gaaagttctt ccaggacaga 182640
acaggatagt cagccatctt cacagtctac ctcttaggcc gtatccagga gcataggtaa 182700
tcagtttcca gccacagtac agcgagccca ggaaaccgca cacggtccct gctgggaaca 182760
cgtaccacca catcgattcg tcgtgccgta gaaccgtaga gttttccgaa cttttataca 182820
cgccggtggc gttagggccg tgtgtgctgc tgtgattgga ggttttgtga gctaggtaac 182880
agctgtgatt tcacctgtcg ccaagactga cagcgattac ccaggtggag cacaatcaca 182940
tagctgatgg acgttggttg atccgttgat tcccatggac attttaacgg cgacagtaca 183000
gctcccgtta aacattagat taatagacgc tagtggatga cagcatgtta tttgcccaaa 183060
tgtgatcgtg gttatacttt cttgtttttt gctcatatgc tgtaaggtgt tcgaggatcg 183120
tggggagtat atgtgttgaa tcggaatcat gtttactgac cgcgccatac ttcgtatacg 183180
aacctaaccg gcgtaaagtg ttttccgata tataaactgg cgcctattgt ggctgtagcg 183240
cccataggta tggcgtatac ccacggtgat gttgtgttat tcgttttttg tgataaaacg 183300

-continued tagcttatgt ttaacgtgtg ttccgtcacg ttatgtgtgt cgttaaaaga cggcgcctgt 183360
acagtatggc tttgagttgt atcttgaatt gttattgcat ctggaggtgt tgtgtacaga 183420
gtggttgttg cgtgttgagg tgttgttacg ttttgaggca cagttgcggt gtacacgggc 183480
tccaaggtgt agttacggag tctttctatg caggtagtgt tgagatattt gtgaatgctg 183540
gttatgttcg attctgtgag gttaaagtgt gtactattta tggcggtata atttagacgg 183600
tcttgccatc ccgaggatgt tagtgttagg taattcgtgt tgtttacgtt tgcttgatat 183660
gtataggtag gtgtactgtt tgtgaggtcg caagtgtgat tttcttgcag agattttatc 183720
catcttctgt gaaaatattg agatacgcga tgaatgtttt cgctatctat attataaagc 183780
gtttcagtgt cacctagggg ttgtttgttg taacttttat tttggaccct gggtgtgaac 183840
catgattcca atgtttgtat agtaaggtgt cctactaata aagacgaact gattcccacc 183900
gtaatgttat accgcacacc cagggtgccg tttacaaaca cggaaatgtt tccgttgcaa 183960
actacatcgg cagatgagtt agattccagg tggtaacgat aggataatga ccgttcgctc 184020
ccaacggatg acacaaagta tccgaatagc aaacacgccc attcaatccg catattttaa 184080
tcacactatt cacacctcac acactgcatt ttttaacatc ttattttttt attttatgcg 184140
tgttctcacc tcttcatctt tttaacaccg gggtaactat cgtaagtcgg taggcgtcga 184200
tagccctcac cacctcgtcg tccccttccc ggcgtgggac accagcgtcc acaacactgc 184260
aggtaacaca ggtagcatag gaaacatacg gtgaaaatac tccaaaatcc caaaaatgcc 184320
gcgattcccc gagtggccca gggagacatc ccggtgtcta tgtcggccgg cggtgctggc 184380
gtcaccggta aaaatttcgg cgggtgtggc tgcgaacggt agcagtcacc ggggagccgg 184440
taacgctgta tcactgtcca acagcggtcg ggttcctcgt ccggacatgc gggtttccag 184500
caatcctcgg cgtcggcgcg gccgatatag aagtagttgc gttgaaaacc gcggtacatc 184560
ccgcagtcgt gattccgtag acgccagggc gtcggcgacc agatctggtc tcccagcgag 184620
tagcgaccta acgccggcgt gcagcaaggt tcgtcgggcc ggctgagcgt ctccagttgc 184680
gtgagaatta cgaagcgttg catgatgagg ccgtggctgt agttgcgcag cacgcattcg 184740
tacatgccgg ccgtgtctgt cgatacgttg aaagtcagcg agaatatttg gccgagatgc 184800
aactgcgaga aattccaagt ggcgtacggc aggcggtatt ggagtccgtt catcagccga 184860
tggcctttga cggcgtccag gatgagctcg tcgctaccgt cgtgggaacg acagaaacgt 184920
gcgcgaatgg agaccatggg ccaggagtgt gtcatgaccg tgcaggggat ggtaacttgc 184980
tctccctcgg cgaccaacac cggcgccggc gacgtggtct cataattctc ggcccacatc 185040
ttttcggcga tgtcagcggt ggcgaagggg aacgaagagg aagaatattc gaagagtcgc 185100
gggcagctca acagcaccca gaacagccac ggcagagttc ggagcgactc ccggcggcac 185160
atgatgattc tttccttccc tttttcgcag agacgctgcg cgcctgctcc tgctccgtgt 185220
gtcggccgct caaacgtcgg gccggcgtgg tggtgaccac cgtgcgacgc agcttctcgc 185280
ccgggatgcc cgcgactgag cgtccggttt ttttgcaggt ctttttttgct gcctcctcct 185340 cgccgtcgcc gtcgcggccg acgtggtgga ccagcaccgc gcaggaactc tcgcgtcgcc 185400
ggcggtacgc gacctgtctc attgctacct cggatgttta agaagggacg ttcatctgcg 185460
tcacagggtc tgatgaagct gccaagagtc gtggctgtgg cgcagcgcgt tctgtacagc 185520
gcgtttcacc gctttctgca tggccgctac cacgtcgggc gggagcggct ccggcggaag 185580
ctcgatgagc agttgctgcg aatctcggcg ctcggcgtcc gccgtttcgt cggacgtggc 185640
gtagaaaacc gaggtggtcg cccagtcgtc cacgctgtcg acggcctctg tcagtgccgg 185700
gttgtcaaaa ccgccatcgg acgcgggtga taaaagaacg tacgatgaca cgctgttagt 185760
acgactctcg tcgtcgctct gggaacgacg tgatggacga cggtagatga cctcgtcttg 185820
ccacgcgtcg aagcggtcgc agcagcgctg gatccaagcg cagcgaagca gcttacggaa 185880
cacgtcgttg ttccaaaagt agagcataaa gagaaagaaa agtagcgtaa cgatgaagcc 185940
gaaaacgacg agggtcggca gggcactacc gccgctgccg ttttttgtgt cgtgcgtgtg 186000
cacggtggta gtggcgttag tctgagctgg ggtcatgaca agtctgaaga gatgagagtg 186060
tgggtgctca tcaggaacag ttgaggtctc tccctaccga agccttagcc tctacggtgt 186120
tttatgatca acgtgtctac gaacgtcatt gtgaaagtga cgtctcaggc tttccgaaac 186180
cgcgtcagat tcaacgtggg tttcggttta gcctgcgtca ccgaggcgga ggtggaaatg 186240
agccgtcctg tgggggagtg tatgaccctg tagtgcccat gggtaacgtc gcgtcggaag 186300
aagtgaatgc ggcattggtg tacgcgtggg ttgttttgct ctctgactcg gaggagttgc 186360
cgcagcagct gcagatttta cgtactagcc aaaagcagca aaagcagcag gtaaataaga 186420
gaaggagtcc agataatgtc cagccgctag cggcaaacag cgcaagttgc gcgactgtcc 186480
aattactacc accaaaactc tcaacacatt gaatcgacgc tgaggttggt gttgcagtgc 186540
tgttgctact agtggatgaa gacgaagaag acgaagtaga ttgactggaa ttagagctgg 186600
tacctgtagt ggtttcactc gccgacgcgg cgagtgcaaa taaaactaat atccacagca 186660
tgttcgttac tatataattg atatactaac tcgtttgtcg taacaatcag cgttatacac 186720
gctgtatcgg catcgtttta ccggaaagtt tatcgtaatg taacccgcgt tgtgtacatt 186780
cgtactgaca gggaaccccc ggtgatgtgc acattatact ctttcattct ggggtttccc 186840
aatgacgtaa aaatttccac tacacaataa aattactgac tcatgtgaaa agtgtgcttt 186900
ttattaacag agcagagggt ttacagtaga tatatgtttg ccagggccac cgttttctaa 186960
caccgatcac cgccaccatt accacccgtt gaactccaca cccgggagcc gcctgatcgc 187020
cagagactcc tcaccgtcca tcgtccgaac aagctcccgc caccgatgct gccaccatca 187080
ccgagagaaa gaaccgcttg ctgcagatac gcttgggctc gcctccgtgc ggacgccgtt 187140
tcgtgcagac gctgagtaga tcgagcagag aatgtcaaaa cgacattatc gcgatccgct 187200
cccctctttt ttcttttcct cattcacgtg tactcttgat ggtaatgtac catggctacg 187260
gtggtgaact gcgtcgcgga tcccgtcacg ggtttcaaca gatcgacgtc ggtcagcggc 187320
gccgtcaccg ccatgtccgg cggaggcacg ctgtttctct ggttagcgac gtggaccgac 187380
gacgaggacg atgaacccgc acggcggtct gttatccgcg acgacgcgta gctgcactgg 187440
gaagacactt cctcccaacg gaccaagatc tcgtcgggcc gttcggagaa acggtatcgt 187500
ctgtccgatt cccgccgtac ggcgccgagg cccagcgacg acaggtccgc gaaccggcgc 187560
tcgtactccc cgtacagctc gcaacagcgg atcagccagc ggtagctcaa aaacatgcgc 187620
accagtttga aggtgtcgtg ccagtggtaa gccagatagc agagaatggc cacgatcagc 187680
acgagcatca cgccgatgat gggtaacccg acgttcagcg gcagatcgtc catggtgacc 187740
gtcctctgtt cggatctacg tcccagtctc tctcttttgt acagcactcg cgcgggaacg 187800
gccccctcaa ccctcttacg tagcgggaga tacggcgttc tcccgcgggc cacttacttg 187860
cacggtcgct tgaacggcgg cttggactgc cacatgcacc gcatccatcc attccggcag 187920
cagcgcgttc gacgatgtcg tacgagtcgc ggatgatgtt accccgccag cacctccgca 187980
ggcaaccgtg tcgtcgttgc tatcgtcgcc ggtttcgggc gatgacagcg ccggcggcgc 188040
gggtctcgtc tcgtccacca tttccaccgt gtcgaagcga cagccgctgc cgtagtacat 188100
agcttcgttc aacggccggc gggccgggtc gccgagttcc gggtcgggca catccatggc 188160
tcgccgtctc cttctctgcc gctcgtggtg ccgacggcac ttctcgggat aatgacagcc 188220
gcaaaataga tcgtggagca tgtctcgcca actgtcctgg tgataatatc ttaagtacgc 188280
gatgagcgcg ccgatggcca taatcataag cgtaagcaaa acggcacaga taacgtgaaa 188340
caccgcggtc atccaagtcg ggcggcgtcg gggacgcggt gggtcggttt ctcttacgcc 188400
ggcgtcactc agccaccaca cccgtagccg acattcccag aaccggtgaa tgcgactcag 188460
ggcctttcga cgccgccatt tatttccaac gtccaagtcc cacgtcattt ctggcatctc 188520
cacgcccttg actgacatac tctctttctc tctcttagct gcggtgaaaa agagggaagg 188580
cgtgtgctgc tatacaactg tacaacggac gcgctcgctc tttcggtctc aggtcatctg 188640
catcgactcg gcgtccttca tgacgctctg caccgccttt tccaacagtt cctcgatgtc 188700
cgaccatcga ggaggcgggg ctaactcgga aaccgacacg ataggcagcg tggtcggctc 188760
cgtcggcgtg cggggtcggg gacagggaca cgagagtccc accttcgaga gattctccag 188820
cccgacggtg cgcggcagtc tcggattccg cggcggcttt tgcggcgtcg gcgttttcgg 188880
gaagggcctg ggcgtcaccg gcggtgtcca gccgaccggc ttgggtttcg tgggcggcgg 188940
cgttttcttg gtgggcggcg tgctcaggtt cttacgcggc gcgggtatcg gcgtcggggg 189000
cctgtgcgac gacagccgcg tggtgggggc ccggaccggc ggcgtaggcg gccgcttctt 189060
gcgcccgggc ggcggagatg gcttccagga tggcggcggc tgatgcagca ccgtgtcgac 189120
gctggtcgag gacgacaaag agctcgacga ggagcaatgc gacggagatc ggccgatgct 189180
ggttggcgtt cccggcgtgg atacgtcggg gatctcgaac cgcgccggag gaaactcggg 189240
tttatctatc ggcagaccat cctctcctat gtagagcgac gtacaccgcg gcacctgcgg 189300
cgtcggcggg tgggtggcca cccgcatgag ccccagttcc agatccagcg gctcgacgac 189360
gtcttctttc ggatttcgat agcagcacgc gcaggcacca cgcttatcag aagcagcacc 189420
cgggagccgg cctcgcgacg aagtctcgtc ggatcgcttg cggcctcggc gctgggtaaa 189480
taaggaaatg gccaggacca gggaagccag tccggtaccg ccgaggagcc cgacgccgag 189540
ccacagccac accatgatct tctctcctgc ttggaatctc aaactccgtg tcgggaagga 189600
ccggtgtacg gacatttatg tcttggattt ctggaaacgt catttttttgg caaggaatgt 189660
gtttattgtc caaacactga ggaaggagat gtgggccaag tcggaaaatt ccttatcaca 189720
ccgggggcgg gttacgttcc ggtctgatgc tgctgctgtt gttgttgtag agccgcggcc 189780
acggccgcct gcacggcagc ttgtaccgcc tcggccacgc cgggtggcat ctgcggcatg 189840
gcggggggag acgcgtcggg cggaccgccg ggcatcgccg tcggctgcga cggtggttgt 189900
gaactcaccg tcggttcgca cggaggtttg tccttcggtc tacccttcgg tttatctttc 189960
gccctacctt tcttcggttt gggttccgat gtcggtgctg gcggctgcgg tgggatgacg 190020
ggctggtggg actcctccga cggcgggggg acggacaccg tcggcgccga aaccggggga 190080
ctttcgacta tctcgcagat caccctgtcg ggatcgtcgc cgtgtccggg acgccgtcga 190140
tgaccgtatt gtaccatgtc gtaaatcatc gtctctttgt aacacgctga acagcagcgg 190200
ctacaaggac ccgaaatgca tttgcagttg cacttacagc tgcagctgca gtagcgaacc 190260
catcggcagg tgaggaggtc gattacggag tctttgaaga attcccggta acggatgaga 190320
tacgcgcaaa ggaaaatcat aaaaacagaa cagccaacca cggctgcaat gccggctcca 190380
gaagagaaat tcgacgacca tcccgccaaa caccaaattc ccaaggctgc gcatgtcatc 190440
cagatcacaa tgatcgcggg gacgccccat tggcattggc acgaaggatc ttgcacatcg 190500
caacccatcg ctactgcgtt ctcccacaaa cgccatcgca ctatttatcc ctacagcggc 190560
tgccgagtca cgtccgccgg cgctcatcgg cagcggcgat gtcctagtaa cactcgtccg 190620
acacttccac catctccagc tcggccggcg gttcggcatc ctccaccagc ggcgtcgtct 190680
catcttttcc gcagcagcga acgcatacct tctccaggca gaacgccacc agctgccgtc 190740
gaacgtacca caggtacacg tgcagacctg cgaacaggac tacggaggtc atgacaacca 190800
cgacgcacac gggaatccag ggatcgagac tttcggaacc catggctatc gtcgccgacg 190860
tgcgcgcgtc tgtctcaccg ccgctcgccc gtcgtcgcgc ggcttgttat acgctagccc 190920
gtcgccgcct cggggcacgg tgccctccta cccacgtaac ttcctccgtg acttaaagtc 190980
gcgtgtggta gatctcctgc tccgtggacg aaccgttcgg caggatagcg gttaaggatt 191040
cggtactaag gccgtgtcgc caacgtcgaa tgctacgttg caaaagctta gacggacggc 191100
catcctccct ctcatcgcaa taataaaaca ccagcagcgc gcacgacgcg atcacggtga 191160
cacccatgac cagacccacg cagatagcca gccccgctag cgtatccagc gccatcccgt 191220
ctgctcccgt cgtcgtctcc tgaacaaagc aactctacag tccccgtttt caaccgtttt 191280
tgtttccttc tccgcgacca aatgctaacg cccgcggtct ttccggccgt gctctacctc 191340
ctggcgcttg tcgtctgggt tgagatgttc tgcctcgtcg ccgtagccgt cgtcgagcgc 191400
gagatcgcct gggcgctgct gctgcggatg ctggtcgttg gcttgatggt ggaagtcggc 191460
gccgccgccg cttggacctt cgtgcgttgt ctcgcctatc agcgctcctt ccccgtgctt 191520
acagccttcc cctgaaaccc acgttaaccg accgtcccga aaacgccgct gttaacacag 191580
gaaaaaaaga aaccacgcag gaaccgcgca ggaaccacgc ggaacatggg acactatctg 191640
gaaatcctgt tcaacgtcat cgtcttcact ctgctgctcg gcgtcatggt cagtatcgtc 191700
gcttggtact tcacgtgaac caccgtcgtc ccggtttaaa aaccatcatc gacggccgtt 191760
ataaagccac ccggacacgt gccgcggcac ttgcctacgg cgctgctcca gggaaactcc 191820
tcttccttct gctcttcctc cttcaccgca gggaccgtct ccctcgacca gggacccgcc 191880
gaagcaactg ccggagcaac ctggaggagt cgcggcatga cggcgcccaa gtgtgtcacc 191940
accactactt atctggtcaa gaccaaggaa cggccctggt ggcccgacaa cgccatcagg 192000
agatggtgga tcagcgttgc catcgtcatc ttcatcggag tatgtctggt ggccctgatg 192060
tactttacgc agcagcaggc acgcagcggg agcagcagca gcggctagac aagtctctgg 192120
cggctacagc tccaagcgcc gtagccggcc cgcctgccga tcgcgacgtc gtggaccatc 192180
gaacagagac tcacgcgtgc gagaccccga ggtacgccac gcggtgccta acgcggtata 192240
ccacacccgt acggtctgca gtgcggcgta caacgtgtgg aaaacgcgtc gtgtcgcaga 192300
gtccgccacg tctctgtctt gtcgctcccc aatcggctcc cgcacacccc ccgcggcacc 192360
cagagggcgg gtgagccaag tgttcttaag gccgttctct gttccatagc ccataaattg 192420
tttattccgg agctcgttgg cgcggaaata gccggataag gggagcaaca accgtcggcg 192480
aaagccgtcc cgctcattca gtccgggttt cgcgtacagt cggacgtgtg accgttgggc 192540
aacggaacgg cgtttcactg ccaaaatcgt atcgggtagt gtacgagacg tcggcgttgc 192600
agaatgcgac tcgcggcgta gctcgctgtc gctatgcggc tcgtcgccgt gtggcgcggc 192660
ctggccggct gtctgcggcc agatctgttg gccttttggt tcctctggct gctgctgcgt 192720
gtgtgctttg gcagacgcgg tggcagtttg cggtctgcgg taagtgagga tgttgccgag 192780
caagcgcact tgcggcgcgt ggtcggcatg cgtgttattg taggtgcgtt gccagatggc 192840
aagtgctgtc aacagcagac gttgtgggtg gtcggtgtat ttttgtgggt tgcggtgaga 192900

-continued gtcggtactc ggtgttttgt gagtcatctc aaccgtctgt gttgctgtta gcagcgtcca 192960
gaacagcgac gcgactttgg ggatggcctc gtgctcaccg ccgcggagag cgccgccgga 193020
cctgctcgtc agcagcgagc tacgcagacg gaatatctgg aggagagtta cgtgtgtcac 193080
aggagagcgc gggtctccgg cggtaacgac ggcggtgtcg tcgacacgtg tgcggcctgc 193140
tgtgctctgc ggaaaagcgc cggtctcgga gaccgtggac gaaaaagaga acgcagcagc 193200
taccgctggc ggcggcggcg gtaatgctgc cgttgatgtt agacgttgtg agtactcgga 193260
gacagcggtg aggcagaagc tcgatcctcc agggaacgac agtcgatgcg tggtagccgc 193320
agcaggtgag gttggggcgg acaacgtgtt gcggaacgtg gcgagaacgt cgtcctcccc 193380
ttcttcaccg ccccacccac cctcggttgg tgtttctttt gtcttgtgtc ttgcagatag 193440
ttccacggac agcgacggca agtccataat caccggtgtg caagtggtgg aacacgacga 193500
agagatcatc gcgccgcaga gtttgtggtg cacggcgttc gaggaagccc tctgggatgt 193560
ggctctgttg gaagtgccgc gttgggtgtg gcagggctgg aagaggtggc gcaatagcga 193620
gtccgggcgt cgatggagtg ctgggtcggc gtcggcttcc agcttgtgtg acttggcggg 193680
cgaggccgtt ggagaattgg tgggatcggt cgtcgcgtac gtgatccttg aacgtctgtg 193740
gttggcagcc agaggctggg tgtgcgaaac aggtgtggaa gccgaggagg ccatggcgcg 193800
acggcgacag cgcatgctgt ggcgtatgtt ctctcgtgga ggcgacggcg aatgcagcag 193860
acggtgtttg atggagatgg cgagcgagga agaaagcgcc gtgttgtgac cagacgacgt 193920
tggatgcggg acgtcggagc acatgggcca tgtgtggtgg cagatggcgg tgtccacttg 193980
tgcctggggc ggcagtgcat agacgaagca acatgtcgct gtgaagagat agagtgtgaa 194040
catagctgta tgcagcgttg cgtgtagaag cggggggatt aagacgttaa taaagaatag 194100
cggcggttct gatagggcga ccgctgaggc gagctgcgtg tgcgtgtgag ttgtgttccc 194160
cgctgcaaaa ggctcccgtc cccggcgtca cccccgtccc tcagtccgtg cgcagcacaa 194220
aaggcccccg tccccaccat ggtccccgcc gcaatcaacg cccgtgtccc cgcaagtccc 194280
cgccgcaagc agcccccgt ccccaccacc gtccctcagc ccggtcccgc aagtccccgc 194340
cgcaagcagc tcccccgtcc ccagcgcaac ccccggctcc ccgtccccaa cggcgcacaa 194400
aaacccccgt ggccgccgca aacgcggcgc cgcgcaaaag ctccgtgcaa acacccgcgg 194460
aaagatccct gagcaaacca agaccgtgag accccacgca ccggcagcgt gcacaaagcg 194520
cagcgcaaaa gctccgtgca aacacccgcg gcccggtcgg ccgcgcgctg acgccccgca 194580
aacctccccg agccctgtcc cgcgcgacaa actccgtagc tgcctcagcg caaaactccc 194640
tcagcccggt cggcgcgctg gcgcttacgt ccctgacaac tccccgagcc ctgtcccgca 194700
ccggcggcgg tcggggtgtg tcgggggtgc ggctgggtgg gtgtgtgccg ggtgcggctg 194760
ggtgtgccgg gtgtgtcggg ggtgtgtcgg ccgggtgtgt cgcgggtgtg tcggcggggt 194820
gtgtcgggtg tgtcgcgggc gtgtgccggg tgtgtcgcgg gcgtgtgccg ggtgtgtcgg 194880
gggtgtgtcg gcggggtgtg cgcgcggctg gatggaagca gtgtgccccg gggcccgcga 194940
ctcccccccc ccgacgcggg tccgcagctt cctctttttt ccctagggac gagtggcggc 195000
ggcgcgcgct tcgtcttctc cgcgtgtcct cgacggggac ttcctctttt tccgcgtctg 195060
gccgccgtcc gtcacccccc gggagttgct ctgcgcgtcc ccagggactc gcgctgccgt 195120
ccccagggac tccccttctt cttcctcttt tccccgggga ttcaaagaca cgcaacagca 195180
aagacagaca cgcaagacag gcgcgccgca cgtcgctttt attcgccgtc gccgtcctcc 195240
gcgaccgccg tgccccacca cacgcaactc caattttcac ccccccgcaa aaaacacccc 195300

-continued cccgcccttc gggcacccag cacacggccc ggaatggatg ccgggcgtcc acctaggtgt 195360
gtgcgcgctc ggcaggcgtc cgcctcgctg tgcgctcggg tggtcgtggc ctgccgcgcg 195420
tctgcctttg ggttttccac ggcgttccag actgcgcggc gccaaggcgg cgccagcaag 195480
cgccgtgcac gccgctgcct ataaaagcca ggtgcgtgtc ggccgtggca cacgggctac 195540
ggaggcgtcc gcgtgtgtaa acggcgtggt cgctgacgcg ggtttggttc ctatatagtg 195600
gacgtcggag gtgtccggcg gccatggccc agcgcaacgg catgtcgccg cgcccccgc 195660 ccctcggtcg cggccgcgga gccggagggc cttcgggggt tggttcctct ccttcgtctt 195720
cttcttgtgt gccgatggga gcgacgtcaa cagcggggac tggtgcgagt actgcgggta 195780
cggcgacgcc ggtccacggc gtccaccgcg tagaaccccg cgggccgccg ggcgcccctc 195840
cgggtagcgg caacaacagc aacttttggc acgggccgga gcgcttgctg ctgtctcaga 195900
ttccggtgga gcgccaggcg ctgacggagc tggaatacca ggccatgggc gccgtgtggc 195960
gcgcggcgtt tttggccaac agcacgggcc gcgccatgcg caagtggtcg cagcgcgacg 196020
cgggcacgct cctgccgctc ggacggccgt acggattcta cgcgcgggtg acgccgcgca 196080
gccagatgaa cggcgtgggc gcgacggacc tgcgtcagct gtcgccgcgg gacgcgtgga 196140
tcgtgctggt ggcgaccgtg gtgcacgagg tggaccccgc ggccgacccg acggtgggcg 196200
acaaggccgg ccatcccgag ggtctgtgcg cgcaggacgg actgtacctg gcgctgggcg 196260
ccgggttccg cgtgttcgtg tacgacctgg cgaacaacac actgatccta gcggcgcgcg 196320
acgcggacga gtggtttcgg cacggcgcgg gcgaggtggt gcggctgtac cgctgcaacc 196380
ggctgggcgt gggcaccccg cgcgcgacgc tgctgcctca gccggcgctt cgacagacgt 196440
tgctgcgcgc cgaggaggcg acggcgctcg gacgggagct gcgccggcgg tgggccggca 196500
cgacggtggc actgcagacg ccgggaaggc gactgcagcc gatggtgctg ctgggcgcgt 196560
ggcaggagct ggcgcagtac gaaccgttcg cgtcggcgcc gcaccccgcg tcgctgctga 196620
cggccgtgcg tcggcacctg aaccagcgtc tgtgctgcgg ctggctggcg ctgggcgcgg 196680
tgctgccgtc gcggtggctg cgctgcgcgg cggggccggc gacagggacg gtggcgggga 196740
cgacgccgat gacggcgggg acgacggcga tggcgacggg gacgacgttg ctggcggggg 196800
cgagcagcac ggagacggag gccgccggcg gggacgcgcc gtgcgcgatc gcgggagccg 196860
tggggtctgc tgtgacttta cctccgcagc cgtacggcac ctccgccggc gggaacgcgg 196920
tgtgcgtgcc aaacgcggac gcgcacgcgg cggtcggaac ggatgcggcg gcggcagcag 196980
cggcggcgcc gacggtgatg gtgggtccga cggcgatggc gggtccggcg gcgtcgggga 197040
ccgtgccgcg cgccatgctg gtggtggtgc tggacgagct gggcgccgtg ttcgggtact 197100
gcccgctgga cgggcacgtg tacccgctag cggcggagct gtcgcacttt ctgcgcgcgg 197160
gcgtgctggg cgcgctggcg ctgggacgcg agtcggcgcc cgccgccgag gccgcgcggc 197220
ggctgctgcc cgagctggac cgcgagcagt gggagcggcc gcgctgggac gcgctgcacc 197280
tgcacccgcg cgccgcgctg tgggcgcgcg agccgcacgg gcagtgggag ttcatgtttc 197340
gcgaacaacg cggtgacccc ataaatgatc ccgtcgcatt tcgtctttcg gacgctcgaa 197400
ctctcggtct cgacctcacc accgtcatga cagagcgtca aagccaattg cctgaaaagt 197460
atatcggctt ctatcagatt aggaaacctc cttggctcat ggaacaacct ccacccccat 197520
ctcgccaaac caaaccggac gctgcaacga tgcccccacc gctcagtgct caggcaagcg 197580
tcagctatgc gctccgatac gatgacgagt cctggcgccc gctcagcaca gttgacgacc 197640
acaaagcctg gttggatctc gacgaatcac attgggtcct cggggacagc cgacccgacg 197700

-continued

```
atataaaaca acgcagactg ctgaaggcca ctcaacgacg aggcgccgaa atcgacagac 197760
ccatgcctgt cgtgcccgaa gaatgttacg accaacggtt cactaccgaa ggccaccagg 197820
tcatcccgtt gtgcgcgtcc gaacccgagg atgacgacga agatcccacc tacgatgaat 197880
taccgtcgcg cccaccccag aaacataagc cgccagacaa acctccgcgc ttatgcaaaa 197940
cgggccccgg cccacctccg ctgccgccaa agcaacggca cggttccacc gacggaaaag 198000
tttctgcgcc ccgacagtcg gagcatcata aaagacagac ccgaccgcca aggccgccac 198060
cgcccaaatt cggggataga accgcggccc atctctcgca aaatatgcga gacatgtacc 198120
tcgatatgtg tacatcttcg ggccacaggc cacggccgcc agcacctccg cggccgaaaa 198180
aatgtcaaac acacgcccct caccacgttc atcattgaaa gtctctccag tccatatgtt 198240
gtcaggacgt gctgtcgttc tccgcttgct gcgaagcccg ttcttccgag tcgtgtcgct 198300
gcgtccagcg tcgcgcccaa gatgggaatt tgggtctctt cacgcgtagc ctcctccacc 198360
acggctgctg atcgccgtca ctaaggaccg acacggagga tgacgaggag cttctccccg 198420
actccgcggt ccgcgaccgg ctacgtagcg cgtgtccctg ccagtctccg cagttacacc 198480
acacgtcgtg agcagcgtgc acctgctgcc gccactgggc ctcggcgtgc tcaggccacc 198540
cgccggagcc cggtctgagc tccgacgcag gatgcgcgta ctcaacgtgc gccttccagt 198600
ccatacagca acaccatagg tcgtgcgagt cgtcggctac ccgccgccag gccagttccc 198660
gcatgggaag gctggacacg ccgaccgaga ggtcaccgag cccggacgcc atatcttctt 198720
cctctccgtc gctgtcatta agcagccagg tcacctcctc cgctccgcgg tccgccggtc 198780
tcgacggacc gcgccgccgt cggcaacacg gaaaacagca cgccagcccg agccgctaag 198840
gccgcatgcc cctgccgccc gactgagcac gcataccccg ctcaactgcg ttttgccacc 198900
cctgccagtg ctctcgctcg agcaccaccc cgcatctccc aaccttttc caataaacga 198960
aaccgacatg acacacgtaa tgggtactcg tggctagatt tattgaaata aaccgcgatc 199020
ccgggcgtct cagcacacga aaaaccgcat ccacatcata gacaagttac agtccacagt 199080
cacatacacg ataaacaata ccaacagggt aatgtttatg gagtaaaaca ctattgtcca 199140
ggccacatgc gtatatgact tccgcaccat cccgtactgc atgttccaca tgtacgcgct 199200
agacgtgtaa tccactcgca gttcggggac gcaacgcagc cagatcacat ccccttgcag 199260
taccagacgc agggctagcg tctcgaagat cggcatcaca tctaagttcc gcacgttcca 199320
ctttaacgac tccccgggaa cgaactccac gtcgtccgcg tgtacgtaca ggttctctcc 199380
cacgccgcca taatcggcct ttggatcgaa gacgaaccga ctcatgttgc ccacgatgct 199440
cccccgagca aataacttgc cgttgtcaat gtggcaccgg ttgtcctcga tctgaaacca 199500
gggatgcttg gccgtggact tccagggccg gagcgcgtct tccccggctt tagtgatgcc 199560
atcgggcagg cggatcaagg gacccatgga agtccaaaga cccacccagg ctttccagag 199620
attgttcatg gtgaaacagc gtgtggactg tacgctcttt cccaatttat atcccagagt 199680
agtgacgtga acccagccac ctcccagatt cctgacgttt tggttgtctt tcctgtcaat 199740
ttctcccgta aacttatgat tatcctagcc cattcccgat aaaaatacac ggagacagta 199800
gatagagtta cgaataaacc ggtttattta ttcaagtgtc tcaggagatt cttgagcgag 199860
cgtggatacc acgccgtcgt cagttcatgg tggcattgag cagccatagc accagagtcc 199920
cggcgcccgg tatcagacac gctgacctac cggacgcctc tgagtccgta ccccgcggcc 199980
tgggtgttag agtccgtacc ttgcagccca ggtaggtttc aggtaccagc tggttcgtac 200040
ctgttaaata aatcgcagac gggcgctcac ccttacggtc aggagcacaa gaacaaccag 200100
```

agagaacaga tatacgagca gggttctgaa cagcagaccc caattgtcgt ctctcatgct 200160
tcgctgaagg taccagttga tggtctgaga gctatagtcc atcctcacct gaggaacaca 200220
cgcagcatat ttcttggggt ctccccacct cgtagacaac gtgatgtcca ccatatccac 200280
ggtgtgcgtc accgggtgcc caccgatgtt ccactcgaaa taggctccgc gctcatcatg 200340
gtggtactgc tcaccggaca cctgcagtct gtccatgtaa gattgagaga cgatacccac 200400
gttcacaaag tgtctctcgc tgaagttgcc cgacatcctc cccttgaagt acagcatgcc 200460
catatggaac cagcattggt tctcctccac ccgaaagtgg gccgatctga tctccgatac 200520
caccacatcc agaggccggg gcaccgagtc cgcgagtctc aggaacaaga cggccaggat 200580
cgcgagcacc aacaccggct tcatgactcc gaaggtccgc tgctcggctc cgctcaccgc 200640
tccggtctgg ctgcagcagt gcttcgctga gaagtagcgt gtggactgca cggtgttttt 200700
gaatatatag cgtttcttgg tgacgttgtt tcccctacgt agtaggcaac tacgtgccaa 200760
aagaggcgtt acggtacttt ccgtactggg atttccaaac cgggactttc cacacggcag 200820
tttcaacacc gggactttcc acacggcagt ttcaacaccg ggacttttca cacggtgatt 200880
tcgccaccgg gactttccgt acggcggttt cgccaccgct gacgttctca tcgccgccca 200940
cgtcaacggt ggcgacaccg tactttccca tgcggtttat aaacgtcaag agtcacgtca 201000
gtcgcccacc ccattacacg gcgatatccc gatagggcat gagggggccc gggtgtcgcg 201060
acatgtcgac gacaggtgcg gattagtggt cgtgtcgcga catggacgtg caggggggatg 201120
tctatcgcga tagagtcgat gtgacagccc gctgcacctc tctgtcgcga catgcgtaca 201180
cgacgggccg gcttgtcggc gattgtcgcg acatatcgtt atcggttaac gaccggagtt 201240
gtctatcgcg acatatcgtc gactatcgcg acagaaaaaa ataccgttcg tagagaatgc 201300
cgtgttgaag gaacgcgctt ttattaagac gattaaacag cattaggagc cgcaacgtcg 201360
aattccacgt ccagtcgatt cgtatgttat gctgcacagc aatgctagaa tgacaaccag 201420
cagggtaatc ccgcaacata gatacaaagt cacagcgaag aatccgtgtc gttctatcaa 201480
gcgaaacgcg ttccaaacgg ccccgtcaca gacgcagtta ttcataagcg ttaacaaccg 201540
gtggctagga tgaatatcca aatcacaggg cagtagccga ctgactcgtt ggcaggtcag 201600
cctaccctca aggtttctat cgtttgaacg ggatttgtgc gttttaggcc tctttttctc 201660
cgcctgcaag cattggtgcg caaagtcctc acctagctgt ttccagctat catctgcatc 201720
tgtgcagtcc cctgtatcgt tgtgacaaac gggtctgtgc gactttgttc tcggaacaca 201780
agcttgttgt cgcggtgaca gagagagaag ggttttcggg tcacgcgaag accgctcacc 201840
gggggtcggc aacgcacaca tcaacagaaa accgagacgg atcaagaggt ccatagtgaa 201900
gaaggagcga tatcgacgta cttacgaaac ggcgattata tatgttctca acaataccgc 201960
cctacgttgt atgatgtaac gtgtgacgta agtctgatcc aacactgaac gctttcgtcg 202020
tgtttttcat gcagctttta cggaccatga caagcctgac gagagcgttc atcggggcat 202080
gaagtacgca ctacacagac aaaccctatg tatttgttac gatagaatac ggaacggagg 202140
aggctttcgc cacacctatc ctgaaagcgt tgcattcttt atgataggtg tgacgatgtc 202200
tttaccattc ccacggctgc tttgcgtgat gatgacattc atcatgtatt tccattcaca 202260
catacctttt gtgcatacga tttatatatg atcatccacg cttataacga gcctaacagt 202320
ttattagccc ttgacaggat aggtcaaaag attatatgta ggttttccgg taaaccgaat 202380
tgtgatgttt ctctgcagga aataaaacag cctggtacct atgaaacgga caatgcagta 202440
ctgtagcagc gtaaccaagt aggtccacat gaacacgtac aaaattatgg taagccatcg 202500
tttttcgtgc cacagcctgt agctgtcgta catgaatgag gacggtctag ggatccaggg 202560
tagttgtaat tgggggcaac attcgtaccg tccagaagac agtcgcacgg gtttcagtga 202620
gatgagtact ttagcgatgt tcgcggggac gctgcgtttc accgtgacgg tgagaatttg 202680
accgtcgttt tgtacttcat gaggcacgtt atacaagcca ctggtatcat gaaggatgac 202740
ctctgatgcg atgtgaggat taaattgtcc ctcaaaccgc caaacgctgg tcatgttacc 202800
accgtcaatt acgcagctga cggtgtgaga taccacgatg ttggacttag gtctgggggc 202860
taattgcctt tttacaaatt ccctttggta ttgcaggtcc tgctgccact gcttttccgt 202920
gcggaaagtc ggcacgtctt ccgcacgttt agcgacgata gacgccacca aggtagatgc 202980
cagaagcagc tggatccgca tggtattacc gtatgtcaat tagaaagttg aacggacacg 203040
gttattgttt ctggcggata taagtatata aacgcgagtt agcctttccc gtccgttttg 203100
tacacccgtt ccccacacaa atgacgaata cggccttttt tttataaaaa taaaccacgt 203160
gtattatata aaaacattta catagaaaag agacacacgg atcaacataa ggacttttca 203220
cacttttggg gtacacaggc gtgccaccgc agatagtaag cgctggatac atggtacaca 203280
gtcctggcca gcacgtatcc caacagcagc accatcgcca tctgtatggc gatcacgacc 203340
ccgagctcta agtgtctgta ttcatagtgt agtcgtcgca ggttatccac tgaattcccg 203400
tagctgaaat aacgtatatg gtaccgaggc tggcaccaca tgggtttgca tttggagcac 203460
ggcaccaaat gcagagtgag atggtccaag tccgtgggca cccactggcg caaacggaat 203520
acggcttcgg tggtctccac gaggcactcc ggggcttgca gacggcccca ctttcgtccg 203580
tgacggcccg accagccgac ccgagccact atccctttct cgggatagaa cgtaccctgt 203640
acacgccaca cagcgtccaa cacgccgtcc ttgacgacgc agctggcctg atagctggac 203700
acgttgttaa gcggcggaaa gcgaaactga cgtgccggcg gagccacata gttcggttca 203760
ccgtgttgtc gcggttcgtc ctccctatag taatagtagt cgtcgtcctc ataggggttg 203820
ccggcgtgag ccagcgttac ccaacagcag cccaggccga cgaggaggcg cagccaccgc 203880
ctcatggcgg cttcgccagt caatcgtctt tagcctcttc ttcccgtgag gtccttccgg 203940
tggcgcggtg ccgacctcgg acccagggac gtatccacct caggtacaca caacaggcta 204000
cctggacacc gaagctgaac aaggctacgt gtttcacaaa ctgcaccagt accacataga 204060
ggaatgtcag gtagcgtctt tccgcaaaca gccgttccaa gtctgagggc gttacccgca 204120
gcggcaacca gggcagcctg gacgccggcc ggcaatggag cacgctccgg ttacaggcac 204180
tgcaggggta aacggttaac atcacgtaag agagtcgtgc gtccacctgt gggagctcag 204240
tttcgtaacg tagagccccg tcattttcca gctggggtgc gccgaccttg aaatgggtcg 204300
cgctccgctc gttaccccag gtgccgtagg ctctcggggc cgtatcggag aagttgccgc 204360
gcacaagcca ggcggccacg agtaccccgt gctggacgta acattcggac acggaactgg 204420
agacacggta gccggacacg tccccaaacc cgcgagggta ctggggcaga cggacggact 204480
tgctatttga caacggacag atacgagacg acgaggacgc agacgactcg tcgttggacc 204540
acgacaatcg gagcgactgc ttggagcggt tcgagagtac acttactgcg atcagacacc 204600
agtgccagaa gaaggaacag gtggacgggg accacaggat catagccgcc ggcaccgcgg 204660
ccggccgcag gaagccgccc ggcgcgtcgt ctgtgtgcgg gagccgaaac accgtgcctc 204720
tttatatcgt cccgacgtga cgcgagtatt acgtgtcagg ggaaaccccc gtcatgacga 204780
acgtgatttg taagtgacgc ggggtgctga cggggttcgg cccgagaggt gacggagcgc 204840
ctcacgtcag tatgatgtcc gatccgcgtc agccccgacg tggttatggt caccgaaacc 204900

-continued cacgtttata tggacgttga aaacagcgcc tgaccacatg attcatcata ccatttctcg 204960
gaatcgggcc catgccggga aagcacattc cttttcagta aacaacaatg acatcataac 205020
aaatcatttt attcgcgagg tggataataa ccgcatatca ggaggaggga tcgggtgatg 205080
acgcaggccc cgcaaaacag tccgaaataa atttttagta tcgccccgta gtcgcctaga 205140
taccagaggt acgtcaagtt catcaaaacg cccatcggcg tcccggaatc gtataccgga 205200
cacacgaagc gttcataaca atcccgggag gcgagtgtta gggtagcaga atagtttcgg 205260
ggtcggtttc cttccggcga cgacagctcc gtgggcagca gaatgtagag cgcctcggta 205320
gccgtcgcgg tgccttccac gaggatgggc tgccggtgcc tttcgtgatt ttctccgtcg 205380
tgtagccaag ccgaggcccg caaagtctta ggcgagggga attgtccata gagtttcact 205440
gcacctttca gtacatgatt ctgaataaca cagccgcacg taaagtaggt cggttctctc 205500
gtctcctccg tggctgccgc caccactccc agccaccaca acaggcaggt cgcgagaggg 205560
ttccggaggc ttccccggcg tagcatggtt tcgggttaaa gcaaagagtc tggtgagtcg 205620
tttccgagcg actcgagatg cactccgctt cagtctatat atcaccactg gtccgaaaac 205680
atccagggaa aatgtcggtg cagccaacct ttcacataca gcccccaaaa cacttgaatc 205740
actgccacca tcatcagcgt atactgcgcc gacttaatcg tgagcgtgta gtacgccatc 205800
agacggcgat cttcgaacaa tagtcgttcg atgtcctcta acgagctcca caggggaacc 205860
caaggcacga ggcaccgggg ttcgcactct acataataag tttggcattg gtggcagggg 205920
gaaaagtaga acaatacgag ttttgtgcgt tggggaacac gatagtcccg gagccagtag 205980
cgttttgcga cgaggctttc ggagatatcc tccaccggcg tcggcactcg atccgcgtag 206040
ccctccagcg tctggtagta cacccggggt gtcggcgtgg gcacggacag gttcccgcgc 206100
agggtccaca gagcctccag tcgaccgccc gatcggagca cgcagcgcgc ctcggaatac 206160
tctactcggt actccgaaac atcgggcaga ggcggtaacg gctccgtctc caccaagggc 206220
ggaggttcat cgaaaagagt caaggataat tcaggcatac tacctgcgac cggggcccag 206280
agggctagga taagcattac aagattcatt ctgtcttaca agggaaggct gttcccctgt 206340
ccagactcaa aagctgtaag gctgtcttat agcatgtagt cttgcacgtc acgaggaaca 206400
gggtggtgat ctagtgacgt cgggagaaca cggtgtttta gggtgcgggg gacaaaggac 206460
agtacgacag attaggtgat agaaacgttt tttttattta tgaaaaagcc agtgtgccgt 206520
gcgacctagg gccccggcgt agtttggata ccagatgggg gccgtcaggg gtactaccac 206580
gagcagaaac ataatgactt ggtccatgta tagcagcata gcggtgcgta gcaggtcgcc 206640
gtccgtgtag caatttgacg gtgagcgata aagcaccgtt aatgtgtcgc ggataagcac 206700
gatcttgagg ccgtagatga agctcacagt cagtgctaaa atgatgcgtt ggtatggttc 206760
ccaggactgc acggcaatga agagccagag tatgggaagc atgaagctta gcaaacagag 206820
gatggctaac cgtcgttgta tgttccaggc catgagccag gctaggcccg tacaccagac 206880
gcagagcatg gatgacagga cataggcctg gattaccacg gtgcgatcga aacacagccc 206940
gatggtggac acggatatcg tagtgagggt ggtatatacc atgaccagca tcagggtccc 207000
gggtcggcgc tgacgttcca gccagtacgc atggcaacgc agagcgcagg gtagcagtgt 207060
gctccagaag ggcagtgtat cgcgcaggta gggggtcgtc acgcgccacg gtatgagcat 207120
gaaaaggatg gtagtggcta tggtggcgct ggtctggaac acgacggtgc cgtagagacg 207180
taccatccag agaaagtgtt gaacgctccg cagggtgtct tcatctttgg tgattacggt 207240
gactcgacgg atcggcggtg gtgacggcgg cgacacgggt gggggtttct ctttcttatg 207300
gccgagtggc tcgccttggt gaaactggat ctgtaccatg acgggtgctc gacgaacagt 207360
cgtcggggct tcaggtaccc ggcaagtttt atagagaaag gggacgatg ggtggtggct 207420 acgagccacc gccaccttcg caatacgagg atctgaaggc ggcaaagacg gtcgtccagg 207480
gcaggcgcca gaggttggga ctgagcacga tcagcgtgat tttaaacatg gtcaccagtc 207540
ctacgtagat cagcagcgag ccgcgtaacg tctgagcagc cggcagttcg tcgcggatgt 207600
aacgcgtgcc gtagaaagtc acggtcatca taaggaagac gatggcgccg tagccgtaga 207660
gtagaatacg ctgatgatgg aacacggtct ggtcgccgat aatccagagc gtgatgaaaa 207720
aaacgctggt gagcacccgt gagcatatga gctcccaacg cttagcgcga aagctgtccc 207780
caaccatgac agcgccggtg caagctatcc acagcgtgag gaccagtgtg tagtcgatga 207840
ggatggcggg caggtcggag caccaggtgt agaaaaccgt ggtaacggag aggaggccta 207900
cgtagctcat ggtcaatacc acgtcgtcgg ggtgcctttc gccctgtatc aagaccaaac 207960
accagagaag ggagggggca aaaaccagca gcagagggga agattcatgt tgacatatgt 208020
tgtgggaatc ggggataccc agccaaatca ttccgcagaa agccgtactg atggcgatgt 208080
gaaagaccac tagggcgtag acccggacga ggacagcaaa acggcgcagc cacataaggc 208140
cgtggtgcag ctgcaggaga gaagcccatt gcggcgaatg tagcgacggc agcggcgggt 208200
ccatgaggcg ggtggtgcgc ccgagtgaac gggtgagcgt ctcggtggag tcttcttata 208260
aaccagcggg tctcaagcaa ccctgctctg gaacgtcgcg gtggtgctgt tgaggatgac 208320
gctgagcgtg ccgttgtcaa tccggtaatg atgataggtg ccaagcttgg ccaggtagct 208380
gaacatttgg tcccagcgtg ccgaccacac cacgggcgtg agcatcagga gtgtggtgtg 208440
ataaatgagt gtttcggtgg cgtaaagtat cagcgagctg cggatgatgt ggctcacggg 208500
cattttggtg gcgatgtagc gcacgtcttg gaaaagaacg gccaggatgc agcccacgaa 208560
cacggtgtag agacacagca gagtcttatg taaccaggtg taagtagaag ccaggacgct 208620
gaccatcacc gtcaaaagtg tggaggtaaa aagcgcgtca cgccacacgg aactgagacg 208680
gtgctcccaa gccacgccgt tgcaggccac gaacaacgtc cacgttaaga tgaggctgga 208740
aacgccaatg ggcgctgtgg cgcacaggtt gagcccggcg gtggtgaacg acagaagcgc 208800
cacatacagc gcaaacacca ggccgttgct ggggtgtctg tgatcggtaa gctccagcgc 208860
gcccagaacc aacaccggtg tgcagctaag caataacggc gaaggatcgt cgcggcactc 208920
gtagcccagc gaggggtaac ctagccaaac cagcgcgcta atgagcacgc taaaagcggt 208980
ttccagcgtc agcaatccgt agacacgcat gacgatcgcg gtccgccgta gccaacacac 209040
cgcatcttcg gaagctgtgg acgctgtttc cgaataccgg gaggagatcg tgcttccctc 209100
ttccaaggat cggaaagtag cgtccgtcgt ttccgcggac gcggcttccc tggtacgctc 209160
cgtttccgac gacgcggttt cccgctgcgt ggaaactgtc tccatgtcgg gaccgcagcg 209220
cccggcggcg tatccgcaag gtctcgaagc tacagcttgt cagaggaaaa gtaggtttgc 209280
aaaaaggtgc gcagggtcat gattctcagc accatcagca aagtgaaaac caggctgaga 209340
aacaccttga cggccgccaa aagcgcgcgt tccagcggcg tctcgtagcg cacagccagg 209400
gccgcttcgt ggaaatgcga gacggctaga caggtaatga gcacgctgaa ggacaagacg 209460
atcttaaagc acaaggacca accacgcctc aagatgacca ccacgattgc cgtgaaggtc 209520
aacgtgatca aagcatggac gaccacaatc tgacggcgga cggtacgttc gggagccaac 209580
aacgctacgc cggtgcagct gagaaaggcc agtaaggtga acaacgcggc cgagatgacc 209640
aacgtaccgt ccaggcagag acatatcacg atcaacggcg gcacgtgaag cagcgtgtaa 209700
aagagcagaa cgccgatatt gctgggatgc gatgtttcgt aacagtgaat gaagatcacc 209760
gacgtgacgg gtatgacaaa gacgaggctg ggcgaggact ccgtgagaca cagacgggaa 209820
tggtgaaacc acgtcgcggg cgccgcgtag cagaaggcgc tcaacaacgc ggtcaagccg 209880
gccagctgcc aacccacggc gccataggtg tgcagcgcca cgcggcaaca atcgacccaa 209940
gccagactgc gggtcaccag ccgggtctct tggatcccgg ggggcacgta gatgaccgtg 210000
ccatcggtgg gtacttgaaa cccttttct cttctcatgg tgcgctgcgt tctctggaaa 210060
cggccgctct gcccgaaaac cagttccgaa cgaaaatcta gggcgagagg gtggacaacg 210120
gcgtcgacga cgaagcatgg gacaggtcgt tcggcgttaa cgtcatcgcg tcggacgacg 210180
gtagttctaa gagacgtaga tcgctcagca ggtcctgaca gttgcggatt cgcaagatca 210240
gaaaaaaaag ggaaatgaac gtaataaaga gctgtagcga cgtatgcgct acatcgcgtg 210300
gcataagaac gtgacggacg aaaaggacct gctgcgaaaa gtggccggcg aagataaggc 210360
ccaccgtgct gtagaagccc aaaagcagcc gcaggggcca agtccagggc cgcgtaaaga 210420
cgatgagaac gttaaccaga aagaccacga cccagacgcc gttgatgagg gtaaattgat 210480
cggacagggt gcagttgtcg cgacagatga agactacttc cgcgcagagc aaggtgatga 210540
ccaacgtgag cacaaacgac gtcaacacct cgcggggctc ctggcaggca cacgtgacac 210600
ctagcgccgg gatgtgcgcc aggaggccgg cgagtaatag caccagctgt cggaacggac 210660
gacggcagcg cgggtgccgg tttcgctgag cgagaaccgg tcgctcatag cggaaataca 210720
cgaagagcgc ggaggccaca ggcaccagga ggagcacttc gggcgcccag acaacgtgac 210780
aaggaaagcc cggacgcgac ttaagagtcg ctgtagggaa gaccagagag aagctaccca 210840
agacggccac cgccgcggag atttgaaaga ggagcaagcc ggcgattcgg acgacaacct 210900
cgaagcgatg cacccagccc agcacggcca ccacggccgc ttcatcatag tcgtcgttgt 210960
tgccgctgtc gaacagccgc cgaaacacga tctgtcgctg ggtcgcggtg ggaaagcgca 211020
gacccatgac agccggaggc tatatgaccg cgcgtctaag gcgcgagatc cgtgggggga 211080
cttttagatg tttgggcggc ccgcggttct aacaggcttg attggtggag acggccggcg 211140
cggcgggtgg gggaaacgac gagtttttcc gttacgccat ggttcgcgtg aggtttctct 211200
gtacctcccg caaaaggtca cagcctgaaa tggaggccgc gttggtggcc ccggtggcgc 211260
gtgacgataa ccaggtcatc caagcgatga gtttgtctaa tgagtcctcg gtggtgaaga 211320
ggataagaat gagcagatac aggtacacca ggttctcata gagacacaaa gtgagcaggt 211380
cggcctcgga ccacgcaatc tcaaacaggc gcgtggtgtc aaagaccgtg acgaccagca 211440
tgaagctcag cgccatggcg taatagccca aaaaaagttt gtgccccaac ggtacgggct 211500
gcaggtaaag tgcgatcaag aacgcgataa cgccgatcac aaacagcgtg acgatgacct 211560
gccatcgacg gtgattatgg ccggctagac ccgtgacgca gctgcagagg ctaaaaagca 211620
cgcaagccaa gaggcccgag aaggtcacca gcgtagagga ggagcaggcg ctggccacga 211680
tcaccgaaag cgtcgtgagc acgctataaa tggtaagcag gcccgggctc ggcggcgacg 211740
tgaacgatcc ttcatcgcgt ttgccatgca gcagggccaa acagatggtg ggcaccatca 211800
aactcaaggg cggcataaag ccggtgcaac agagaaagac ggtgccttta agatgcggaa 211860
aagccagcac caggcccaga cagagcaaga aggtgcaggt gccctgcacg gccacggtgc 211920
tgtagacccg catacaaagt aaaaagcgac gtacgtcgtt cgtcgagacg gaggaaatca 211980
taatgactcc gcgcgagggt cgcgggggtg gggcgcccca ggccgtcccg gtggcctctg 212040
agttcggaga catgacggcg gtggctatca acaggcgcgt atgagaaacc gtttatagag 212100

-continued tgtaatagaa tcaccgtcat tcccacacgg cgttccccca taaagtcacg tcacactcga 212160
gtaagcgtga aaaagcttta ttgttgaata aaaaacacga gtacaacacc gagttgcggt 212220
gtcctgtctg tctactgggt gggggaggtt catcgtctgt ctctagaggg aaggtgggga 212280
acgtctaagc gagcgggagc gtgtcatctc ccccatcttt ttacaacaag ctgaggagac 212340
tcacgccgtc gatgcgtccg ccgtgtttct cggcgtactg ctgcacccag acgtggccgc 212400
taaagatggc gacgctcatg tttaggagac tcatgacgat ggtgtacaac acgacgctga 212460
cacagacgct gtttttagac agcgttccac gctggtagat gagatccagg gtctcgtaaa 212520
taagcacggc cgaagcggcg gtcaccacca ggacgtagag tccgctgtag atcttgctga 212580
cccacagcac gggcgaaaag taaagcaata ggtaaaagac gatgacggac cagccgtagc 212640
caatcccgat gactttccag cgcgtgggat tgttgccggc caggtaggtg agaccgctgc 212700
agagaacgaa aaagaccatc accagggcaa acgacagacc gatgacgcgc ctttctccgc 212760
aaaagcccgt gcacacggtg atgccggtgt tgatcagcag gcacgccacc gtgagatgag 212820
caaaattggt ggtgtgtggg cgaaactcgg cgaaaccgcg tagcatggcc agcgtggaca 212880
cgggcacgat ggaggacagg gctggcacta tgccgttggc gcactgtccc tgcacatcgg 212940
ggaaggcgag ccaagccagc aggcagaccg tgagggtaca agccagctgc cacacgagcc 213000
cgtgatagac ctccatgagc agcttgaagc gtttcaacca ctggaagagc tgctgttcgg 213060
ccaccagcgc gtggctgcga tggagcggca cgatggtgac cgtcggcgac tcatggtgtt 213120
cggaaaccga ggcggtgtcg cccatgctgc cgcttacgac cgctgtcggt ctaaggtagg 213180
cgtcgatgaa acagtccgtc ttatcagcac ccggttaccg cggatttgat tgacgtcacg 213240
agtgtggtca aaccgtggcg gcaccctgta tccgacccgt cgtcatgggc tccacaacca 213300
gagcctcaga agatggtaca tgccgatgaa taaagccaca ttttcgacat agaggcgtag 213360
cgagggctga aaactctccg ggaaagaact ctgacaggtg atcagggaca gatcgtgaat 213420
tagcatcagc gtcaccgtca acagcgtcgt cgcgtgtaaa ccgagaaaga acggggtcgc 213480
ggcccgcagc agccaaagtc ccagcgccgt agcgcagagc agagacagga ccgacggtag 213540
ccacagccgc cggagagacg agccaggatc gcaacccaaa agcgaggccc ccagacagcc 213600
gagatctacc gccagggcga gaagagccgc gccgagaaag gcctgcggcg acggctggca 213660
cattagcaag gtcagaaagg ctagcgcgtg cggcaggcag taagccaaca ggagtgggag 213720
tttgcgggga caacggtcga gcgacggacc gcgtagcagc aggaacaggc agccgacggg 213780
cacgacgagg ctgagatgag aaagcggcgg tgggtcgtcg tcccgtcccc gctcgcatag 213840
ctcggccacc ggtggcggca tgagccacca gctgagcacg ctgagggcga cggtggcggt 213900
aagctggaag gcgacgagga cggaggcgcg cagccatacc gccagcctct ctaggtaggg 213960
gactacctcc tcgacggtcc attctagcgg gacgacatga agcatggcga caagcgcggc 214020
tgctctgaaa acgggcacgg ttttataggc attaggacgt ccccgtcgta ctggcggctg 214080
tcaaagtccc gttgtccaaa gacgcgccgt ccgaaagact aatccaacgg ggacccgaga 214140
gcatgagcaa caacgtgaga aagatggcca tgctgtccag gtagagacag acggcatgac 214200
ggatgcactg gttaggtggg cagaaaaaga tgaccatgag actgtcgtag gccagaatac 214260
ccaaaaagaa gctgatggag aaggcgcaca acgtcaccac tatcttctgc agccagtcgg 214320
cgtcgcttag cagagcgagc gtgaggaacg aaagcagcat caccacgtag acgcagctga 214380
tgcatttcca acgacgtcgg tcacggccac ctagaaacgc cagccccgta aaggagataa 214440
acaacgccag ggtcatcacg taggaaccta ctagtacgcg gctttcagag cacatttgga 214500

-continued agatggccgc cgtcaggctg ttggccaaca gatagatgaa aagcaccgtg gcgttactag 214560
ggtgctcgtt gcccaacgtg tacgtgatga acatgcagac gatgggcacg agcacggtga 214620
gaaagaagct gtagttctcg acgcaaaagt tgcggttttg tgggaacccc aaccaaaaaa 214680
cgcttcccaa gccgaagctg aaagccagct gaaagatgaa gatggcgtac acgcgcagcc 214740
atacggtgaa ctttttgaac cactcgagag cctccatgcg ggagagcagc agcgcgttag 214800
cctcctgcgc ctgcatggtg gcgacggtct cggcacaaag ccgctgcggc gcacctaccc 214860
ttctcttata cacaagcgag cgagtggggc acggtgacgt ggtcacgccg cggacacgtc 214920
gattaggaga cgaactggga cgacgccgct gctgtggcag cgaccgtcgt agcgaccgtc 214980
gtctgagcag tgtgggcgct gccgggctcg gagggcatga agtagagcac ggagacaaag 215040
aggtacatga ggtccatgta caagcagagc gcgcccggga tataactctc atactcgatg 215100
tcgtgcagga tgtcctgcgt atcgcacacc accgaggtca cgatgacggc caaaccggct 215160
atcatcacca ggatctcact taccgcctcg ggaaaaagag aaaatatggc gaacagtaag 215220
agaatcagcg tggatgcgcc cgtcaatagg gaacgctgta attccacgtc gcgggcaaac 215280
agatacgtag cgagcgtaag gaaacaaaat agcgtcactg tggccaccat ggcataaatg 215340
actgaacgat gactaaagtg gaagcctgac gccgtgacag ccacgctggt aagcaacgtg 215400
tacgtcagta agatccatac gtttttggga aagttgggct cggcccaacg caacagacct 215460
aagcacacga tggagatcat taagcaagac agcgtcagac gcacgctgga aaagagctgc 215520
tccagccggt gcggcaacac cagccagcaa aaggcgcaga cgctcataag gatgaggcat 215580
tgcacccaga taaggatgta gatgcgcagc aggaagaccg accgggctat ctggacctga 215640
ccgcggagcg acatggcggc aacgccggcg gttatcgccg agattcgtct aaatacacga 215700
agcgaactag aaaacgcaca cacgttattt gcaaaaagaa agcagctgcc ggcttattat 215760
tttattaaaa atttatctgt gcagaatcat aagtttatga tgaataaaaa cggggaaagg 215820
gaatctgctt ttagggaccc gggtctggtc cgtcgtctcc catctggtcg ggttcgggga 215880
tggggacctg tttcagcgtg tgtccgcggg cgtgcatggc ttttgctcgc cggccgcgct 215940
gtaaccaggc ctctttctct gtggtcggcg agtcttccga cgggtaggga gtctgggagt 216000
ccatcgcttc aggcccaccg ctcgttccct cgaccgtcgt gtcgtcctcg ttttcgctat 216060
tacacggggt ttctggagta tcgcctatac ggttggcgat tctccggggg cggccgctct 216120
cgtcctcgtc gctgctatcg ccgcccggta attcgacgcc gcattcgttg tacggagcgc 216180
ggcacatggg cggcggaaag aacttgggca tgcgaaagca gcgttgtcca tccacggtct 216240
gcgtggtttc atcgttatcc tcccataatc ccccctgtag cgccggcagc gtttcgacgc 216300
tgtgagaggg gaaggcccag ttctggttgt cttgcagcgc gcccgtgggc agtaggtccg 216360
tgcggcccca ggcgctgctg ttgttgggta ccttgtcagt gccgcgagta ggtcgcagaa 216420
accagtccag agcgctctct agctgcgagc gtgtgatggt gcccagtgcg ccgtgccagc 216480
gcagcacgtc tcttttcagc gtgtggtgac agacgggcag ctcctccaac cgacactcgc 216540
cgcgcaatcc gcggtcgaag cggcagagac cacgcagttt aagcagaccg cacttgagaa 216600
acatgtgaaa attatcggca atgcgataca ggtctgagtc ctcgatcttg tgtaggtaga 216660
ccacgccaaa cttgtcgagc agcaccaggc cgctgggcac aaaaggcccg taggccaggt 216720
aatagcccac gaggccgacg acgtaccact cgcagcacaa gcgttgacga ataaagttca 216780
gaagatcgcg aaagtccgcg gccggcatgt ggtcaaaagg ccggcaggcg cgcaggccct 216840
cgatggagcc cagcatgagc aacggctcca cctcggtgcg acccggcgtg cggatgacca 216900
ggttgagacc gctcatttcg cgggccgtct tggccacggc cgcagcgtca gtggggtcgg 216960
tgcagaggaa tttttgcaca tgatagcgcg gttcggtggt ggcgaacggc gtttgtgggt 217020
gccgatacac atattcgcac cagagtagac cgttcttgga aaaggctttg atatcactgg 217080
ccacctcgta gagcccgtcg gtctcccagt cgtagacgta gacggtgccg taatgactta 217140
gcatgagcac gcagggcagt tcctgcgcct gcttggtgtt tcgtgttaga tcgctgtcgg 217200
gtggacgcac ggctagtaca ccgacggctt ccagggtgtc atcgcagcag agatagtcgg 217260
cggccagaga acgtgcgtaa atctgcggga tggcggcctg ttcgcgcatc actaggaacc 217320
agttggcggg gttgcgcagt gctacggtgg ttccttggtg gcgctgcacg taggttctca 217380
gcgccggagg atcgtactgg cgcagataga ggccttgcag catcgataac gtcttttgaa 217440
agacggtgtt tctaaattgg aaaacgccgt agtcgcagcg gatagcatct tcgcagcgct 217500
cgtcgcgctg tcggagatag gtgccccagg cttcggcggc ggctttggtg agtagggaca 217560
tgccggcgga gccgtctcga cagcgagtcg gataaagcgc gctgcgcgaa agcttaatat 217620
aggagcagcg tcagacgaat cgcggctggt ggcccggggg gtgggacgcg ccgcctacac 217680
aaagtgctcc cgaaaatcga aactcttgac ccactccgga gacaaatccg tattcagatt 217740
gatgcgtcgc gcttccactt cggcttccga aacctcggcc tccgtccggt aggcgttaac 217800
aatacgctga cccaggtgcc aacgctcttt ctctgccaaa cgccgttgct caaaccactc 217860
gtctacgtcc ttgaggtcaa agacagtgtc ctcctcaagg tcaaagccta ggtcttccca 217920
ctcgtcgtca tcgctctcgt ggccgccggc catacgcgcg gcaactgcgt cttcccctcc 217980
tcttctttca acgttgggta ccacgttgtt ttcttcgggt tccatgggtt ctgcgccact 218040
gtcgtcatcg tcctctccct gctcctcatc gtccgccaag gcgtcgtgga tcacctccag 218100
gttctgattg tcgggtacga cgtggttatc ttcgtcgtcg tcgcgtggca tgggcggcgg 218160
ccgacggcgg acgaccggca tggcgcggcc gtcgtttcct tcgtcttcct cttcaccgtc 218220
tcccaaggaa cgcggtcgac gacgttccgc gaagtcgccg cggaccacgc gcgcctgcca 218280
aatggtaaac gcgtcccaac cgtcccagtt attgagcatt tcggcgcgaa aacggtcgcc 218340
tcgacagagc cagcgaaact gccgcgcgta gtcgcggtct acgccgctgt cgaacatggt 218400
aaagtgcaga cgcgccgcct cgcccatgtg tacgcagcct ccattgcgtt ccagcctggc 218460
cgcgcgccgc agaccgtgtt cgtagcggcg acgcacgtac accttcatga ggccggcgcg 218520
aaaaagttcc tctaggctgt cggccagacg gtagatttca ccggctagac gctgcagggg 218580
cggcgagcgg tccagatgcg acttgacaat caccacgtaa aaacgacaga aacggtcgaa 218640
gatgatgagg aaggacgtgt caaagaaacc accggcgcgg taggagccca cggcgcccag 218700
caggtaccag cggcaacgca gttgcagcgt gacgtacatt tcgcactcgg ccaagcgggc 218760
ggctggcgct acctcgaagg gccagcaatc cgtcaagcag ccgaaactgg tcaggagttt 218820
caacgttttg gcatggcgcc caggtgtgtg aaagttcacg tcgcgtccgt ggtgttcgcc 218880
aacgcaggcg gccaacgcgt cggcgtcatg agcgtgacgc agcagcatcg ctactacgtc 218940
gtgcggtacc cgcgtagcaa acggcgtctg tggctgacgg tacacggctt cggtgtacat 219000
cataccgtaa cgtgccagct cgtccagatg acgcgcgcac agcagcagaa tctcttgcga 219060
gggttcgtag atgtagaggc gcgtaccgcc acccatgcag agcaccagct ccgtctcttc 219120
gtagtgatct tccaccatga tcacgcactt gcctagcacg ataaggcgtt cggggcaaca 219180
aatcacgtcg tccagcagtt ggtcgcgcag ctccggcatg gtgctgccag gccgcacctg 219240
caggaaccag ttgtgcggaa tgccgagcga caacacctgg tcgacgtggt tacggaccca 219300
gtcgcgaagc acgtcggcgc tgtactggca ctcaaagatg ccctgaaagt cgcccatgac 219360
ccgcagaaaa gtttcgtagc gcgtgtggca atagaggaat tcatcgtttc gcgtaaacgt 219420
gggagctccg tcttcccagc gtgtacgcca catgtcaaaa gaggccgcca gctagacacc 219480
ccagaaaaga agcagagaaa gagagttctt tgtgcgacac gttttattcc gcgtcctccg 219540
ctcgacgctc aaatctggat gtactcgcgc acacccgtca ggctctttaa gggaaaaggg 219600
tccgagtacg tcactaaccg cgactgatgc accagggcgg taatcacccg ctctgcgccc 219660
tcgcgcgtcg acgaacgcgt cgtcaccagg cagtgcagcc gcgggcccgt atcgtcctga 219720
tgaccagcgg cctcgcgctc ggctgcttcc acaccgacaa tgtcgggatc caacacgtag 219780
ctctgcgagt tggtgtcgta gcggtgtagc accaacgtgt tggggtccag acgctcccac 219840
gcgccctcgt gcgggtcaaa acgctccgtt aaacagagcc agtcatactg ctgctgcaga 219900
atacgccgct cgcgctcgcg tcgctcatcg ggcaacgcgg cgtcttcgtt gaagagaatg 219960
tcccgcttgt ggtctacggc acgctcgtgg tggtgcgggc acagatgacg gtgttccata 220020
cgcgtctgac gttgacgctc gcgctcaaaa cgccggtgtc gaaagaccat tttcagcaac 220080
cccatgcgga aaaactccgt gatggtgttg gcaacgcgcc gcacgtagtg gttggggtcg 220140
tccatctgga tggcgtacac ggcaccgaac cagtccaaca gtaccagcac ttcggccaca 220200
aaactgcgtc ccggtcgcgg acgtcccgtc acgcctagca cataccacgg cgtggccaga 220260
ttagcacgga cagcccacca ccaacgacgg ctctccacct cggtgagcgc acaaaagggc 220320
caaatgcggt gtaactgctg caccgttttc atcagccgca taatcaccgt gccgtaaccc 220380
ggtgtatgca acttcacgtc gcaacccagg attcgttcgg ccgtggcgta cgagccctca 220440
ggcgtggtgt cattgagaaa caaaacatgc atggtacgcg cgcccttagg gtatcgtcgc 220500
ggaacaggta ccgtcattct ccgcagagtg gtgtgaatca cgtcgcgata cgcaatctcc 220560
gaacgtgaca caccgtaacg tgccagttcg tccaggttgt gcgataccaa caccatgtac 220620
ttttcacgag tgtcgtaggc gtagacgcga gaaaagcgac ccataaaaac cacgtacggg 220680
gtagccacca tgccatcatg gtaatcgcga cgtggctcgg gcaacaaaat aacagcgtat 220740
cccaacggcg tcagcggctc gcggcaacag atgagctttg acgccgcctg tttggcggcg 220800
gtaatgatcc cgtcctccgt acgtaacatc acatgccagc ccttgggggg acccaaggac 220860
agacagcgtc cctcgttacg atgaacgtaa cgcgtgattt ccattggctc caggcaaaag 220920
aacagttcct taaaatcccg caacacttgt cggtataacg ccatgggatc ctcggccgcc 220980
acaggcagcg cggggagctc cggcggcaca actgcagcgc cgtcagggcc agaacccgca 221040
gccggatcca tcattgcgcg acactctcag ccggacaacc ggcgtcactg acagaagccg 221100
agccaaatac agagaaagca acgctacacc gtcaccccgc tcccaagcgc cgcggaaagt 221160
gctccgattt ttcaccgtcg ttcgcgacgt tgatttgcct cggtctgaga accgacctag 221220
cgttcggacc ggtgcgcaga aacagccggc ggtccgagcc actgagcggt tcacagcccc 221280
ggccgccgat agttaccgga gagacgttcg agctgcaggt acatcggcgc tccccgctcc 221340
gccaccccgc gcccgcccca gtttatactc tccgacgccc cgtccaacgc gcctgtggag 221400
ggccaatcgg accgcgggag ctctccaagt ggatgacagg cacagccggg tgcccgaccg 221460
tgaagagccc tcatccacct gaacagaccg ctaaccgaag gaccccgaat cgcgtccgtc 221520
ggtcccgacg tccgtcgcca tctggctccc tgctgctggc tacctctcgg atttcaaaaa 221580
agagcacgtg ccgatgacgg tgcacaggaa agagccaaag tgtcacggcg tcttttttta 221640
tttgtattcc tttcctgttt tgtactcgta aactgttaac gttgttttta catccaaaag 221700

-continued ggcaagtaag aaacaggatg aggcatggta ggtttgggcg cggggcggcc ctccagcacg 221760
gcggcccggg ccgcccggcg ggtgagcacc cggcgttgcg ccgtatctat cttgtgtttc 221820
ttctgtgtct ttttcctatc ttgttccgcg acggcctctt tcatcacgtt cagcatgcgt 221880
tcctcgacgc cctccaggga tcctggggag gagggagtcc tagtgaggct tccaatgttg 221940
ttttgtggat tttcggtttc ctcttcttgg tcgtcatcgt cggacgtgtc gtcttcctct 222000
tgatcctctt cttcgtccga gtagtagacg catagtccct ggttcatcag gctgggattc 222060
attaggttct gacggggaat ccgctgctgt agacgtttaa ccgcccgttc caggcgagag 222120
ctcatgccgc accagacgct gtaacgccgc acgggcccgt agcgggctgt ttgttcgcgt 222180
acatgatcgt tgagctcttg ccaatattgt ttggcacact ccagatcgga ggtttgtgga 222240
tagtcgggtc ggatccgcgg atcccaactg acatcggcgg tgccagagac ttcgtccaga 222300
ctgttacgca tagagcacca gtcgggtcgg acgataaacc tgtccttgcg gattaaccat 222360
ttataacgta gttcgtgatg gcgtgtagag gcccgtacac gctccacggt cccaaagcgg 222420
tcccagaagg gaaagttttc gtgagggcag cgacccggca cttccagacg ttcggcgtcg 222480
tccacggcgt agtgaaaacg ccggccggcc tggtaaattt tgagcagacc cacggttaac 222540
aacatatcca cgctgtcagc caaccgccag atctcgcgcc gagacacgtc aaaatagaaa 222600
aattcgcagg ctcggtcgac caggatcacg aaatcggcgt gaaagacgcc ggagggtagc 222660
gactcgccca ccacacccat tatcatggtt tcacagcata agcggtccac aaagaacttc 222720
aacaggtcgt tgaattgctc cgtctccata cagataaagg gccagacgcc tttgaggttc 222780
tcggcctggc cgcagagcag caacggacgg gtcatctcgc ccggagtgcg cagaggcacg 222840
cattcgccgc gataacgaca ggtcacacgc tgcaattcgc tgatgctgtt gtcgtgcagg 222900
cgaagatcgc agataatatg atccggttgc gtggttagca gcggcgtgcg catttgctcg 222960
ccatagatgg cctcgcagtg caacagcccg tgtcgtgcaa aatcgtccag actgtgcgcc 223020
aggtagtaaa gcaccccgcg atagcggtct agacaccaca cggtttcgta acgtcctagc 223080
aggagcacca gacgggcctg gctaggtggc tcaatttcct ctacatacac gaaaaagtcg 223140
tcgtcgtccg agtcctcgtc ctcagaagag gaccgcggcc cgtgtactct gggcaacacg 223200
gtggtagaga actgcaggac gcccagggac tcgagcgact cttcgcagca gatgagctga 223260
ccccagggcg tttcgggccc gtcggtgaca gccgcgctgc caaagatgtc ctcaaactct 223320
acaaaatcta gacgccatcc gggtggcgct gaaacgggaa ggctaatgtt catatcagca 223380
tagctacgaa ctaagtggcg gatgtcctgc cgcaagtctt ggcagagaat gagctttcgt 223440
aaacccttga gggtcctccg aacaacggcc ccagacgcgt agcgatagga ctggcgcatg 223500
gtgccgcggc gtggagcggc acttggcagc ctattttatg gagtttcttc aatgacgtgg 223560
cttgttcacg tcgttcgtgg gctgcggttg gcagctccgg tctgtaaacc acccgaaaag 223620
actagcatcg acgtcaaaga ctcacgtaat ttgggacatg tgcgaccgca aagtgcgtca 223680
aaatagcacg tgactttggg acataaaaag taccgtgagc tctagacgtg gtttttgtga 223740
ttgacactta caccaggtaa gccaagggac ggtgaaactg tatgtgagga acctgggtgc 223800
ttagacaact aacgtgtaat gctttttaca ggaccgttca acaggtgata ctacctgcaa 223860
ggcaatgact acatctacta caactaccac tagtatcatg ctacaggtga gcaacgtaac 223920
gaatcacacc ttgaacagca ccgaaattta tcagttgttc gagtacactc gattcggggt 223980
gtggttgatg tgcatcgtgg gcacgtttct gaacgtgctg gtgattacca ccatcctgta 224040
ctaccgtcgt aagaaaaaat ctccgagcga tacctacatc tgcaacctgg ctatagccga 224100

-continued

```
tctgctgatt gttgtcggcc tgccgttttt tctagaatat gccaagcatc accctaaact 224160
cagccgagag gtggtttgtt cgggactaaa cgcttgtttc tacatttgtc tttttgccgg 224220
cgtttgtttt ctcatcaacc tgtcgatgga tcgttactgc gtcatcgtct ggggtgtaga 224280
attgaaccgc gttcgaaata acaagcgagc cacctgttgg gtggtgattt tctggatatt 224340
ggccgcgctc atggggatgc cacactatct gatgtacagt cataccaaca acgagtgtgt 224400
tggtgaattt gctaacgaga cttcgggttg gttccccgtc tttttgaaca ccaaagtcaa 224460
tatttgcggc tacctggcgc ccatcgtgct gatggcgtac acgtacaacc gtatggtgcg 224520
gtttatcatt aactacgtgg gtaaatggca catgcagacg ctccacgttc ttttagttgt 224580
ggttgtatct tttgccagct tttggttccc cttcaacctg gcactatttt tagaatccat 224640
ccgtctttta gtgggaacgc aaaacgagac tctccaaacc gttattactt tctgtctata 224700
cgtcggtcag tttttggcct acgttcgcgc ttgtctgaat cctgggatct acatcctagt 224760
aggcactcaa atgaggaagg acatgtggac aaccctaagg gtattcgcct gttgctgcgt 224820
gaagcaggag ataccttacc aggatattga tattgagcta caaaaggaca tacaaagaag 224880
ggccaaaaac accaaacgta cccattatga cagaaaacat gcacctatgg agtccgggga 224940
ggaggaattt ctgttgtaat tcgatcctct ctcacgcgtc cgccgcacat ctatttttgc 225000
taattgcacg tttcttcgtg gtcacgtcgg ctcgaagagg ttggtgtgaa aacgtcatct 225060
cgccgacgtg gtgaaccgct catatagacc aaaccggacg ctgcctcagt ctctcggtgc 225120
gtggaccaga cggcgtccat gcaccgaggg cagaactggt gctaccatga cgccgacgac 225180
gacgaccgcg gaactcacga cggagtttga ctacgacgat gaagcgactc cctgtgtcct 225240
caccgacgtg cttaatcagt caaagccagt cacgttgttt ctgtacggcg ttgtctttct 225300
tttcggttcc atcggcaact tcttggtgat cttcaccatc acctggcgac gtcggattca 225360
atgctccggc gatgtttact ttatcaacct cgcggccgcc gatttgcttt tcgtttgtac 225420
actacctctg tggatgcaat acctcctaga tcacaactcc ctagccagcg tgccgtgtac 225480
gttactcact gcctgtttct acgtggctat gtttgccagt ttgtgtttta tcacggagat 225540
tgcactcgat cgctactacg ctattgttta catgagatat cggcctgtaa aacaggcctg 225600
ccttttcagt attttttggt ggatctttgc cgtgatcatc gccattccac actttatggt 225660
ggtgaccaaa aaagacaatc aatgtatgac cgactacgac tacttggagg tcagttaccc 225720
gatcatcctc aacgtagaac tcatgctcgg tgctttcgtg atcccgctca gtgtcatcag 225780
ctactgctac taccgcattt ccagaatcgt tgcggtgtct cagtcgcgcc acaaaggtcg 225840
cattgtacgg gtacttatag cggtcgtgct tgtctttatc atcttttggc tgccgtacca 225900
cctgacgctg tttgtggaca cgttgaaact gctcaaatgg atctccagca gctgcgagtt 225960
cgaaaaatca ctcaagcgcg cgctcatctt gaccgagtca ctcgcctttt gtcactgttg 226020
tctcaatccg ctgctgtacg tcttcgtggg caccaagttt cggcaagaac tgcactgtct 226080
gctggccgag tttcaccagc gactgttttc ccgcgatgta tcctggtacc acagcatgag 226140
cttttcgcgt cggagctcgc cgagccgaag agagacgtct tccgacacac tgtccgacga 226200
ggcgtgtcgc gtctcacaaa ttataccgta ataaaaaagc gctacctcgg ccttttcata 226260
caaaccccgt gtccgcccct cttttccccg tgcccgatat acacgatatt aaacccacga 226320
ccatttccgt gcgattagcg aaccggaaaa gtttatgagg aaaaagacgt aggaaaggat 226380
catgtagaaa aacatgcggt gtttccgatg gtggctctac agtgggtggt ggtggctcac 226440
gtttggatgt gctcggaccg tgacggtggg tttcgtcgcg cccacggtcc gggcacaatc 226500
```

aaccgtggtc cgctctgagc cggctccgcc gtcggaaacc cgacgagaca acaatgacac 226560
gtcttacttc agcggcacct ctttccattc ttccgtgtcc cctgccacct cagtggaccg 226620
tcaatttcga cggaccacgt acgaccgttg ggacggtcga cgttggctgc gcacccgcta 226680
cgggaacgcc agcgcctgcg tgacgggcac ccaatggagt accaactttt ttttctctca 226740
gtgtgagcac taccctagtt tcgtgaaact caacggggtg cagcgctgga cacctgttcg 226800
gagacctatg ggcgaggttg cctactacgg gggttgttgt atggtgggcg ggggtaatcg 226860
tgcgtacgtg atactcgtga gcggttacgg gaccgccagc tacggcaacg ctttacgcgt 226920
ggattttggg cgcggcaact gcacggcgcc gaaacgcacc taccctcggc gcttggaact 226980
gcacgatggc cgcacagacc ctagccgttg cgatccctac caggtgtatt tctacggtct 227040
acagtgtcct gagcaactgg ttatcaccgc ccacggcggc gtgggtatgc gccgctgtct 227100
taccggctct cgtcccaccc cgtcccggcc ccaccggcat gacttggaga acgagctaca 227160
tggtctgtgt gtggatcttc tggtgtgcgt ccttttatta gctctgctgc tgttggagct 227220
cgttcccatg gaagccgtgc gtcacccgct gcttttctgg cgacgcgtgg cgttatcgcc 227280
gtccacttcc aaggtggatc gcgccgtcaa gctgtgtctt cggcgcatgc tgggtctgcc 227340
gcccccaccg tcagtcgcac cacctgggga aaagaaggag ctaccggctc aggcggcctt 227400
gtcgccgcca ttgaccacct ggtcactacc gccgtttccg tccacgcgga tacctgacag 227460
tccgccgcca ccgtaccagc ttcgtcacgc tacgtcacta gtgacggtac ccacgctgct 227520
gttatatacg tcatccgaca tcggtgacac agcttcagaa acaacgtgtg tggcgcacgc 227580
tacttatggg gaacccccgg agcccgctcg atcgacggct acggttcagg aatgtaccgt 227640
tcttaccgcc ccaaattgcg gcatcgtcaa caacgacggc gcggtctctg aaggccaaga 227700
ccatggagat gcggttcacc atagcctgga tgtggtttcc cagtgtgctg ctgatagtgg 227760
ggttgttgac gcctccgagt aacggctgca ctgttgatgt cggacgaaac atgtccattc 227820
gagaacagtg ccgccttcga aacggtgcga cgttctccaa gggagacatc gaaggtaact 227880
tcagtgggcc cgtcgtcgtg gagttggact acgaagacat cgatattact ggcgaacggc 227940
agcgacttcg gttccatctc agcggcctcg ggtgtcctac aaaggaaaat ataagaaaag 228000
acaatgaaag cgacgccaac ggtggaattc gctgggctct atatatacaa accggcgacg 228060
ccaagtacgg tattcgtaat cagcatttga gtatacggtt aatgtatcct ggggaaaaaa 228120
atacacaaca gctgttgggt tctgatttca gttgcgaacg tcaccggaga ccgtccacgc 228180
cgttgggaaa gaacgccgaa gtgcctcccg cgacccgcac gtcttctaca tacagcgtcc 228240
tcagcgcttt tgtagtgtgg atcggatccg gcctcaatat catctggtgg accggcatcg 228300
tgcttctggc ggtggacgct ctcggacttg gcgagcgttg gctgaggtta gcactgtccc 228360
accgggacaa acatcacgca tcgcgaaccg cggcgctcca gtgtcaacgc gacatgttac 228420
ttcggcaacg tcgacgggct cggcggctgc acgccgtttc tgaaggcaaa ctgcaggaag 228480
agaagaaacg acagtctgct ctggtctgga acgttgaggc gcgacccttt ccgtccacac 228540
atcagctgat tgtgctgccc cctcctgtag cgtcagctcc tcctgcagtt ccctcgcagc 228600
cccccgagta ttcgtctgtg tttccgcctg tataaaaata aagagacggg aggctgatcg 228660
cggccttcag cgtctcattt gtctttactc tcgagtgcgg tcggtgtctc gtcggtgaga 228720
cgaggccgcc gcccgacaag ttcgatctca tgtcgctctt ggagcgcgaa gagagttggc 228780
gtcgcgtagt cgactactcg cacaacctgt ggtgtacgtg cggtaactgg cagagccacg 228840
ttgagattca ggacgaagag cccaactgcg agcagccgga gcccgcacac tggctggaat 228900

-continued acgtggcggt ccagtggcag gcccgggttc gcgattctca cgatcgctgg tgtctctgca 228960
acgcctggcg tgatcacgcc ttgcgcggcc gttggggtac ggcgtattcc tcgggttcct 229020
cagcctcttc ctccggtttc gtcgcggaga gcaagttcac ctggtggaaa cgactgcgcc 229080
acagtacccg gcgctggttg tttcgccgcc ggcgagctcg atacactcca tctaactgtg 229140
gggaaagtag cactagcagc ggccagagta gcggtgacga gagtaactgc agtctacgca 229200
cccacggcgt gtacacacgg ggtgaacaac actaatcgat aagtcgcgtg taggcgactg 229260
gctacatcaa ccggatatct gcggggattt aaaaagacga cccgttgtca tccggcttag 229320
agcaaaccgt ccttttatca tcttccgtcg ccatggctat gtacacatcc gaatccgaac 229380
gcgactggcg tcgtgtaatc cacgactcgc acggcctgtg gtgcgactgc ggcgactggc 229440
gagagcacct ctattgtgtg tacgacagcc attttcagcg acgacccacg acccgagccg 229500
aacggagggc cgccaattgg cggcgacaga tgcggcggtt acaccgtctg tggtgttttt 229560
gtcaggattg gaagtgtcac gcgttatacg ccgagtggga cggcaaagaa tccgacgacg 229620
attcgtcggc gtcttcctcg ggcgaagcgc cagagcaaca ggtccccgct tggaagaccg 229680
tgcgggcctt ctcgcgggcc taccaccacc gcattaaccg gggtctgcgg ggcacgcccc 229740
caccgcgcaa cttgccggga tacgagcacg cctccgaggg ctggcggttt tgcagtcgac 229800
gagaacggcg agaggacgat cttcgcacgc gggctgagcc ggaccgcgtg gtgttccagt 229860
tagggggagt acctcctcgc cgtcaccggg aaacttacgt gtaagaacac ggcgtgacaa 229920
taaacaacat agcgtaaatc cccgtgtgat gtgtgtggtt gacgttcggg aaacatgtcc 229980
ccatcatcag cgtcacaact gacgtgggtt ggtcactgac gtgcaggatg ttacgcgagt 230040
cagagaatcg cataagaacg gggtggtgag cgggttccca caggagtatc tggcgcaaaa 230100
gcaccatgag cctcaggttc cccgagaggg cgggttacga gaaattggga taccgcccgc 230160
atgccaaacg cgtgtgggtg catgacccgt tgggattgac gcggtttatc atgaggcaac 230220
tcatgatgta cccgctggtg ttgccgttca cttttccgtt ttacgtgccg cggtcctagc 230280
acgtcagtgg tgacgctgat aattgcaaca tgggcaatgg cgaacccgct tgggacgaac 230340
gtcaatacca cgtcaaacca ccgtgacttg gctgaacgtt gaaacataaa gccaaagcgc 230400
cgtcggcact tggcttcaga gcagcgcctc ggggcgatgc gacggcgatg aacttagagc 230460
aactcatcaa cgtccttggt ctgctcgtct ggattgccgc tcgtgctgtc agccgcgttg 230520
gtccacatgg ctccggactc gcttatcgtg agcttcatga tttccacggg tatctgcagc 230580
tggaccttct gggaccagtg gtggcgggga atcgttcagt ccggacctgg agagagcagg 230640
cggaccgaac cagagggacc ttcgctcggc gttcaggcct taatactagc cgcatcttac 230700
ctgtcggcag catgtatcgg ggctccgaca ccttatccgc cggcttgtat cgtcccgaag 230760
aagaggtgtt cctcctcttg aaccgctgcc atgggccact gtcaacgccg aaaaacgctt 230820
gtctggctga ggtcggtgtc gctaatgcca ctttttgtc tcgcttcaat gtcggtgatt 230880
ttcacggagc gtcatgggaa aacggtaccg ctcccgatgg agagcccggg gtatgctgaa 230940
attcctctta agattccgta aacgacgtcg tccagtcgtt gtgccgcgat tcgtacggtt 231000
catcgtctac gtcgttttgt tcaccgtcgc tgtgcaacgt gtgaaacaag agcgtgatgc 231060
gcaccttcgg cggtatgaag aacggttacg gaaaaaccac gcacggcgtc ggcagtcttt 231120
tccgtgactt ggggcgatgg gtccgagctg cggtatgggt cacggcggcg tgtgttttat 231180
tgacgaagat gccgatgtgt gactaaaaac gtcccagccc tagagcgatg tgtttcaata 231240
aaaattatgt agtatcatag tatgcgtgtc ctggtttttc atttttggat gtatttgtca 231300
cataaaaggc gatagaatgt ggggacgaaa catatccaga tacgcagttt tgttattcga 231360
acaaaacccg tgtgatgcaa aaaacagtac tgcaggatga aagtcccatg gggggggggg 231420
gacagacagt agtcgttttt gccgctgggc gtacggtatg cttatattta tgactataat 231480
atgtgcactc gtgtgtcgat gttcctattg ggaagggtgt gaatgtagga ggtataaaga 231540
atggtgggat gtggagaggc atcgctagac acaggttgat cgttgtgcta gccccacctg 231600
agcagcgtca tgggtaaagc ggtgattaag cgtgaaaaca ccgtaggggg gggggcagga 231660
agcttggtgg cagtggccgt tggatacctt atgtgtctgt attggtatat ttgcaaatcg 231720
agtgcgccgg tatagtttaa cgatgattat attatgtatg cgcagtatac aatgccctaa 231780
aacgtaacag tatgggatga atgccaataa ataacatata aaagccagaa gtatacatac 231840
aagggttgct agacacaggt ttgtttctgt gctagcccaa cggcacttgt acaatccatg 231900
caaccagaaa aatgatgcga aaccaacgtc gtgggggggg ggggatgaaa agtctgttaa 231960
tcattggtct cgcggtgcaa gttgctgcgt tttacgtgta ttgttacacg ggtcgcgtat 232020
cgctataatc ggatgtgtgt tactcattcg tggcgtcgtt atagtattgt gaaaaagaat 232080
tctcgtaagc atgttgacaa ctgcaaaata aaaccatttt attgagcatt gtaatggtag 232140
tgtgtggcta cattagaaaa cgtgacgcgt cgcatgtcgc ggcacaatct ggcagcgggg 232200
tcggggtagg gtacggtggg aggcatgtac acagatggaa caaaagcaga agtaacgtga 232260
gacggagcat atagtccagt atccagcggt tcctgagtag caccacccat caactgaatg 232320
ccctcatgag taaaagtctg cgggcggcag cccttgggga ccgttggcat gggacgatca 232380
atctccaaac cacagcgtaa cacggttttc ttccaacgtc gttggtacac gtcgttttta 232440
cggttactcc ccagaaccca gaaagtctcg tccaagtcgt accaggagtc ttccccaggg 232500
agacgtggcg gtttccaatc ctcatcgtcc cgtcgcaaag cacgtcccaa actggcttgg 232560
ggagtcaacg gtggttctgt gggtcgggtg tagcgcgagt gttttccctt catgagcgat 232620
tcgtcctcct tgcctttagg ctttttggtc tttttgtgta tcatctggcc gccggcctcc 232680
ataaccaccg tggccaagtc cagtcccaga gcttgagcgt cggcgcggcg tcgagcgtct 232740
tgcaggtagt cttccacatt tgcacagatg gccgggtgtt tggtggctag ggtgaggacc 232800
tcagcctcgc cgcggcccgg acgtagcaaa aaagctaact gcccgtgcgg ctcgcgcgcc 232860
cacagcgcgg cgcgcgggtg caggtgcagc gcgtcccagc gcggccgctc ccactgctcg 232920
cggtccagct cgggcagcag ccgccgcgcg gcctcggcgg cgggcgccga ctcgcgtccc 232980
agcgccagcg cgcccagcac gcccgcgcgc agaaagtgcg acagctccgc cgctagcggg 233040
tacacgtgcc cgtccagcgg gcagtacccg aacacggcgc ccagctcgtc cagcaccacc 233100
accagcatgg cgcgcggcac ggtccccgac gccgccggac ccgccatcgc cgtcggaccc 233160
accatcaccg tcggcgccgc cgctgctgcc gccgccgcat ccgttccgac cgccgcgtgc 233220
gcgtccgcgt ttggcacgca caccgcgttc ccgccggcgg aggtgccgta cggctgcgga 233280
ggtaaagtca cagcagaccc cacggctccc gcgatcgcgc acggcgcgtc cccgccggcg 233340
gcctccgtct ccgtgctgct cgcccccgcc agcaacgtcg tccccgtcgc catcgccgtc 233400
gtccccgccg tcatcggcgt cgtccccgcc accgtccctg tcgccggccc cgccgcgcag 233460
cgcagccacc gcgacggcag caccgcgccc agcgccagcc agccgcagca cagacgctgg 233520
ttcaggtgcc gacgcacggc cgtcagcagc gacgcggggt gcggcgccga cgcgaacggt 233580
tcgtactgcg ccagctcctg ccacgcgccc agcagcacca tcggctgcag tcgccttccc 233640
ggcgtctgca gtgccaccgt cgtgccggcc caccgccggc gcagctcccg tccgagcgcc 233700

-continued gtcgcctcct cggcgcgcag caacgtctgt cgaagcgccg gctgaggcag cagcgtcgcg 233760
cgcggggtgc ccacgcccag ccggttgcag cggtacagcc gcaccacctc gcccgcgccg 233820
tgccgaaacc actcgtccgc gtcgcgcgcc gctaggatca gtgtgttgtt cgccaggtcg 233880
tacacgaaca cgcggaaccc ggcgcccagc gccaggtaca gtccgtcctg cgcgcacaga 233940
ccctcgggat ggccggcctt gtcgcccacc gtcgggtcgg ccgcggggtc cacctcgtgc 234000
accacggtcg ccaccagcac gatccacgcg tcccgcggcg acagctgacg caggtccgtc 234060
gcgcccacgc cgttcatctg gctgcgcggc gtcacccgcg cgtagaatcc gtacggccgt 234120
ccgagcggca ggagcgtgcc cgcgtcgcgc tgcgaccact tgcgcatggc gcggcccgtg 234180
ctgttggcca aaaacgccgc gcgccacacg gcgcccatgg cctggtattc cagctccgtc 234240
agcgcctggc gctccaccgg aatctgagac agcagcaagc gctccggccc gtgccaaaag 234300
ttgctgttgt tgccgctacc cggaggggcg cccggcggcc cgcggggttc tacgcggtgg 234360
acgccgtgga ccggcgtcgc cgtacccgca gtactcgcac cagtccccgc tgttgacgtc 234420
gctcccatcg gcacacaaga agaagacgaa ggagaggaac caacccccga aggccctccg 234480
gctccgcggc cgcgaccgag gggcgggggg cgcggcgaca tgccgttgcg ctgggccatg 234540
gccgccggac acctccgacg tccactatat aggaaccaaa cccgcgtcag cgaccacgcc 234600
gtttacacac gcggacgcct ccgtagcccg tgtgccacgg ccgacacgca cctggctttt 234660
ataggcagcg gcgtgcacgg cgcttgctgg cgccgccttg gcgccgcgca gtctggaacg 234720
ccgtggaaaa cccaaaggca gacgcgcggc aggccacgac cacccgagcg cacagcgagg 234780
cggacgcctg ccgagcgcgc acacacctag gtggacgccc ggcatccatt ccgggccgtg 234840
tgctgggtgc ccgaagggcg ggggggtgtt ttttgcgggg gggtgaaaat tggagttgcg 234900
tgtggtgggg cacggcggtc gcggaggacg gcgacggcga ataaaagcga cgtgcggcgc 234960
gcctgtcttg cgtgtctgtc tttgctgttg cgtgtctttg aatccccggg gaaaagagga 235020
agaagaaggg gagtccctgg ggacggcagc gcgagtccct ggggacgcgc agagcaactc 235080
ccggggggtg acggacggcg gccagacgcg gaaaaagagg aagtccccgt cgaggacacg 235140
cggagaagac gaagcgcgcg ccgccgccac tcgtccctag ggaaaaaaga ggaagctgcg 235200
gacccgcgtc gggggggggg agtcgcgggc cccggggcac actgcttcca tccagccgcg 235260
cgcacacccc gccgacacac ccccgacaca cccggcacac gcccgcgaca cacccggcac 235320
acgcccgcga cacacccgac acaccccgcc gacacacccg cgacacaccc ggccgacaca 235380
cccccgacac acccggcaca cccagccgca cccggcacac acccacccag ccgcaccccc 235440
gacacacccc gaccgccgcc ggtgcgggac agggct 235476

<210> SEQ ID NO 2
<211> LENGTH: 548
<212> TYPE: DNA
<213> ORGANISM: Human cytomegalovirus
<220> FEATURE:
<221> NAME/KEY: gene
<222> LOCATION: (1)..(548)

<400> SEQUENCE: 2
atgggtgtac aatgtaacaa taaactgcta ttactagtcg tactaataac aattgcaatc 60
atcctaacat tctagtacaa tttcacatga aaagcatcct acaggaaact tactacaaac 120
tgaatatata caaataccca tcacagtagc tgagggaaac acaatttact ttaatgctag 180
cgataactcc tgtaatgtca tgccatccat aatttcaagg tctgaaatta tagaatgtaa 240

-continued ctatgaatga gtcgagaatt tatacacagg acgtctatca ctgtgacatt ccatgtaata 300
tcaacgatga acgtaaacaa cgtagactac tttgacaact gtaacaacta taaatagagc 360
cgagtatatt atcaccgtgt tatcttcacg ttattctgaa cacacgaact cctacgtagc 420
cactcacgtt gattggacaa ttgccgcggc aacgatgata attatctgca tcctaacata 480
cgtcaatgtt tcaccaaaca gaagacgcag actacaaact agaaataacg tcaagtacat 540
aacgtaat 548

<210> SEQ ID NO 3
<211> LENGTH: 447
<212> TYPE: DNA
<213> ORGANISM: Human cytomegalovirus
<220> FEATURE:
<221> NAME/KEY: gene
<222> LOCATION: (1)..(447)
<223> OTHER INFORMATION: complement

<400> SEQUENCE: 3
ctacttacct ttatcgtcgg aggggaaagc gctaagatac cccacctgag tgaaaggacc 60
tttgcagttt gtccgtgcat aacaggtaac tgataaaatg tctggatttt tggtgttgtt 120
caacaggtta actttgcagg tggcgttcag agacacctgg ttgtagctgt agctggcttc 180
gcaattcaca ttatacaggt gcccctcttt ctgcgtcgtg gttgccacgg aggtagaggc 240
ggacgtggag gtagagccgg acgtgaaagt agaggtttgt accgtggtgg tgacggtaga 300
agtaacgtta ttgggggtac ttatcgacgt agtggatgtg acggtgatat taggggaagt 360
gacggcactt gtagtgctac ttcccattcc tgggtgcgtg ttactcagga gcgcggctgc 420
gagcgcaatc gccagtgcgg gacacat 447

<210> SEQ ID NO 4
<211> LENGTH: 335
<212> TYPE: DNA
<213> ORGANISM: Human cytomegalovirus
<220> FEATURE:
<221> NAME/KEY: gene
<222> LOCATION: (1)..(335)
<223> OTHER INFORMATION: complement

<400> SEQUENCE: 4
tatttattga attatcaacg ttacttagtt acaataagaa accaagtatc cacttgttca 60
ggaccgttat caactctccg ctttaaatca taagatcctt cgttgccttg cgttacgttg 120
caaaacgtca atcctgtatg actacaatta cacacaccgt gaatcggcgg cgttgctagc 180
gtgtaattct tcgtcccctc cacactacac acgtcggtat catttttacc atcaaaaaac 240
gaccaaatcg ttttcaggtt agcactaacg gttttatcat caccggtctt tacatgaaca 300
ttagccattc cctcgactct gtaattcaac gtcaa 335

<210> SEQ ID NO 5
<211> LENGTH: 20
<212> TYPE: RNA
<213> ORGANISM: Human cytomegalovirus

<400> SEQUENCE: 5
uaacuagccu ucccgugaga 20

<210> SEQ ID NO 6
<211> LENGTH: 22
<212> TYPE: RNA
<213> ORGANISM: Human cytomegalovirus

<400> SEQUENCE: 6
ucaccagaau gcuaguuugu ag 22

<210> SEQ ID NO 7
<211> LENGTH: 22
<212> TYPE: RNA
<213> ORGANISM: Human cytomegalovirus

<400> SEQUENCE: 7
ucguugaaga caccuggaaa ga 22

<210> SEQ ID NO 8
<211> LENGTH: 21
<212> TYPE: RNA
<213> ORGANISM: Human cytomegalovirus

<400> SEQUENCE: 8
ugcgucucgg ccucguccag a 21

<210> SEQ ID NO 9
<211> LENGTH: 20
<212> TYPE: RNA
<213> ORGANISM: Human cytomegalovirus

<400> SEQUENCE: 9
ggggaugggc uggcgcgcgg 20

<210> SEQ ID NO 10
<211> LENGTH: 22
<212> TYPE: RNA
<213> ORGANISM: Human cytomegalovirus

<400> SEQUENCE: 10
aagugacggu gagauccagg cu 22

<210> SEQ ID NO 11
<211> LENGTH: 21
<212> TYPE: RNA
<213> ORGANISM: Human cytomegalovirus

<400> SEQUENCE: 11
ucguccuccc cuucuucacc g 21

<210> SEQ ID NO 12
<211> LENGTH: 22
<212> TYPE: RNA
<213> ORGANISM: Human cytomegalovirus

<400> SEQUENCE: 12
cgacauggac gugcaggggg au 22

<210> SEQ ID NO 13
<211> LENGTH: 21
<212> TYPE: RNA
<213> ORGANISM: Human cytomegalovirus

<400> SEQUENCE: 13
ugacaagccu gacgagagcg u 21

<210> SEQ ID NO 14
<211> LENGTH: 22
<212> TYPE: RNA
<213> ORGANISM: Human cytomegalovirus

<400> SEQUENCE: 14
uuaugauagg ugugacgaug uc 22

<210> SEQ ID NO 15
<211> LENGTH: 21
<212> TYPE: RNA
<213> ORGANISM: Human cytomegalovirus

<400> SEQUENCE: 15
aaccgcucag uggcucggac c 21

<210> SEQ ID NO 16
<211> LENGTH: 22
<212> TYPE: RNA
<213> ORGANISM: Human cytomegalovirus

<400> SEQUENCE: 16
agcggucugu ucagguggau ga 22

<210> SEQ ID NO 17
<211> LENGTH: 21
<212> TYPE: RNA
<213> ORGANISM: Human cytomegalovirus

<400> SEQUENCE: 17
auccacuugg agagcucccg c 21

<210> SEQ ID NO 18
<211> LENGTH: 22
<212> TYPE: RNA
<213> ORGANISM: Human cytomegalovirus

<400> SEQUENCE: 18
gauugugccc ggaccguggg cg 22

<210> SEQ ID NO 19
<211> LENGTH: 671
<212> TYPE: DNA
<213> ORGANISM: Human herpesvirus 5
<220> FEATURE:
<221> NAME/KEY: gene
<222> LOCATION: (1)..(671)
<223> OTHER INFORMATION: strain AD169 substrain varUK

<400> SEQUENCE: 19
atgggcatgc aatgcaacac taaattgtta ttgccagtcg cactaatacc ggttgtaatc 60
atcctaattg gtactctagt gcccatactt ttacatgaac aaaaaaaggc gttttactgg 120
cgactttttc tgcaaagtca acatgtagaa gcacccatta cagtaacgca gggagacaca 180
gtctacctag atgctagcaa taatccctgt aattattcca gcttttggta ccacggtaat 240
tgcgaacttt gtggatggaa cggatatcta cgcaatgtta cacattacta cacaaacaca 300
tcgtgttccc cgcaattcat gtgcataaac gaaactaaag gtctgcagtt atataatgta 360
acattaaacg attcaggtgc ttatactgaa cacgtttacg aatgtgatct ttcatgtaac 420
attactactt ataacgaata tgaaatactc aattacttcg ataactgtaa ctacaccata 480
aatagcacca agcatattat caccgtggtg tcttcacgtc attctaaaca aacaaattcc 540
cacgtatcca ctcacgctgg ttgggcagcc gccgtggtga cggtaattat gatctacgtt 600
ttgatccact ttaacgttcc ggcaactctg agacacaaac tacgaactag aaacaacgta 660
aatcgcatag c 671

<210> SEQ ID NO 20
<211> LENGTH: 675
<212> TYPE: DNA
<213> ORGANISM: Human herpesvirus 5
<220> FEATURE:
<221> NAME/KEY: gene
<222> LOCATION: (1)..(675)
<223> OTHER INFORMATION: strain AD169 substrain varUC

<400> SEQUENCE: 20
atgggcatgc aatgcaacac taaattgtta ttgccagtcg cactaatacc ggttgtaatc 60
atcctaattg gtactctagt gcccatactt ttacatgaac aaaaaaaggc gttttactgg 120
cgactttttc tgcaaagtca acatgtagaa gcacccatta cagtaacgca gggagacaca 180
gtctacctag atgctagcaa taatccctgt aattattcca gcttttggta ccacggtaat 240
tgcgaacttt gtggatggaa cggatatcta cgcaatgtta cacattacta cacaaacaca 300
tcgtgttccc cgcaattcat gtgcataaac gaaactaaag gtctgcagtt atataatgta 360
acattaaacg attcaggtgc ttatactgaa cacgtttacg aatgtgatct ttcatgtaac 420
attactactt ataacgaata tgaaatactc aattacttcg ataactgtaa ctacaccata 480
aatagcacca agcatattat caccgtggtg tcttcacgtc attctaaaca aacaaattcc 540
cacgtatcca ctcacgctgg ttgggcagcc gccgtggtga cggtaattat gatctacgtt 600
ttgatccact ttaacgttcc ggcaactctg agacacaaac tacgaactag aaacaacgta 660
aatcgcatag cgtga 675

<210> SEQ ID NO 21
<211> LENGTH: 665
<212> TYPE: DNA
<213> ORGANISM: Human herpesvirus 5
<220> FEATURE:
<221> NAME/KEY: gene
<222> LOCATION: (1)..(665)
<223> OTHER INFORMATION: strain Towne

<400> SEQUENCE: 21
atgggtatac aatgtaacac taaactactg ttactagccg cgctaatagc aactgcaacc 60
attctaacta gcattttagt tccggtactt ttacatgaac aagaaaaaac attttaccgg 120 cgattttttta cgcaaagtca acatgtagaa agacccatca cggtaactca gggagataca 180
gtttacctga acggtagtaa taatccctgc aactattcca gtttctggaa ctacggcagt 240
tgcgaacttt gtggatggaa cggatacata cataaacagt accacgaaaa caaatcatgc 300
tctccgcgat ttacatgttt taacgacaca aaaggtctca gacttaataa cgttacatct 360
agcgattcag gaacatacac ggaatacgtg tatgaatgcg atttgccatg taatacaagt 420
gactatgatg aatatgacat actaaactat cttgacaatt gtactactac cataaacagc 480
accaattata ttattaccgt attgtctcca cgtcattcta aacacaccaa ttcccacata 540
tccacgctgg ttggacagct gccgtggtga cggtaattat aatctgcgtt ttgacttact 600
ttaacgttcc ggcaaccctg aaacgcaaac tacgaactag aaacaacgct acccacatac 660
cgtga 665

<210> SEQ ID NO 22
<211> LENGTH: 675
<212> TYPE: DNA
<213> ORGANISM: Human herpesvirus 5
<220> FEATURE:
<221> NAME/KEY: gene
<222> LOCATION: (1)..(675)

<223> OTHER INFORMATION: strain HAN38

<400> SEQUENCE: 22
atgggcatgc aatgcaacac taaattgtta ttgccagtcg cactaatacc ggttgtaatc 60
atcctaattg gtactctagt gccgatactt ttacatgaac aaaaaaaggc gttttactgg 120
cgactttttc tgcaaagtca acatgtagaa gcacccatta cagtaacgca gggagacaca 180
gtctacctag atgctagcaa taatccctgt aattattcca gcttttggta ccacggtaat 240
tgcgaacttt gtggatggaa cggatatcta cgcaatgtta cacattacta cacaaacaca 300
tcgtgttccc cgcaattcat gtgcataaac gaaactaaag gtctgcagtt atataatgta 360
acattaaacg attcaggcgc ttatactgaa cacgtttacg aatgtgatct ttcatgtaac 420
attactactt ataacgaata tgaaatactc aattacttcg ataactgtaa ctacaccata 480
aatagcacca agcatattat caccgtggtg tcttcacgtc attctaaaca aacagattcc 540
cacgtatcca ctcacgctgg ttgggcagcc gccgtggtga cggtaattat gatctacgtt 600
ttgatccact ttaacgttcc ggcaactctg agacacaaac tacgaactag aaacaacgta 660
aatcgcatag cgtga 675

<210> SEQ ID NO 23
<211> LENGTH: 936
<212> TYPE: DNA
<213> ORGANISM: Human herpesvirus 5
<220> FEATURE:
<221> NAME/KEY: gene
<222> LOCATION: (1)..(936)
<223> OTHER INFORMATION: strain HAN20

<400> SEQUENCE: 23
atgccagcca cagacacaaa cagcacccac accacgccgc ttcacccaga cgcccaacac 60
acgttaccct tacaccacag caacacacaa ccgcatgtcc aaacctcgga caaacacgcc 120
cacgaacaac accgcacaca gatggagctc gacgccgcag actacgctgc ttgcgcacag 180
gcccgccaac acctctacga tcaaacacaa ccccaactac acgcataccc caacaccaac 240
ccacaggaca gcgctcattt tcccacagag aatcaacatc aactcacgca tccacttcac 300
aacattggcg agggcgcagc gctcggctac cccgtccccc gcgcggaaat ccgccgcggc 360
ggtggcgact gggccgacag cgcaagcgac tttgacgccg actgctggtg catgtgggga 420
cgcttcggaa ccatgggccg ccaacctgtc gtcaccttac tgttggcgcg ccaacgcgac 480
ggcctcgctg actggaacgt cgtacgctgc cgcggcacag gctttcgcgc acacgattcc 540
gaggacggcg tctctgtctg gcgtcagcac ctggtttttt tactcggagg ccacggccgc 600
cgtgtacagt tagaacgtcc atccgcggga gaagcccaag ctcgaggcct cttgccacgc 660
atccgggtca cccccatctc cacatctcca cgtcggaaac cgccgcaccc cgccacatcc 720
accgcatcgc accacccaca tgcttcgcct cggtcagatc acacgctttt tcctgtccca 780
tctacaccct cagccacggt tcacaatccc cgaaactacg ccgtccaact tcacgccgaa 840
acgacccgca catggcgctg ggcacaacgc ggtgaacgtg gcgcgtggat gccggccgag 900
acatttacgt gtccaaagga taaacgtccc tggtag 936

<210> SEQ ID NO 24
<211> LENGTH: 660
<212> TYPE: DNA
<213> ORGANISM: Human herpesvirus 5
<220> FEATURE:
<221> NAME/KEY: gene
<222> LOCATION: (1)..(660)

<223> OTHER INFORMATION: strain HAN13

<400> SEQUENCE: 24
atgggtgtac aatataacac taaactgctg ttattagccg tattagcaat tatcccagct 60
ggcattctag tacaggcaat ttcacatgag caaaaaacat cctaccggca acttttgctg 120
caaagtgaac gtgtgcaaat acccatcaca acagtcgagg gagatacaat ttgctttaac 180
gttagtaaca acccctgcaa cttttccagt tattggaatc acaataattg tgaactttgc 240
ggttggacac cgtttttctt tgaatatgct ggatatactg aaaacacgtc gtgtcaccca 300
cgatttacct gtcttcatga tactaaaggt ctaaaactat acaatgtaac catgaatgac 360
tcgggaattt atacacaaca cgtttatcac tgtgatattc catgtaacat cagcgatgat 420
cgtaaatata acgtagatga cattgataac tgcaacgcta ctataaatgt aaccgactat 480
attattaccg tgttgtcttc acgttattct aaacgcaccg attaccacgt agatacttac 540
attggttatg caaccactgt ggtgacaata gtatttatct gtgttttaac ttgcattaac 600
gtctcagcaa ctctaaggca cagactacga actagaaaca acgttaacag cataacgtga 660

<210> SEQ ID NO 25
<211> LENGTH: 657
<212> TYPE: DNA
<213> ORGANISM: Human herpesvirus 5
<220> FEATURE:
<221> NAME/KEY: gene
<222> LOCATION: (1)..(657)
<223> OTHER INFORMATION: strain 3157

<400> SEQUENCE: 25
atgagtgtac gatgtaacag taaactgctg ctactagccg tactaataac aattatccta 60
tctagcattc tggtacaggc aattccacat aaacaaaaaa catcctacca gcagctcttg 120
ctgcaaagtg gacatgtaca aatacccatc acagtagccg aaggagatac aatttgcttt 180
aacgttagtg ataacccctg caacttttct agttactgga atcacaataa ctgcgaactt 240
tgcggttgga caccatttta ctcggaatat gctggatatt ccgaaaacaa gtcgtgtcac 300
ccacgattta cctgtcttca cgatactaaa ggtctgaaac tacacaacgt aactacaaat 360
gattcaggaa tttatacccg aaacgtttat tactgtgaca ttccatgcaa catcagcgat 420
gatcataaac ataacgtaga ggactttaac aactgtaaca ccactataaa tagaactcac 480
tatattatta ctgtctcgtc ttcacgttat tctaaccgca ccaattccca cgtagccact 540
cacgttggtt ggacagccac cgtggtgata attatctgcg ttttaactta cgttaacgtt 600
acaacaaccc tgaagcacag actacgaact agaaacaacg tcaaccacac aatgtga 657

<210> SEQ ID NO 26
<211> LENGTH: 648
<212> TYPE: DNA
<213> ORGANISM: Human herpesvirus 5
<220> FEATURE:
<221> NAME/KEY: gene
<222> LOCATION: (1)..(648)
<223> OTHER INFORMATION: strain 3301

<400> SEQUENCE: 26
atgagcgtac aatgtaacac taaattgcta ttactaattg cattaatacc gattgcaatt 60
atcctaactg gaactctagt gccggtaatt ttacatgaac aaaaaaaggc gttttactgg 120 cgacttttc tgcaaagtca acaaagtcaa catatagacg cacctattac agtaattcag 180
ggagatacag tttatctcaa cgctagtaac aacccctgca attattccag cttttggtac 240

-continued

```
catggtaatt gtgaactttg tggatggaac ggacacttac acaattttac agaataccac    300

acaaatacat cgtgttcccc gaaattcatc tgcataaacg aaactaaagg actgcagtta    360

cataatgtaa cattgaacga ttcaggaaca tataccgagg acgtttacga gtgcgacctt    420

ttatgtaaca ttactaactg cacctacacc ataaacagta ctaaatatat tatcactgtg    480

ctctccccac atcattctaa acacaccaat tcccacgtat ccactcacgt tggttggaca    540

cttgccgtgg ttacgattat tataatctgc gttctgattt actttaacgt tccaacaacc    600

ctaagacaca aactacaaac tagaaacaac gtaaaccgca taacgtga                 648
```

<210> SEQ ID NO 27
<211> LENGTH: 675
<212> TYPE: DNA
<213> ORGANISM: Human herpesvirus 5
<220> FEATURE:
<221> NAME/KEY: gene
<222> LOCATION: (1)..(675)
<223> OTHER INFORMATION: strain JP

<400> SEQUENCE: 27

```
atgggcatgc aatgcaacac taaattgtta ttgccagtcg cactaatacc ggttgtaatc     60

atcctaattg gtactctagt gcccatactt ttacatgaac aaaaaaaggc gttttactgg    120

cgactttttc tgcaaagtca acatgtagaa gcacccatta cagtaacgca gggagacaca    180

gtctacctag atgctagcaa taatccctgt aattattcca gcttttggta ccacggtaat    240

tgcgaacttt gtggatggaa cggatatcta cgcaatgtta cacattacta cacaaacaca    300

tcgtgttccc cgcaattcat gtgcataaac gaaactaaag gtctgcagtt atataatgta    360

acattaaacg attcaggtgc ttatactgaa cacgtttacg aatgtgatct ttcatgtaac    420

attactactt ataacgaata tgaaatactc aattacttcg ataactgtaa ctacaccata    480

aatagcacca agcatattat caccgtggtg tcttcacgtc attctaaaca aacaaattcc    540

cacgtatcca ctcacgctgg ttgggcagcc gccgtggtga cggtaattat gatctacgtt    600

ttgatccact ttaacgttcc ggcaactctg agacacaaac tacgaactag aaacaacgta    660

aatcgcatag cgtga                                                      675
```

<210> SEQ ID NO 28
<211> LENGTH: 675
<212> TYPE: DNA
<213> ORGANISM: Human herpesvirus 5
<220> FEATURE:
<221> NAME/KEY: gene
<222> LOCATION: (1)..(675)
<223> OTHER INFORMATION: strain Toledo

<400> SEQUENCE: 28

```
atgggcatgc aatgcaacac taaattgtta ttgccagtcg cactaatacc ggttgcaatc     60

atcctaattg gtactctagt gccgatactt ttacatgaac aaaaaaaggc gttttactgg    120

cgactttttc tgcaaagtca acatgtagaa gcacccatta cagtaacgca gggagacaca    180

gtctacctag acgctagcaa taatccctgt aattattcca gcttttggta ccacggtaat    240

tgcgaacttt gtggatggaa cggatatcta cgcaatgtta cacattacta cacaaacaca    300

tcgtgttccc cgcaattcat ctgcataaac gaaactaaag gtctgcagtt atataatgta    360

acattaaacg attcaggcgc ttatactgaa cacgtttacg aatgtgacct ttcgtgtaac    420

attactacta ataacgaata tgaaatactc aattattttg ataactgtaa ctacaccata    480

aatagcacca agcatattat caccgtggtg tcttcacgtc attctaaaca aacaaattcc    540
```

```
cacgtatcca ctcacgctgg ttgggcagtc gccgtggtga cggtaattat gatctacgtt    600

ctgatccact ttaacgtccc ggcaactctg agacacaaac tacgaactag aaacaacgta    660

aatcgcatag cgtga                                                     675
```

<210> SEQ ID NO 29
<211> LENGTH: 657
<212> TYPE: DNA
<213> ORGANISM: Human herpesvirus 5
<220> FEATURE:
<221> NAME/KEY: gene
<222> LOCATION: (1)..(657)
<223> OTHER INFORMATION: strain Merlin

<400> SEQUENCE: 29

```
atgggtgtac aatgtaacag taaactgctg ctactagccg tactaataac aattatccta     60

tctagcattc tggtacaggc aattccacat aaacaaaaaa catcctacca gcagctcttg    120

ctgcaaagtg aacatgtaca aatacccatc acagtagccg aaggagatac aatttgcttt    180

aacgttagtg ataacccctg caacttttct agttactgga atcacaataa ctgcgaactt    240

tgcggttgga caccatttta ctcggaatat gctggatatt ccgaaaacaa gtcgtgtcac    300

ccacgattta cctgtcttca cgatactaaa ggtctgaaac tacacaacgt aactacaaat    360

gattcaggaa tttatacccg aaacgtttat tactgtgaca ttccatgcaa catcagcgat    420

gatcataaac ataacgtaga ggactttgac aactgtaaca ccactataaa tagaactcac    480

tatattatta ctgtctcgtc ttcacgttat tctaaacgca ccaattccca cgtagccact    540

cacgttggtt ggacagccac cgtggtgata attatctgcg ttttaactta cgttaacgtt    600

acaacaaccc tgaagcacag actacgaact agaaacaacg tcaaccacac aatgtga       657
```

<210> SEQ ID NO 30
<211> LENGTH: 1126
<212> TYPE: DNA
<213> ORGANISM: Human herpesvirus 5
<220> FEATURE:
<221> NAME/KEY: gene
<222> LOCATION: (1)..(1126)
<223> OTHER INFORMATION: complement, strain AD169 substrain varUK

<400> SEQUENCE: 30

```
ctaccactgc ttgaagtagg gcaccgggtg tttcttttcc tcaacgggct cctccagtct     60

cttataggac cagtcccgcc ggcgcgccag catgtaggtc acgtacaaaa gaataatcac    120

catgaacacc aggaaagcca gcacgccgta ggccagcagc cggtcctcga acagcgggtc    180

gctcttgata aacacgtagg tggtggtaaa acttcggccc gcaatctgaa cgtggagacg    240

cacgacagta tacgtgccgt tgaggtagaa gacaaactcg cgtaaccgtt gtccgttata    300

cgtcacgtta ctaatattcc acggcggaat gagctggttg ccctgatgca gatgcacggt    360

gctgttgggg tgatagaggc tgctaccgtt gagcaagcag tgttcgtgtt cctgaagcag    420

cacgcggacc cgcatcgtgg tggcgttcag gcgagtcccg tacacggcgt agatgggata    480

ggtgaaaagg tcccaagtgg cgttgtgatg gcggccccag ctgaagaaag agcacgtgta    540

ctcagtggtc tcctgcggcc tgagtcccga gataagcagc tcttgagcag tagcgttgta    600

ggagagatgt agttttcctg tggataaaat tcataagttg tttattttgt tggcaggttg    660

gcgggggagg aaaaggggtt gaacagaaag gtaggtgcta cttaccttca ttatcggggg    720

ggaaggcgct aagatacccc acctgagtga agggaccctt gcagtctgtc cgtgcataac    780

aagtaactga taaaatgtct ggatttttgg tgttattcaa caggataact ttgcaggtgg    840
```

```
cgtttagaga cacttggtcg tggctgtagc tggcttcgca attcacagta tacaggtgcc    900

cctctttctg cgtcgtggct atcacggaag tggaggcgga cgaggtagag gtttgtaccg    960

tggtggtgac agcagaagtg acgttgttag aggtacttat tgacgtagta gacgtgacgg   1020

tggtattact aggggaagtg acggcgcttg tggtgctact tttcaccccc gggtgcatgt   1080

cgcccaagag cgcaactacg agcgcgatcg ccagtacgga acacat                  1126


<210> SEQ ID NO 31
<211> LENGTH: 1126
<212> TYPE: DNA
<213> ORGANISM: Human herpesvirus 5
<220> FEATURE:
<221> NAME/KEY: gene
<222> LOCATION: (1)..(1126)
<223> OTHER INFORMATION: complement, strain AD169 substrain varUC

<400> SEQUENCE: 31

ctaccactgc ttgaagtagg gcaccgggtg tttcttttcc tcaacgggct cctccagtct     60

cttataggac cagtcccgcc ggcgcgccag catgtaggtc acgtacaaaa gaataatcac    120

catgaacacc aggaaagcca gcacgccgta ggccagcagc cggtcctcga acagcgggtc    180

gctcttgata aacacgtagg tggtggtaaa acttcggccc gcaatctgaa cgtggagacg    240

cacgacagta tacgtgccgt tgaggtagaa gacaaactcg cgtaaccgtt gtccgttata    300

cgtcacgtta ctaatattcc acggcggaat gagctggttg ccctgatgca gatgcacggt    360

gctgttgggg tgatagaggc tgctaccgtt gagcaagcag tgttcgtgtt cctgaagcag    420

cacgcggacc cgcatcgtgg tggcgttcag gcgagtcccg tacacggcgt agatgggata    480

ggtgaaaagg tcccaagtgg cgttgtgatg gcggccccag ctgaagaaag agcacgtgta    540

ctcagtggtc tcctgcggcc tgagtcccga gataagcagc tcttgagcag tagcgttgta    600

ggagagatgt agttttcctg tggataaaat tcataagttg tttattttgt tggcaggttg    660

gcgggggagg aaaaggggtt gaacagaaag gtaggtgcta cttaccttca ttatcggggg    720

ggaaggcgct aagataccce acctgagtga agggacccct gcagtctgtc cgtgcataac    780

aagtaactga taaaatgtct ggatttttgg tgttattcaa caggataact ttgcaggtgg    840

cgtttagaga cacttggtcg tggctgtagc tggcttcgca attcacagta tacaggtgcc    900

cctctttctg cgtcgtggct atcacggaag tggaggcgga cgaggtagag gtttgtaccg    960

tggtggtgac agcagaagtg acgttgttag aggtacttat tgacgtagta gacgtgacgg   1020

tggtattact aggggaagtg acggcgcttg tggtgctact tttcaccccc gggtgcatgt   1080

cgcccaagag cgcaactacg agcgcgatcg ccagtacgga acacat                  1126


<210> SEQ ID NO 32
<211> LENGTH: 1144
<212> TYPE: DNA
<213> ORGANISM: Human herpesvirus 5
<220> FEATURE:
<221> NAME/KEY: gene
<222> LOCATION: (1)..(1144)
<223> OTHER INFORMATION: complement, strain Towne

<400> SEQUENCE: 32

ctaccactgc ttgaagtagg gcaccgggtg tttcttttcc tcaacgggct cctccagtct     60

cttataggac cagtcccgcc ggcgcgccag catgtaggtc acgtacaaaa gaataattac    120

catgaacacc aggaaagcca gcacgccgta ggccagcagc cggtcctcga acagcgggtc    180

gctcttgata aacacgtagg tggtggtaaa acttcggccc gcgatctgaa cgtggagacg    240
```

```
cacgacagta tacgtgccgt tgaggtagaa gacaaactcg cgtaaccgtt gtccgttata    300
cgtcacgtta ctaatattcc acggcggaat gagctggtcg ccctgatgca gatgcacggt    360
gctgtttggg tgatagaggc tgctaccgtt gagcaagcag tgttcgtgtt cctgaagcag    420
cacgcggacc cgcatcgtgg tagcgttcaa gcgagtcccg tacacggcgt agatgggata    480
ggtgaaaagg tcccaagtgg cgttgtgatg gcggccccag ctgaaaaaag agcacgtgta    540
ctcagtggtc tcctgcggcc tgagtcccga gataagcagc tcttgagcag tagcgttgta    600
ggagagatgt agttttcctg tggataaaat tcatatgctg tttattctgt tagcaggttg    660
gtgggggagg aaggggaata gaacagaggc ggtattactt acctttatca ccgggcgcaa    720
aagcgctaag ataccccacc tgagtgaagg gacccttgca gtctgtccgt gcataacagg    780
taatggacaa aatgtcggga tttacggtgt tgttcaacag ggacacttta caggtggcgt    840
tgagagacac ctggtcgtag ctgtagctgg cttcgcaatt cacagtatac aggtgcccct    900
ctttctgcgt cgtggctgcc acggaggtag cggcggatgt gaaggtagag ccggacgtgg    960
aaatagaggt ttgtaccgtg gtgctgacgg cagaagtgac gttattagag gtacttattg   1020
acgtagtgga cgtgacggtg gtattaatgg gggaagtgac ggcgcttgtg gtgctacttt   1080
ccactcccgg gtgcgtgtcg cctaagagcg taaccatgag cgcgatcgcc agtacgggac   1140
acat                                                                1144
```

<210> SEQ ID NO 33
<211> LENGTH: 1152
<212> TYPE: DNA
<213> ORGANISM: Human herpesvirus 5
<220> FEATURE:
<221> NAME/KEY: gene
<222> LOCATION: (1)..(1152)
<223> OTHER INFORMATION: complement, strain HAN38

<400> SEQUENCE: 33

```
ttcgggtcct accactgctt gaagtagggc accgggtgtt tcttttcctc aacgggctcc     60
tccagtctct tataggacca gtcccgccgg cgcgccagca tgtaggtcac gtacaaaaga    120
ataattacca tgaacaccag gaaagccagc acgccgtagg ccagcagccg gtcctcgaac    180
agcgggtcgc tcttgataaa cacgtaggtg gtggtaaaac ttcggcccgc gatctgaacg    240
tggagacgca cgacagtata cgtgccgttg aggtagaaga caaactcgcg taaccgttgt    300
ccgttatacg tcacgttact aatattccac ggcggaatga gctggtcgcc ctgatgcaga    360
tgcacggtgc tgttggggtg atagaggctg ctaccgttga gcaagcagtg ttcgtgttcc    420
tgaagcagca cgcggacccg catcgtggta gcgttcaagc gagtcccgta cacggcgtag    480
atgggatagg tgaaaaggtc ccaagtggcg ttgtgatggc ggccccagct gaagaaagag    540
cacgtgtact cagtggtctc ctgcggcctg agtcccgaga taagcagctc ttgagcagta    600
gcgttgtagg agagatgtag ttttcctgtg gataaaattc atatgctgtt tattctgtta    660
gcaggttggt gggggaggaa ggggaataga acagaggcgg tattacttac ctttatcacc    720
gggcgcaaaa gcgctaagat accccacctg agtgaaggga cccttgcagt ctgtccgtgc    780
ataacaggta atggacaaaa tgtcgggatt tacggtgttg ttcaacaggg acactttaca    840
agtggcgttg agagacacct ggtcgtagct gtagctggct tcgcaattca cagtatacag    900
atgcccctct ttctgcgttg tggctgccac ggaggtagcg gcggatgtga aggtagagcc    960
ggacgtggaa atagaggttt gtaccgtggt gctgacggca gaagtgacgt tattagaggt   1020
acttattgac gtagtggacg tgacggtggt attaatgggg gaagtgacgg cgcttgtggt   1080
```

gctactttcc actcccgggt gcgtgtcgcc taagagcgta accatgagcg cgatcgccag 1140
tacgggacac at 1152

<210> SEQ ID NO 34
<211> LENGTH: 1124
<212> TYPE: DNA
<213> ORGANISM: Human herpesvirus 5
<220> FEATURE:
<221> NAME/KEY: gene
<222> LOCATION: (1)..(1124)
<223> OTHER INFORMATION: complement, strain HAN20

<400> SEQUENCE: 34
ctaccactgc ttgaagtagg gcaccgggtg tttcttttcc tcaacgggct cctccagtct 60
cttataggac cagtcccgcc ggcgcgccag catgtaggtc acgtacaaaa gaataattac 120
catgaacacc aggaaagcca gcacgccgta ggccagcagc cggtcctcga acagcgggtc 180
gctcttgata aacacgtagg tggtggtaaa acttcggccc gcgatctgaa cgtggagacg 240
cacgacagta tacgtgccgt tgaggtagaa gacaaactcg cgtaaccgtt gtccgttata 300
cgtcacgtta ctaatattcc acggcggaat gagctggtcg ccctgatgca gatgcacggt 360
gctgttgggg tgatagaggc tgttaccgtt gagcaagcag tgttcgtgtt cctgaagcag 420
cacgcggacc cgcatcgtgg tggcgttcag gcgagtcccg tacacggcgt agatgggata 480
ggtgaaaagg tcccaagtgg cgttgtgatg gcggccccag ctgaagaaag agcacgtgta 540
ctcagtggtc tcctgcggcc tgagtcccga gataagcagc tcttgagcag tagcgttgta 600
ggagagatgt agttttcctg cggataaaat taatgtttat tttgatatca ggttgacgag 660
ggaggaaaag gggttgaaca gaaaggtagg tgctacttac cttcattatc gggggggaaaa 720 gcgctaagat accccacctg agtgaaggga cctttgcagt cggtccgtgc ataacaagta 780
actgataaaa tgtctggatt tttggtgtta ttcaacagga taactttgca ggtggcgttt 840
agagacactt ggtcgtagct gtagctggct tcgcaattca cagtatacag gtgcccctct 900
ttctgcgtcg tggctatcac ggaggtggag gcggacgagg tagaggtttg taccgtggtg 960
gtgacagcag aagtgacgtt gttagaggta cttattgacg tagtggatgt ggcggtggta 1020
ttactagggg aagtaacggc gcttgtggtg ctactttcca ctcccgggtg cgtgtcgtcc 1080
aaaagcgcaa ccacgagtac gatcgccagt acgggacaca tcat 1124

<210> SEQ ID NO 35
<211> LENGTH: 1364
<212> TYPE: DNA
<213> ORGANISM: Human herpesvirus 5
<220> FEATURE:
<221> NAME/KEY: gene
<222> LOCATION: (1)..(1364)
<223> OTHER INFORMATION: complement, strain HAN13

<400> SEQUENCE: 35
atgggtgtac aatataacac taaactgctg ttattagccg tattagcaat tatcccagct 60
ggcattctag tacaggcaat ttcacatgag caaaaaaacat cctaccggca acttttgctg 120
caaagtgaac gtgtgcaaat acccatcaca acagtcgagg gagatacaat ttgctttaac 180
gttagtaaca acccctgcaa cttttccagt tattggaatc acaataattg tgaactttgc 240
ctaccactgc ttgaagtagg gcaccgggta tttcttttcc tcaacgggct cctccagtct 300
cttataggac cagtcccgcc ggcgcgccag catgtaggtc acgtacaaaa gaataattac 360
catgaacacc aggaaagcca gcacgccgta ggccagcagc cggtcctcga acagcgggtc 420
gctcttgata aacacgtagg tggtggtaaa acttcggccc gcgatctgaa cgtggagacg 480
cacgacagta tacgtgccgt tgaggtagaa gacaaactcg cgtaaccgtt gtccgttata 540
cgtcacgtta ctaatattcc acggcggaat gagctggtcg ccctgatgca gatgcacggt 600
gctgttgggg tgatagaggc tgctaccgtt gagcaagcag tgttcgtgtt cctgaagcag 660
cacgcggacc cgcatcgtgg tggcgttcag gcgagtcccg tacacggcgt agatgggata 720
ggtgaaaagg tcccaagtgg cgttgtgatg gcggccccag ctgaagaaag agcacgtgta 780
ctcagtggtc tcctgcggcc tgagtcccga gataagcagc tcttgagcag tagcgttgta 840
ggagagatgt agttttcctg cggataaaat taatgtttat tttgatatca ggttgacgag 900
ggaggaaaag gggttgaaca gaaaggtagg tgctacttac cttcattatc gggggraaaa 960
gcgctaagat accccacctg agtgaaggga cctttgcagt cggtccgtgc ataacaagta 1020
actgataaaa tgtctggatt tttggtgtta ttcaacagga taactttgca ggtggcgttt 1080
agagacactt ggtcgtagct gtagctggct tcgcaattca cagtatacag gtgcccctct 1140
ttctgcgtcg tggctatcac ggaggtggag gcggacgtgg aggtagaggt ttgtaccgtg 1200
gtggtgacag cagaagtgac gttgttagag gtacttattg acgtagtaga cgtgacggtg 1260
gtattactaa gggaagtgac ggcgcctgtg gtgctacttt tcacccccgg gtgtgtgtcg 1320
cccaagagcg cgactacgag cgcgatcgcc agtacggagc acat 1364

<210> SEQ ID NO 36
<211> LENGTH: 1121
<212> TYPE: DNA
<213> ORGANISM: Human herpesvirus 5
<220> FEATURE:
<221> NAME/KEY: gene
<222> LOCATION: (1)..(1121)
<223> OTHER INFORMATION: complement, strain 3157

<400> SEQUENCE: 36
ctaccactgc ttgaagtagg gcaccgggtg tttcttttcc tcaacgggct cctccagtct 60
cttataggac cagtcccgcc ggcgcgccag catgtaggtc acgtacaaaa gaataattac 120
catgaacacc aggaaagcca gcacgccgta ggccagcagc cggtcctcga acagcgggtc 180
gctcttgata aacacgtagg tggtggtaaa acttcggccc gcgatctgaa cgtggagacg 240
cacgacagta tacgtgccgt tgaggtagaa gacaaactcg cgtaaccgtt gtccgttata 300
cgtcacgtta ctaatattcc acggcggaat gagctggtcg ccctgatgca gatgcacggt 360
gctgttgggg tgatagaggc tgctaccgtt gagcaagcag tgttcgtgtt cctgaagcag 420
cacgcggacc cgcatcgtgg tggcgttcag gcgagtcccg tacacggcgt agatgggata 480
ggtgaaaagg tcccaagtgg cgttgtgatg gcggccccag ctgaagaaag agcacgtgta 540
ctcagtggtc tcctgcggcc tgagtcccga gataagcagc tcttgagcag tagcgttgta 600
ggagagatgt agttttcctg cggataaaat taatgtttat tttgatatca ggttgacgat 660
ggaggaaaag gggttgaaca gaaaggtagg tgctacttac cttcgttatc gggggraaaa 720
gcgctaagat accccacctg agtgaaggga cctttgcagt cggtccgtgc ataacaagta 780
actgataaaa tgtctggatt tttggtgtta ttcaacagga taactttgca ggtggcgttt 840
agagacactt ggtcgtagct gtagctggct tcgcaattca cagtatacag gtgcccctct 900
ttctgcgtcg tggctatcac ggaggtggag gcggacgagg tagaggtttg taccgtggtg 960
gtgacagcag aagtgacgtt gttagaggta cttattgacg tagtggatgt ggcggtggta 1020
ttactagggg aagtaacggc gcttgtggtg ctactttcca ctcccgggtg cgtgtcgccc 1080

-continued

```
aaaagcgcaa ccacgagtac gatcgccagt acgggacaca t                    1121


<210> SEQ ID NO 37
<211> LENGTH: 1129
<212> TYPE: DNA
<213> ORGANISM: Human herpesvirus 5
<220> FEATURE:
<221> NAME/KEY: gene
<222> LOCATION: (1)..(1129)
<223> OTHER INFORMATION: complement, strain 3301

<400> SEQUENCE: 37

ctaccactgc ttgaagtagg gcaccgggtg tttcttttcc tcaacgggct cctccagtct     60

cttataggac cagtcccgcc ggcgcgccag catgtaggtc acgtacaaaa gaataattac    120

catgaacacc aggaaagcca gcacgccgta ggccagcagc cggtcctcga acagcgggtc    180

gctcttgata aacacgtagg tggtggtaaa acttcggccc gcgatctgaa cgtggagacg    240

cacgacagta tacgtgccgt tgaggtagaa gacaaactcg cgtaaccgtt gtccgttata    300

cgtcacgtta ctaatattcc acggcggaat gagctggttg ccctgatgca gatgcacggt    360

gctgttgggg tgatagaggc tgctaccgtt aagcaagcag tgttcgtgtt cctgaagcag    420

cacgcggacc cgcatcgtgg tggcgttcaa gcgagtcccg tacacggcgt agatgggata    480

ggtgaaaagg tcccaagtgg cgttgtgatg gcggccccag ctaaagaagg agcacgtgta    540

ctcagtagtc tcctgcggcc tgagtcccga gataagcagc tcttgagcag tagcgttata    600

ggagagatgt agttttcctg tggataaaat tcataagttg tttattttgt tagcaggttg    660

gcgggggagg aaggggaaca aaacagacaa gtacgtatta cttaccttta tcgttggagg    720

gaaaggcgct aagatacccc acctgagtga agggaccctt gcagtctgtt cgtgcataac    780

aggtaacaga taaaatgtct ggattttttg tgttgttcaa tagagtaact ttgcaggtgg    840

cgttgagaga cacctggtcg tagctgtagc tggcttcgca attcacagta tacaggtgcc    900

cctctttctg cgtcgtggct atcacggagg tggaggcgga cgtggaggta gaggtttgta    960

ccgtggtggt gacagcagaa gtgacgttgt tagaggtact tattgacgta gtagacgtga   1020

cggtggtatt actaagggaa gtgacggcgc ctgtggtgct acttttcacc cccgggtgtg   1080

tgtcgcccaa gagcgcgact acgagcgcga tcgccagtac ggagcacat              1129


<210> SEQ ID NO 38
<211> LENGTH: 1144
<212> TYPE: DNA
<213> ORGANISM: Human herpesvirus 5
<220> FEATURE:
<221> NAME/KEY: gene
<222> LOCATION: (1)..(1144)
<223> OTHER INFORMATION: complement, strain JP

<400> SEQUENCE: 38

ctaccactgc ttgaagtagg gcaccgggtg tttcttttcc tcaacgggct cctccagtct     60

cttataggac cagtcccgcc ggcgcgccag catgtaggtc acgtacaaaa gaataattac    120

catgaacacc aggaaagcca gcacgccgta ggccagcagc cggtcctcga acagcgggtc    180

gctcttgata aacacgtagg tggtggtaaa acttcggccc gcgatctgaa cgtggagacg    240

cacgacagta tacgtgccgt tgaggtagaa gacaaactcg cgtaatcgtt gtccgttata    300

cgtcacgtta ctaatattcc acggcggaat gagctggtcg ccctgatgca gatgcacggt    360

gctgttgggg tgatagaggc tgctaccgtt gagcaagcag tgttcgtgtt cctgaagcag    420

cacgcggacc cgcatcgtgg tagcgttcaa gcgagtcccg tacacggcgt agatgggata    480
```

ggtgaaaagg tcccaagtgg cgttgtgatg gcggccccag ctgaagaaag agcacgtgta 540
ctcagtggtc tcctgcggcc tgagtcccga gataagcagc tcttgagcag tagcgttgta 600
ggagagatgt agttttcctg tggataaaat tcatatgctg tttattctgt tagcaggttg 660
gtgagggagg aaggggaata gaacagaggc ggtattactt acctttatca ccgggcgcaa 720
aagcgctaag ataccccacc tgagtgaagg gacccttgca gtctgtccgt gcataacagg 780
taatggacaa aatgtcggga tttacggtgt tgttcaacag ggacacttta caggtggcgt 840
tgagagacac ctggtcgtag ctgtagctgg cttcgcaatt cacggtatac aggtgcccct 900
ctttctgcgt cgtggctgcc acggaggtag cggcggatgt gaaggtagag ccggacgtgg 960
aaatagaggt ttgtaccgtg gtgctgacgg cagaagtgac gttattagag gtacttattg 1020
acgtagtgga cgtgacggtg gtattaatgg gggaagtgac ggcgtttgtg gtgctacttt 1080
ccactcccgg gtgcgtgtcg cctaagagcg taaccatgag cgcgatcgcc agtacgggac 1140
acat 1144

<210> SEQ ID NO 39
<211> LENGTH: 1143
<212> TYPE: DNA
<213> ORGANISM: Human herpesvirus 5
<220> FEATURE:
<221> NAME/KEY: gene
<222> LOCATION: (1)..(1143)
<223> OTHER INFORMATION: complement, strain Toledo

<400> SEQUENCE: 39
ctaccactgc ttgaagtagg gcaccgggtg tttcttttcc tcaacaggct cctccagtct 60
cttataggac cagtcccgcc ggcgcgccag catgtaggtc acgtacaaaa gaataatcac 120
catgaacacc aggaaagcca gcacgccgta ggccagcagc cggtcttcga acagcgggtc 180
gctcttgata aacacgtagg tggtggtaaa acttcggccc gcgatctgaa cgtggagacg 240
cacgacagta tacgtgccgt tgaggtagaa gacaaactcg cgtaaccgtt gtccgttata 300
cgtcacgtta ctaatattcc acggcggaat gagctggttg ccttgatgca gatgcacggt 360
gctgttgggg tgatagaggc tgctaccgtt gagcaagcag tgttcgtgtt cctgaagcag 420
cacgcggacc cgcatcgtgg tggcgttcaa gcgagtcccg tacacggcgt agatgggata 480
ggtgaaaagg tcccaagtgg cgttgtgatg gcggccccag ctgaagaaag agcacgtgta 540
ctcagtggtc tcctgcggtc tgagtcccga gataagcagc tcttgagccg tggcattgta 600
ggacagatgt agttttcctg tggataaaat tcataaactg tttattttga tgtcaggtta 660
gcgggggagg aaggggaata gacggaaagg taggtgctac ttacctttat cgtcggaggg 720
gaaagcgcta agatacccca cctgagtgaa aggacctttg cagtttgtcc gtgcataaca 780
ggtaactgat aaaatgtctg gatttttggt gttgttcaac aggttaactt tgcaggtggc 840
gttcagagac acctggtcgt agctgtagct ggcttcgcaa ttcacattat acaggtgccc 900
ctctttctgc gtcgtggttg ccacggaggt agaggcggac gtggaggtag agccggacgt 960
gaaagtagag gtttgtaccg tggtggtgac ggtggaagta acgttattgg gggtatttat 1020
cgacgtagtg aatgtgacgg tgatattagg ggaagtgacg gcacttgtag tgctacttcc 1080
cattcccggg tgcgtgttac tcaagagcgc ggctgcgagc gcaatcgcca gtgcgggaca 1140
cat 1143

<210> SEQ ID NO 40
<211> LENGTH: 1126
<212> TYPE: DNA

<213> ORGANISM: Human herpesvirus 5
<220> FEATURE:
<221> NAME/KEY: gene
<222> LOCATION: (1)..(1126)
<223> OTHER INFORMATION: complement, strain Merlin

<400> SEQUENCE: 40
ctaccactgc ttgaagtagg gcaccgggtg tttcttttct tcaacgggct cctccagtct 60
cttataggac cagtcccgcc ggcgcgccag catgtaggtc acgtacaaaa gaataattac 120
catgaacacc aggaaagcca gcacgccgta ggccagcagc cggtcctcga acagcgggtc 180
gctcttgata aacacgtagg tggtggtaaa acttcggccc gcgatctgga cgtggagacg 240
cacgacagta tacgtgccgt tgaggtagaa gacaaactcg cgtaaccgtt gtccgttata 300
cgtcacgtta ctaatattcc acggcggaat gagctggtcg ccctgatgca gatgcacggt 360
gctgttgggg tgatagaggc tgctaccgtt gagcaagcag tgttcgtgtt cctgaagcag 420
cacgcggacc cgcatagtgg tagcgttcaa gcgagtcccg tacacggcgt aaatgggata 480
ggtgaaaagg tcccaagtgg cgttgtgatg gcggccccag ctgaagaaag agcacgtgta 540
ctcagtggtc tcctgcggcc tgagtcccga gataagcagc tcttgagcag tagcgttgta 600
ggagagatgt agttttcctg tggaaaaaat taatgagttg tttattttgt tagcaggttg 660
gcgagggagg aaggggaaca aaacagaaag gtacgtgtta cttaccttta tcgttggagg 720
gaaaagcgct aagatatccc acctgagtga agggaccctt gcagtctgtc cgtgcataac 780
aagtaactga taaaatgtct ggatttttgg tattattcaa caggataact ttgcaggtgg 840
cgtttagaga cacttggtcg tagctgtagc tggcttcgca attcacagta tacaggtgcc 900
cctctttctg cgtcgtggct atcacggagg tggaggcgga cgaggtagag gtttgtaccg 960
tggtggtgac agcagaactg acgttgttag aggtacttat tgacgtagta gacgtgacgg 1020
tggtattact aggggaagtg acggcgcttg tggtgctact tttcactccc gggtgcatgt 1080
cgcccaagag cgcaactacg agcgcgatcg ccagcacgga acacat 1126

<210> SEQ ID NO 41
<211> LENGTH: 324
<212> TYPE: DNA
<213> ORGANISM: Human herpesvirus 5
<220> FEATURE:
<221> NAME/KEY: gene
<222> LOCATION: (1)..(324)
<223> OTHER INFORMATION: complement, strain Towne

<400> SEQUENCE: 41
ctaattttta gtagtcaaat accataattc accgctgtac tcgtctttat tctctccgaa 60
ccaacgacca aggtcgacaa cgccatcgtt acccttcgtg atattgcaca gatctaaaga 120
tgtatgagta caattcgtta cacaaacgct tgatccatta ttcactagag gtgcatgtct 180
ccctgttaca ttacataacc atccttgatt cagatggctc catttcgtag tcatcgggtc 240
gtttttgtgt tcaatggtta cattgtcacc acttttaacc tctactttat tgaaacccgc 300
accttcatgt ataaacaccg tcat 324

<210> SEQ ID NO 42
<211> LENGTH: 324
<212> TYPE: DNA
<213> ORGANISM: Human herpesvirus 5
<220> FEATURE:
<221> NAME/KEY: gene
<222> LOCATION: (1)..(324)
<223> OTHER INFORMATION: complement, strain HAN13

<400> SEQUENCE: 42
ctaattttta gcagtcaaat accataattc accgctgtac tcgtctctat tctctccaaa 60
ccaacgacca agatcgacaa cgccgtcatt acccttcgta atattacaca aatctagaga 120
cgtatgggta caattcgtta cacagacgct tgatccgtta ttcactaaag gtgcatgcct 180
cccggttaca ttacataacc atcctttatc ccaatggctc catctagtag tcatcggatc 240 tttttgtgt tcaatggtta cattattacc actggtaact tccactctat taaaacccgc 300
actttcatgt ataaacaccg ttat 324

<210> SEQ ID NO 43
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain AD169 substrain varUK

<400> SEQUENCE: 43
ttagctgact tccaagtgcc acacatcacc actgtattca tccatgtttt caccgaacca 60
acgagacaga tcgaagaagc cagaatctcc cgactttaaa ttacataaat ccaacgtatt 120
atgaccacag ctcgacacac aaatagttgc gttactattc acagtagcat tacctatacc 180
cgtaacgttg cacaaccact gatcaccatt gttaccaaaa acggttttcc acttagttgt 240
caacggatct ttcctatgcg taatggtaaa attactacca gtcgtcgctt ttagctcatt 300
acgagtatta tccgcatcca catatatcaa cgtcat 336

<210> SEQ ID NO 44
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain AD169 substrain varUC

<400> SEQUENCE: 44
ttagctgact tccaagtgcc acacatcacc actgtattca tccatgtttt caccgaacca 60
acgagacaga tcgaagaagc cagaatctcc cgactttaaa ttacataaat ccaacgtatt 120
atgaccacag ctcgacacac aaatagttgc gttactattc acagtagcat tacctatacc 180
cgtaacgttg cacaaccact gatcaccatt gttaccaaaa acggttttcc acttagttgt 240
caacggatct ttcctatgcg taatggtaaa attactacca gtcgtcgctt ttagctcatt 300
acgagtatta tccgcatcca catatatcaa cgtcat 336

<210> SEQ ID NO 45
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain JP

<400> SEQUENCE: 45
ttagctgact tccaagtgcc acacatcacc actgtattca tccatgtttt caccgaacca 60
acgagacaga tcgaagaagc cagaatctcc cgactttaaa ttacataaat ccaacgtatt 120
atgaccacag ctcgacacac aaatagttgc gttactattc acagtagcat tacctatacc 180

-continued

```
cgtaacgttg cacaaccact gatcaccatt gttaccaaaa acggttttcc acttagttgt    240

caacggatct ttcctatgcg taatggtaaa attactacca gtcgtcgctt ttagctcatt    300

acgagtatta tccgcatcca catatatcaa cgtcat                              336


<210> SEQ ID NO 46
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain Toledo

<400> SEQUENCE: 46

ttagctgact tccaagtgcc acacatcacc actgtattca tccatgtttt caccgaacca     60

acgagacaga tcgaagaagc cagaatctcc cgactttaaa ttacataaat ccaacgtatt    120

atgaccacag ctcgacacac aaatagttgc gttactattc acagtagcat tacctatacc    180

cgtaacgttg cacaaccact gatcaccatt gttaccaaaa acggttttcc acttagttgt    240

caacggatct ttcccatgcg taatggtcaa attactacca gtcgtcgctt ttagctcatt    300

acgagtatta tccgcatcca catatatcaa cgtcat                              336


<210> SEQ ID NO 47
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain 3301

<400> SEQUENCE: 47

ttagctaact tccaagtacc acacatcacc actgtattca tccatgtttt caccgaacca     60

acgagacaga tcgaagaagc cagaatctcc cgactttaaa ttacataaat ccaacgtatt    120

atgaccacag ctcgacacac aaatagttgc gttactattc acagtagcat tacctatacc    180

cgtaacgttg cacaaccact gatcaccatt gttaccaaaa acggttttcc acttagttgt    240

caacggatct ttcctatgcg taatggtaaa attactacca gtcgtcgctt ttagctcatt    300

acgagtatta tccgcatcca catatatcaa cgtcat                              336


<210> SEQ ID NO 48
<211> LENGTH: 546
<212> TYPE: DNA
<213> ORGANISM: Human herpesvirus 5
<220> FEATURE:
<221> NAME/KEY: gene
<222> LOCATION: (1)..(546)
<223> OTHER INFORMATION: complement, strain Merlin

<400> SEQUENCE: 48

aacgaattac acgtagttta ttacatgaaa actgtaagaa caccaattca ctaagcgata     60

caacatttag ctgacttcca agtgccacac atcaccactg tattcatcca tgttttcacc    120

gaaccaacga gacagatcga agaagccaga atctcccgac tttaaattac ataaatccaa    180

cgtattatga ccacagctcg acacacaaat agttgcgtta ccattcacag tagcattacc    240

tatacccgta acgttgcaca accactgatc accattgtta ccaaaaacgg ttttccactt    300

agttgtcaac ggatctttcc tatgcgtaat ggtaaaatta ctcccagtcg tcgcttttag    360

ctcattacga gtattatccg catccacata tatcaacgtc atagctaggc acgctataag    420
```

```
taccccccccc ccacaatgga atgttgccaa accggttctt tcccgttata gccatagcgt    480

tcccaggcaa aagcaaacgc caaacctaat gcagtgaaaa gcgcttgcag ccagaaccag    540

cttatg                                                                546


<210> SEQ ID NO 49
<211> LENGTH: 336
<212> TYPE: DNA
<213> ORGANISM: Human herpesvirus 5
<220> FEATURE:
<221> NAME/KEY: gene
<222> LOCATION: (1)..(336)
<223> OTHER INFORMATION: complement, strain HAN20

<400> SEQUENCE: 49

ttatttgact tccaagtgcc acacatcacc actatattca tccatgtttt caccgaacca     60

acgagacaga tcgaagaagc cagaatcttc cgactttaaa ttacataaat ccaacgtatt    120

atgaccacag ctcgacacac aaatagttgc gttactattc acagtggcat tacctatacc    180

cgtaacgttg cacaaccact gatcaccatt gtcaccaaaa acggttttcc acttagttgt    240

caacggatct ttcctatgcg taatggtaaa attactacca gtcgtcgctt ttagctcatt    300

acgagtatta tccgcatcca catatatcaa cgtcat                              336


<210> SEQ ID NO 50
<211> LENGTH: 309
<212> TYPE: DNA
<213> ORGANISM: Human herpesvirus 5
<220> FEATURE:
<221> NAME/KEY: gene
<222> LOCATION: (1)..(309)
<223> OTHER INFORMATION: complement, strain 3157

<400> SEQUENCE: 50

ttatttattg aattatcaac gttacttagt tacaataaga aaccaagtat ccacttgttc     60

aggaccgtta tcaactctcc gctttaaatc ataagatcct tcgttgcctt gcgttacgtt    120

gcaaaacgtc aatcctgtat gactacaatt acacacaccg tgaatcggcg gcgttgctag    180

cgtgtaattc ttcgtcccct ccacactaca cacgtcggta tcatttttac catcaaaaaa    240

cgaccaaacc gttttcaggt tagcactaac ggttttatca tcaccggtct ttacatgaac    300

attagccat                                                             309


<210> SEQ ID NO 51
<211> LENGTH: 316
<212> TYPE: DNA
<213> ORGANISM: Human herpesvirus 5
<220> FEATURE:
<221> NAME/KEY: gene
<222> LOCATION: (1)..(316)
<223> OTHER INFORMATION: complement, strain HAN38

<400> SEQUENCE: 51

ttaagattgt gaaacaacgg gaaacgattc tcccggttct tcataaccac catactttgt     60

tttaacgcta taaacacctt cttgtattga cgtcatatgt atgattacat gcactgatac    120

aaacagtaat gtttgacgct acaacaccaa tatcattaaa ccgtacagta cataacaccg    180

tatcgccact gtcgtcacta gaaccacctc cgatcttttt ccaggtagaa tacacgtcag    240

gattccacgt tactgttcca gtactgttca gacgtatctt aacttccgta aatccataaa    300

taccgtggtt ccacgt                                                     316
```

FULL GENOME DNA OF HUMAN CYTOMEGALOVIRUS STRAIN JHC ISOLATED FROM KOREAN PATIENT AND OPEN READING FRAMES THEREOF

CROSS-REFERENCE TO RELATED APPLICATIONS

This application claims the benefits of Korean Patent application No. 10-2011-0061865, filed on Jun. 24, 2011 in the Korean Patent Office, and the U.S. Patent Application No. 61/441,508, filed on Feb. 10, 2011, in the U.S. Patent and Trademark Office, the disclosure of which is incorporated herein by reference in its entirety.

TECHNICAL FIELD

The following disclosure relates to analysis of full genome DNA sequences of human cytomegalovirus strains (hereinafter, referred to as 'HCMV') and, more particularly, to a full genome DNA of a human cytomegalovirus strain JHC isolated from a Korean patient as well as open reading frames thereof.

BACKGROUND

Human cytomegalovirus (that is, 'HCMV') belongs to beta-herpesvirus and contains double-stranded DNA with a length of 230 to 240 Kbp, which is the largest of the human viruses. HCMV is a ubiquitous pathogen and found worldwide both in developed industrial societies and in isolated aboriginal groups. Although most of the HCMV infections are not symptomatic, severe clinical outcomes may arise in neonates, immuno-compromised hosts and recipients of organ transplants.

Since HCMV was first and successfully isolated from the salivary glands, adenoid tissues and urine in the 1950's, HCMV isolation has been performed worldwide from various parts of the infected human. Genome-wide analyses of HCMV genetic contents became possible when the genome of the widely used laboratory strain AD169 was fully sequenced by plasmid cloning and a Sanger method. An analysis result of 230 Kbp genome has identified ~150 to at most up to 192 open reading frames ('ORFs'), which may potentially encode a protein. Most low-passage strains have 19 ORFs encompassing ~15 Kbp in UL/b' region that are absent from the high-passage strain AD169. This region is inverted within the genome relative to its counterpart in AD169.

Due to the large genome size of HCMV, there have been difficulties in obtaining the whole genome sequences of HCMV. As sequencing technologies have recently developed, almost 20 whole genome sequences have been determined for HCMV. Cloning of the entire HCMV genome into bacterial artificial chromosome has enabled analysis of full genome sequences of well-known strains such as Toledo, Towne, TB40/E, etc., as well as clinically isolated ones ('isolates') such as FIX, PH and TR. In recent years, high-throughout sequencing technology using Illumina Genome Analyzer has been used to obtain complete genome sequences of Towne and AD169 variants as well as several clinical isolates. In order to determine the whole genome sequences for clinical isolates, polymerase chain reaction (PCR) sequencing techniques have been applied.

Until now, all of the full genome sequences of HCMV isolates are from European countries or the United States, while full genome sequences of HCMV isolated from Asian people, especially, Korean people have not been reported.

SUMMARY

The inventors of the present invention have found a full genome sequence of a HCMV strain JHC isolated from a Korean patient and conducted analysis of open reading frames (ORFs) as well as phylogenetic analysis of the foregoing strain. The present invention was completed under the foregoing discovery.

The first object of the present invention is to provide a full genome DNA of a HCMV strain JHC.

The second object of the present invention is to provide ORFs of the full genome DNA of the HCMV strain JHC.

The third object of the present invention is to provide a protein encoded by an ORF of the full genome DNA of the HCMV strain JHC.

The fourth object of the present invention is to provide a transformant containing the full genome DNA of the HCMV strain JHC or ORFs thereof.

The fifth object of the present invention is to provide a method for genome analysis of HCMV strains using the full genome DNA of the HCMV strain JHC or ORFs thereof.

According to a first aspect of the present invention, there is provided a full genome DNA of a HCMV strain JHC having a DNA sequence defined by SEQ. ID NO. 1.

According to a second aspect of the present invention, there is provided an ORF of the full genome DNA of the HCMV strain JHC described above. In one embodiment, the ORF may be selected from UL1 having a DNA sequence defined by SEQ. ID NO. 2, UL119 having a DNA sequence defined by SEQ. ID NO. 3 and RL6 having a DNA sequence defined by SEQ. ID NO. 4.

According to a third aspect of the present invention, there is provided a protein encoded by the foregoing ORF of the full genome DNA of the HCMV strain JHC.

According to a fourth aspect of the present invention, there is provided a transformant including the full genome DNA of the HCMV strain JHC or ORFs thereof.

According to a fifth aspect of the present invention, there is provided a method for genome analysis of HCMV strains, including:

determining a genome sequence of a HCMV strain as a subject of the analysis; and comparing the determined genome sequence with that of the full genome DNA of the HCMV strain JHC described above or ORFs thereof, and analyzing the genome of the HCMV strain as the subject of the analysis.

Other features and aspects will be apparent from the following detailed description, the drawings, and the claims.

BRIEF DESCRIPTION OF THE DRAWINGS

FIG. 4A illustrates a nucleotide sequence alignment of HCMV RL6 gene;

DETAILED DESCRIPTION OF EMBODIMENTS

Figure 1A:
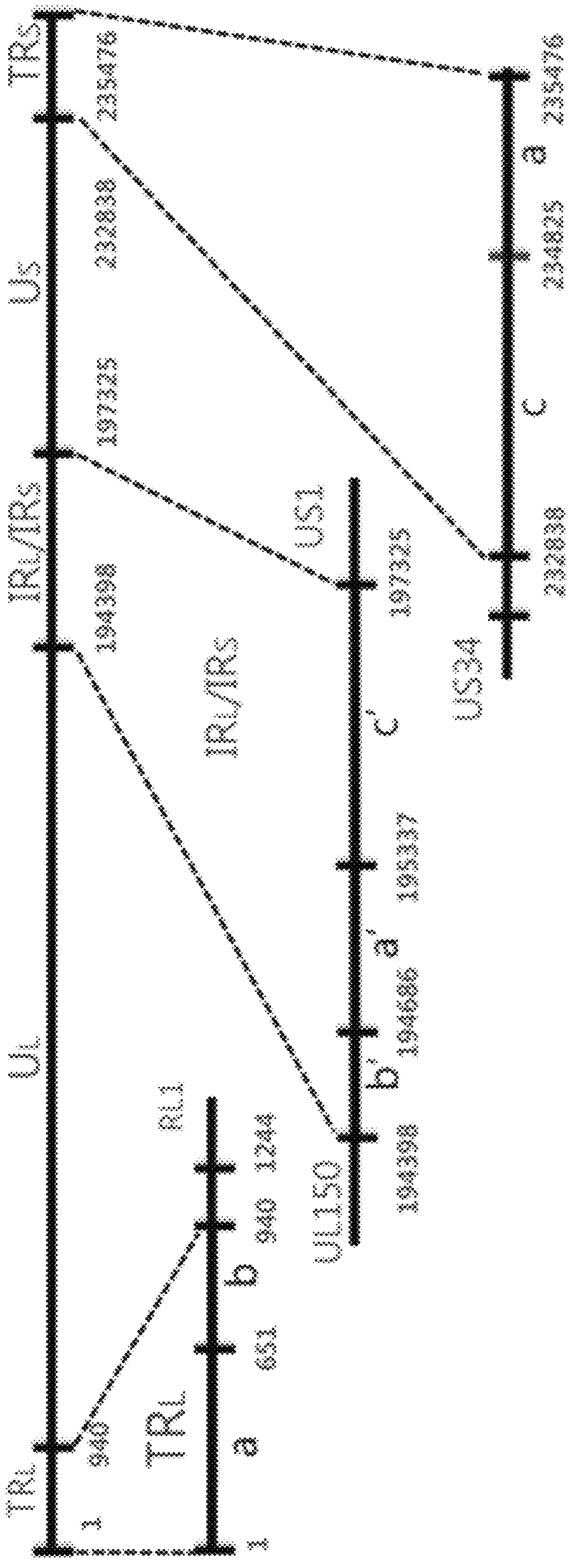
FIG. 1A illustrates a genome map of HCMV strains JHC.

In the description, the term "open reading frame" or an ORF refers to a DNA sequence translated into an amino acid sequence, which ranges from a translation start codon (e.g., ATG) to a stop codon (e.g., TGA, TAA, TAG).

The term "transformant" refers to a genetically modified cell by acquiring a foreign gene, for example, includes transformed micro-organisms, i.e., bacteria such as *E. coli.*

The present invention relates to an analysis of a full genome sequence of a JHC strain isolated from a Korean patient. This virus was isolated from patients who have received bone marrow transplant and exhibited resistance to ganciclovir ('GCV') treatment. Such isolated virus was found to have GCV sensitivity. This fact was considered in respects to selecting minor viral species with a growth advantage in cell culture. This virus was named JHC and the present invention has determined a full genome sequence of the JHC virus strain. The JHC strain is the first Asian strain of which a full genome sequence has been determined.

A genomic architecture of the strain JHC is typical of HCMV, which comprises unique long (Ul) and unique short (Us) regions surrounded by repeat sequences. The strain JHC has 19 ORFs known as Ul/b' that are absent from the highly lab-adapted AD 169, at 3' end of the Ul region. All the clinical isolates with limited passages of in vitro cell culture have Ul/b' sequences, and the strain JHC is not exceptional.

As a result of sequence analysis, it was found that most ORFs in the strain JHC are substantially identical to those in other strains. The exception is only two ORFs (UL1 and UL119) showing early stops and one ORF (RL6) having an unusual start codon. Early stops are usually generated by frame-shift mutation due to insertion or deletion of 3n+1 or 3n−1 nucleotides. For the strain JHC, deletion of 4 or 8 nucleotides may cause frame-shift mutations. These ORFs are not essential for HCMV replication and premature translation termination may not be too detrimental for virus replication. RL6 is a member of RL11 family and is the most variable of 164 ORFs among the 12 HCMV strains used in the present invention. The strain JHC contains an unusual start codon TTG.

The strain JHC has all gene information for 14 micro-RNA (microRNA, miRNA) sequences and a miRNA sequence is almost 100% conserved in the strain JHC, and likewise with other HCMV strains. The only exception is a sequence of miR-UL70-1-5p wherein the first base T is substituted by C and this substitution is also found in the strains Merlin, HAN13, HAN20 and 3157.

Recent studies suggest accumulation of mutations during adaption to in vitro cell culture. Most widely affected genes are RL13 and UL128 locus (UL128 consisting of genes UL128, UL130 and UL131A.

Hereinafter, preferred embodiments of the present invention will be described in detail with reference to examples, however, such examples are for illustrative purposes only and not intended to limit the scope of the present invention.

EXAMPLE 1

Virus and DNA Sequencing

The HCMV strain JHC was isolated from a Korean patient who has undergone bone marrow transplant (Jung G S, Kim Y Y, Kim J I, Ji G Y, Jeon J S, Yoon H W, Lee G C, Ahn J H, Lee K M, Lee C H., 2011, Full Genome Sequencing and Analysis of Human Cytomegalovirus Strain JHC Isolated From a Korean Patient, Virus Res. March; 156 (1-2):113-20. Epub January 19). The patient exhibited resistance to ganciclovir treatment, but the isolated virus was sensitive to ganciclovir and did not contain M460V mutation in UL97 gene. The virus from the patient's blood was inoculated into human foreskin fibroblast (HFF) cells and the plaque was purified and subjected to 3 additional passages in HFF cells. The virus used for sequencing was a product obtained after four passages.

DNA was extracted from the strain JHC stock with QIAamp DNA Mini Kit (QIAGEN) at a concentration of 5 μl g/100 μl. DNA sequence was determined by a high throughout sequencing method using a Genome Sequencer FLX standard system of Roche Diagnostics serviced by Macrogen. 77,390 sequence fragments with an average length of ~250 bp long were obtained and these were assembled and viewed using Consed program. An average quality of the sequence fragments was 99.99%. A total of 98.26% of 231,387 sequences was matched with the derived consensus sequence and the coverage was 154 reads per nucleotide. These were aligned against two reference strains AD169-varUK (NC_001347.6) and Merlin (NC_006273.2) and 4 large contigs were obtained. Gaps between the contigs were filled by PCR Sequencing using primers obtained from the adjacent contigs.

The completed entire genome sequence of the strain JHC was represented by SEQ. ID NO. 1. As shown with SEQ. ID NO. 1, it was found that the genome of the strain JHC has a length of 235,476 bp.

EXAMPLE 2

Analysis of Open Reading Frames

A location of open reading frames (ORFs) of the strain JHC in the full genome sequence was determined by Blast search for two reference strains AD169-varUK and Merlin. The resulting data included the first and last nucleotide positions of each ORF in the strain JHC genome and direction of the ORFs. The ORF information was verified by ORF finding programs such as CLC Sequence Viewer (version 6.1) and ORF Finder provided by NCBI. When the results of the blast search did not coincide with those of ORF finding programs, the nucleotide sequences of the corresponding ORFs were examined with BioEdit Sequence Alignment Editor (Department of Microbiology, North Carolina State University, version 5.0.9) and manually edited to determine the position of the start and stop codons. Finally, all the allocated ORFs were confirmed by identification of the translated amino acid sequences.

Results of the foregoing analysis are shown in the following items (1) to (4).

(1) JHC Genome Architecture and ORF Mapping

The architecture of the JHC genome is typical of HCMV in that the genome may be divided into 6 regions, that is, TRL, UL, IRL, IRS, US and TRS, and lengths thereof were 940 bp, 193,457 bp, 940 bp, 2,639 bp, 35,512 bp and 2,639 bp, respectively. A genome map of the strain JHC is shown in FIG. 1A. An overall genome length and architecture were very similar to those of HCMV strains, except that the strain AD169-varUK contains much longer TRL and IRL/IRS regions than clinical isolates due to the presence of duplicated RL genes in these regions. G+C content of the JHC genome is approximately 57.5%, similar to other analyzed HCMV strains. The following Table 1 shows HCMV strains analyzed in the present invention, and GenBank accession numbers, genome lengths and GC contents thereof.

TABLE 1

HCMV strains analyzed in this study and their GenBank accession numbers, genome lengths and GC contents

| Strain | Source | Genome length (bp) | % GC |
|---|---|---|---|
| AD169-varUK | NC_001347.6 | 230,290 | 57.2 |
| AD169-varUC | FJ527563.1 | 231,781 | 57.6 |
| Towne | FJ616285.1 | 235,147 | 57.5 |
| HAN38 | GQ396662.1 | 236,112 | 57.6 |
| HAN20 | GQ396663.1 | 235,728 | 57.5 |
| HAN13 | GQ221973.1 | 236,219 | 57.5 |
| 3157 | GQ221974.1 | 235,154 | 57.5 |
| 3301 | GQ466044.1 | 235,703 | 57.5 |
| JP | GQ221975.1 | 236,375 | 57.5 |
| Toledo | GU937742.1 | 235,398 | 57.5 |
| Merlin | NC_006273.2 | 235,646 | 57.5 |
| JHC | The present invention | 235,476 | 57.5 |

Figure 1B:
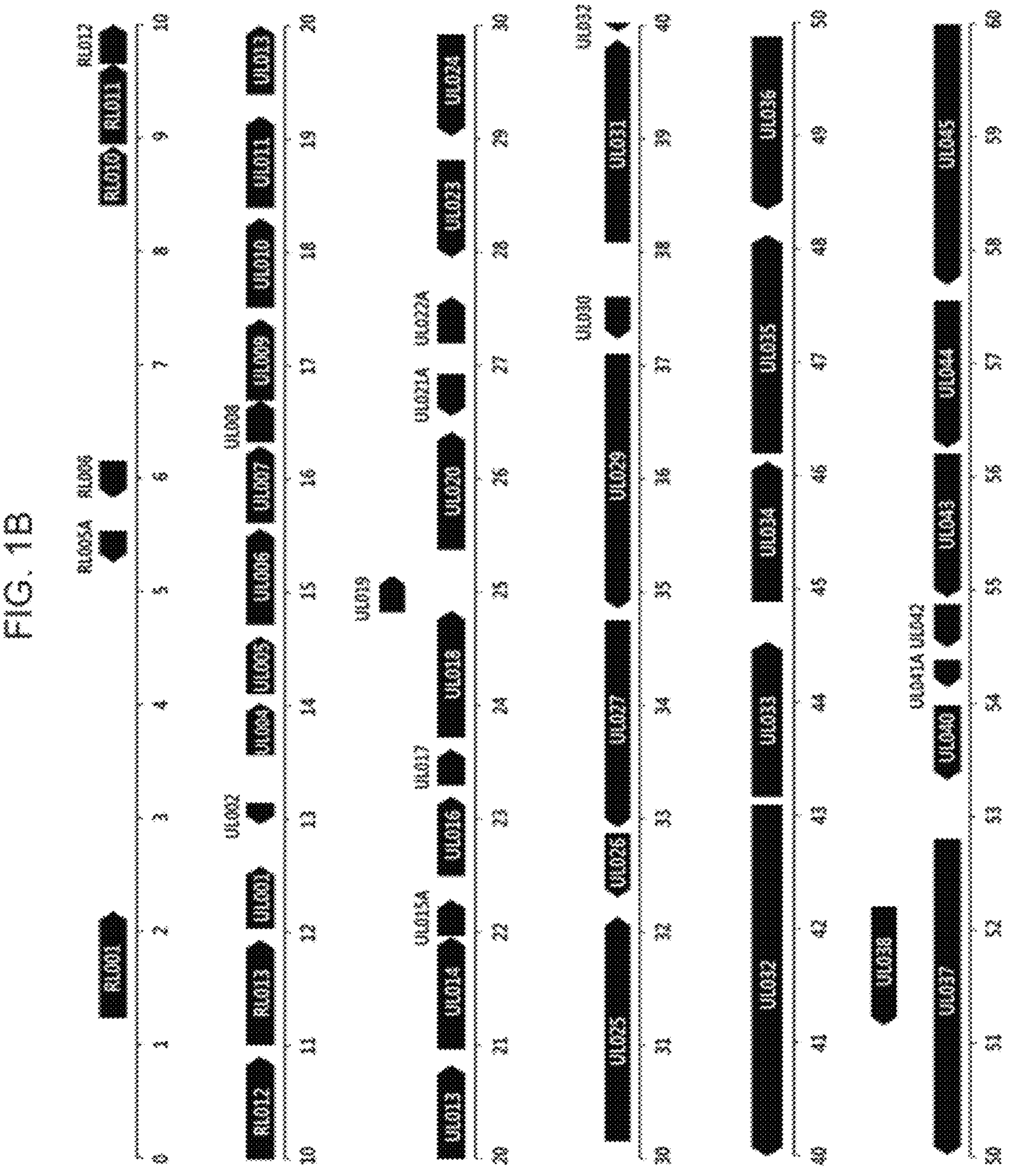
FIG. 1B illustrates an ORF map of HCMV strains JHC.
Figure 1B:
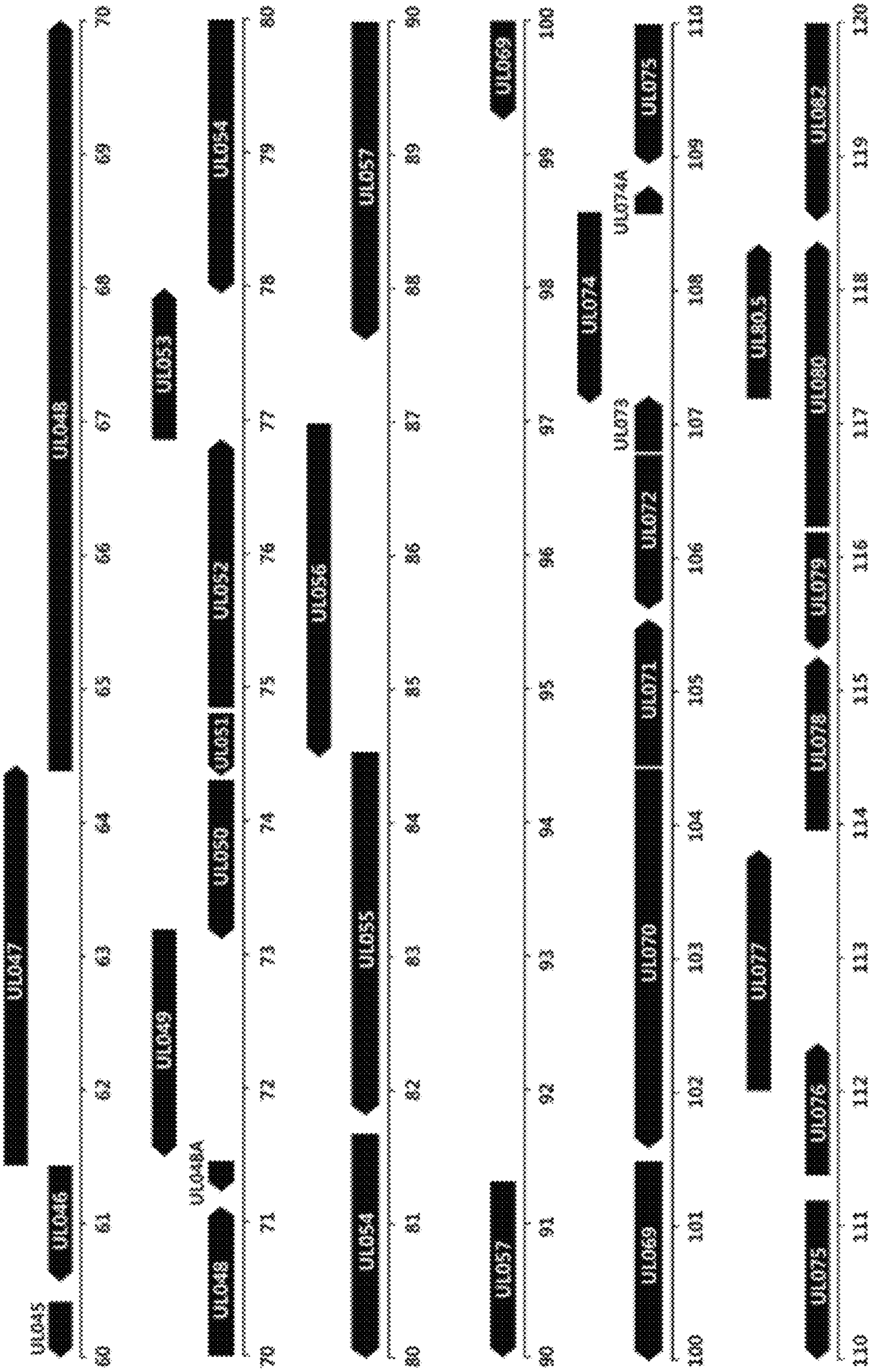
Figure 1B:
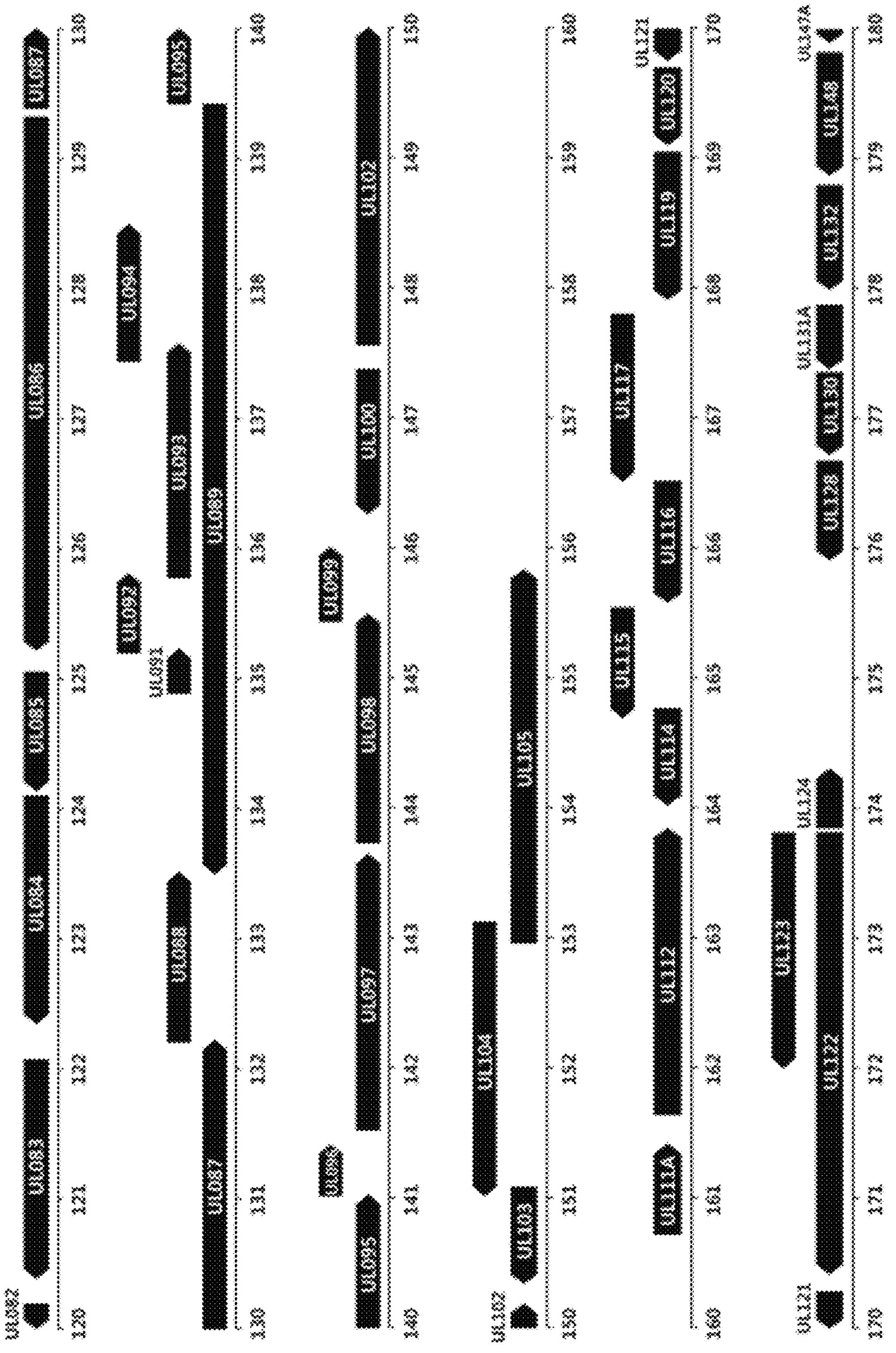
Figure 1B:
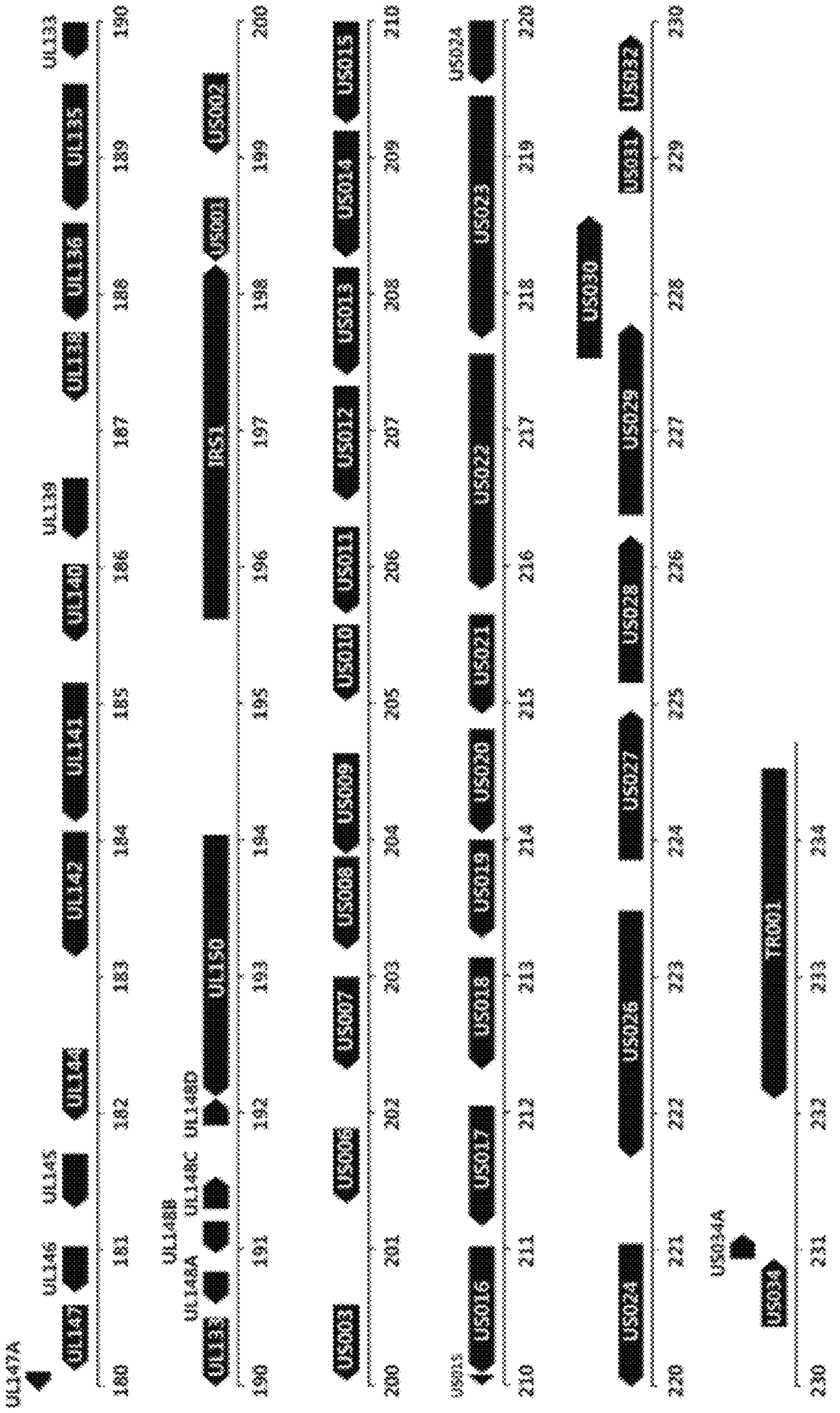

The strain JHC includes 165 ORFs. Among these strains, 7 are RL genes, 125 are UL genes and 31 are US genes. Two other ORFs are IRS and TRS. Like other clinical isolates, 19 ORFs between UL133 and UL150 are located at 3' end of the UL region of the strain JHC. This region is occupied by duplicated RL genes in AD169-varUK strain, and ORFs UL141, 142 and 144 are not located in AD169-varUC strain. Among the 165 ORFs in the strain JHC, 67 are in forward direction and 98 are in reverse direction. The directions of ORFs are 100% conserved among the 12 HCMV strains analyzed in the present invention. The ORF map of the strain JHC is shown in FIG. 1B.

(2) Analysis for Characteristics of the Strain JHC ORFs

Although ORF sequences are somewhat diverse among different strains, ORF lengths are relatively similar among different strains. 78 of the 165 ORFs have the same lengths regardless of the strains. Two ORFs of the strain JHC were 3 nucleotides shorter (UL56) or longer (UL99) than the other strains and this fact suggests insertion or deletion events specific for the strain JHC. 3 nucleotides ACA in the UL56 of the strain were deleted at position 1337-1339 of the other HCMV strains. In the UL99 of the strain JHC, insertion of GAA was found at position 344-345 of the other HCMV strains.

Figure 3A:
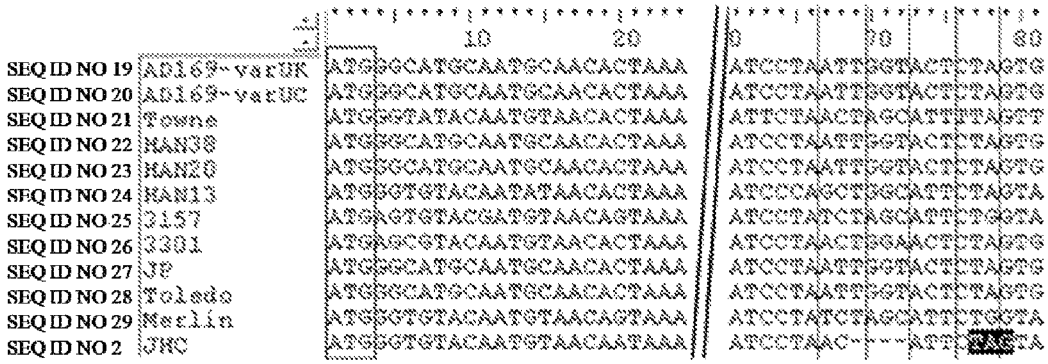
FIG. 3A illustrates a frame-shift mutation caused by deletion of 4 nucleotides in UL1 of the strain JHC.
Figure 3B:
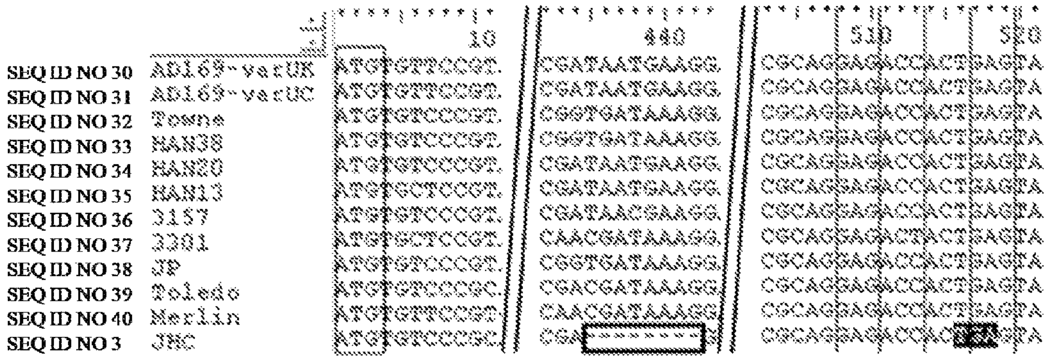
FIG. 3B illustrates a frame-shift mutation caused by deletion of 8 nucleotides in UL119 of the strain JHC.

Comparison of the strain JHC ORFs with those of other strains revealed two early stops and one unusual start codon. Two UL genes of the strain JHC are truncated due to formation of early stop codons. In UL1, deletion of 4 nucleotides (consensus: TGGC) at position 69-72 resulted in a frame-shift and generated a new stop codon TAG at codon number 25 (see FIG. 3A). In UL119 of the strain JHC, a frame-shift mutation was observed due to a deletion of 8 nucleotides (consensus: TGATAAAG) at nucleotide position 435-442, resulting in a new stop codon TGA at nucleotide position 505-507 (see FIG. 3B).

Figure 4B:
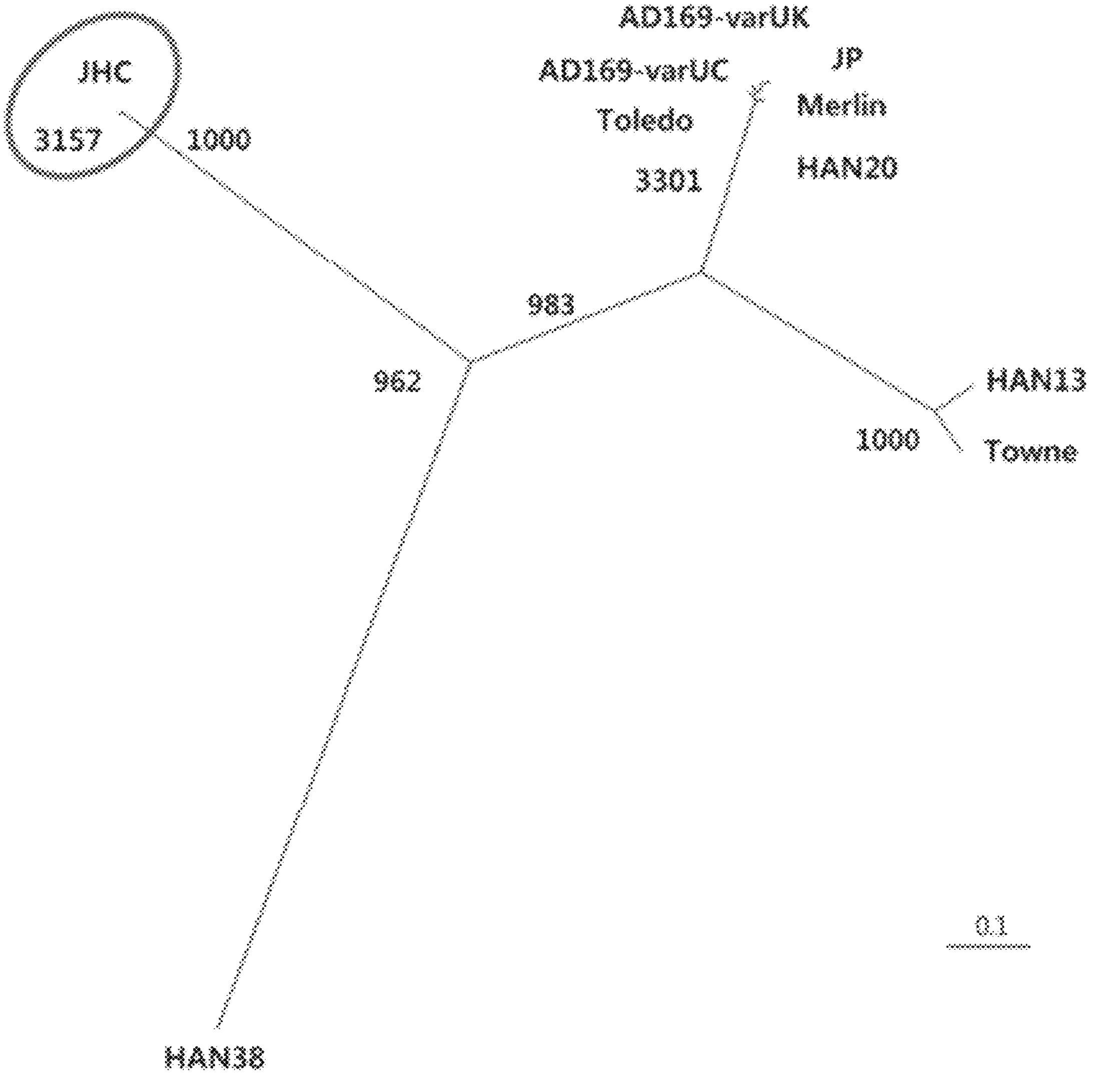
FIG. 4B illustrates a phylogenetic tree drawn using a neighbor-joining method based on a nucleotide sequence of HCMV UL6A.
Figure 4C:
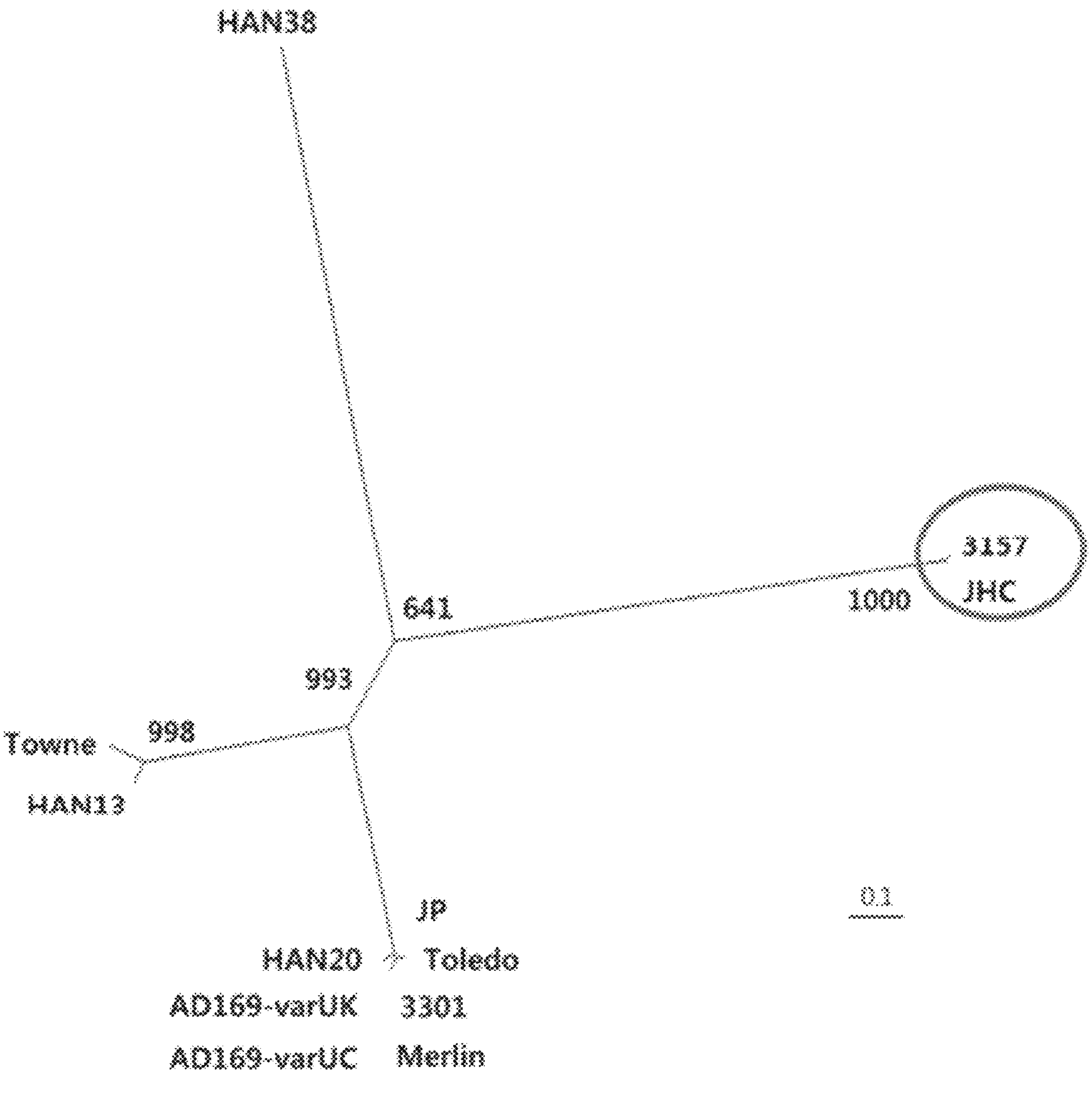
FIG. 4C illustrates a phylogenetic tree drawn using a neighbor-joining method based on an amino acid sequence of HCMV UL6A.

The strain JHC includes an ORF having unusual start codons. RL6 starts with TTG in the strains JHC and 3157. HAN13 has an unusual ATA start codon and the strain HAN38 starts with ACG (see FIG. 4A). All other strains include common ATG start codons. Sequence alignment data shown in FIG. 4A suggest that HCMV may be divided into 4 groups based on the RL6 sequence diversity. JHC is clustered with the strain 3157 and this cluster is distinct from the other groups. Towne and HAN13 form another cluster and strains AD169-varUK, AD169-varUC, Toledo, Merlin, 3301 and HAN20 form a third cluster in both the nucleotide sequence (FIG. 4B) and the amino acid sequence (FIG. 4C). HAN38 is separated from the others and forms a fourth cluster. The strains JHC and 3157 are highly similar in their nucleotide and amino acid sequences.

(3) Analysis of Micro RNAs

HCMV is known to have genetic information for at least 14 micro RNAs (miRNAs). It was examined whether these miRNA sequences are conserved in the strain JHC as well as in the other strains. The 12 HCMV strains investigated in the present invention include all genetic information for miRNAs. The locations of the miRNA sequences on the genomes of the strain JHC and two reference strains AD169-varUK and Merlin are shown in the following Table 2.

TABLE 2

| miRNA[a] | Mature miRNA sequence (5'->3')[b] | Genome location[c] AD169-UK | Merlin | JHC |
|---|---|---|---|---|
| miR-UL22A-1-5p | UAACUAGCCUUCccGUGAgA (SEQ. ID NO. 5) | 27,650-27,669 | 27,992-28,011 | 27,753-27,772 |
| miR-UL22A-1-3p | UCACcAGAAuGCUaGUUuguAG (SEQ. ID NO. 6) | 27,687-27,708 | 28,029-28,050 | 27,790-27,811 |
| miR-UL36-1 | UCGUUGaAGACACCUGGAAAGA (SEQ. ID NO. 7) | 49,564-49,543 | 49,914-49,893 | 49,674-49,653 |
| miR-UL70-1-5p | UGCGUCUCGGCCUCGUCCAGa (SEQ. ID NO. 8) | 104,021-104,041 | 104,405-104,424 | 104,157-104,176 |
| miR-UL70-1-3p | GGGGAUGGGCUGgCGCGCGG (SEQ. ID NO. 9) | 104,062-104,081 | 104,445-104,464 | 104,197-104,216 |
| miR-UL112-1 | AAGUGACGGUGAGAUCCAGGCU (SEQ. ID NO. 10) | 164,162-164,183 | 164,557-164,578 | 164,280-164,301 |
| miR-UL148D-1 | UCGUCCUCCCCUUCUUCACCG (SEQ. ID NO. 11) | Not present | 193,587-193,607 | 193,370-193,390 |
| miR-US4-1 | CGACAUGGACGUGCAGGGGGAU (SEQ. ID NO. 12) | 196,090-196,111 | 201,371-201,392 | 201,098-201,119 |

TABLE 2-continued

| miRNA[a] | Mature miRNA sequence (5'->3')[b] | Genome location[c] AD169-UK | Merlin | JHC |
|---|---|---|---|---|
| miR-US5-1 | UGAcAAGCCUGACGAGAgcGU (SEQ. ID NO. 13) | 197,036-197,056 | 202,317-202,337 | 202,048-202,068 |
| miR-US5-2 | UUAUGAUAGGuGUGACGAUGUC (SEQ. ID NO. 14) | 197,163-197,184 | 202,444-202,465 | 202,179-202,200 |
| miR-US25-1 | AACCGCUCAGUGGCUCGGACC (SEQ. ID NO. 15) | 216,245-216,225 | 221,539-221 519 | 221,271-221,251 |
| miR-US25-2-5p | Agcggucuguucagguggauga (SEQ. ID NO. 16) | 216,466-216,445 | 221,760-221.739 | 221,492-221,471 |
| miR-US25-2-3p | Auccacuuggagagcuccccgc (SEQ. ID NO. 17) | 216,408-216,388 | 221,702-221,682 | 221,434-221,414 |
| miR-US33-1 | GAUUGUGCCCGGACCGUGGGCG (SEQ. ID NO. 18) | 221,468-221,447 | 226,768-226,747 | 226,500-226,479 |

[a]miRNAs are named according to Dolken, et al. (2009).
[b]Nucleotides not conserved in between human and chimpanzee CMV are indicated by small letters.
[c] miRNA sequences located on the genome in reverse direction are underlined.

Five miRNA sequences (miR-UL36-1, miR-US25-1, miR-US25-2-5p, miR-US25-2-3p and miR-US33-1) are present in reverse direction. The miRNA sequences are near 100% conserved in the strain JHC and other HCMV genomes. The exceptions are miR-UL70-1-5p and miR-UL148D-1. AD169-varUK does not contain miR-UL148D-1 since the region between UL133 and UL150 is deleted and replaced by RL sequences (see Table 2). The sequence of miR-UL70-1-5p in the strain JHC is 5'-CGCGTCTCGGCCTCGTCCAGA-3' (SEQ. ID NO. 19). The first base T was substituted by C in the strain JHC and this substitution is also found in the strains Merlin, HAN13, HAN20 and 3157.

(4) Mutation Related with Passage in Cell Culture

Certain mutations in RL13 and UL128 locus (UL128L: UL128, UL130 and UL131A) genes are known to be required in order to allow HCMV to grow in fibroblasts. Thus, it was examined whether the strain JHC as well as other HCMV strains have experienced mutations in these genes. Results of the examination are shown in the following Table 3.

TABLE 3

| Strain | Passage history[a] | RL13 Length[b] | RL13 Mutation | UL128 Length | UL128 Mutation | UL130 Length | UL130 Mutation | UL131A Length | UL131A Mutation | Unusual start codon in RL6 |
|---|---|---|---|---|---|---|---|---|---|---|
| AD169-UK | several times | 147 | Frame shift[c] | 171 | — | 214 | — | 74 | frameshift | — |
| AD169-UC | several times | 147 | frameshift | 171 | — | 214 | — | 74 | frameshift | — |
| Towne | several times | 42 | frameshift | 171 | — | 229 | read-through[e] | 129 | — | — |
| Toledo | several times | 209 | 279 bp del | 100 | Nonsense[d] | 214 | — | 129 | — | — |
| HAN13 | 3 | 294 | — | 171 | — | 214 | — | 129 | — | ATA |
| 3157 | 3 | 70 | frameshift | 171 | — | 214 | — | 129 | — | TTG |
| Merlin | 3 | 293 | — | 130 | nonsense | 214 | — | 129 | — | — |
| JHC | 3 | 306 | — | 171 | — | 214 | — | 129 | — | TTG |
| HAN38 | 2 | 301 | — | 171 | — | 214 | — | 129 | — | ACG |
| HAN20 | 2 | 302 | — | 171 | — | 214 | — | 129 | — | — |
| 3301 | unpassaged | 307 | — | 171 | — | 214 | — | 129 | — | — |
| JP | unpassaged | 302 | — | 171 | — | 214 | — | 129 | — | — |

[a]According to the information in GenBank.
[b]Expected number of amino acid residues in each protein. Underlined parts indicate significant loss of amino acids.
[c]Frame-shift mutation due to insertion or deletion resulting in early stops: insertion of 1 bp in RL13, insertion of 1 bp in UL131A of AD169-UK and AD169-UC, insertion of 1 bp in RL13 of Towne and 2 bp in RL13 of 3157.
[d]Nonsense mutation due to substitution in UL128 gene; T302A in strain Toledo and C391T in strain Merlin.
[e]Read-through mutation due to insertion of 2 Ts at nucleotide position 610.

As shown in the above Table 3, the strain JHC and 3 other strains (HAN13, HAN20, HAN38) with limited passages in fibroblasts did not exhibit significant alterations in RL13 or UL128L genes. On the other hand, early stops were observed in two strains with limited passages due to frame-shift mutation in RL13 of the strain 3157 and nonsense mutation caused by substitution of C391T in UL128 of the strain Merlin. In the case of two strains without a history of in vitro cell passage, significant alterations were not observed in RL13 or UL128L genes. Four strains analyzed in the present invention are known to have extensive in vitro cell passages and all exhibited early stops due to frame-shift mutation or end truncation, which is caused by deletion of 279 bp in RL13. Nonsense mutation in UL128 of the strain Toledo was also observed. In addition, read-through mutation was found in UL130 of the strain Toledo while UL128 of the strain Toledo exhibited early stops. In both of the AD169 strains, early stops were observed due to frame-shift mutation. Furthermore and interestingly, it was found that 4 of the afore-mentioned 6 strains with limited passages in cell culture include unusual start codons in RL6, which were not observed in any of the strains with extensive passages or without passage.

EXAMPLE 3

Phylogenetic Analysis

Based on full nucleotide sequences of 12 HCMV strains, phylogenetic trees were constructed using a neighbor-joining method.

The nucleotide sequence of the strain JHC was multiple-aligned with those of 11 other HCMV strains registered in NCBI GeneBank database, by way of ClustalW (ver. 1.83), followed by manual editing. The resulting output files were used for construction of phylogenetic trees through Dnadist and neighbor programs included in Phylip package (version 3.6). Distance matrix was obtained by Kimura-2-parameter. Cluster analysis was performed by the neighbor-joining method and resulting tree files were viewed by the Treeview program (version 1.6.6). Significance of the phylogenetic trees was verified by bootstrap analysis. Phylogenetic trees were constructed from one thousand replicates generated by Seqboot program and the consensus tree was identified by the Consense program.

Figure 2A:
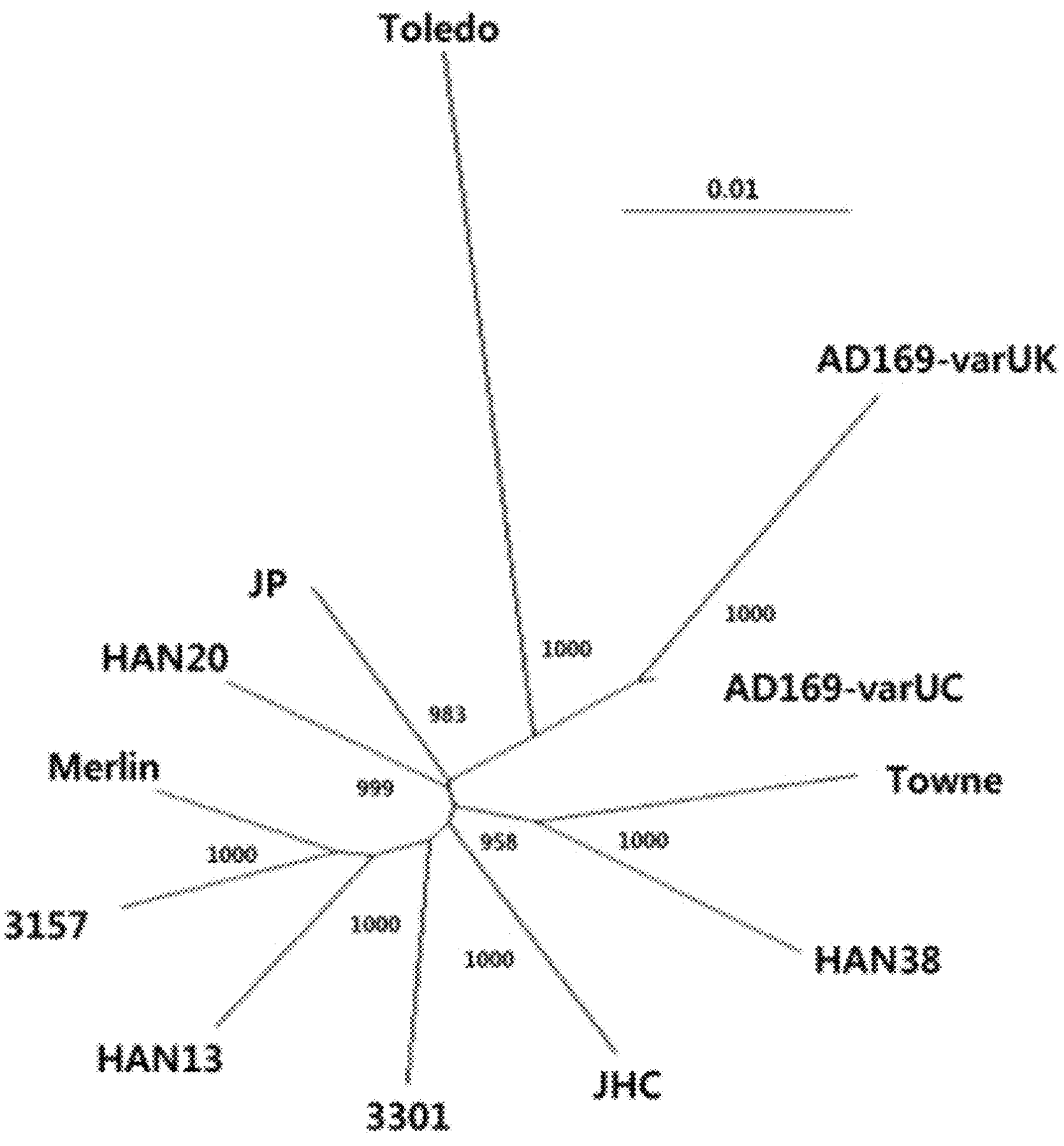
FIG. 2A illustrates a phylogenetic tree of HCMV based on full genomic nucleotide sequences.
Figure 2B:
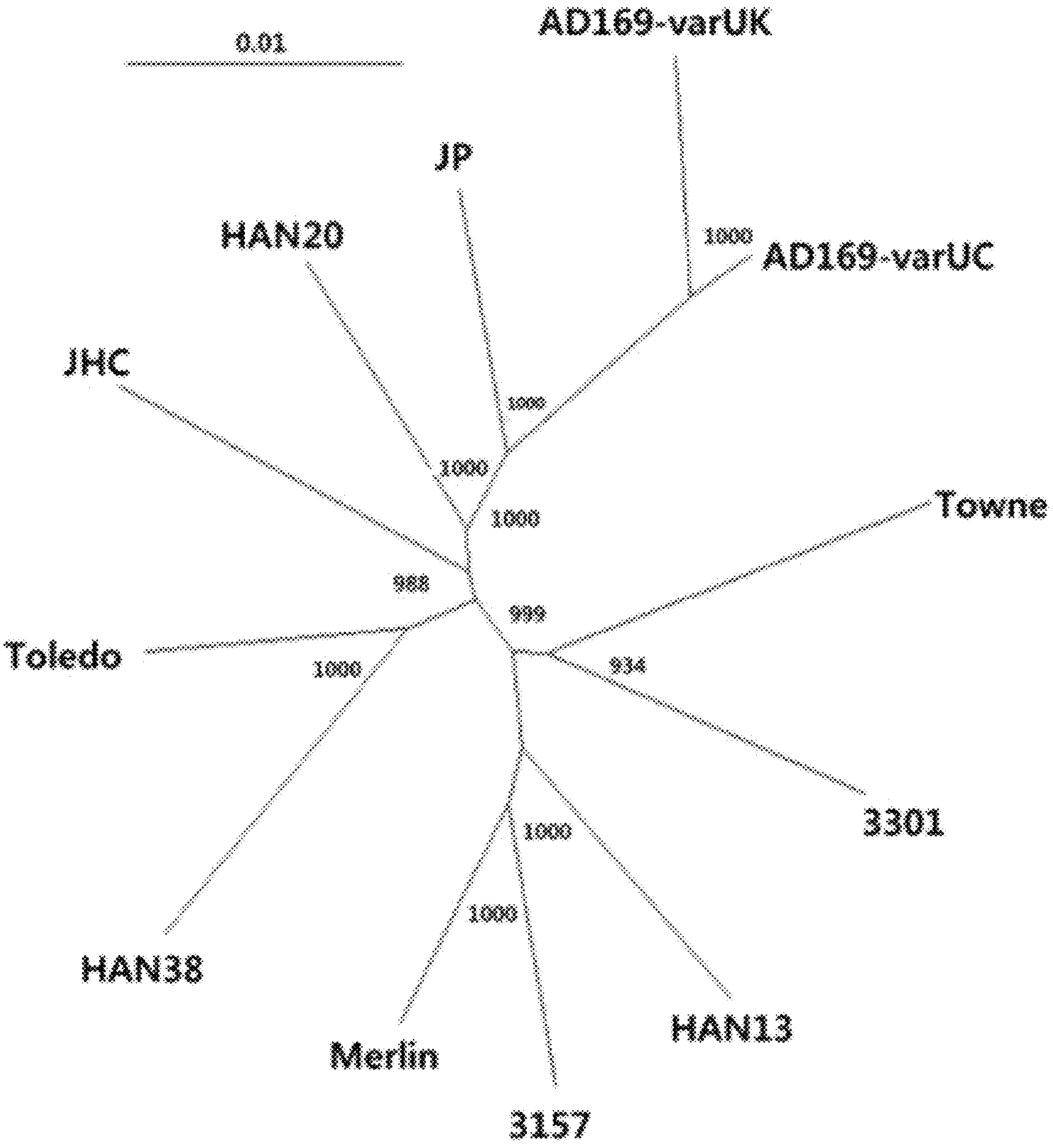
FIG. 2B illustrates a phylogenetic tree of HCMV based on common genomic nucleotide sequences.

Results of the foregoing examination are shown in FIG. 2. Contrary to expectation, there were no clear clustering of the 3 lab-adapted strains AD169-varUK, AD169-varUC and Towne or separation from the other clinical strains (FIG. 2A). The strain JHC was placed in the middle of the other strains. Since the lab-adapted strains AD169-varUK did not contain UL/b' sequences, the phylogenetic tree was constructed after deleting all these sequences from the full genome. All of the 12 strains were randomly distributed in the phylogenetic tree and there was no clear clustering of any specific strains, except for the two AD169 strains (see FIG. 2B). Therefore, it is considered that HCMV strains are not grouped on the basis of the full nucleotide sequences, at least among the 12 strains analyzed in the present invention.

As is apparent from the detailed description, the present invention has determined the whole nucleotide sequence of a JHC strain firstly isolated from an Asian, that is, a Korean patient, other than American and/or European people. Accordingly, the present invention may be helpful to understand molecular characteristics of HCMVs through phylogenetic analysis and gene comparative studies and, in addition, JHC strains may be used as a reference strain for HCMVs of Korean or other Asian people.

What is claimed is:

1. An isolated host cell transformed with an isolated DNA sequence of an HCMV strain JHC, wherein the DNA sequence is SEQ ID NO: 1, SEQ ID NO: 2, SEQ ID NO: 3, or SEQ ID NO: 4.

* * * * *